(12) United States Patent
Poupot et al.

(10) Patent No.: US 10,106,565 B2
(45) Date of Patent: Oct. 23, 2018

(54) PHOSPHORYLATED DENDRIMERS AS ANTIINFLAMMATORY DRUGS

(71) Applicant: CENTRE NATIONAL DE LA RECHERCHE SCIENTIFIQUE, Paris (FR)

(72) Inventors: Mary Poupot, Aigrefeuille (FR); Remy Poupot, Aigrefeuille (FR); Jean-Jacques Fournie, Corronsac (FR); Damien Portevin, London (GB); Severine Fruchon, Toulouse (FR); Jean-Luc Davignon, Beauzelle (FR); Cedric-Olivier Turrin, Toulouse (FR); Anne-Marie Caminade, Toulouse (FR); Jean-Pierre Majoral, Ramonville-Saint-Agne (FR); Olivier Rolland, Toulouse (FR)

(73) Assignees: CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR); UNIVERSITE PAUL SABATIER (TOULOUSE III), Toulouse (FR)

( * ) Notice: Subject to any disclaimer, the term of this patent is extended or adjusted under 35 U.S.C. 154(b) by 629 days.

(21) Appl. No.: 13/932,499

(22) Filed: Jul. 1, 2013

(65) Prior Publication Data
US 2013/0336997 A1 Dec. 19, 2013

Related U.S. Application Data

(63) Continuation-in-part of application No. 12/525,416, filed as application No. PCT/IB2008/002547 on Aug. 1, 2008.

(51) Int. Cl.
| | |
|---|---|
| A61K 31/66 | (2006.01) |
| A61K 31/675 | (2006.01) |
| C07F 9/6593 | (2006.01) |
| C07F 9/38 | (2006.01) |
| C07F 9/6581 | (2006.01) |
| C07F 9/26 | (2006.01) |
| C07F 9/40 | (2006.01) |
| C08G 83/00 | (2006.01) |
| C08G 73/02 | (2006.01) |

(52) U.S. Cl.
CPC ............ *C07F 9/65815* (2013.01); *C07F 9/26* (2013.01); *C07F 9/3808* (2013.01); *C07F 9/3873* (2013.01); *C07F 9/405* (2013.01); *C07F 9/4009* (2013.01); *C07F 9/65817* (2013.01); *C08G 73/0206* (2013.01); *C08G 73/028* (2013.01); *C08G 83/004* (2013.01)

(58) Field of Classification Search
CPC .................................................. C07F 9/65815
USPC ......... 514/89, 63, 93, 102, 105, 107, 79, 75, 514/141
See application file for complete search history.

(56) References Cited

U.S. PATENT DOCUMENTS

2008/0317699 A1 12/2008 Avila et al.

FOREIGN PATENT DOCUMENTS

| WO | 9803573 | 1/1998 |
|---|---|---|
| WO | 03080121 | 10/2003 |
| WO | 03089010 | 10/2003 |
| WO | 2006024769 | 3/2006 |
| WO | 2006040579 | 4/2006 |
| WO | 2007106437 | 9/2007 |

OTHER PUBLICATIONS

Kornek et al., American Journal of Pathology, vol. 157, No. 1, Jul. 2000.*
Broadley et al., Brain, 2000, 123, 1102-1111.*
Huskisson et al., The Lancet, 1976, pp. 393-395.
Poupot M et al., "Design of phosphorylated dendritic architectures to promote human monocyte activation", The FASEB Journal, vol. 20, No. 13, Nov. 1, 2006, pp. 2339-2351, XP009116041.
Rolland O et al., "Tailored control and optimisation of the number of phosphonic acid termini on phosphorus-containing dendrimers for the ex-vivo activation of human monocytes", Chemistry—A European Journal, vol. 14, No. 16, May 29, 2008, pp. 4836-4850, XP009116043.
Fruchon S et al., "Anti-inflammatory and immunosuppressive activation of human monocytes by a bioactive dendrimer", Journal of Leukocyte Biology, vol. 85, No. 3, Mar. 2009, pp. 553-562, XP009115979.
International search report dated May 12, 2009 in corresponding PCT/IB2008/002547.

\* cited by examiner

*Primary Examiner* — Shobha Kantamneni
(74) *Attorney, Agent, or Firm* — Young & Thompson

(57) ABSTRACT

Dendrimers with monophosphonic or bisphosphonic terminations for the treatment of inflammatory diseases.

1 Claim, 19 Drawing Sheets

Structure of dendrimer Gc1 (or (Aza2P)$_{12}$ or ABP)

Structure of dendrimer (Aza2P)₁₀-Julo-D

Structure of dendrimer (Aza2P)₁₀-Biot-D

Inhibition of the proliferation of CD4 T lymphocytes by dendrimer Gc1 at 20 µM.

Inhibition of the proliferation of purified CD4 T lymphocytes by dendrimer Gc1 at 20 µM.

Inhibition of the proliferation of purified CD4 T lymphocytes by dendrimers Gc1, $(Aza2P)_{10}$-Julo-D and $(Aza2P)_{10}$-Biot-D at 20 μM.

Figure 7

The primer pairs used for quantitative RT-PCR.

| gene name | primers | sequence 5' → 3' | product (pb) |
|---|---|---|---|
| GAPDH | F | cca tgt tcg tca tgg gtg tg | 73 |
| | R | gtg cag gag gca ttg ctg at | |
| MRC1 | F | tga acg gaa tga ttg tgt agc ttt a | 184 |
| | R | cag gtt gga aga cgg ttt aga ag | |
| IL-10 | F | aac aag agc aag gcc gtg g | 93 |
| | R | gaa gat gtc aaa ctc act cat ggc | |
| CCL18 | F | cct cgt cta tac ctc ctg gca g | 98 |
| | R | tgg tta gga gga tga cac ctg g | |
| IL-1RN | F | tct gtt ctt ggg aat cca tgg | 96 |
| | R | tca gtg atg tta act gcc tcc ag | |
| CD23 | F | cta agg atg gag ttg cag gtg tc | 81 |
| | R | gca ctt ccg ttg gaa att gat c | |
| CCL5 | F | ctg cat ctg cct ccc cat at | 97 |
| | R | tag aaa tac tcc ttg atg tgg gca c | |
| IL-1β | F | gaa ctg aaa gct ctc cac ctc c | 114 |
| | R | gag gcc caa ggc cac ag | |
| IL-6 | F | tga gag tag tga gga aca gc cag | 122 |
| | R | tgg cat ttg tgg ttg ggt c | |
| IL-12 | F | tga tgg ccc tgt gcc tta g | 90 |
| | R | gat cca tca gaa gct tgc at tc | |

Figure 8(1)

24 of the 78 up-regulated genes in monocytes activated by dendrimer Gc1 (*da*-monocytes)

| Affymetrix identifier | Gene Symbol | Donor 1 | p-value | Donor 2 | p-value | Donor 3 | p-value | Gene Description |
|---|---|---|---|---|---|---|---|---|
| 1552398_a_at | CLEC12A | 2,49 | 0,00002 | 1,95 | 0,0001 | 3,58 | 0,00002 | C-type lectin domain family 12, member A |
| 1553413_at | FLJ13744 | 3,15 | 0,00010 | 1,17 | 0,4419 | 3,57 | 0,00086 | Hypothetical protein FLJ13744 |
| 1555141_a_at | LOC150159 | 3,26 | 0,00055 | 3,12 | 0,00004 | 0,68 | 0,09428 | CG10806-like |
| 1560869_a_at | — | 2,57 | 0,00002 | 2,22 | 0,00002 | 4,26 | 0,00002 | Full length insert cDNA clone YQ50C11 |
| 1568768_s_at | BRE | 2,92 | 0,00009 | 9,80 | 0,00049 | 1,81 | 0,08894 | brain and reproductive organ-expressed (TNFRSF1A modulator) |
| 1569352_at | KIAA1450 | 2,68 | 0,00002 | 3,36 | 0,00002 | 3,45 | 0,00039 | KIAA1450 protein |
| 200755_s_at | CALU | 2,31 | 0,00002 | 2,60 | 0,00134 | 1,28 | 0,25285 | calumenin |
| 202759_s_at | PALM2-AKAP2 | 2,06 | 0,00002 | 2,16 | 0,00002 | 2,22 | 0,00002 | PALM2-AKAP2 protein |
| 202760_s_at | PALM2-AKAP2 /// AKAP2 | 2,02 | 0,00002 | 2,30 | 0,00002 | 3,57 | 0,00002 | A kinase (PRKA) anchor protein 2 /// PALM2-AKAP2 protein |
| 202877_s_at | C1QR1 | 2,46 | 0,00002 | 2,54 | 0,00027 | 3,18 | 0,00035 | complement component 1, q subcomponent, receptor 1 |
| 203276_at | LMNB1 | 2,87 | 0,00003 | 2,30 | 0,00077 | 1,09 | 0,4381 | lamin B1 |
| 203474_at | IQGAP2 | 1,84 | 0,00002 | 2,00 | 0,00002 | 4,03 | 0,00003 | IQ motif containing GTPase activating protein 2 |
| 203548_s_at | LPL | 1,15 | 0,5 | 2,08 | 0,00031 | 6,37 | 0,00002 | lipoprotein lipase |
| 203710_at | ITPR1 | 2,15 | 0,00086 | 1,96 | 0,00011 | 3,68 | 0,00062 | inositol 1,4,5-triphosphate receptor, type 1 |
| 204014_at | DUSP4 | 3,86 | 0,00003 | 3,72 | 0,00002 | 7,14 | 0,00086 | dual specificity phosphatase 4 |
| 204142_at | ENOSF1 | 2,48 | 0,00011 | 1,98 | 0,00108 | 4,46 | 0,00010 | enolase superfamily member 1 |
| 204221_x_at | GLIPR1 | 1,7 | 0,00249 | 2,03 | 0,00097 | 2,04 | 0,00165 | GLI pathogenesis-related 1 (glioma) |
| 204438_at | MRC1 | 2,77 | 0,00044 | 4,18 | 0,00069 | 11,90 | 0,00003 | mannose receptor, C type 1 |
| 204475_at | MMP1 | 37,04 | 0,00002 | 21,74 | 0,00002 | 34,48 | 0,00002 | matrix metalloproteinase 1 (interstitial collagenase) |
| 204935_at | PTPN2 | 2,27 | 0,00003 | 2,16 | 0,00003 | 1,78 | 0,00031 | protein tyrosine phosphatase, non-receptor type 2 |
| 204951_at | RHOH | 3,04 | 0,00002 | 4,07 | 0,00002 | 3,32 | 0,00044 | ras homolog gene family, member H |
| 205239_at | AREG | 2,86 | 0,00002 | 2,50 | 0,00003 | 1,75 | 0,0037 | amphiregulin (schwannoma-derived growth factor) |
| 205680_at | MMP10 | 2,05 | 0,00006 | 5,68 | 0,00002 | 4,78 | 0,00010 | matrix metalloproteinase 10 (stromelysin 2) |
| 205965_at | BATF | 2,25 | 0,00069 | 2,41 | 0,00005 | 1,7 | 0,02293 | basic leucine zipper transcription factor, ATF-like |

Figure 8(2)

27 of the 78 up-regulated genes in monocytes activated by dendrimer Gc1 (*da*-monocytes)

| Affymetrix identifier | Gene Symbol | Donor 1 | p-value | Donor 2 | p-value | Donor 3 | p-value | Gene Description |
|---|---|---|---|---|---|---|---|---|
| 206181_at | SLAMF1 | 6,41 | 0,00002 | 8,55 | 0,00002 | 1,19 | 0,14568 | signaling lymphocytic activation molecule family member 1 |
| 206239_s_at | SPINK1 | 2,74 | 0,00002 | 2,82 | 0,00008 | 3,42 | 0,00002 | serine protease inhibitor, Kazal type 1 |
| 206341_at | IL2RA | 1,39 | 0,00003 | 2,70 | 0,00002 | 2,19 | 0,00062 | interleukin 2 receptor, alpha |
| 206569_at | IL24 | 2,84 | 0,00003 | 3,97 | 0,00003 | 4,90 | 0,00002 | interleukin 24 |
| 207433_at | IL10 | 2,93 | 0,00002 | 2,83 | 0,00010 | 0,99 | 0,17741 | interleukin 10 |
| 207442_at | CSF3 | 3,48 | 0,00003 | 3,16 | 0,00002 | 0,39 | 0,76745 | colony stimulating factor 3 (granulocyte) |
| 208303_s_at | CRLF2 | 2,29 | 0,00002 | 3,34 | 0,00183 | 1,92 | 0,0412 | cytokine receptor-like factor 2 |
| 209146_at | SC4MOL | 8,62 | 0,00149 | 1,5 | 0,00015 | 2,60 | 0,00002 | sterol-C4-methyl oxidase-like |
| 209210_s_at | PLEKHC1 | 4,72 | 0,00002 | 4,29 | 0,00002 | 5,05 | 0,00002 | pleckstrin homology domain containing, family C (with FERM |
| 209395_at | CHI3L1 | 2,31 | 0,00008 | 4,52 | 0,00007 | 1,12 | 0,2609 | chitinase 3-like 1 (cartilage glycoprotein-39) |
| 209813_x_at | TRGC2 / TRGV9 | 3,01 | 0,00002 | 2,92 | 0,00002 | 4,61 | 0,00002 | T cell receptor gamma constant 2 /// T cell receptor gamma constant 2 /// T cell receptor gamma variable 9 /// T cell receptor gamma variable 9 |
| 209924_at | CCL18 | 3,77 | 0,00002 | 2,76 | 0,00002 | 4,05 | 0,00011 | chemokine (C-C motif) ligand 18 (pulmonary and activation-regulated) |
| 210139_s_at | PMP22 | 2,71 | 0,00027 | 3,69 | 0,00005 | 1,24 | 0,00019 | peripheral myelin protein 22 |
| 210511_s_at | INHBA | 2,38 | 0,00002 | 2,67 | 0,00002 | 5,71 | 0,00002 | inhibin, beta A (activin A, activin AB alpha polypeptide) |
| 211144_x_at | TRGC2 | 2,56 | 0,00002 | 2,54 | 0,00015 | 5,24 | 0,00002 | T cell receptor gamma constant 2 |
| 212230_at | PPAP2B | 2,23 | 0,00002 | 1,73 | 0,00003 | 2,82 | 0,00005 | phosphatidic acid phosphatase type 2B |
| 212942_s_at | KIAA1199 | 3,94 | 0,00002 | 5,81 | 0,00002 | 1,49 | 0,00086 | KIAA1199 |
| 213073_at | ZFYVE26 | 2,04 | 0,00004 | 1,98 | 0,00003 | 2,72 | 0,00002 | zinc finger, FYVE domain containing 26 |
| 213246_at | C14orf109 | 1,42 | 0,00002 | 2,07 | 0,00003 | 2,07 | 0,00002 | chromosome 14 open reading frame 109 |
| 213807_x_at | MET | 0,97 | 0,5 | 2,47 | 0,00165 | 3,44 | 0,00069 | met proto-oncogene (hepatocyte growth factor receptor) |
| 214234_s_at | CYP3A5 | 2,43 | 0,00010 | 2,78 | 0,00031 | 2,04 | 0,0333 | cytochrome P450, family 3, subfamily A, polypeptide 5 |
| 214581_x_at | TNFRSF21 | 6,67 | 0,00011 | 4,05 | 0,00002 | 1,49 | 0,03097 | tumor necrosis factor receptor superfamily, member 21 |
| 215561_s_at | IL1R1 | 1,32 | 0,00492 | 7,69 | 0,00015 | 4,41 | 0,00011 | interleukin 1 receptor, type I |
| 215724_at | PLD1 | 4,41 | 0,00165 | 2,83 | 0,00203 | 2,30 | 0,00183 | phospholipase D1, phophatidylcholine-specific |
| 215856_at | CD33L3 | 1,41 | 0,00077 | 3,06 | 0,00009 | 2,65 | 0,00149 | CD33 antigen-like 3 |
| 216243_s_at | IL1RN | 2,16 | 0,00002 | 3,45 | 0,00003 | 2,75 | 0,00002 | interleukin 1 receptor antagonist |
| 216609_at | TXN | 2,03 | 0,00008 | 1,69 | 0,00304 | 2,67 | 0,00002 | Thioredoxin |

Figure 8(3)

27 of the 78 up-regulated genes in monocytes activated by dendrimer Gc1 (*da*-monocytes)

| Affymetrix identifier | Gene Symbol | Donor 1 | p-value | Donor 2 | p-value | Donor 3 | p-value | Gene Description |
|---|---|---|---|---|---|---|---|---|
| 219911_s_at | SLCO4A1 | 3,68 | 0,00002 | 2,46 | 0,00002 | 1,48 | 0,00304 | solute carrier organic anion transporter family, member 4A1 |
| 220322_at | IL1F9 | 2,85 | 0,00002 | 4,22 | 0,00002 | 4,10 | 0,00002 | interleukin 1 family, member 9 |
| 220643_s_at | FAIM | 2,53 | 0,00015 | 2,67 | 0,00021 | 5,59 | 0,00002 | Fas apoptotic inhibitory molecule |
| 220745_at | IL19 | 3,11 | 0,00002 | 4,65 | 0,00002 | 4,22 | 0,00002 | interleukin 19 |
| 220865_s_at | TPRT | 3,05 | 0,00002 | 2,89 | 0,00002 | 4,17 | 0,00015 | trans-prenyltransferase |
| 221081_s_at | FLJ22457 | 2,49 | 0,00006 | 1,7 | 0,00003 | 2,28 | 0,00086 | hypothetical protein FLJ22457 |
| 222108_at | AMIGO2 | 1,09 | 0,11171 | 2,12 | 0,00069 | 4,67 | 0,00039 | amphoterin induced gene 2 |
| 222735_at | TMEM38B | 2,11 | 0,00027 | 1,65 | 0,00002 | 3,72 | 0,00005 | transmembrane protein 38B |
| 222939_s_at | SLC16A10 | 2,74 | 0,00002 | 2,29 | 0,00002 | 2,72 | 0,00002 | solute carrier family 16 (monocarboxylic acid transporters), member 10 |
| 223282_at | SDCCAG33 | 1,64 | 0,00035 | 8,47 | 0,00134 | 2,81 | 0,00077 | serologically defined colon cancer antigen 33 |
| 224071_at | IL20 | 2,27 | 0,00035 | 47,62 | 0,00008 | 0,76 | 0,5 | interleukin 20 |
| 224964_s_at | GNG2 | 2,36 | 0,00002 | 3,15 | 0,00002 | 2,62 | 0,00003 | guanine nucleotide binding protein (G protein), gamma 2 |
| 225436_at | LOC58489 | 2,99 | 0,00002 | 3,53 | 0,00002 | 1,34 | 0,01543 | hypothetical protein from EUROIMAGE 588495 |
| 225763_at | MK2S4 | 3,05 | 0,00002 | 2,54 | 0,00015 | 2,07 | 0,00304 | protein kinase substrate MK2S4 |
| 226034_at | — | 3,21 | 0,00006 | 4,65 | 0,00002 | 4,22 | 0,09428 | Homo sapiens, clone IMAGE:3881549, mRNA |
| 226435_at | PAPLN | 2,54 | 0,00108 | 2,34 | 0,00062 | 1,18 | 0,00712 | papilin, proteoglycan-like sulfated glycoprotein |
| 227210_at | SFMBT2 | 2,18 | 0,00002 | 1,42 | 0,01421 | 2,34 | 0,00002 | Scm-like with four mbt domains 2 |
| 228425_at | — | 6,94 | 0,00024 | 0,49 | 0,88199 | 3,28 | 0,00010 | Homo sapiens, clone IMAGE:4826696, mRNA |
| 228426_at | CLEC2D | 1,4 | 0,00492 | 2,48 | 0,00021 | 2,62 | 0,00002 | C-type lectin superfamily 2, member D |
| 228527_s_at | MSCP | 2,80 | 0,00004 | 3,34 | 0,00021 | 1,75 | 0,00003 | Mitochondrial solute carrier protein |
| 231369_at | ZNF333 | 1,47 | 0,48058 | 2,02 | 0,00120 | 2,87 | 0,00002 | Zinc finger protein 333 |
| 236220_at | — | 2,51 | 0,00002 | 1,54 | 0,00031 | 3,73 | 0,00149 | Transcribed locus |
| 238297_at | PHACTR1 | 3,46 | 0,01202 | 4,03 | 0,00011 | 14,49 | 0,00120 | Phosphatase and actin regulator 1 |
| 238790_at | LOC374443 | 2,36 | 0,00097 | 1,53 | 0,00039 | 2,40 | 0,00002 | CLR pseudogene |
| 239427_at | — | 6,33 | 0,00009 | 5,75 | 0,00003 | 2,84 | 0,55808 | Transcribed locus |
| 243016_at | TYMS | 2,98 | 0,00008 | 1,61 | 0,17741 | 2,78 | 0,00062 | Thymidylate synthetase |
| 243675_at | — | 4,44 | 0,00003 | 4,27 | 0,00003 | 5,15 | 0,00005 | Transcribed locus |

Figure 9(1)

20 of the 62 down-regulated genes in monocytes activated by dendrimer Gc1 (*da*-monocytes)

| Affymetrix identifier | Gene Symbol | Donor 1 | p-value | Donor 2 | p-value | Donor 3 | p-value | Gene Description |
|---|---|---|---|---|---|---|---|---|
| 1552386_at | FLJ33641 | -2,44 | 0,00002 | -2,63 | 0,00002 | -1,94 | 0,00002 | hypothetical protein FLJ33641 |
| 1554600_s_at | LMNA | -2,69 | 0,00002 | -2,34 | 0,00006 | -2,58 | 0,00002 | lamin A/C |
| 1555349_a_at | ITGB2 | -5,45 | 0,00011 | -2,45 | 0,00007 | -2,53 | | integrin, beta 2 (antigen CD18 (p95), lymphocyte function-associated antigen 1; macrophage antigen 1 (mac-1) beta subunit) |
| 1555991_s_at | LOC150297 | -2,90 | 0,00008 | -2,88 | 0,00044 | -2,87 | 0,00002 | hypothetical protein LOC150297 |
| 1569600_at | DLEU2 | -2,21 | 0,00019 | -1,7 | 0,00017 | -2,86 | 0,00008 | Deleted in lymphocytic leukemia, 2 |
| 200644_at | MARCKSL1 | -1,98 | 0,00002 | -3,10 | 0,00002 | -3,81 | 0,00002 | MARCKS-like 1 |
| 201005_at | CD9 | -2,97 | 0,00002 | 2,05 | 0,004 | -2,57 | 0,00002 | CD9 antigen (p24) |
| 201065_s_at | GTF2I / GTF2IP1 | -1,34 | 0,00002 | -2,02 | 0,00027 | -2,36 | 0,00027 | general transcription factor II, i /// general transcription factor II, i, pseudogene 1 |
| 201235_s_at | BTG2 | -2,20 | 0,00035 | -1,53 | 0,3305 | -3,65 | 0,00006 | BTG family, member 2 |
| 201506_at | TGFBI | -1,76 | 0,00002 | -2,35 | 0,00002 | -2,94 | 0,00002 | transforming growth factor, beta-induced, 68kDa |
| 201809_s_at | ENG | -2,34 | 0,00087 | -1,63 | 0,00004 | -6,34 | 0,00003 | endoglin (Osler-Rendu-Weber syndrome 1) |
| 202086_at | MX1 | -2,08 | 0,00002 | -1,84 | 0,01014 | -3,17 | 0,00003 | myxovirus (influenza virus) resistance 1, interferon-inducible protein p78 (mouse) /// myxovirus (influenza virus) resistance 1, interferon-inducible protein p78 (mouse) |
| 202275_at | G6PD | -2,24 | 0,00087 | -1,33 | 0,0065 | -2,52 | | glucose-6-phosphate dehydrogenase |
| 202627_s_at | SERPINE1 | -3,16 | 0,00120 | -1,12 | 0,31891 | -2,28 | 0,00024 | serine (or cysteine) proteinase inhibitor, clade E (nexin, plasminogen activator inhibitor type 1), member 1 |
| 202869_at | OAS1 | -2,73 | 0,00002 | -4,32 | 0,0412 | -2,63 | 0,00009 | 2,5'-oligoadenylate synthetase 1, 40/46kDa |
| 203085_s_at | TGFBI | -1,18 | 0,0065 | -2,25 | 0,00002 | -5,46 | 0,00002 | transforming growth factor, beta 1 (Camurati-Engelmann disease) |
| 203104_at | CSF1R | -1,75 | 0,00003 | -2,12 | 0,00002 | -3,81 | 0,00002 | colony stimulating factor 1 receptor, formerly McDonough feline sarcoma viral (v-fms) oncogene homolog /// colony stimulating factor 1 receptor, formerly McDonough feline sarcoma viral (v-fms) oncogene homolog |
| 203153_at | IFIT1 | -2,30 | 0,00134 | -1,33 | 0,5 | -2,59 | 0,00031 | interferon-induced protein with tetratricopeptide repeats 1 /// interferon-induced protein with tetratricopeptide repeats 1 |
| 203560_at | GGH | -2,01 | 0,00005 | -2,70 | 0,00005 | -1,1 | 0,5 | gamma-glutamyl hydrolase (conjugase, folylpolygammaglutamyl |
| 203595_s_at | IFIT5 | -2,25 | 0,00035 | -1,77 | 0,02476 | -3,62 | 0,00008 | interferon-induced protein with tetratricopeptide repeats 5 |

Figure 9(2)

19 of the 62 down-regulated genes in monocytes activated by dendrimer Gc1 (*da*-monocytes)

| Affymetrix identifier | Gene Symbol | Donor 1 | p-value | Donor 2 | p-value | Donor 3 | p-value | Gene Description |
|---|---|---|---|---|---|---|---|---|
| 204058_at | ME1 | -6,56 | 0,00031 | -2,59 | 0,00031 | -1,24 | 0,05402 | Malic enzyme 1, NADP(+)-dependent, cytosolic |
| 204072_s_at | FRY | -3,56 | 0,00002 | -8,47 | 0,00002 | -3,23 | 0,00002 | furry homolog (Drosophila) |
| 204326_x_at | MT1X | -2,41 | 0,00003 | -1,83 | 0,00249 | -2,59 | 0,00002 | metallothionein 1X |
| 204745_x_at | MT1G | -2,01 | 0,00149 | -1,49 | 0,21319 | -2,60 | 0,00003 | metallothionein 1G |
| 204747_at | IFIT3 | -2,19 | 0,00004 | -1,16 | 0,76745 | -2,19 | 0,00031 | interferon-induced protein with tetratricopeptide repeats 3 |
| 204774_at | EVI2A | -2,08 | 0,00002 | -2,25 | 0,00002 | -1,41 | 0,05768 | ecotropic viral integration site 2A |
| 204961_s_at | NCF1 | -2,11 | 0,00039 | -3,38 | 0,00448 | -4,02 | 0,00002 | neutrophil cytosolic factor 1 (47kDa, chronic granulomatous disease, autosomal 1) |
| 204972_at | OAS2 | -2,50 | 0,00002 | -1,11 | 0,12455 | -2,85 | 0,00015 | 2'-5'-oligoadenylate synthetase 2, 69/71kDa |
| 205249_at | EGR2 | -2,69 | 0,00017 | -3,14 | 0,00004 | -2,12 | 0,02122 | early growth response 2 (Krox-20 homolog, Drosophila) |
| 207704_s_at | GAS7 | -2,64 | 0,00003 | -1,28 | 0,5 | -2,02 | 0,00039 | growth arrest-specific 7 |
| 208771_s_at | LTA4H | -1,94 | 0,00002 | -2,34 | 0,00005 | -2,25 | 0,00002 | leukotriene A4 hydrolase |
| 209116_x_at | HBB | -2,10 | 0,00002 | -1,87 | 0,33059 | -3,59 | 0,00002 | hemoglobin, beta /// hemoglobin, beta |
| 209160_at | AKR1C3 | -2,99 | 0,00005 | -3,02 | 0,00003 | -1,92 | 0,00087 | aldo-keto reductase family 1, member C3 (3-alpha hydroxysteroid dehydrogenase, type II) |
| 209761_s_at | SP110 | -2,21 | 0,00002 | -1,16 | 0,5 | -2,80 | 0,00008 | SP110 nuclear body protein |
| 210222_s_at | RTN1 | -1,61 | 0,00005 | -3,17 | 0,00087 | -3,82 | 0,00002 | reticulon 1 |
| 210705_s_at | TRIM5 | -2,09 | 0,00005 | -2,02 | 0,00055 | -1,3 | 0,08894 | tripartite motif-containing 5 |
| 211571_s_at | CSPG2 | -2,01 | 0,00002 | -2,11 | 0,00002 | -1,73 | 0,00002 | chondroitin sulfate proteoglycan 2 (versican) |
| 212859_x_at | MT1E | -2,30 | 0,00002 | -1,91 | 0,00007 | -2,86 | 0,00004 | metallothionein 1E (functional) |
| 213294_at | FLJ38348 | -2,01 | 0,00002 | -2,28 | 0,00005 | -2,76 | 0,00002 | Hypothetical protein FLJ38348 |

Figure 9(3)

23 of the 62 down-regulated genes in monocytes activated by dendrimer Gc1 (*da*-monocytes)

| Affymetrix identifier | Gene Symbol | Donor 1 | p-value | Donor 2 | p-value | Donor 3 | p-value | Gene Description |
|---|---|---|---|---|---|---|---|---|
| 213425_at | WNT5A | -1,48 | 0,00011 | -2,67 | 0,00002 | -2,63 | 0,00035 | wingless-type MMTV integration site family, member 5A /// wingless-type MMTV integration site family, member 5A |
| 213475_s_at | ITGAL | -2,32 | 0,00002 | -2,38 | 0,00008 | -4,45 | 0,00002 | integrin, alpha L (antigen CD11A (p180), lymphocyte function-associated antigen 1; alpha polypeptide) |
| 213629_x_at | MT1F | -1,81 | 0,00002 | -2,10 | 0,00165 | -2,58 | 0,00002 | metallothionein 1F (functional) |
| 214084_x_at | ABR | -4,31 | 0,00031 | -3,66 | 0,00108 | -4,54 | 0,00008 | Active BCR-related gene |
| 217028_at | CXCR4 | -2,45 | 0,00002 | -2,64 | 0,00002 | -1,32 | 0,00027 | chemokine (C-X-C motif) receptor 4 |
| 217546_at | MT1K | -16,74 | 0,00035 | -9,54 | 0,00493 | -15,82 | 0,00005 | metallothionein 1K |
| 218400_at | OAS3 | -2,28 | 0,00002 | -2,14 | 0,02476 | -2,75 | 0,00002 | 2'-5'-oligoadenylate synthetase 3, 100kDa |
| 218589_at | P2RY5 | -2,31 | 0,00004 | -2,08 | 0,00017 | -3,24 | 0,00002 | purinergic receptor P2Y, G-protein coupled, 5 |
| 219691_at | SAMD9 | -2,36 | 0,00004 | -1,59 | 0,00203 | -2,76 | 0,00003 | sterile alpha motif domain containing 9 |
| 219890_at | CLEC5A | -2,05 | 0,00003 | -2,35 | 0,00002 | -1,44 | 0,00002 | C-type lectin domain family 5, member A |
| 221087_s_at | APOL3 | -3,33 | 0,00003 | -1,32 | 0,00249 | -2,02 | 0,00031 | apolipoprotein L, 3 |
| 221530_s_at | BHLHB3 | -2,26 | 0,00003 | -3,14 | 0,00009 | -0,97 | 0,5 | basic helix-loop-helix domain containing, class B, 3 |
| 221698_s_at | CLEC7A | -2,30 | 0,00002 | -2,85 | 0,00069 | -1,62 | 0,00004 | C-type lectin domain family 7, member A /// C-type lectin domain family 7, member A |
| 222876_s_at | CENTA2 | -3,35 | 0,00134 | -1,23 | 0,28497 | -3,30 | 0,00010 | centaurin, alpha 2 |
| 224583_at | COTL1 | -1,74 | 0,00003 | -2,09 | 0,00002 | -2,84 | 0,00002 | coactosin-like 1 (Dictyostelium) |
| 224701_at | PARP14 | -2,13 | 0,00021 | -1,29 | 0,00062 | -2,71 | 0,00007 | poly (ADP-ribose) polymerase family, member 14 |
| 229389_at | ATG16L2 | -3,09 | 0,00013 | -3,71 | 0,00031 | -1,11 | 0,06557 | ATG autophagy related 16-like 2 (S. cerevisiae) |
| 230422_at | FPRL2 | -2,98 | 0,00004 | -8,77 | 0,00004 | -4,34 | 0,00002 | formyl peptide receptor-like 2 |
| 235751_s_at | VMO1 | -3,87 | 0,00493 | -5,45 | 0,00031 | -14,27 | 0,00005 | vitelline membrane outer layer 1 homolog (chicken) |
| 239448_at | SMAD3 | -2,44 | 0,00003 | -3,28 | 0,00002 | -2,86 | 0,00002 | SMAD family member 3 |
| 239979_at | EPSTI1 | -3,53 | 0,00003 | -1,08 | 0,02122 | -2,15 | 0,00002 | Epithelial stromal interaction 1 (breast) |
| 242943_at | ST8SIA4 | -1,97 | 0,00035 | -6,92 | 0,00024 | -2,83 | 0,00013 | ST8 alpha-N-acetyl-neuraminide alpha-2,8-sialyltransferase 4 |
| 243509_at | LOC256021 | -2,02 | 0,00002 | -1,59 | 0,00004 | -2,55 | 0,00027 | Hypothetical protein LOC256021 |

**RT-PCR quantification of mRNA expression for 9 selected genes in *da*-monocytes.**

**Phenotype of *da*-monocytes compared to *alt*- and *class*-monocytes.**

Figure 12(1)
Immuno-suppressive properties of *da*-monocytes (dendrimer Gc1 at 20 µM).
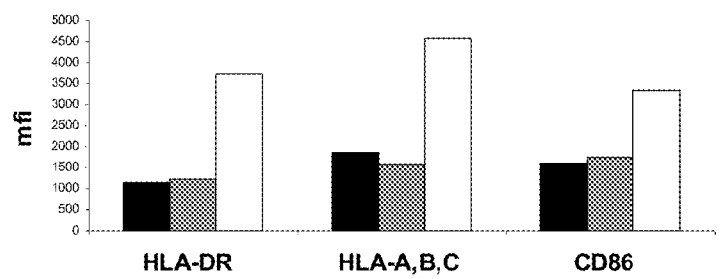
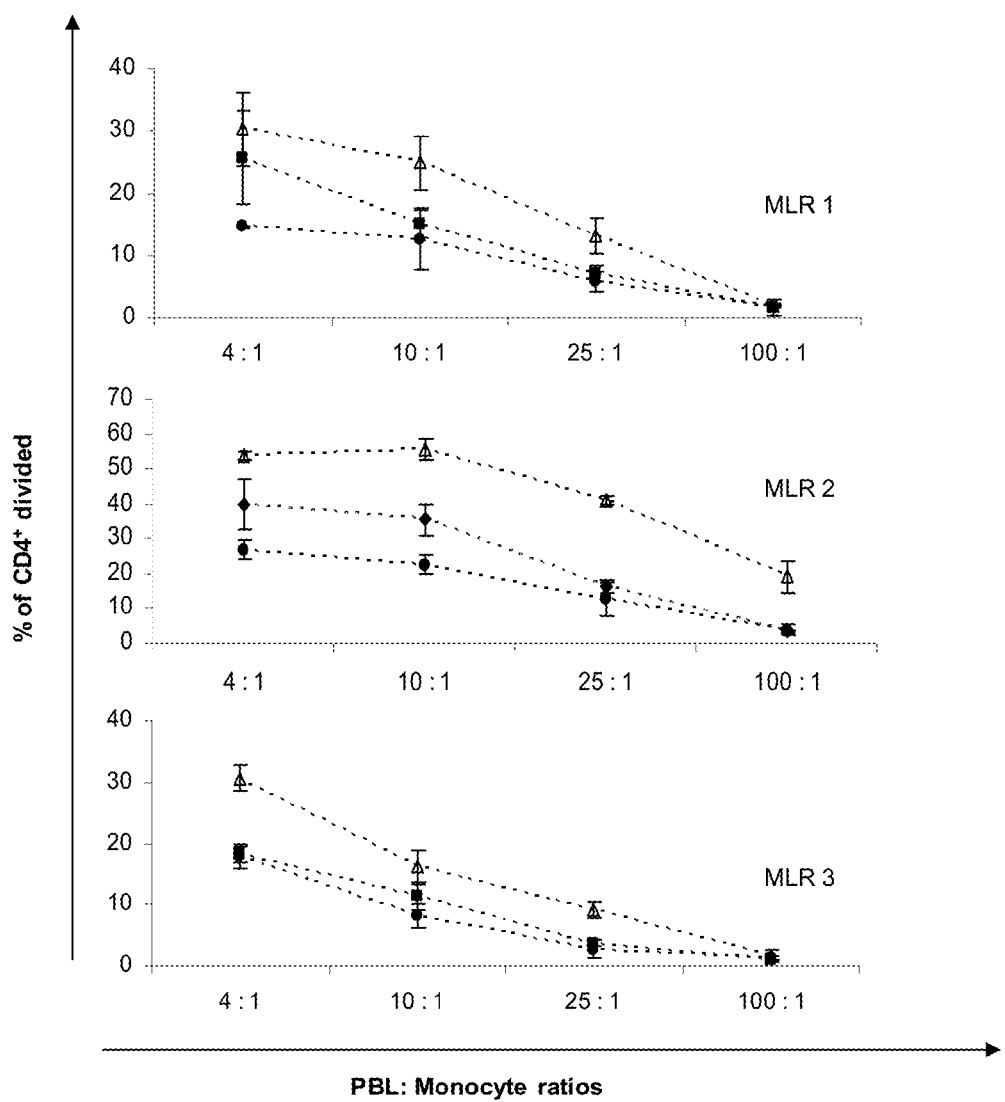
PBL: Monocyte ratios

Figure 12(2)

Statistical analysis of the results of the MLR shown in Figure 12(1) B

|  | MLR1 | | | | MLR2 | | | | MLR3 | | | |
|---|---|---|---|---|---|---|---|---|---|---|---|---|
|  | 4:1 | 10:1 | 26:1 | 100:1 | 4:1 | 10:1 | 26:1 | 100:1 | 4:1 | 10:1 | 26:1 | 100:1 |
| *ali*-monocytes versus *da*-monocytes | 0,023 | ns | ns | ns | 0,011 | 0,002 | ns | ns | ns | ns | ns | ns |
| *ali*-monocytes versus *class*-monocytes | ns | 0,014 | 0,004 | ns | 0,009 | <0,001 | <0,001 | <0,001 | <0,001 | 0,019 | <0,001 | ns |
| *class*-monocytes versus *da*-monocytes | 0,004 | 0,005 | 0,001 | ns | <0,001 | <0,001 | <0,001 | <0,001 | <0,001 | <0,001 | <0,001 | ns |

*Da*- and *alt*-monocytes induce the proliferation of IL10-producing CD4⁺ T cells.

Figure 14
Inhibition of the differentiation of monocytes in osteoclasts by dendrimer Gc1 at 20 µM.
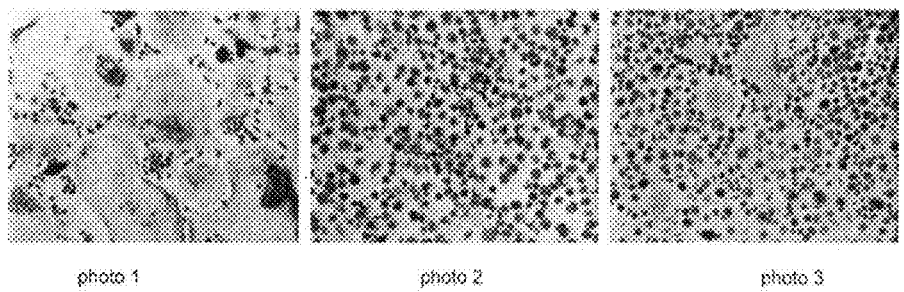
Figure 15
*In vitro* inhibition of bone resorption in presence of Gc1 at different concentrations
A
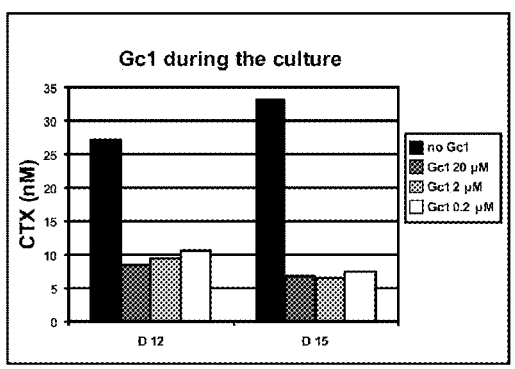
B
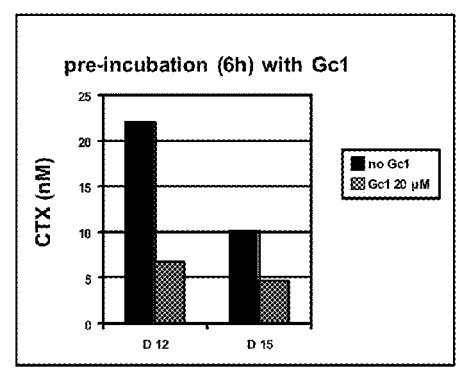

Comparison of the effect of dendrimer Gc1 (A), AMP (B), or PPI (C) (10 mg/kg) on the development of arthritis Efficacy of dendrimer Gc1 in a mouse model of Experimental Autoimmune Encephalomyelitis (EAE)

PHOSPHORYLATED DENDRIMERS AS ANTIINFLAMMATORY DRUGS

The present invention relates to the use of phosphorylated dendrimers for the treatment of uncontrolled inflammatory processes.

Dendrimers are macromolecules constituted by monomers which combine according to a tree-like process around a plurifunctional central core.

Dendrimers, also called "cascade molecules", are highly branched functional polymers with a defined structure. These macromolecules are effectively polymers since they are based on the combination of repeating units. However, dendrimers differ fundamentally from standard polymers to the extent that they have specific properties due to their tree-like construction. The molecular weight and the form of the dendrimers can be precisely controlled (Fréchet, J. M. J. et al. (2001) *Dendrimers and other dendritic polymers*, John Wiley and Sons, New York, N.Y.; Newkome, G. R. et al. (2001) *Dendrimers and dendrons: concepts, syntheses, applications* 2nd ed Ed., Wiley-VCH, Weinheim).

The dendrimers are constructed stepwise, by the repetition of a sequence of reactions allowing the multiplication of each repeating unit and terminal functions. Each sequence of reactions forms what is called a "new generation". The tree-like construction is carried out by the repetition of a sequence of reactions which makes it possible to obtain a new generation and a growing number of identical branches at the end of each reaction cycle. After a few generations, the dendrimer generally assumes a highly branched and pluri-functionalized globular form due to the numerous terminal functions present at the periphery. These structural features, together with the high density of chemical reactive functions on the outer shell of these molecules enhanced their use in biology and medicine (Cloninger, M. J. (2002) *Curr Opin Chem Biol* 6(6), 742-748). Dendrimers can be used as drug carriers that are able to enhance aqueous solubility, improve drug transit across biological barriers and target the drug delivery to injured tissues (Lee, C. C. et al. (2005) *Nat Biotechnol* 23(12), 1517-1526; Cheng, Y. et al. (2008) *Front Biosci* 13, 1447-1471). Dendrimers also act as drugs themselves. Among others, dendrimers glucosamine conjugates were safely used to prevent scar tissue formation via immuno-modulatory and anti-angiogenic effects (Shaunak, S. et al. (2004) *Nat Biotechnol* 22(8), 977-984). Multiple antigenic peptide dendrimers have proved to be promising compounds for immune response modification or immuno-diagnosis (Crespo, L. et al. (2005) *Chem Rev* 105(5), 1663-1681; Singh, P. (2007) *Biotechnol Appl Biochem* 48(Pt 1), 1-9). Polyanionic (with sulfonate groups) dendrimers were shown to provide an efficient microbicide activity against different viruses (McCarthy, T. D. et al. (2005) *Mol Pharm* 2(4), 312-318). Cationic phosphorus-containing dendrimers reduce the replication of the abnormal scrapie isoform of the prion protein in mice (Solassol, J. et al. (2004) *J Gen Virol* 85(Pt 6), 1791-1799). Recently the inventors reported the effects of synthetic molecules belonging to the dendrimer family on the innate immune system (Poupot, M. et al. (2006) *Faseb J* 20(13), 2339-2351; Griffe, L. et al. (2007) *Angew Chem Int Ed Engl* 46(14), 2523-2526; Rolland, O. et al. (2008) *Chem. Eur. J.,* 14(16), 4836-4850).

Mononuclear phagocytes, including monocytes and macrophages (MΦ, the tissue-counterpart of the former), are essential in innate immunity as a first line of defense against bacterial and parasitic infections. They also ensure the engaging of the delayed adaptive immune response. Monocytes/MΦ are a heterogeneous population encompassing a large spectrum of phenotypes from pro-inflammatory to anti-inflammatory responses, depending on the stimulus they receive. Indeed, MΦ activation can take several aspects. Besides the classical activation pathway, a so-called alternative activation mechanism emerged. The classical activation pathway of MΦ is mediated by interferon (IFN)-γ as primer and then triggering by tumor necrosis factor (TNF) or bacterial lipopolysaccharides (LPS). These MΦ produce mediators making them effector cells in type Th-1 cellular immune responses and are cytotoxic effectors against intracellular pathogens. The "alternative activation" of MΦ describes closely related responses induced either by interleukin (IL)-4 or IL-13 or by IL-10 or glucocorticoids. These MΦ appear to be involved in immuno-suppression and tissue repair. This dual classification with pro-inflammatory classically-activated MΦ and anti-inflammatory alternatively-activated MΦ has been recently broadened with the proposition of type 2-activated MΦ. Although they are activated, after IFN-γ priming or not, by ligation of $Fc_\gamma R$ and Toll-like receptors (TLR) triggering, type 2 MΦ rather display anti-inflammatory responses. The closely interlinked pathways of MΦ activation and the intricate responses displayed by these cells explain the still confusing classification of polarized mononuclear phagocytes. During infection, MΦ are critical mediators of inflammatory processes aimed at the removal of pathogens. However, inflammation is also associated with deleterious effects for the tissues and must be repressed to allow complete healing. Due to their dual pattern of activation, MΦ play a pivotal role both in triggering and resolving inflammation.

The inventors surprisingly discovered that some phosphorylated dendrimers lead to an anti-inflammatory type activation of the monocytes.

Thus one of the purposes of the present invention is to propose a novel anti-inflammatory treatment using synthetic and essentially non-toxic compounds with low production costs.

Thus, the present invention relates to dendrimers with monophosphonic or bisphosphonic terminations for the treatment of inflammatory diseases, in particular auto-immune diseases.

Said treatment is mediated by an anti-inflammatory type activation of the monocytes.

Some dendrimers used according to the present invention and their preparation are disclosed in the international application WO 2006/024769.

According to a particular embodiment of the invention, the dendrimers with monophosphonic or bisphosphonic terminations are of generation n and comprise a central core § with a valency of m which can establish m−2 bonds, providing that m is greater than 2, or m−1 bonds, providing that m is greater than 1, or m bonds with linkage chains, preferably identical to each other, m representing an integer from 1 to 20, in particular of 1 to 10 and more particularly of 1 to 8 and n representing an integer from 0 to 12, which linkage chains are constituted by:
  generation chains attached in a tree-like structure around the core on each of the bonds, when n is greater than or equal to 1, a generation chain of a given generation being linked to
    a generation chain of the generation immediately below the given generation, or to the core when the given generation is 1, and to
    at least 2 generation chains of the generation immediately above the given generation, or optionally to at least one intermediate chain when the given generation is n, a terminal group being attached to the end of each generation chain of generation n, or if appropriate to the end of each intermediate chain, or intermediate chains attached around the core on each of the bonds, when n is 0, a terminal group being attached to the end of each intermediate chain;

said terminal group being represented by the formula:

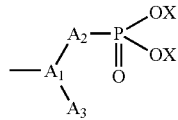

where $A_1$ represents N; a P=Y group, where Y represents O, S, or no atom; an N—R group; or a C—R group; R representing H or a linear, branched or cyclic hydrocarbon chain with 1 to 16 members, optionally containing one or more heteroatoms, said heteroatoms being preferably chosen from oxygen, sulphur, nitrogen, phosphorus, silicon and/or one or more double or triple bonds, each of said members being optionally substituted by at least one substituent chosen from a hydroxyl group, a —NR'R" group, an alkoxy group of 1 to 16 carbon atoms, an alkyl group of 1 to 16 carbon atoms, a halogen atom, a —$NO_2$ group, a —CN group, a —$CF_3$ group, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, R' and R" representing independently of each other H or an alkyl group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$;

$A_2$ represents a single bond or a linear, branched or cyclic hydrocarbon chain with 1 to 6 members, each of said members optionally containing one or more heteroatoms, said heteroatoms being preferably chosen from a sulphur, oxygen, phosphorus or nitrogen atom, more preferably nitrogen, and being optionally substituted by at least one substituent chosen from H, an alkyl group of 1 to 16 carbon atoms, a halogen, a $NO_2$ group, a NRR' group, a —CN group, a —$CF_3$ group, a hydroxyl group, an alkoxy group of 1 to 16 carbon atoms, an aryl or heteroaryl group of 1 to 24 carbon atoms, the heteroelement being preferably chosen from oxygen, nitrogen or sulphur, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, R and R' representing independently of each other H or a linear, branched or cyclic hydrocarbon chain with 1 to 16 members, optionally containing one or more heteroatoms, said heteroatoms being preferably chosen from oxygen, sulphur, nitrogen, phosphorus, silicon and/or one or more double or triple bonds, each of said members being optionally substituted by at least one substituent chosen from a hydroxyl group, a NR"R'" group, an alkoxy group of 1 to 16 carbon atoms, an alkyl group of 1 to 16 carbon atoms, a halogen atom, a $NO_2$ group, a —CN group, a —$CF_3$ group, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, R" and R'" representing independently of each other H or an alkyl group of 1 to 16 carbon atoms, an aryl group of 6 to 24 carbon atoms or an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$;

$A_3$ represents H, or a linear, branched or cyclic hydrocarbon chain with 1 to 6 members, each of said members being optionally chosen from a heteroatom, said heteroatom being preferably chosen from sulphur, nitrogen, phosphorus or silicon, more preferably nitrogen, each member being able to be optionally substituted by at least one group chosen from a hydroxyl group, a NR"R'" group, an alkoxy group of 1 to 16 carbon atoms, an alkyl group of 1 to 16 carbon atoms, a halogen atom, a $NO_2$ group, a —CN group, a —$CF_3$ group, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, R" and R'" representing independently of each other H or an alkyl group of 1 to 16 carbon atoms, an aryl group of 6 to 24 carbon atoms, or an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$ or

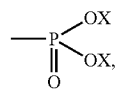

in particular $A_3$ can represent

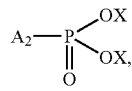

each $A_2$ being identical or different;

each OX, identical or different for each phosphonic group, represents OH, Oalkyl, where the alkyl group comprises from 1 to 16 carbon atoms, Oaryl, where the aryl group comprises from 6 to 24 carbon atoms, Oaralkyl, where the aralkyl group comprises from 7 to 24 carbon atoms, Oalkylaryl, where the alkylaryl group comprises from 7 to 24 carbon atoms, OSiR'$_1$R'$_2$R'$_3$, where R'$_1$, R'$_2$ and R'$_3$, identical or different, represent an alkyl group of 1 to 16 carbon atoms, or O$^-$M$^+$, where M$^+$ is a cation of elements of group IA, IB, IIA, IIB or IIIA, IIIB of the periodic table of the elements, preferably M$^+$ is chosen from the cations of the sodium, potassium, copper, calcium, barium, zinc, magnesium, lithium and aluminium atoms, or hydrocarbon groups of 1 to 100 carbon atoms, or nitrogenous groups of 0 to 100 carbon atoms, such as $NR_1R_2R_3R_4^+$, where, independently of each other $R_1$, $R_2$, $R_3$ and $R_4$ represent H or a linear, branched or cyclic hydrocarbon chain with 1 to 16 members, optionally containing one or more heteroatoms, said heteroatoms being preferably chosen from oxygen, sulphur, nitrogen, phosphorus, silicon and/or one or more double or triple bonds, each of said members being optionally substituted by at least one substituent chosen from a hydroxyl group, a NR"R'" group, an alkoxy group of 1 to 16 carbon atoms, an alkyl group of 1 to 16 carbon atoms, a halogen atom, a $NO_2$ group, a —CN group, a —$CF_3$ group, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, R" and R'" representing independently of each other H or an alkyl group of 1 to 16 carbon atoms, an aryl group of 6 to 24 carbon atoms or an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, m represents an integer from 1 to 20, in particular from 1 to 10 and more particularly from 1 to 8;

n represents an integer from 0 to 12, said central core § representing a group comprising from 1 to 500 atoms, and optionally containing one or more heteroatoms, said heteroatoms being preferably chosen from oxygen, sulphur, nitrogen, phosphorus or silicon.

According to another particular embodiment of the invention, the core § establishes m bonds with m identical linkage chains constituted:

either by generation chains attached in a tree-like structure around the core on each of the bonds, the end of each chain generation furthest from the central core being attached either to a terminal group or to an intermediate chain, the end of each intermediate chain being attached to a terminal group, or by intermediate chains attached around the core on each of the bonds, the end of each intermediate chain being attached to a terminal group.

According to this embodiment, for a given dendrimer, all of the generation chains of the generation furthest from the central core are attached to an identical substituent which can be either a terminal group or an intermediate chain.

According to an alternative embodiment of the invention, the core establishes m−2 or m−1 bonds, m representing an integer from 3 to 20, in particular from 3 to 10 and more particularly from 3 to 8, with respectively m−2 or m−1 identical linkage chains constituted:

either by generation chains attached in a tree-like structure around the core on each of the bonds, the end of each chain generation furthest from the central core being attached either to a terminal group or to an intermediate chain, and the end of each intermediate chain being attached to a terminal group, or by intermediate chains attached around the core on each of the bonds, the end of each intermediate chain being attached to a terminal group;

the 1 or 2 remaining bonds being attached to linkage groups, identical or different, optionally linked together, in particular by means of a covalent bond, constituted:

either by part of the linkage chains defined above, or by a hydrogen atom, or by hydrocarbon groups comprising from 1 to 500 carbon atoms, said hydrocarbon groups being in particular constituted by H or by a linear, branched or cyclic hydrocarbon chain with 1 to 200 members, optionally containing one or more double or triple bonds, each of said members being optionally chosen from a heteroatom, said heteroatom being preferably chosen from a nitrogen, oxygen, phosphorus, silicon or sulphur atom, an aryl group of 6 to 24 carbon atoms, a heteroaryl group of 1 to 24 carbon atoms, a carboxyl group, a >C=NR group, each member being able to be optionally substituted by at least one substituent chosen from a hydroxyl group, a NR"R'" group, an alkoxy group of 1 to 16 carbon atoms, an alkyl group of 1 to 16 carbon atoms, a halogen atom, a $NO_2$ group, a —CN group, a —$CF_3$ group, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, R" and R'" representing independently of each other H or an alkyl group of 1 to 16 carbon atoms, an aryl group of 6 to 24 carbon atoms or an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, the first member of said hydrocarbon chain preferably being oxygen or nitrogen.

In particular the hydrocarbon groups comprising from 1 to 500 carbon atoms defined above can be fluorophores, or any functional chemical group.

According to another particular embodiment of the invention, the generation chains are chosen from any linear, branched or cyclic hydrocarbon chain with 1 to 12 members, optionally containing one or more double or triple bonds, each of said members being optionally chosen from a heteroatom, said heteroatom being preferably chosen from nitrogen, oxygen, sulphur, phosphorus or silicon, an aryl group of 6 to 24 carbon atoms, a heteroaryl group of 1 to 24 carbon atoms, the heteroelement being preferably chosen from oxygen, nitrogen or sulphur, a carboxyl group, a >C=NR group, each member being able to be optionally substituted by at least one substituent chosen from an alkyl group of 1 to 16 carbon atoms, a halogen atom, a —$NO_2$ group, an —NRR' group, a —CN group, a —$CF_3$ group, a hydroxyl group, an alkoxy group of 1 to 16 carbon atoms, an aryl group of 6 to 24 carbon atoms, or an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, R and R' representing independently of each other H or an alkyl group of 1 to 16 carbon atoms, an aryl group of 6 to 24 carbon atoms, or an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$.

According to yet another particular embodiment of the invention, the intermediate chains are chosen from the groups corresponding to the formula:

-J-K-L- where
J represents an oxygen or sulphur atom, or a NR— group;
K represents an aryl group of 6 to 24 carbon atoms, a heteroaryl group of 1 to 24 carbon atoms, the heteroelement being preferably chosen from oxygen, nitrogen or sulphur, an alkyl group of 1 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, each being able to be optionally substituted by a halogen atom or a NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$,
L represents a linear, branched or cyclic hydrocarbon chain with 0 to 10 members, in particular with 0 to 6 members, optionally containing one or more double or triple bonds, each of said members optionally being able to be a heteroatom, said heteroatom being preferably chosen from oxygen, sulphur, nitrogen, phosphorus, silicon, each member being able to be optionally substituted by at least one substituent chosen from an alkyl group of 1 to 16 carbon atoms, a halogen, an oxygen atom, —NO$_2$, —NRR', —CN, —CF$_3$, —OH, an alkoxy group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$;
R and R' representing independently of each other H or an alkyl group of 1 to 16 carbon atoms, an aryl group of 6 to 24 carbon atoms, or an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$;

According to a more particular embodiment of the invention, the core is chosen from:
a nitrogen or silicon atom;
a group of formula

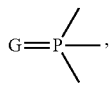

in which G represents an oxygen, nitrogen, sulphur, selenium, tellurium atom or an =NR group, R representing H or an alkyl group of 1 to 16 carbon atoms, an aryl group of 6 to 24 carbon atoms, an aralkyl group of 7 to 16 carbon atoms, such as the thiophosphoryl group of formula

or an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$
a bis-phenyloxy group of formula

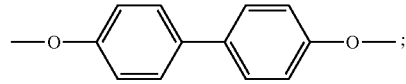

a 1,2-diamino-ethane group of formula

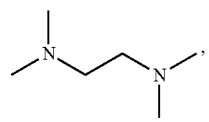

a 1,4-diamino-butane group of formula

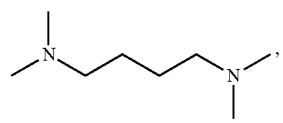

a cyclotriphosphazene group of formula

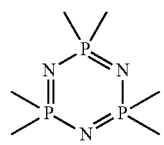

also denoted N$_3$P$_3$ or P$_3$N$_3$,
a cyclotetraphosphazene group of formula

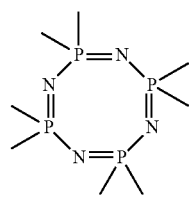

also denoted N$_4$P$_4$ or P$_4$N$_4$.

The present invention relates in particular to the use as defined above, of dendrimers of structure PAMAM, DAB or PMMH.

The dendrimers of structure PAMAM are in particular described by Tomalia, D. A. et al. (1985) *Polym. J.* (Tokyo) 17, 117; Tomalia, D. A. et al. (1986) *Macromolecules* 19, 2466.

The dendrimers of structure DAB are in particular described by de Brabander-van den Berg, E. M. M. et al. (1993) *Angew. Chem. Int. Ed. Engl.* 32, 1308.

The dendrimers of structure PMMH are in particular described in "A general synthetic strategy for neutral phosphorus containing dendrimers" by Launay, N. et al. (1994) *Angew. Chem.* 106, 1682/*Angew. Chem. Int. Ed. Engl.* 33, 1589 and in "Synthesis of bowl-shaped dendrimers from generation 1 to generation 8" Launay, N. et al. (1997) *J. Organomet. Chem.* 529, 51.

An example of a dendrimer of type PAMAM for which n=4 and m=4 is represented below:

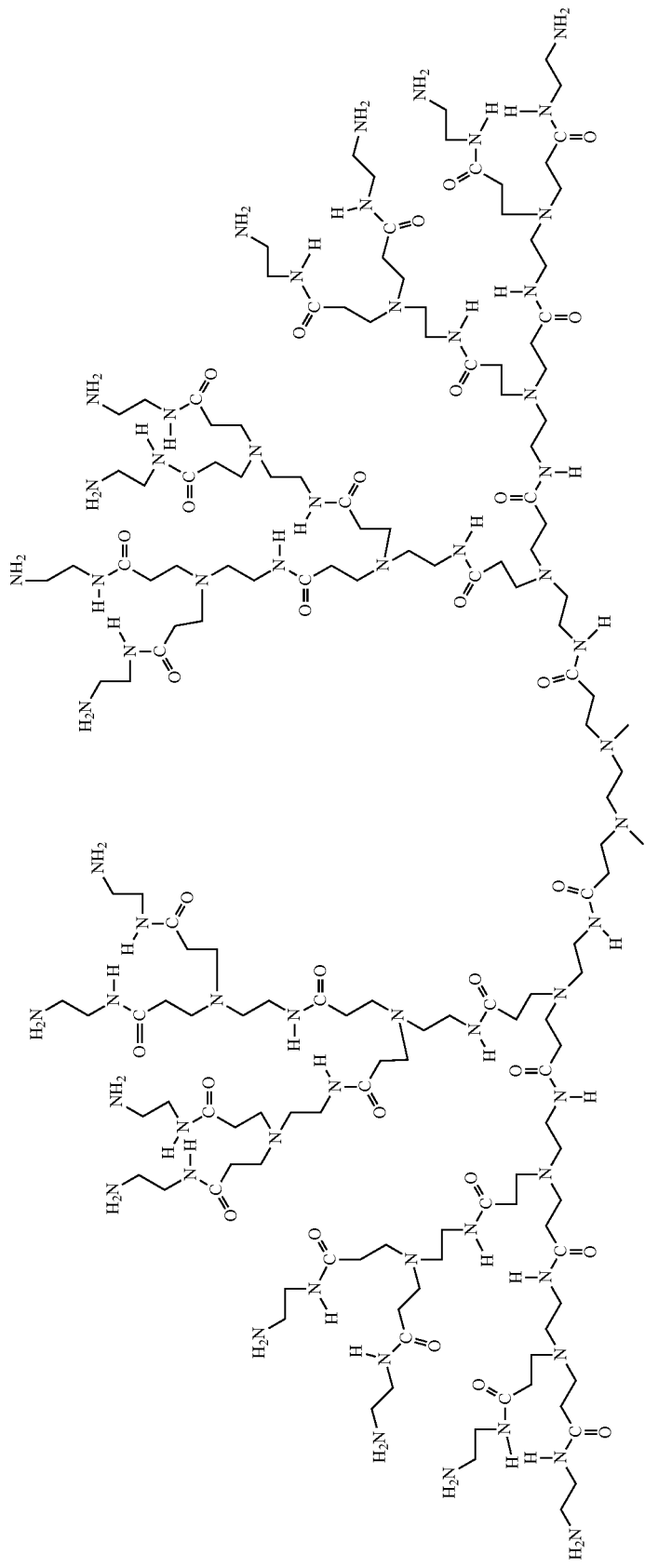

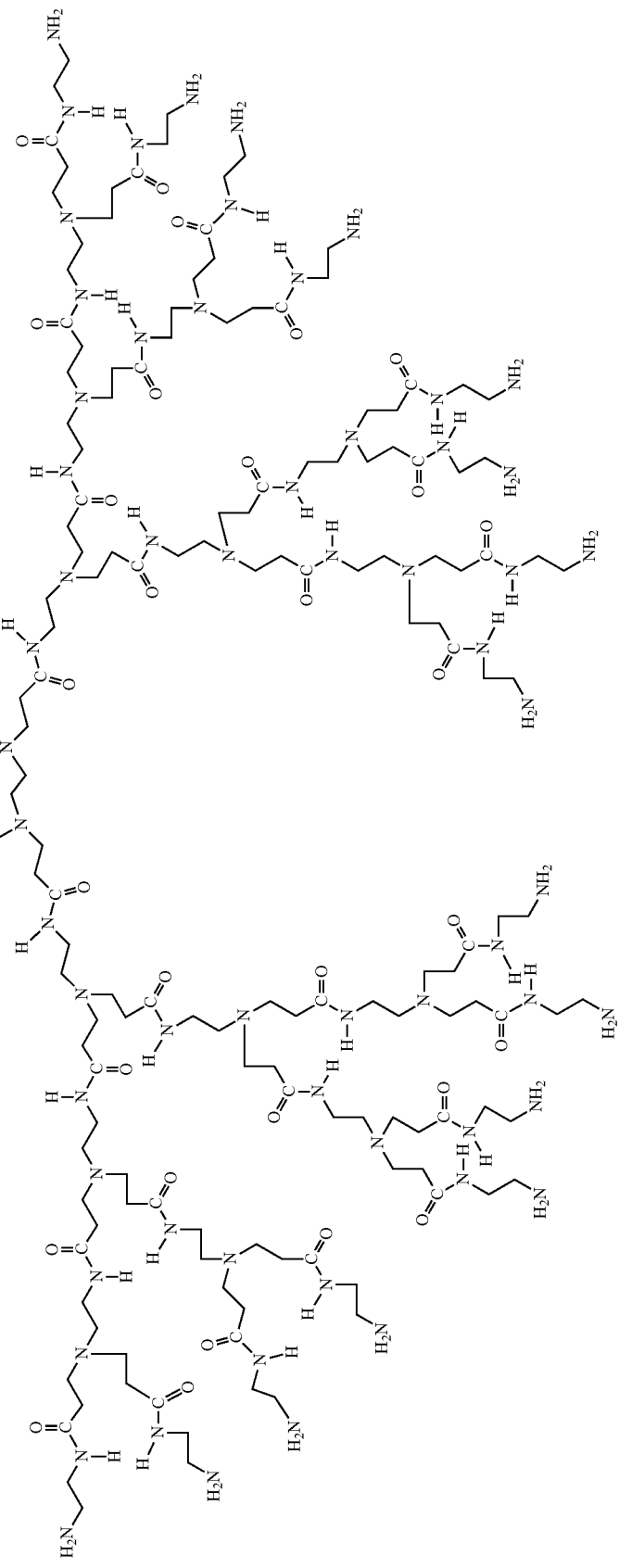
-continued

An example of a dendrimer of type DAB, for which n=5 and m=4 is represented below:

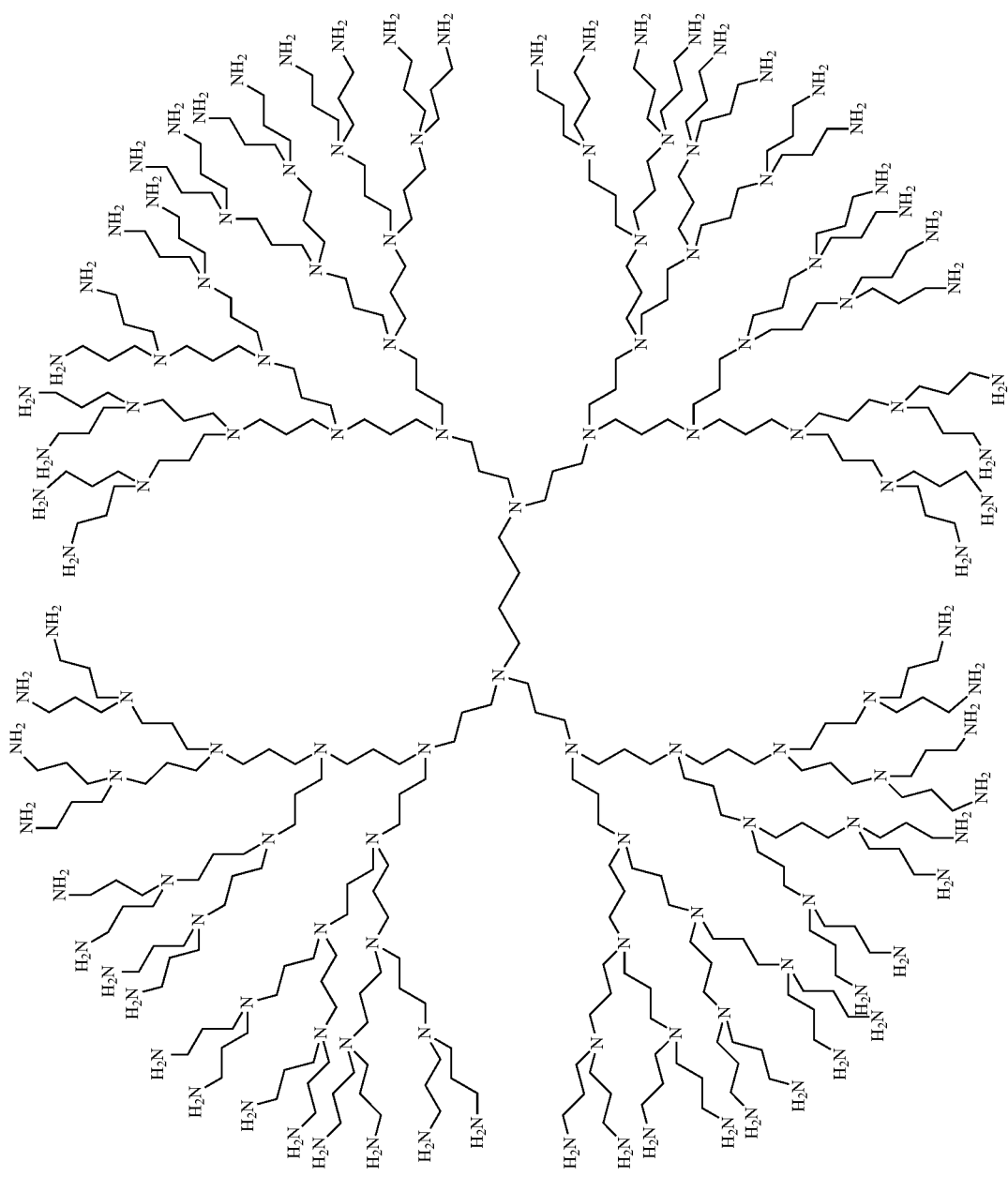

An example of a dendrimer of type PMMH with a thiophosphoryl core, for which n=4 and m=3 is represented below:

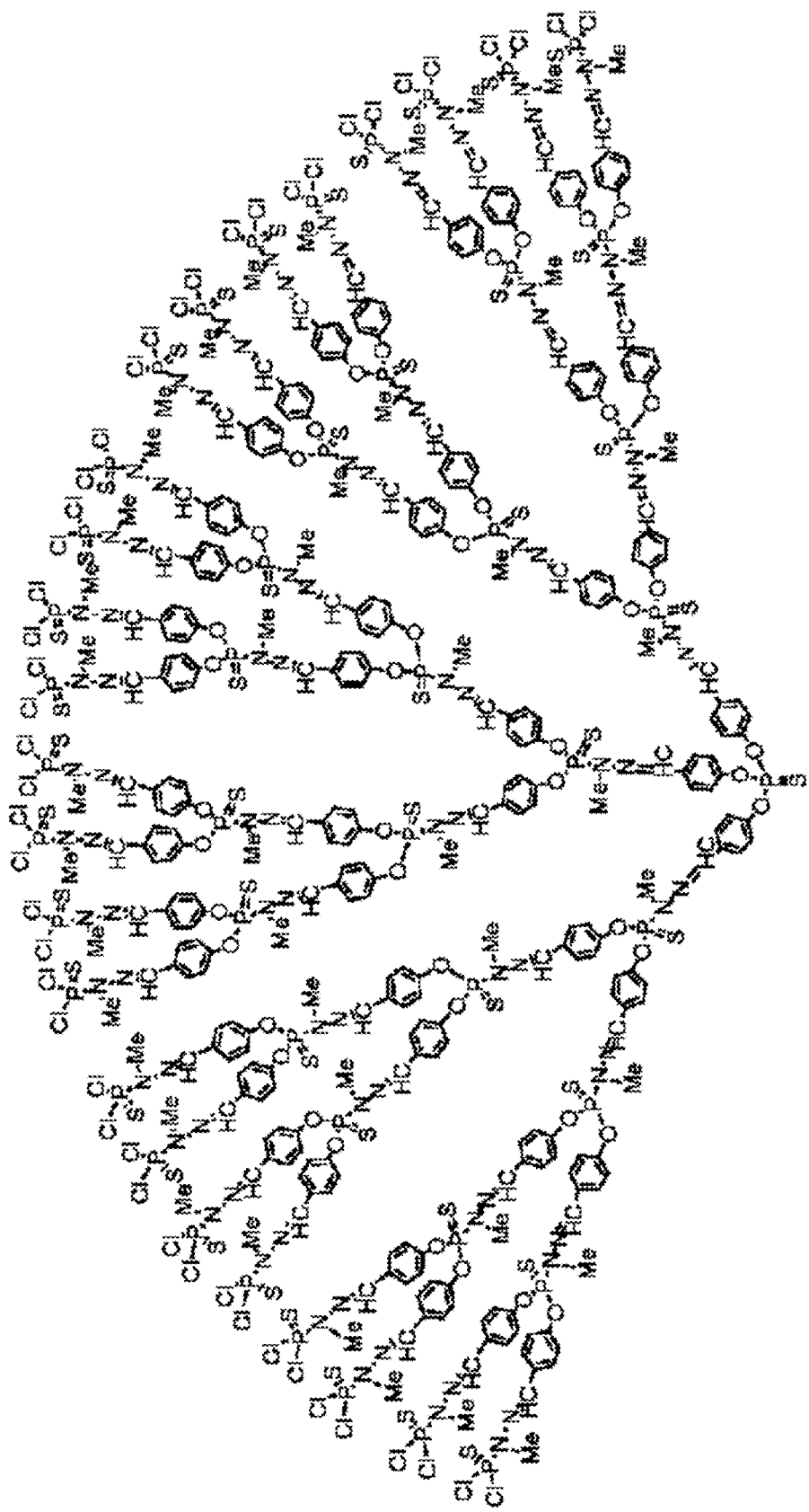

An example of a dendrimer of type PMMH with a cyclotriphosphazene core, for which n=2 and m=6, without an intermediate chain, is represented below:

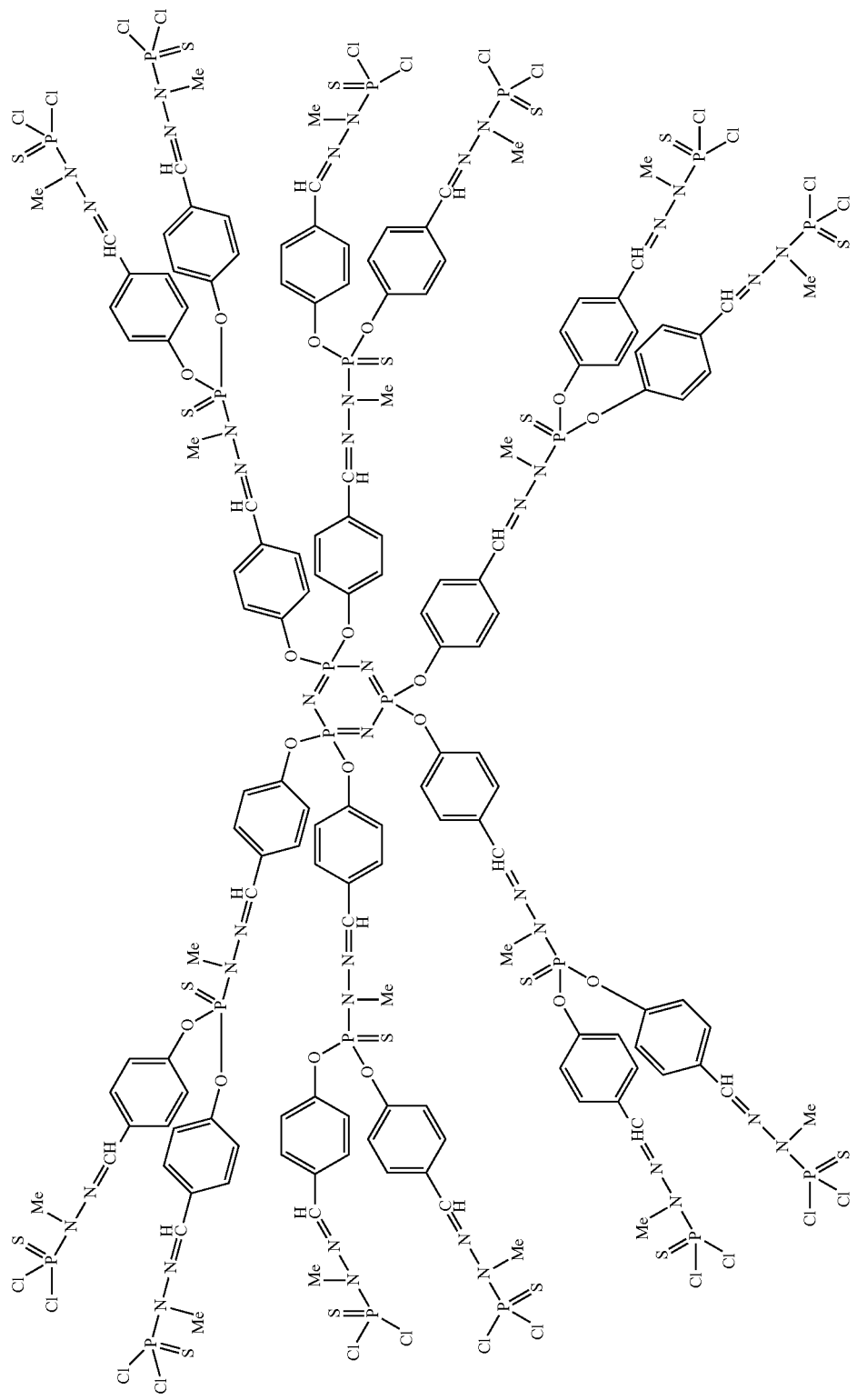

Another example of a dendrimer of type PMMH with a cyclotriphosphazene core, for which n=2 and m=6, with an intermediate chain, is represented below:

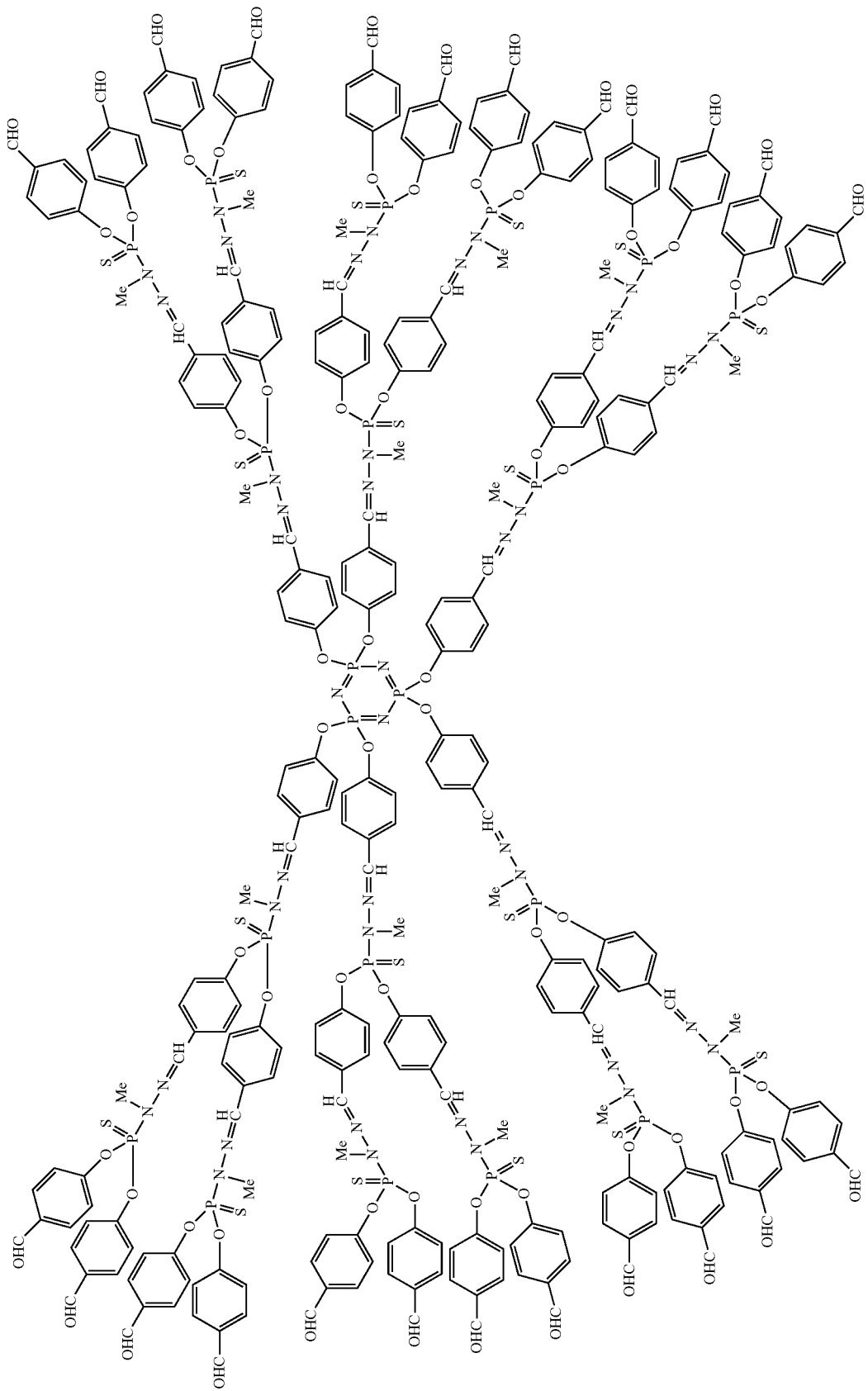

In a particular embodiment, the invention relates to the use of dendrimers with monophosphonic or bisphosphonic terminations corresponding to the following general formula (1a):

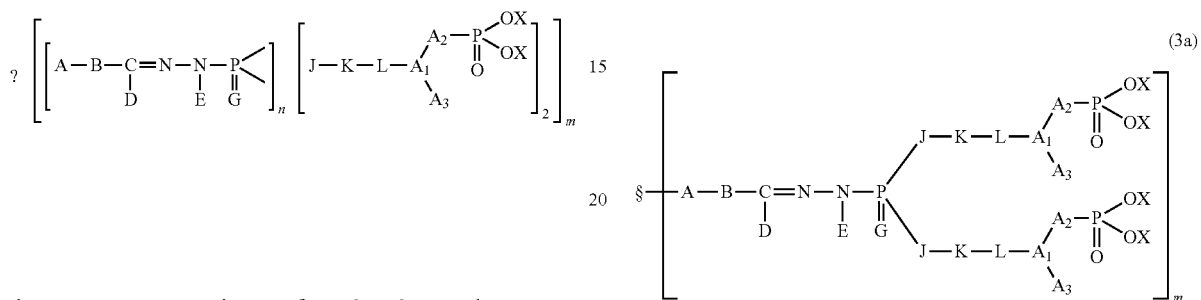

(1a)

where n represents an integer from 0 to 3, namely:

when n=0, formula (1a) corresponds to the following formula (2a),

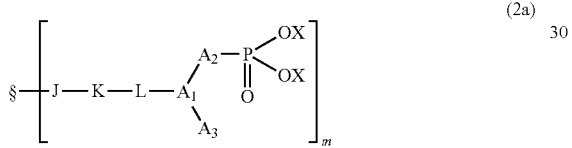

(2a)

when n=1, formula (1a) corresponds to the following formula (3a),

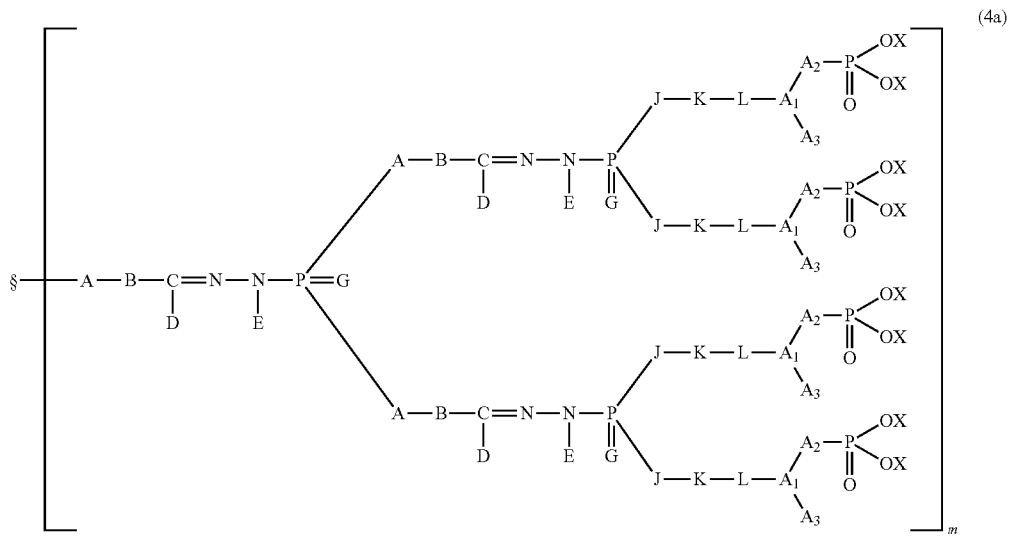

(3a)

when n=2, formula (1a) corresponds to the following formula (4a), (4a)

and when n=3, formula (1a) corresponds to the following formula (5a),

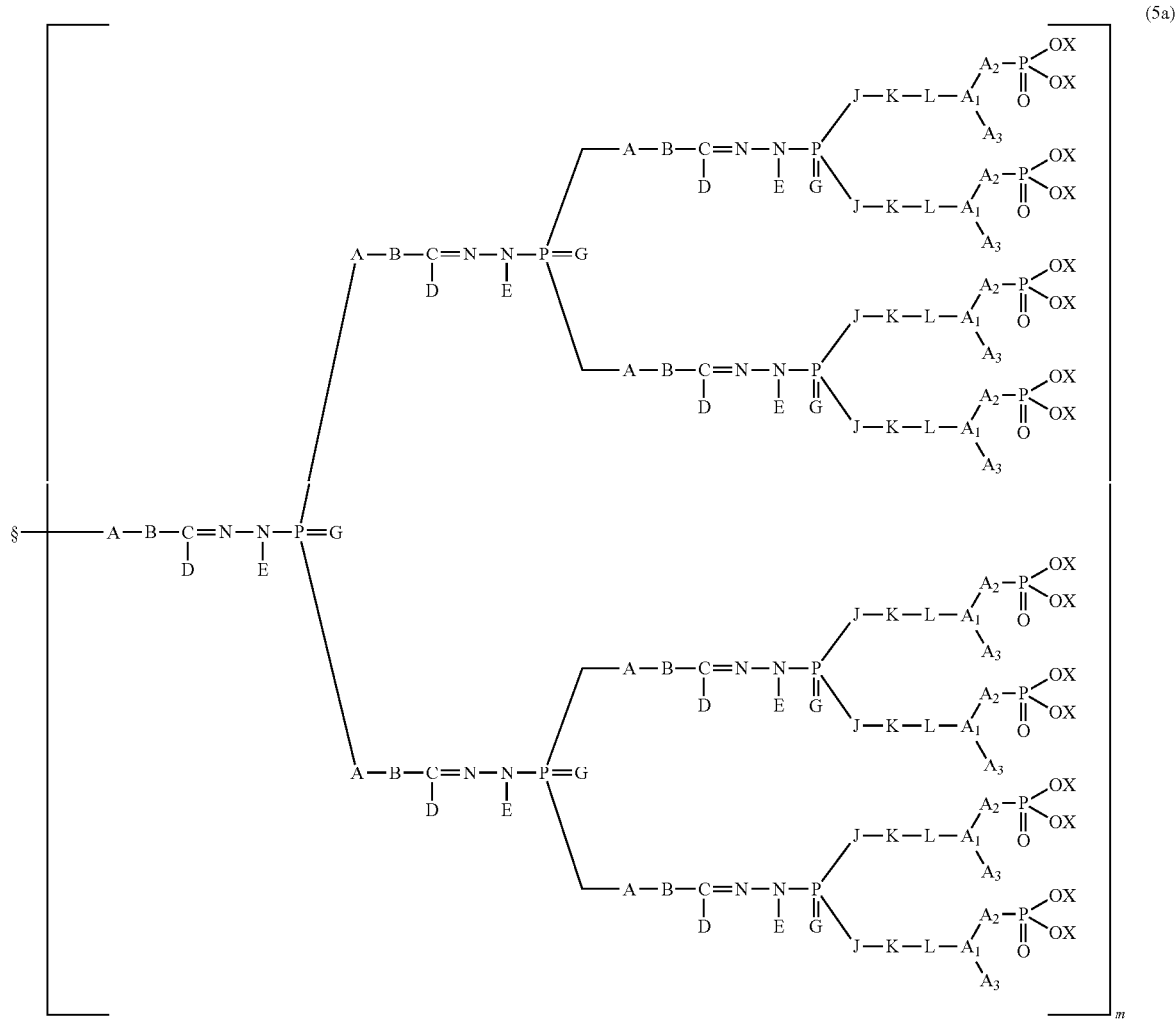

and in which formulae:
the central core § is chosen from the following groups:

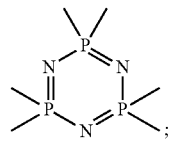

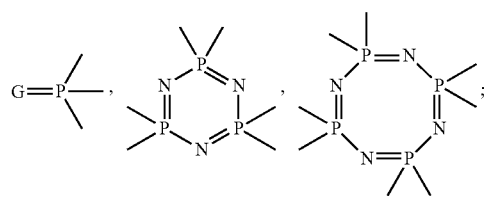

the central core representing preferably the following group:

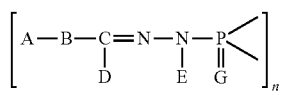

m represents 3, 6 or 8;
the generation chain corresponds to the formula:
where $$\left[ A-B-\underset{D}{C}=N-\underset{E}{N}-\underset{G}{P} \right]_n$$

A represents an oxygen, sulphur, phosphorus atom or a NR— group;
B represents an aryl group of 6 to 24 carbon atoms, a heteroaryl group of 1 to 24 carbon atoms, an alkyl group of 1 to 16 carbon atoms, an oligoethyleneglycol group, a polyethyleneglycol group, two aryl groups of 6 to 24 carbon atoms linked by an oxygen, a nitrogen, a sulphur, an alkyl group of 1 to 16 carbon atoms, an heteroalkyl group of 1 to 24 carbon atoms, an oligoethyleneglycol group, each being able to be optionally substituted by a halogen atom or a $NO_2$, —NRR', —CN, —$CF_3$, —OH group, an alkyl group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 $g \cdot mol^{-1}$ to 3000 $g \cdot mol^{-1}$; according to the invention, when B represents two aryl groups of 6 to 24 carbon atoms linked by an oxygen, a nitrogen, a sulphur, an alkyl group of 1 to 16 carbon atoms, an heteroalkyl group of 1 to 24 carbon atoms, an oligoethyleneglycol group selected from the groups comprising $C_6H_4$—O—$C_6H_4$ and $C_6H_4$—$(CH_2CH_2O)q$-$C_6H_4$ with q=1 to 12.

D represents a hydrogen atom, an alkyl group of 1 to 16 carbon atoms, an alkoxy group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 $g \cdot mol^{-1}$ to 3000 $g \cdot mol^{-1}$, each being able to be optionally substituted by a halogen atom or a —$NO_2$, —NRR', —CN, —$CF_3$, —OH group, an alkyl group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 $g \cdot mol^{-1}$ to 3000 $g \cdot mol^{-1}$;

E represents a hydrogen atom, an alkyl group of 1 to 16 carbon atoms, an alkoxy group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 $g \cdot mol^{-1}$ to 3000 $g \cdot mol^{-1}$, each being able to be optionally substituted by a halogen atom or a $NO_2$, —NRR', —CN, —$CF_3$, —OH group, an alkyl group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 $g \cdot mol^{-1}$ to 3000 $g \cdot mol^{-1}$;

G represents an oxygen, nitrogen, sulphur, selenium, tellurium atom or an =NR group; R and R' representing independently of each other H or an alkyl group of 1 to 16 carbon atoms, an aryl group of 6 to 24 carbon atoms, or an aralkyl group of 7 to 16 carbon atoms, an oligoethyleneglycol group comprising preferentially 1 to 12 ethyleneglycol moieties, a polyethyleneglycol group having a molecular weight ranging preferentially from 300 $g \cdot mol^{-1}$ to 3000 $g \cdot mol^{-1}$;

the intermediate chain corresponds to the formula:

-J-K-L- where

J represents an oxygen atom, a sulphur atom, or a —NR— group;

K represents an aryl group of 6 to 24 carbon atoms, a heteroaryl group of 1 to 24 carbon atoms, the heteroelement being preferably chosen from oxygen, nitrogen or sulphur, an alkyl group of 1 to 16 carbon atoms, an oligoethyleneglycol group comprising preferentially 1 to 12 ethyleneglycol moieties, a polyethyleneglycol group having a molecular weight ranging preferentially from 300 $g \cdot mol^{-1}$ to 3000 $g \cdot mol^{-1}$, each being able to be optionally substituted by a halogen atom or a $NO_2$, —NRR', —CN, —$CF_3$, —OH group, an alkyl group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 $g \cdot mol^{-1}$ to 3000 $g \cdot mol^{-1}$;

L represents a linear, branched or cyclic hydrocarbon chain with 0 to 10 members, optionally containing one or more double or triple bonds, each of said members being able to be optionally a heteroatom, said heteroatom being preferably chosen from oxygen, sulphur, nitrogen, phosphorus, silicon, each member being able to be optionally substituted by at least one substituent chosen from an alkyl group of 1 to 16 carbon atoms, a halogen, an oxygen atom, —$NO_2$, —NRR', —CN, —$CF_3$, —OH, an alkoxy group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 $g \cdot mol^{-1}$ to 3000 $g \cdot mol^{-1}$;

R and R' representing independently of each other H or an alkyl group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 $g \cdot mol^{-1}$ to 3000 $g \cdot mol^{-1}$;

the terminal group corresponds to the formula:

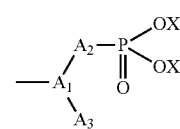

where $A_1$, $A_2$, $A_3$ and X have been defined previously, each X being identical or different.

In a more particular embodiment, the invention relates to the use of a dendrimer of general formula (1a) in which $A_3$ represents:

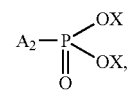

said general formula (1a) then corresponding to the following general formula (1):

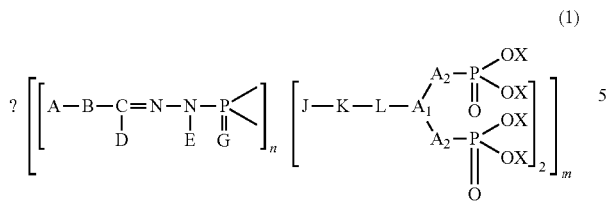

(1)

§, A, B, C, D, E, G, J, K, L, $A_1$, $A_2$, X, m and n being as defined above, the central core § representing preferably the following group:

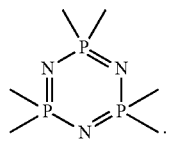

In a particular embodiment of the invention, the dendrimers with bisphosphonic terminations correspond to the following general formula (1) where n represents an integer from 0 to 3, namely:

when n=0, formula (1) corresponds to the following formula (2),

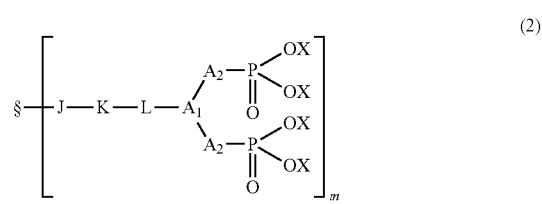

(2)

when n=1, formula (1) corresponds to the following formula (3),

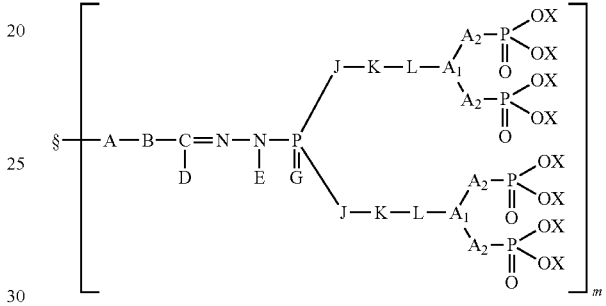

(3)

when n=2, formula (1) corresponds to the following formula (4),

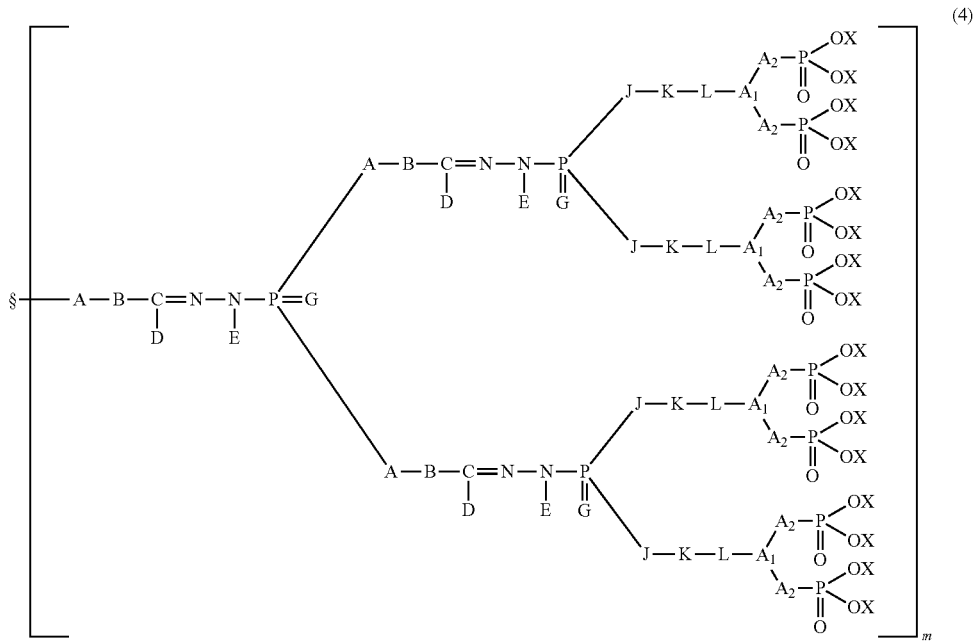

(4)

and when n=3, formula (1) corresponds to the following formula (5),
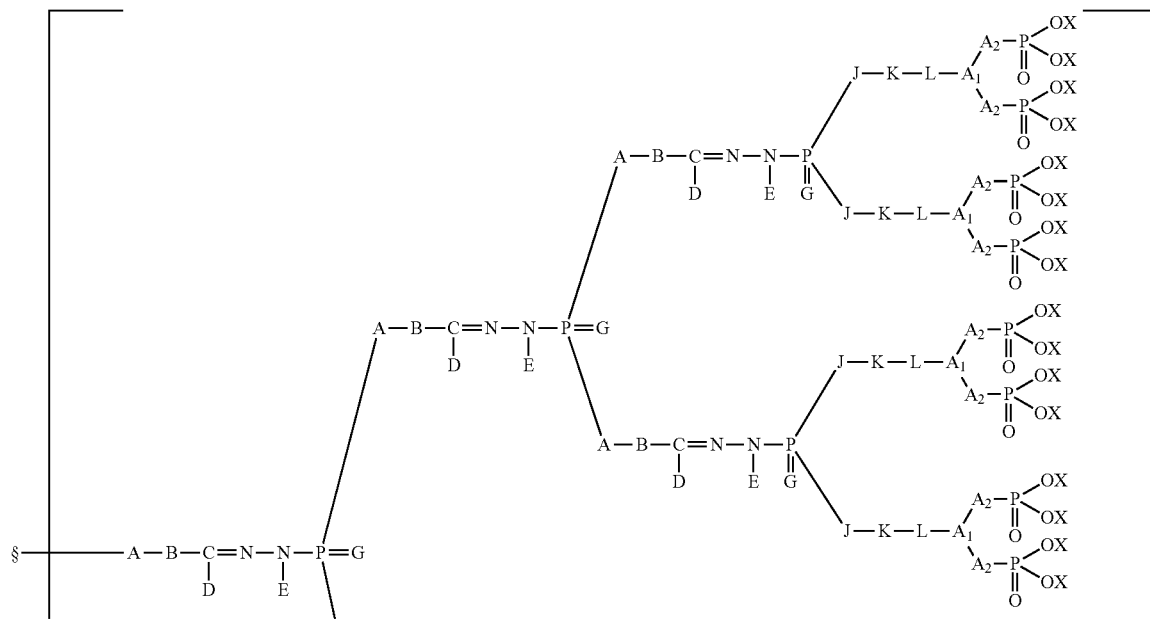
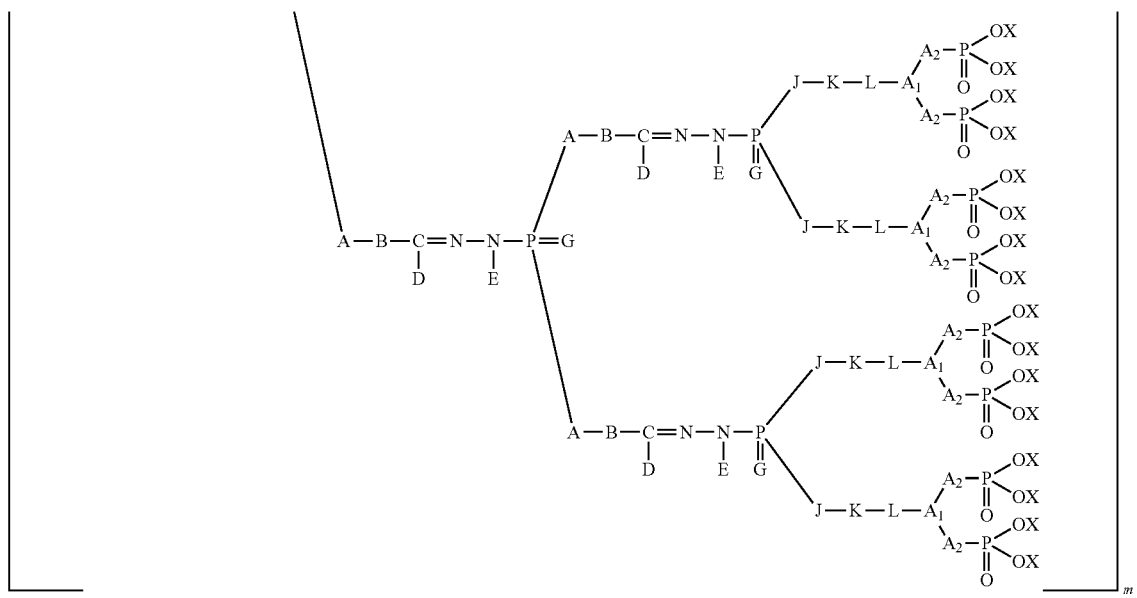
(5)

and in which formulae:

the central core § is chosen from the following groups:

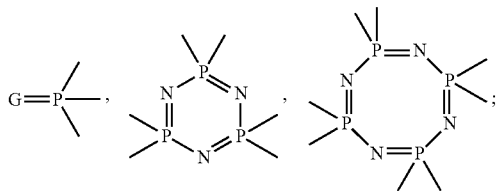

the central core representing preferably the following group:

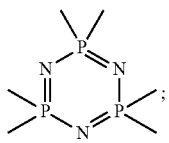

m represents 3, 6 or 8;
the generation chain corresponds to the formula:

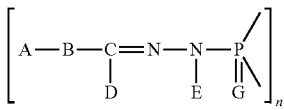

where
A represents an oxygen, sulphur, phosphorus atom or a NR— group;
B represents an aryl group of 6 to 24 carbon atoms, a heteroaryl group of 1 to 24 carbon atoms, an alkyl group of 1 to 16 carbon atoms, an oligoethyleneglycol group, a polyethyleneglycol group, two aryl groups of 6 to 24 carbon atoms linked by an oxygen, a nitrogen, a sulphur, an alkyl group of 1 to 16 carbon atoms, an heteroalkyl group of 1 to 24 carbon atoms, an oligoethyleneglycol group, each being able to be optionally substituted by a halogen atom or a $NO_2$, —NRR', —CN, —$CF_3$, —OH group, an alkyl group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$; According to the invention, when B represents two aryl groups of 6 to 24 carbon atoms linked by an oxygen, a nitrogen, a sulphur, an alkyl group of 1 to 16 carbon atoms, an heteroalkyl group of 1 to 24 carbon atoms, an oligoethyleneglycol group selected from the groups comprising $C_6H_4$—O—$C_6H_4$ and $C_6H_4$—$(CH_2CH_2O)q$-$C_6H_4$ with q=1 to 12.
D represents a hydrogen atom, an alkyl group of 1 to 16 carbon atoms, an alkoxy group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$; each being able to be optionally substituted by a halogen atom or a $NO_2$, —NRR', —CN, —$CF_3$, —OH group, an alkyl group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$;
E represents a hydrogen atom, an alkyl group of 1 to 16 carbon atoms, an alkoxy group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, each being able to be optionally substituted by a halogen atom or a $NO_2$, —NRR', —CN, —$CF_3$, —OH group, an alkyl group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$;
G represents an oxygen, nitrogen, sulphur, selenium, tellurium atom or an =NR group;
R and R' representing independently of each other H or an alkyl group of 1 to 16 carbon atoms, an aryl group of 6 to 24 carbon atoms, or an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$;
the intermediate chain corresponds to the formula:

-J-K-L- where
J represents an oxygen atom, a sulphur atom, or a —NR— group;
K represents an aryl group of 6 to 24 carbon atoms, a heteroaryl group of 1 to 24 carbon atoms, the heteroelement being preferably chosen from oxygen, nitrogen or sulphur, an alkyl group of 1 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, each being able to be optionally substituted by a halogen atom or a $NO_2$, —NRR', —CN, —$CF_3$, —OH group, an alkyl group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$;
L represents a linear, branched or cyclic hydrocarbon chain with 0 to 10 members, in particular with 0 to 6 members, optionally containing one or more double or triple bonds, each of said members optionally being able to be a heteroatom, said heteroatom being preferably chosen from oxygen, sulphur, nitrogen, phosphorus, silicon, each member being able to be optionally substituted by at least one substituent chosen from an alkyl group of 1 to 16 carbon atoms, a halogen, an oxygen atom, —$NO_2$, —NRR', —CN, —$CF_3$, —OH, an alkoxy group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$;

R and R' representing independently of each other H or an alkyl group of 1 to 16 carbon atoms, an aryl group of 6 to 24 carbon atoms, or an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$;

the terminal group corresponds to the formula:

where $A_1$, $A_2$ and X have been defined previously, each X being identical or different.

According to a preferred embodiment, the invention relates to the use as defined above of a dendrimer of general formula (1) of structure PMMH, in which § represents m represents 6;
n represents 0, 1, or 2;
A represents an oxygen atom;
B represents a benzene group;
D represents hydrogen;
E represents a methyl group;
G represents a sulphur atom;
J represents an oxygen atom;
K represents a benzene group;
L represents a non-substituted linear saturated hydrocarbon chain with two carbon atoms;
$A_1$ represents a nitrogen atom;
$A_2$ represents a $CH_2$ group;
X represents a methyl group, or a hydrogen or sodium atom;
said dendrimer being designated GCn, n being defined above.

According to a particularly preferred embodiment, the invention relates to the use as defined above of compounds of the following formulae:

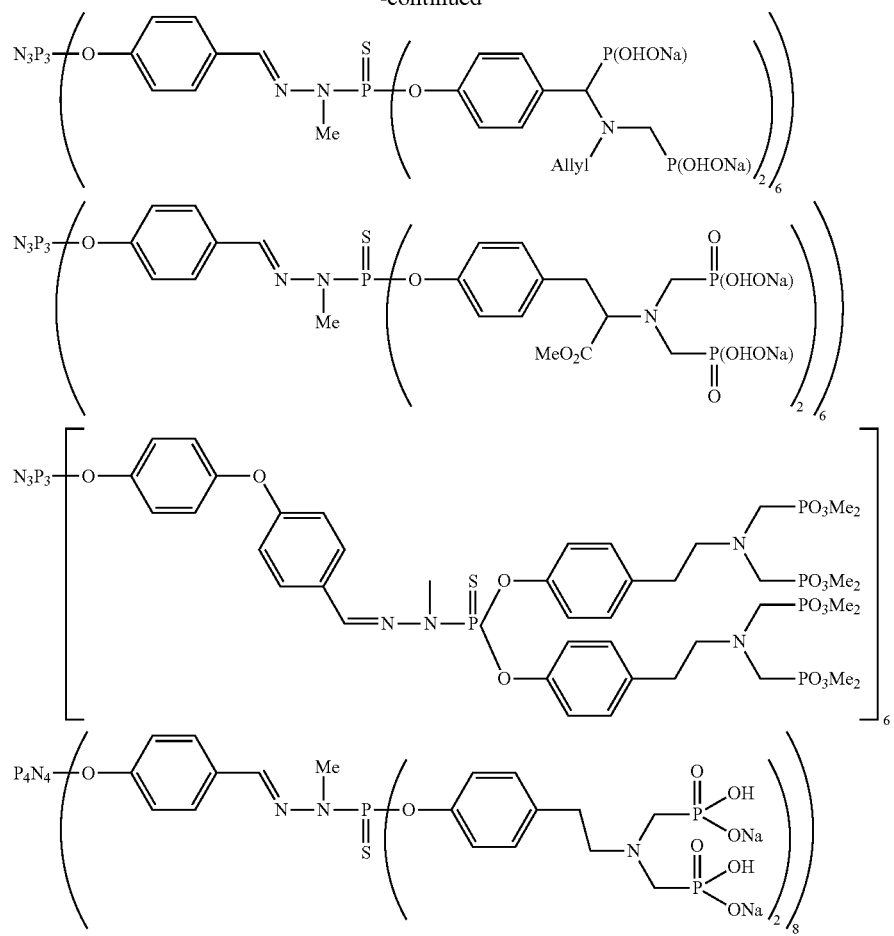
or of Gc compounds of the following formulae:

Gc1a
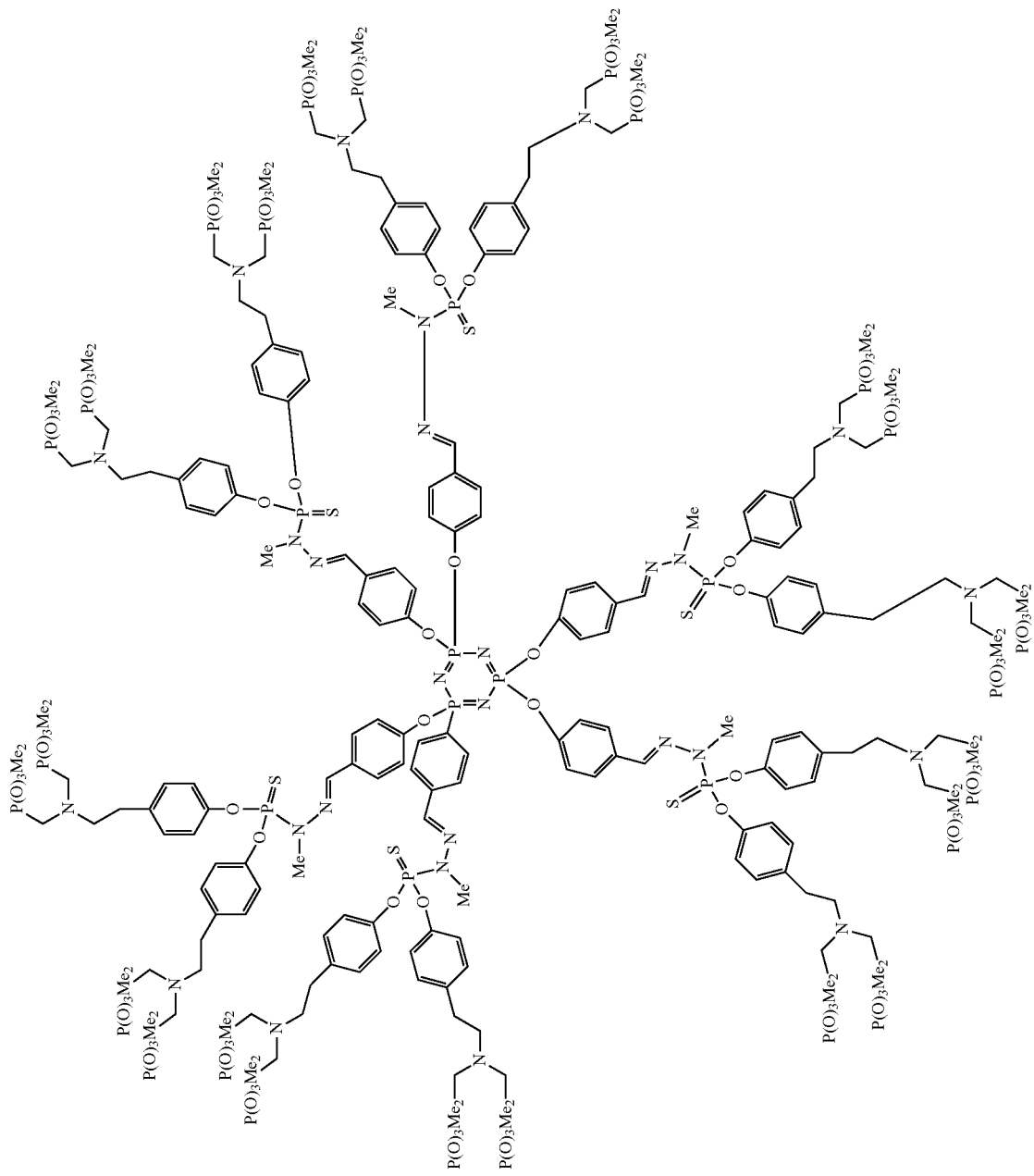

-continued
Gc1b
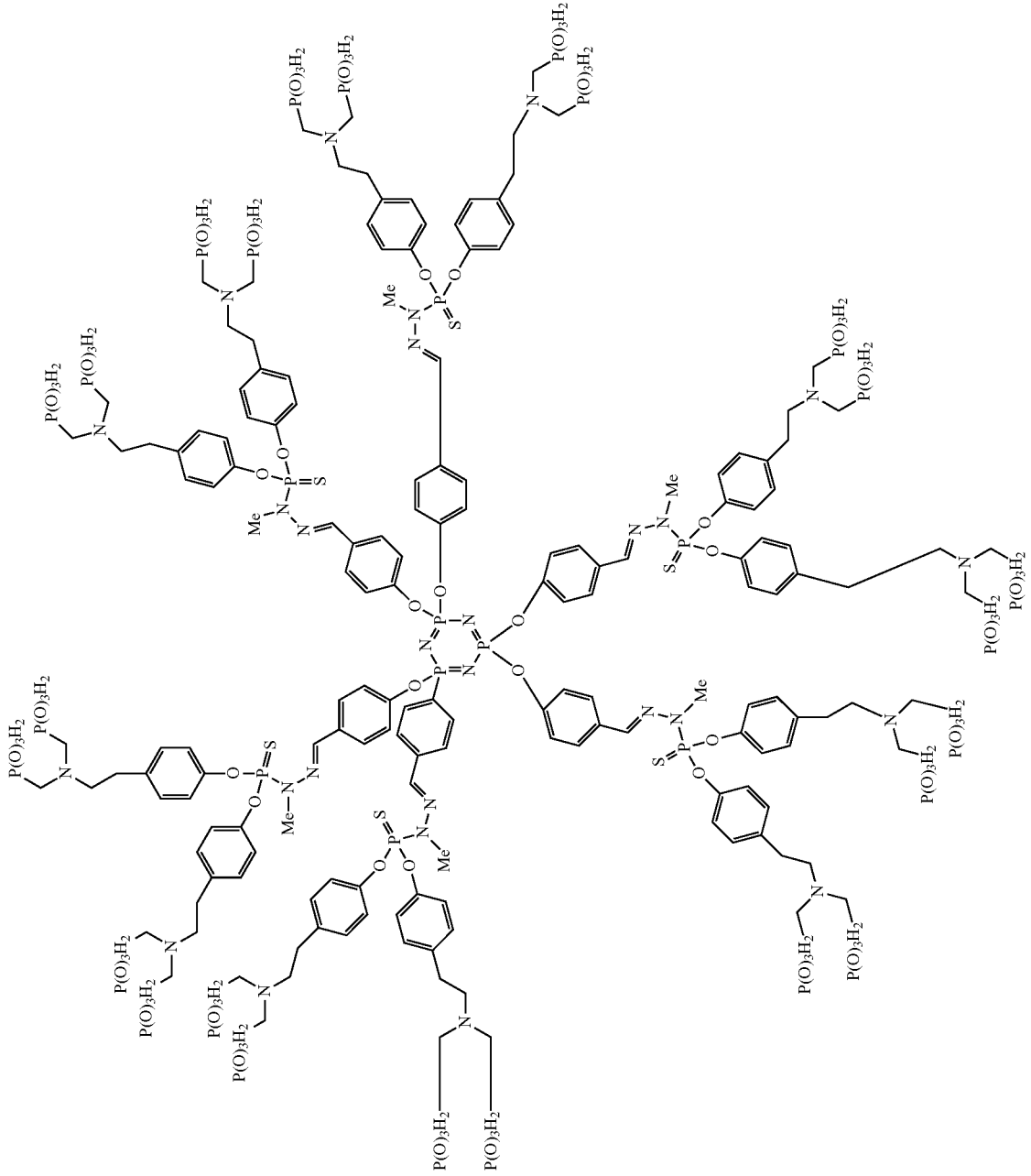

-continued
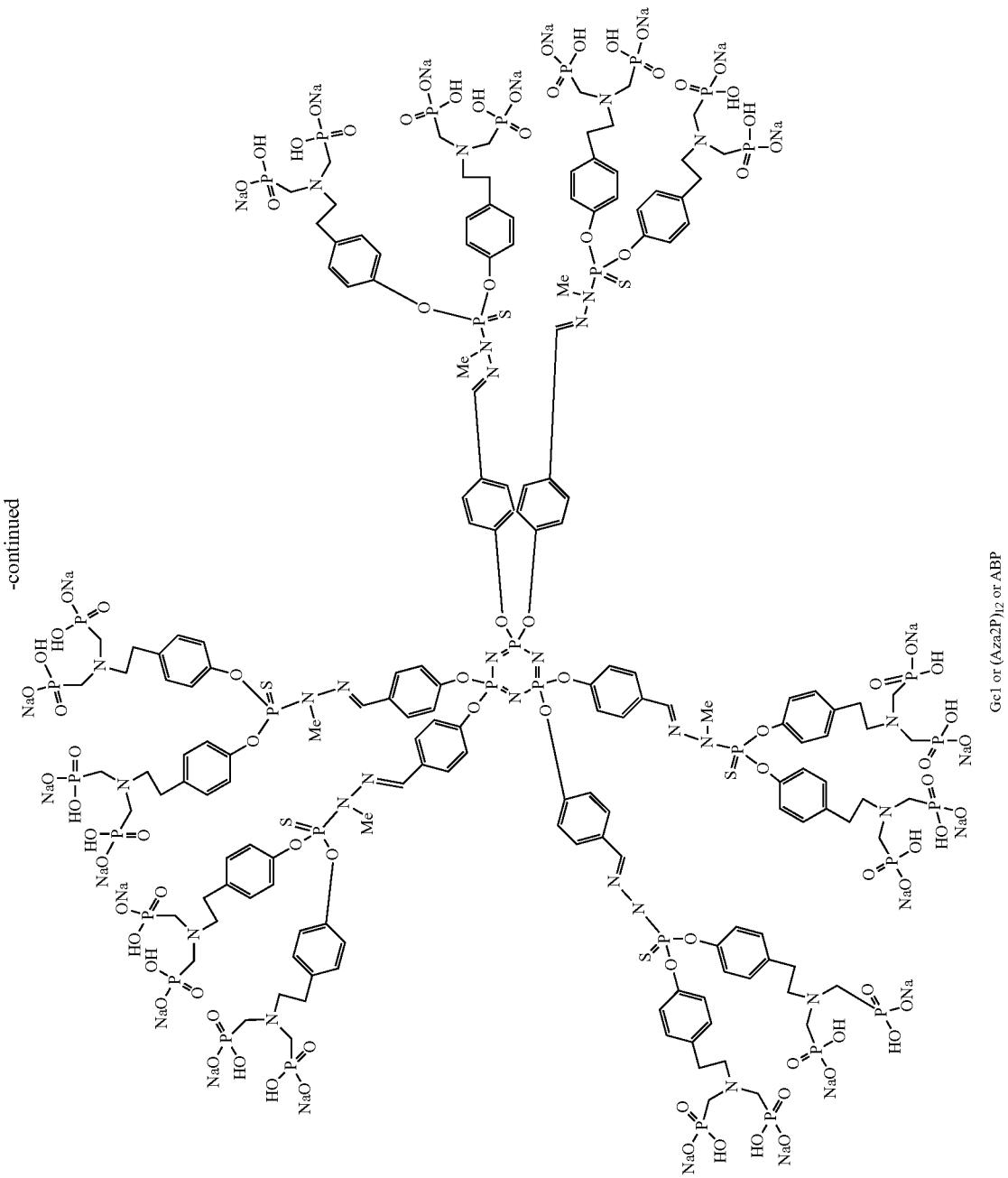
Gc1 or (Aza2P)₁₂ or ABP

The present invention also relates to the use of dendrimers with bisphosphonic terminations corresponding to the following general formula (7):

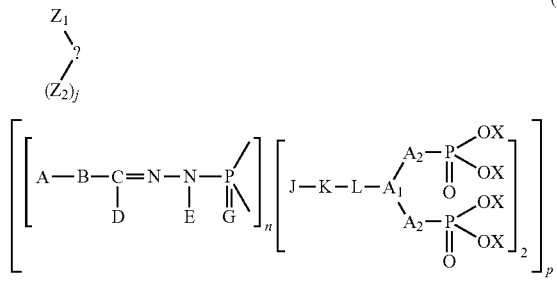 (7)

where n represents an integer from 0 to 3, m represents 3, 6 or 8, p represents m−1 or m−2, and j represents 0 when p represents m−1 and 1 when p represents m−2, namely:

when p=m−1, formula (7) corresponds to the following formula (8):

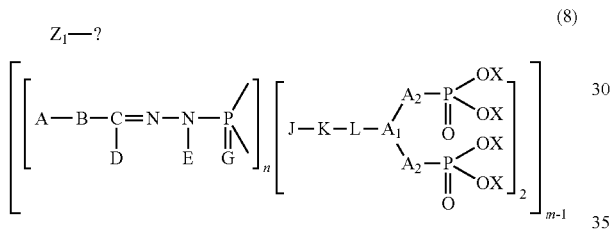 (8)

when p=m−2, formula (7) corresponds to the following formula (9):

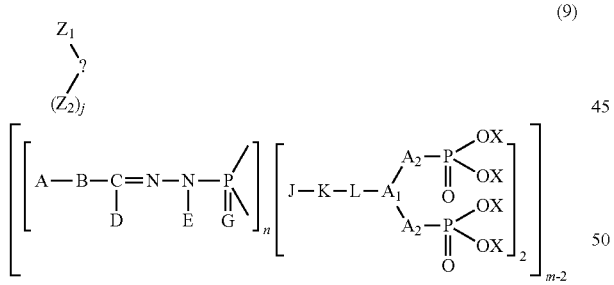 (9)

and in which formulae:

the central core § is chosen from the following groups:

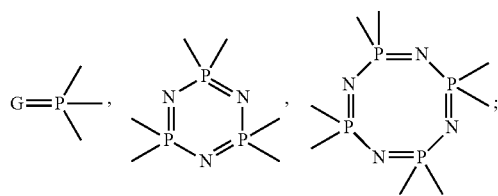

the generation chain corresponds to the formula:

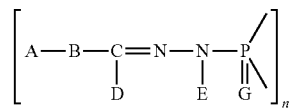

where

A represents an oxygen, sulphur, phosphorus atom or a NR— group;

B represents an aryl group of 6 to 24 carbon atoms, a heteroaryl group of 1 to 24 carbon atoms, an alkyl group of 1 to 16 carbon atoms, an oligoethyleneglycol group, a polyethyleneglycol group, two aryl groups of 6 to 24 carbon atoms linked by an oxygen, a nitrogen, a sulphur, an alkyl group of 1 to 16 carbon atoms, an heteroalkyl group of 1 to 24 carbon atoms, an oligo-ethyleneglycol group, each being able to be optionally substituted by a halogen atom or a $NO_2$, —NRR', —CN, —$CF_3$, —OH group, an alkyl group of 1 to 16 carbon atoms, an aryl group of 6 to 24 carbon atoms, an aralkyl group of 7 to 16 carbon atoms, an oligoethyl-eneglycol group comprising preferentially 1 to 12 ethyleneglycol moieties, a polyethyleneglycol group having a molecular weight ranging preferentially from 300 g·mol$^{-1}$ to 3000 g·mol$^{-1}$. According to the invention, when B represents two aryl groups of 6 to 24 carbon atoms linked by an oxygen, a nitrogen, a sulphur, an alkyl group of 1 to 16 carbon atoms, an heteroalkyl group of 1 to 24 carbon atoms, an oligoethyleneglycol group selected from the groups comprising $C_6H_4$—O—$C_6H_4$ and $C_6H_4$—$(CH_2CH_2O)q$-$C_6H_4$ with q=1 to 12.

D represents a hydrogen atom, an alkyl group of 1 to 16 carbon atoms, an alkoxy group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, each being able to be optionally substituted by a halogen atom or a $NO_2$, —NRR', —CN, —$CF_3$, —OH group, an alkyl group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$;

E represents a hydrogen atom, an alkyl group of 1 to 16 carbon atoms, an alkoxy group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, each being able to be optionally substituted by a halogen atom or a $NO_2$, —NRR', —CN, —$CF_3$, —OH group, an alkyl group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$;

G represents an oxygen, nitrogen, sulphur, selenium, tellurium atom or an =NR group;

R and R' representing independently of each other H or an alkyl group of 1 to 16 carbon atoms, an aryl group of 6 to 24 carbon atoms, or an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$;

the intermediate chain corresponds to the formula:

-J-K-L- where

J represents an oxygen atom, a sulphur atom, or a —NR— group;

K represents an aryl group of 6 to 24 carbon atoms, a heteroaryl group of 1 to 24 carbon atoms, the heteroelement being preferably chosen from oxygen, nitrogen or sulphur, an alkyl group of 1 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, each being able to be optionally substituted by a halogen atom or a NO$_2$, —NRR', —CN, —CF$_3$, —OH group, an alkyl group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$;

L represents a linear, branched or cyclic hydrocarbon chain with 0 to 10 members, in particular with 0 to 6 members, optionally containing one or more double or triple bonds, each of said members optionally being able to be a heteroatom, said heteroatom being preferably chosen from oxygen, sulphur, nitrogen, phosphorus, silicon, each member being able to be optionally substituted by at least one substituent chosen from an alkyl group of 1 to 16 carbon atoms, a halogen, an oxygen atom, —NO$_2$, —NRR', —CN, —CF$_3$, —OH, an alkoxy group of 1 to 16 carbon atoms, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$;

R and R' representing independently of each other H or an alkyl group of 1 to 16 carbon atoms, an aryl group of 6 to 24 carbon atoms, or an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$;

the terminal group corresponds to the formula:

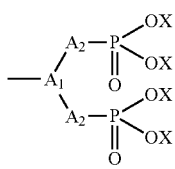

where A1, A2 and X have been defined previously, each X being identical or different;

$Z_1$ and $Z_2$ being identical or different, optionally linked together, in particular by means of a covalent bond, and representing H or a linear, branched or cyclic hydrocarbon chain with 1 to 16 members, optionally containing one or more double or triple bonds, each of said members being optionally chosen from a heteroatom, said heteroatom being preferably chosen from a nitrogen, oxygen, phosphorus, silicon or sulphur atom, an aryl group of 6 to 24 carbon atoms, a heteroaryl group of 1 to 24 carbon atoms, a carboxyl group, a >C=NR group, each member being able to be optionally substituted by at least one substituent chosen from a hydroxyl group, a NR"R'" group, an alkoxy group of 1 to 16 carbon atoms, an alkyl group of 1 to 16 carbon atoms, a halogen atom, a NO$_2$ group, a —CN group, a —CF$_3$ group, an aryl group of 6 to 24 carbon atoms, an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, R" and R' representing independently of each other H or an alkyl group of 1 to 16 carbon atoms, an aryl group of 6 to 24 carbon atoms or an aralkyl group of 7 to 16 carbon atoms, an oligoethyleneglycol group comprising preferentially 1 to 12 ethyleneglycol moieties, a polyethyleneglycol group having a molecular weight ranging preferentially from 300 g·mol$^{-1}$ to 3000 g·mol$^{-1}$, the first member of said hydrocarbon chain preferably being oxygen or nitrogen.

The invention relates more particularly to the use as defined above, of a dendrimer of general formula (8) of structure PMMH, in which § represents

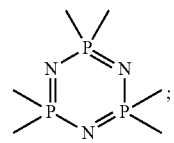

m represents 6;

p represents 5;

n represents 0, 1, or 2;

A represents an oxygen atom;

B represents a benzene group;

D represents hydrogen;

E represents a methyl group;

G represents a sulphur atom;

J represents an oxygen atom;

K represents a benzene group;

L represents a non-substituted linear saturated hydrocarbon chain with two carbon atoms;

$A_1$ represents a nitrogen atom;

$A_2$ represents a CH$_2$ group;

X represents a methyl group, or a hydrogen or sodium atom;

$Z_1$ represents a phenyloxy group;

said dendrimer being designated GCn', n being defined above.

Preferably, the present invention relates in particular to the use as defined above:
of the compounds of the following formulae:
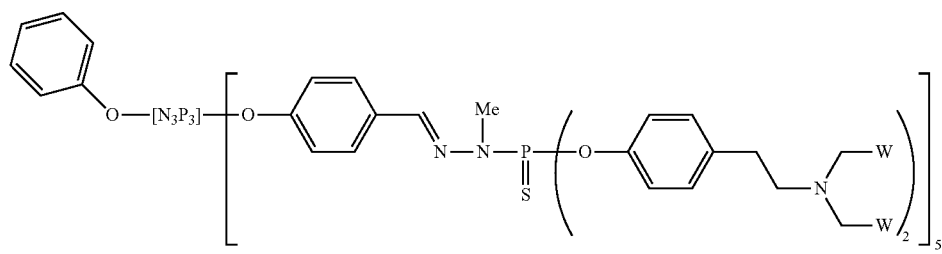
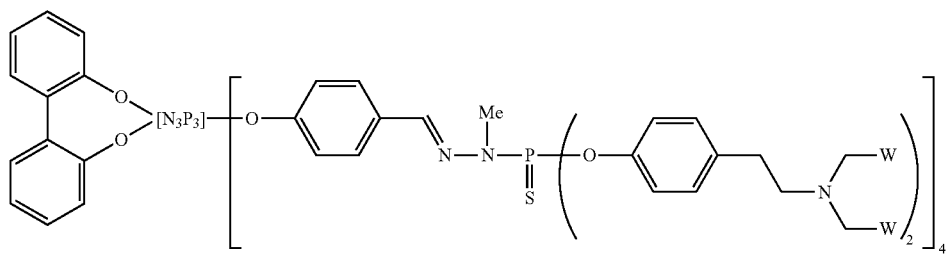
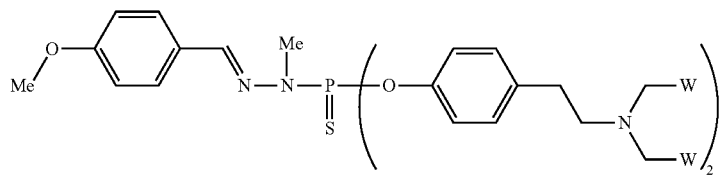
in which W represents $PO_3Me_2$, $PO_3HNa$, $PO_3H_2$, said compounds corresponding, in particular, to compound GC1' of the following formula (10):
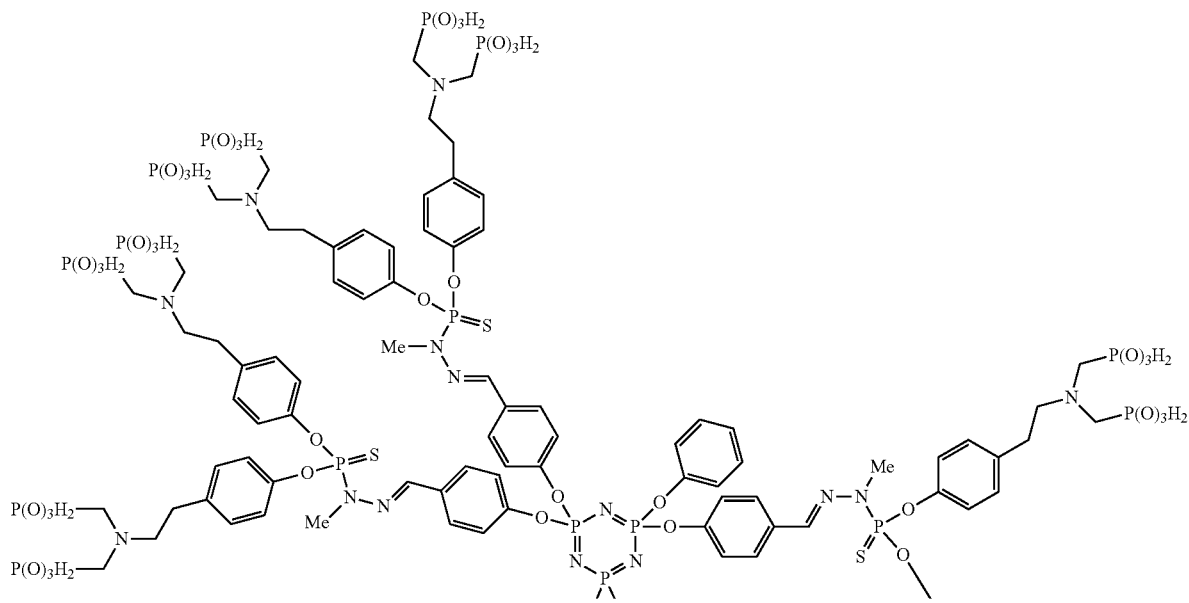
(10)

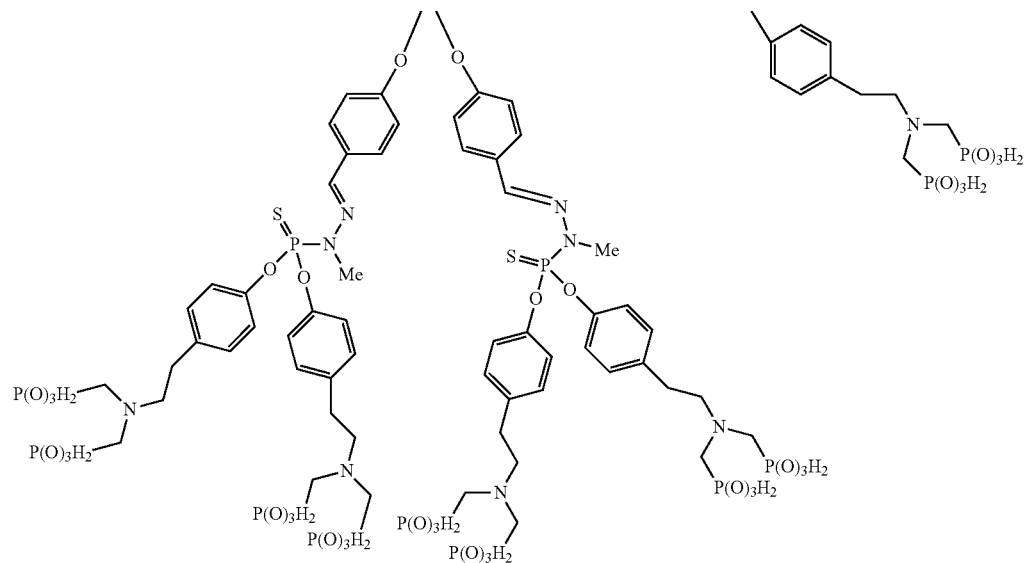
or of the formula (10a)
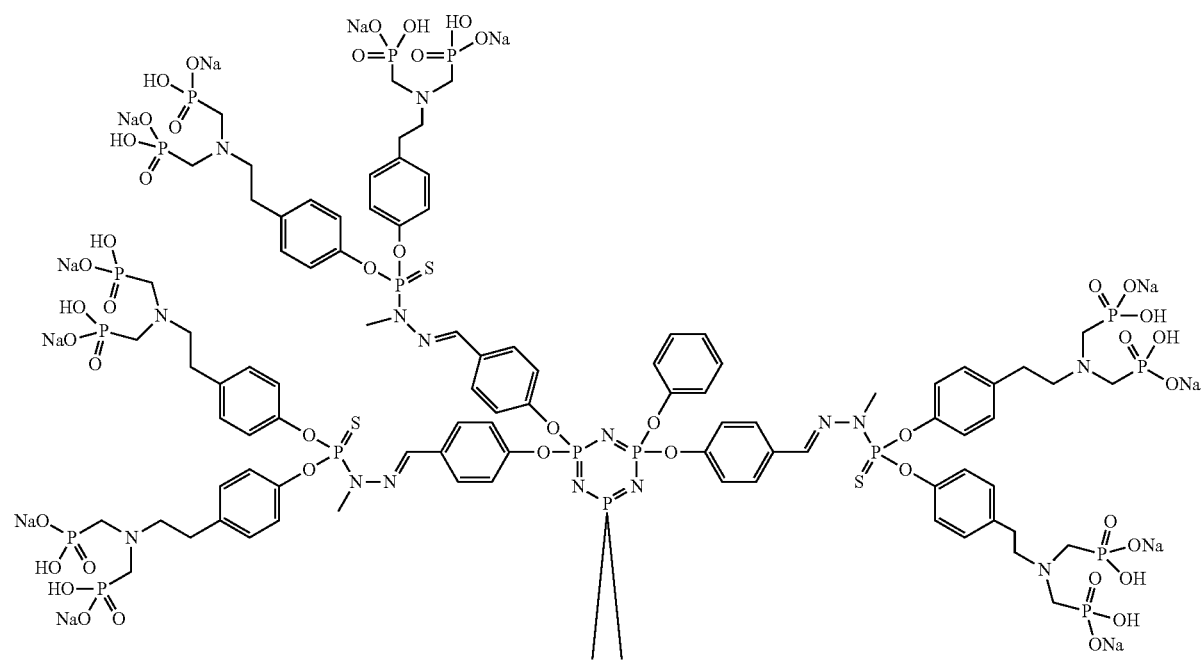

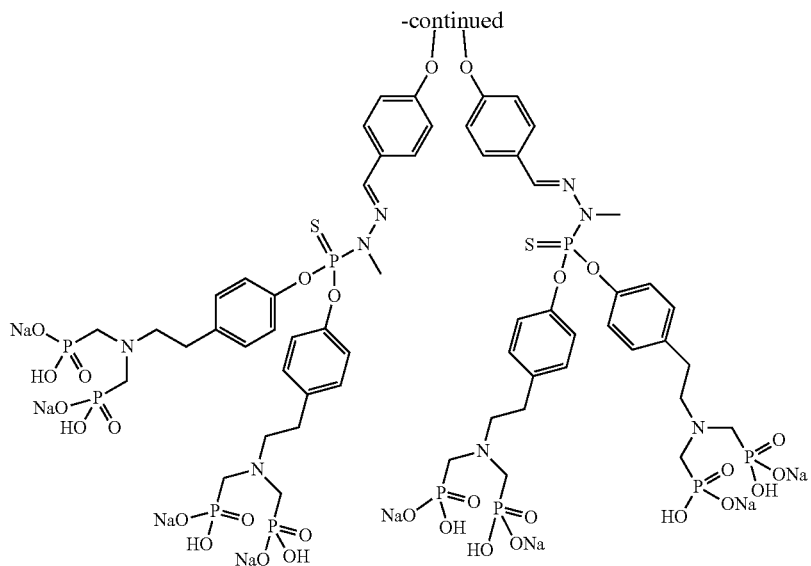
or compounds of the following formula:
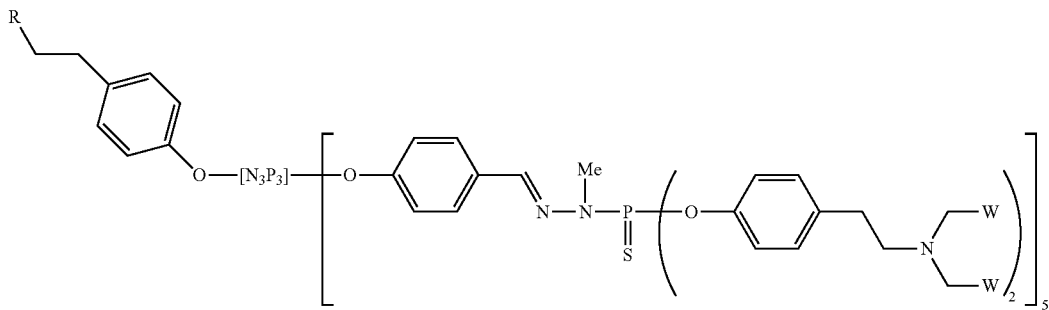
in which W represents $PO_3Me_2$, $PO_3HNa$, or $PO_3H_2$ and R is selected from the group comprising (a) fluorescent groups chosen from:
and (b) a biotinyl group of formula
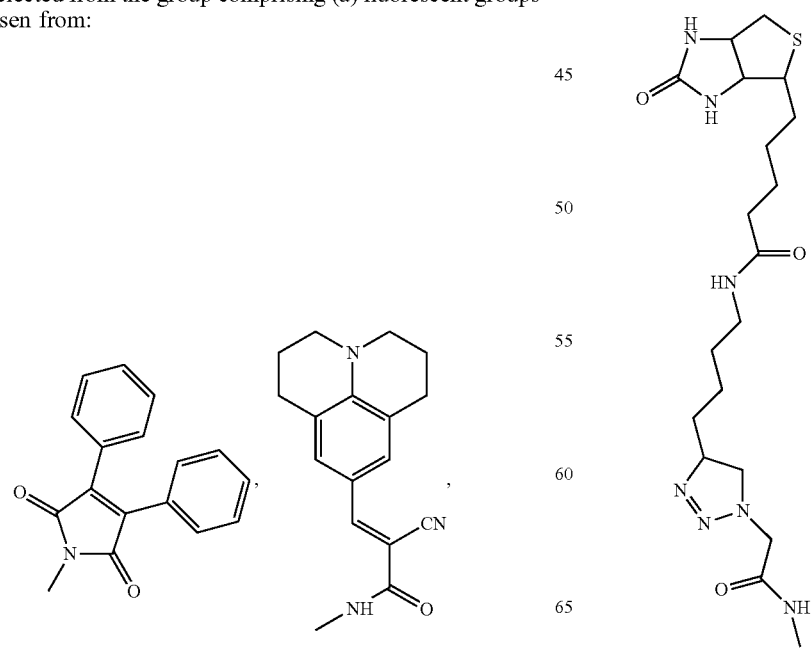

said compounds corresponding in particular to the compounds of the following formulae:
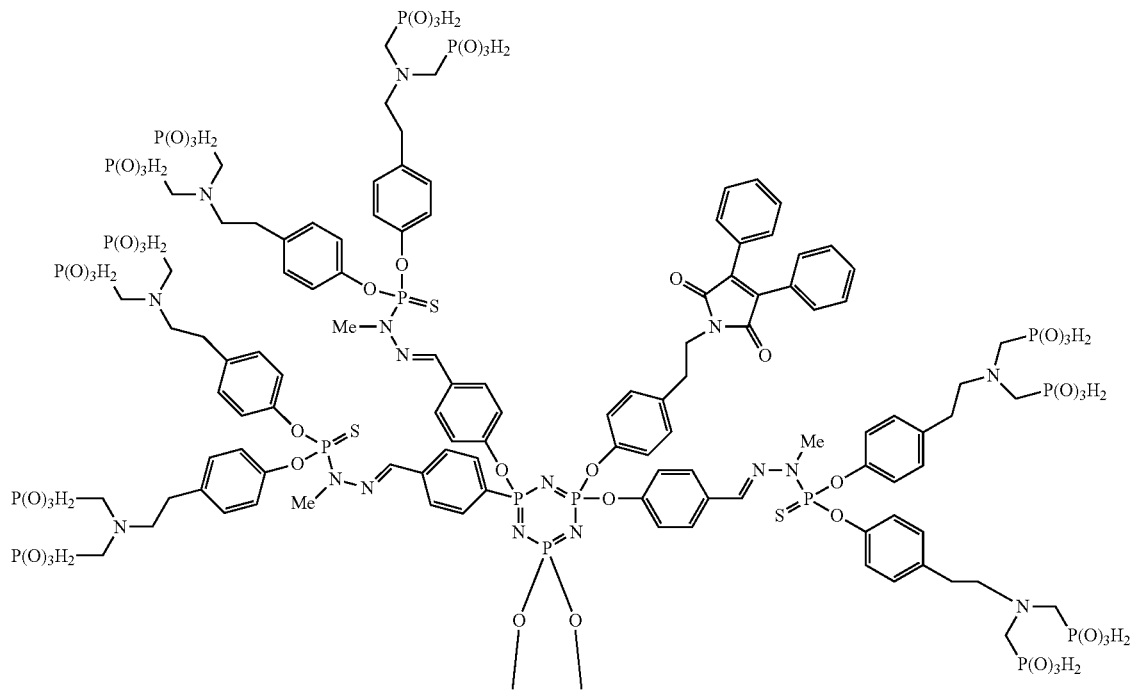
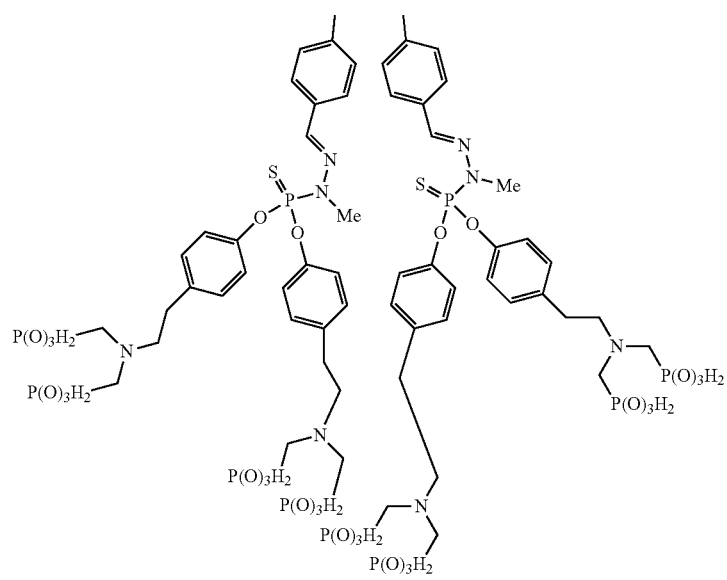

-continued
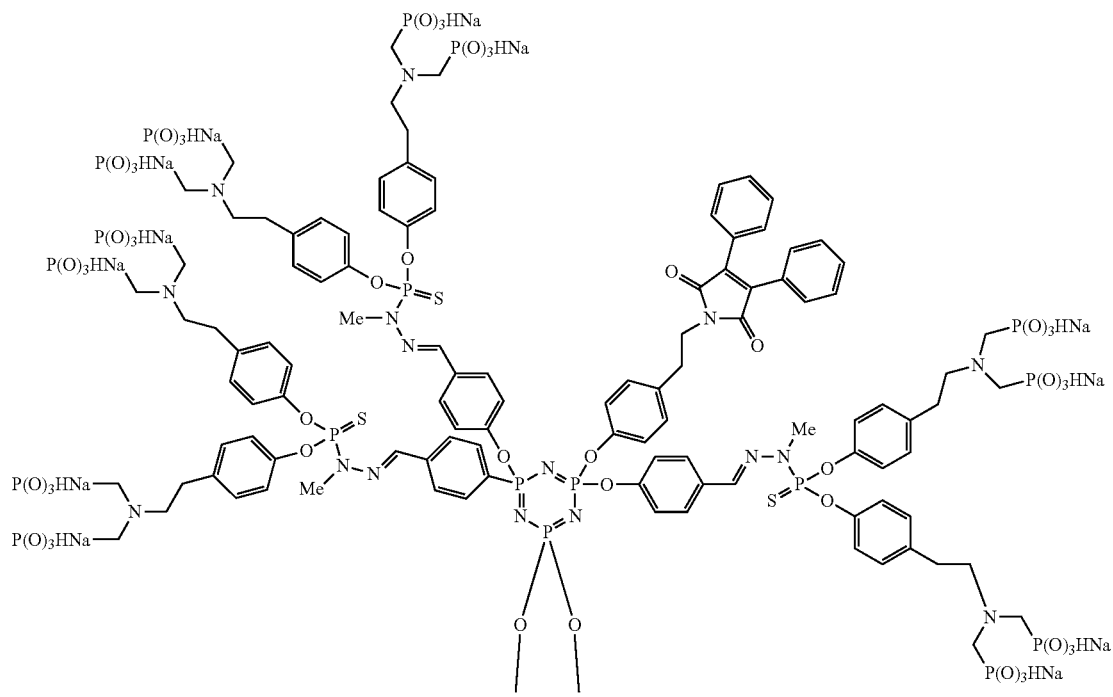
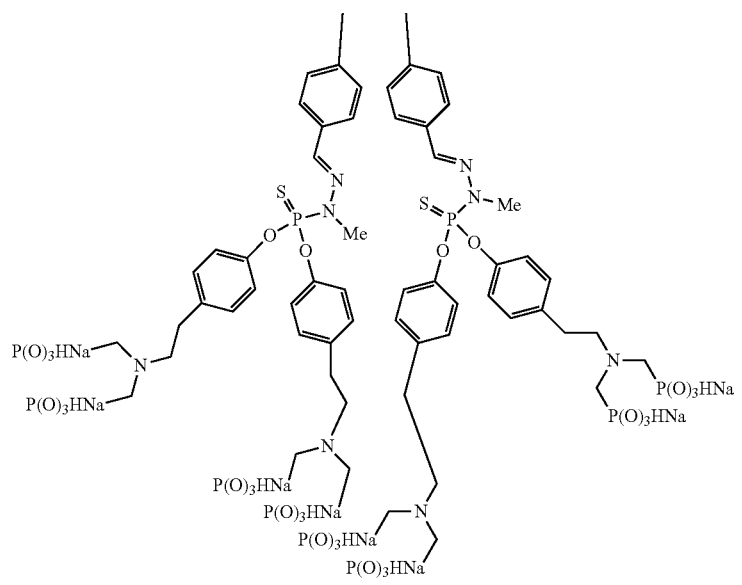

-continued
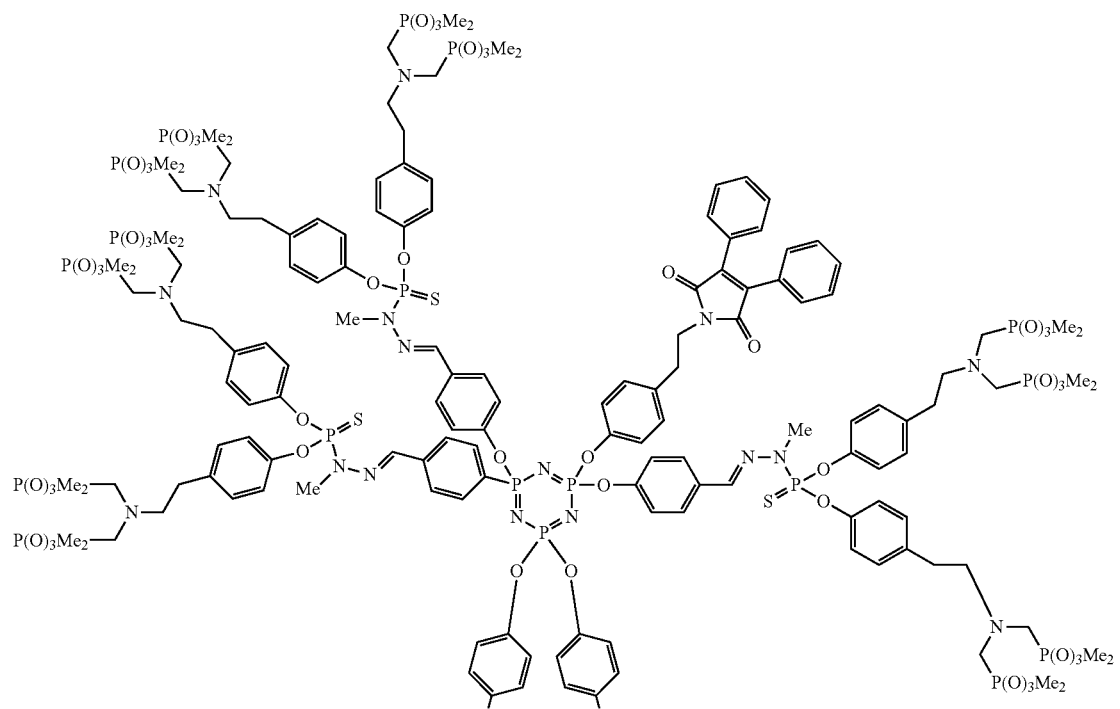
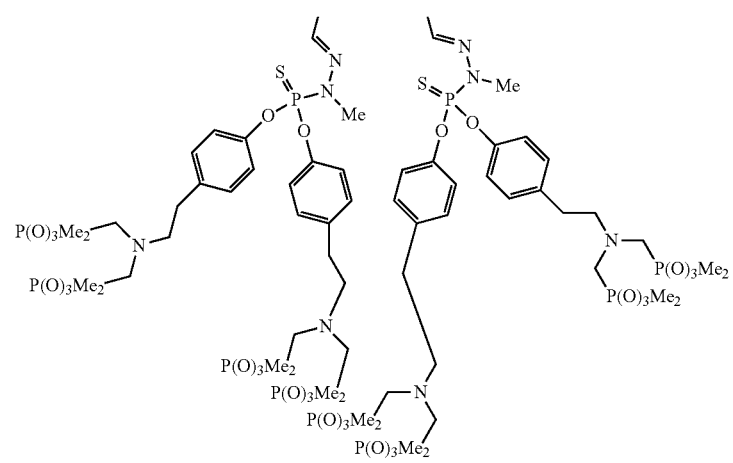

-continued
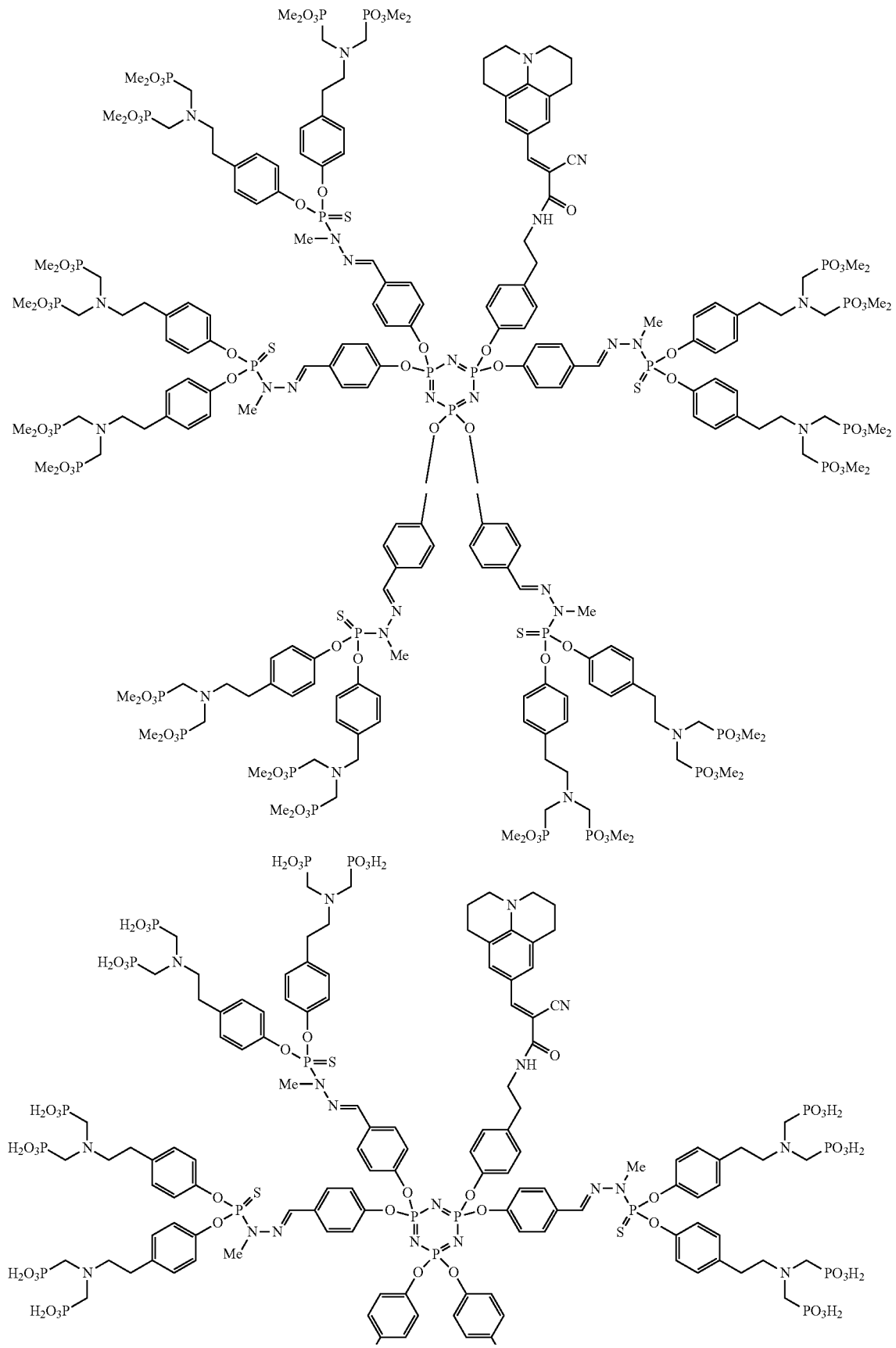

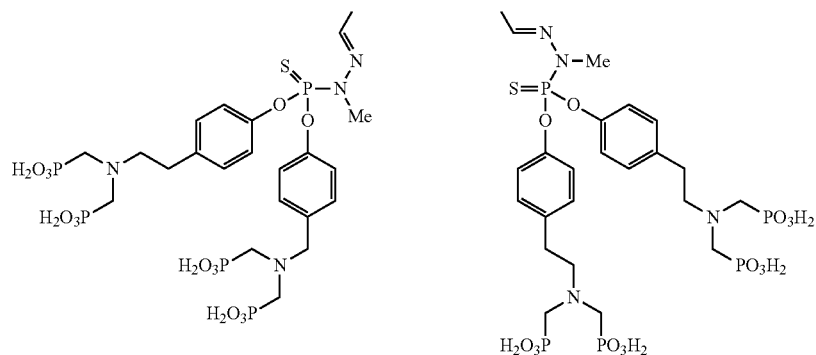
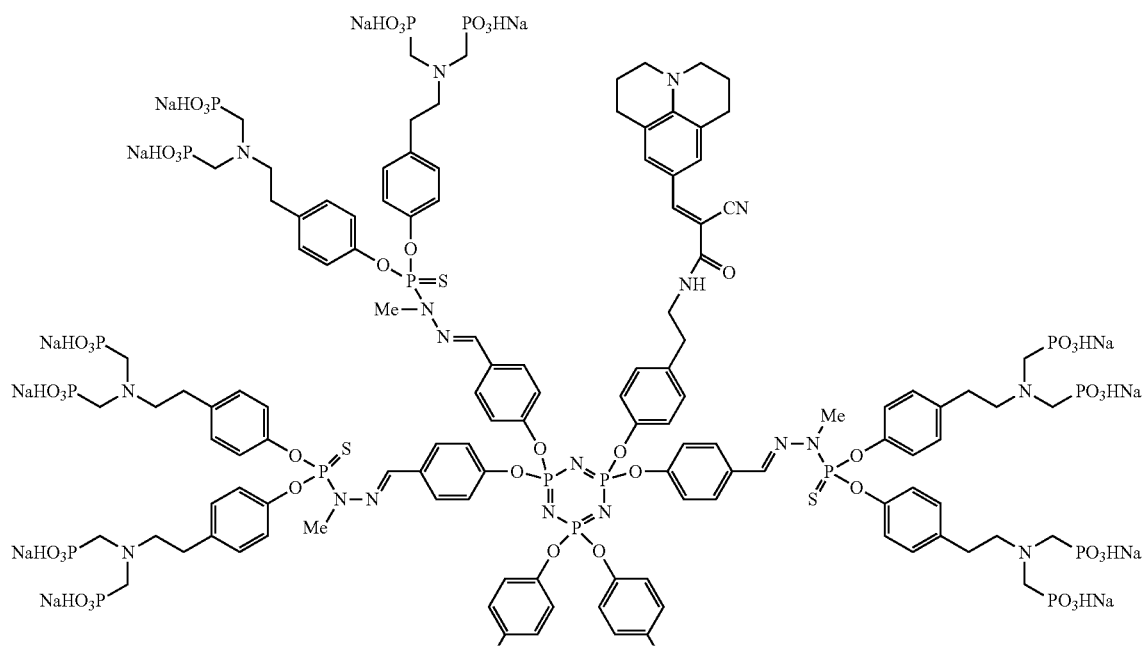
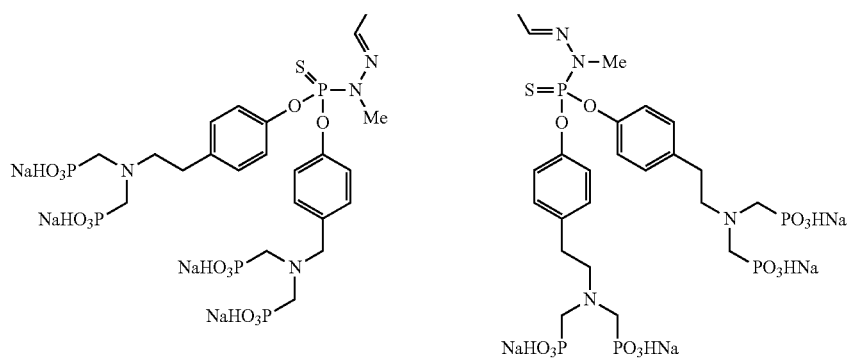
Aza2P-Julo-D 73
74
-continued
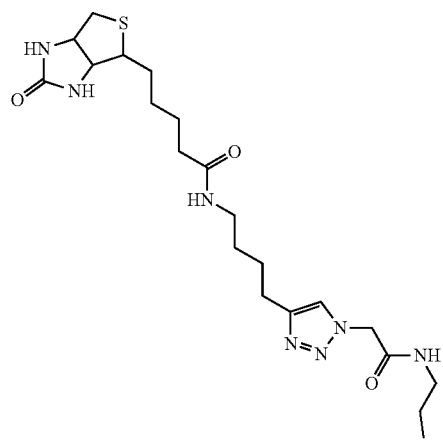
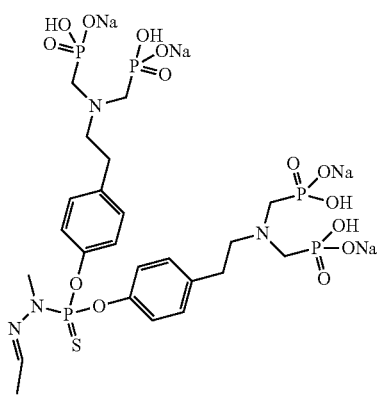
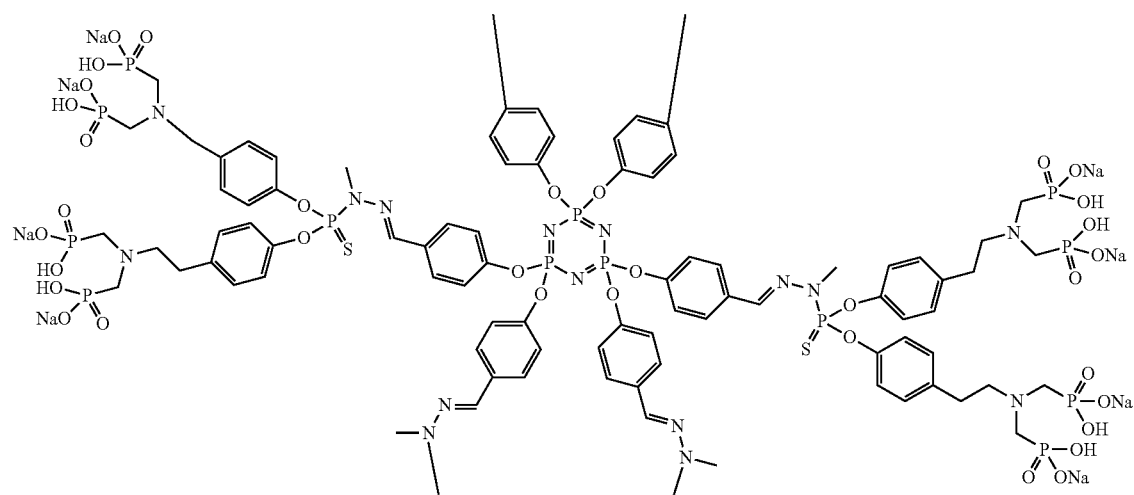
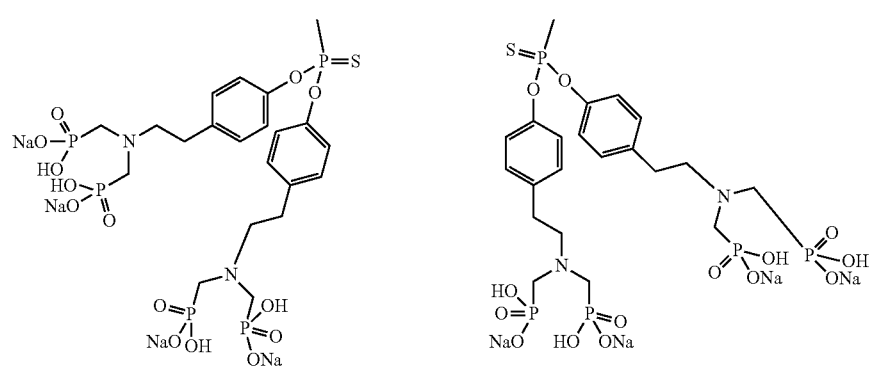
(Aza2P)₁₀-Biot-D The present invention also relates to the use of dendrimers with bisphosphonic terminations of the following formula:

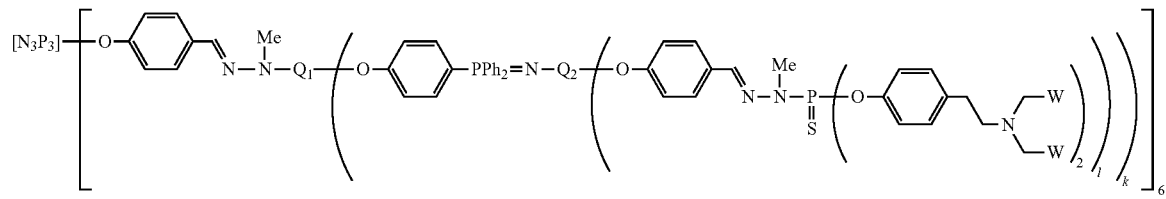

in which W represents $PO_3Me_z$, $PO_3HNa$, or $PO_3H_2$, $Q_1$ and $Q_2$, identical or different, represent P=S or cyclotriphosphazene ($N_3P_3$), l represents 2 when $Q_2$ represents P=S or 5 when $Q_2$ represents $N_3P_3$ and k represents 2 when $Q_1$ represents P=S or 5 when $Q_1$ represents $N_3P_3$, said dendrimers being in particular represented by the following formulae:

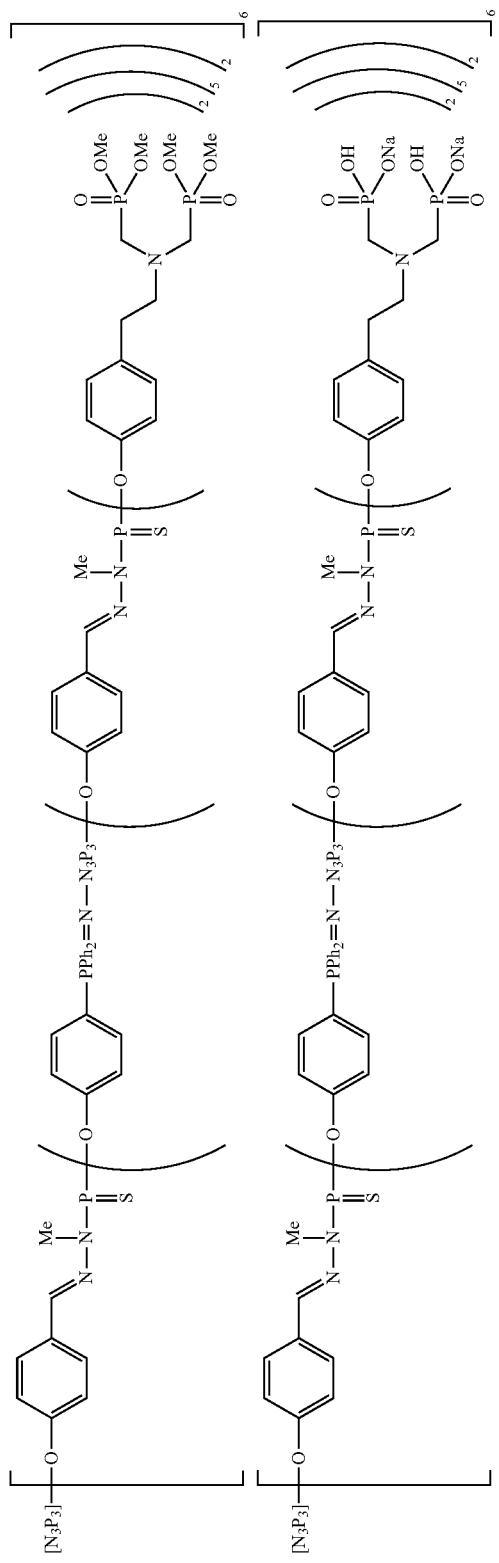
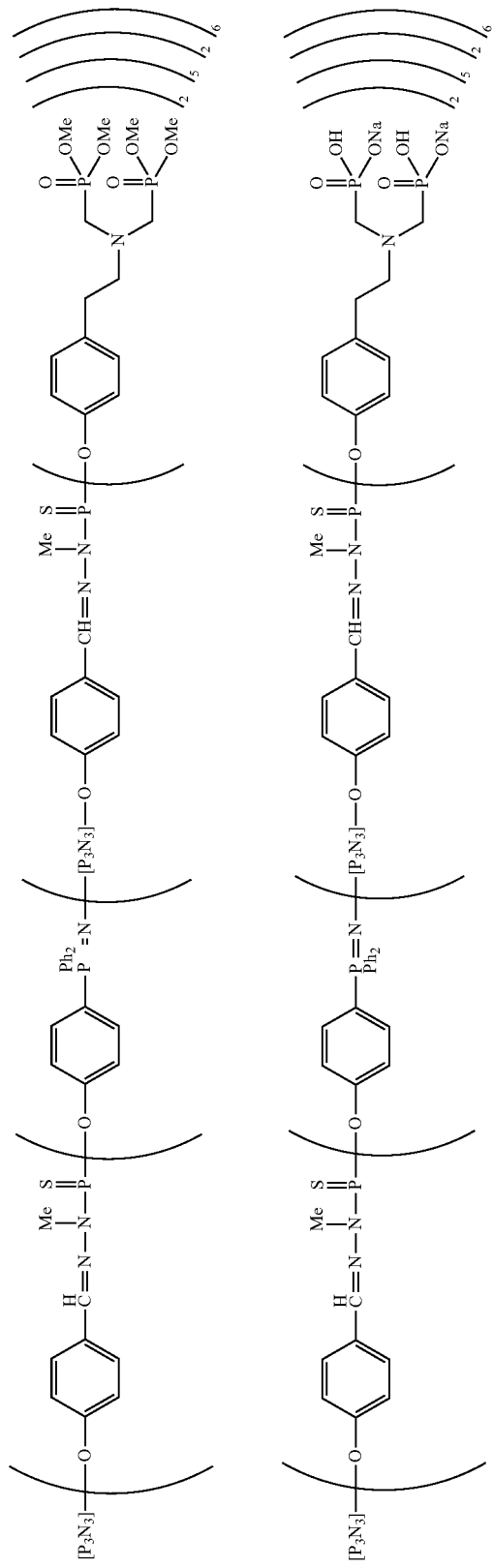

-continued
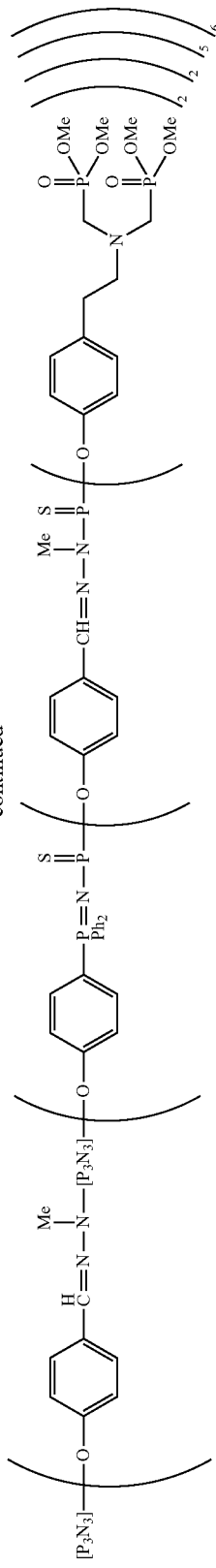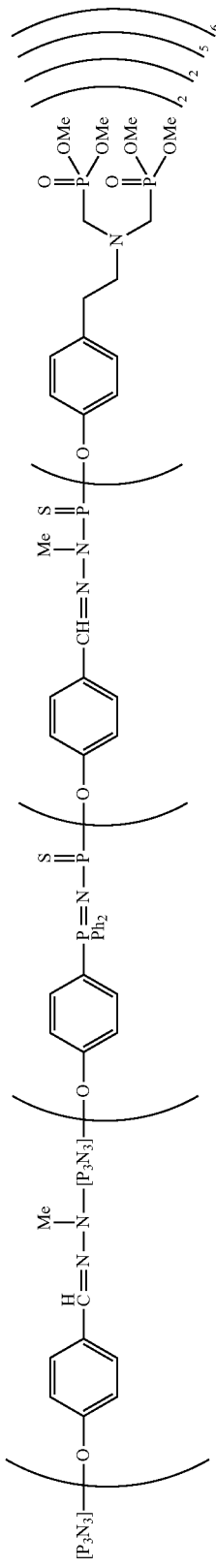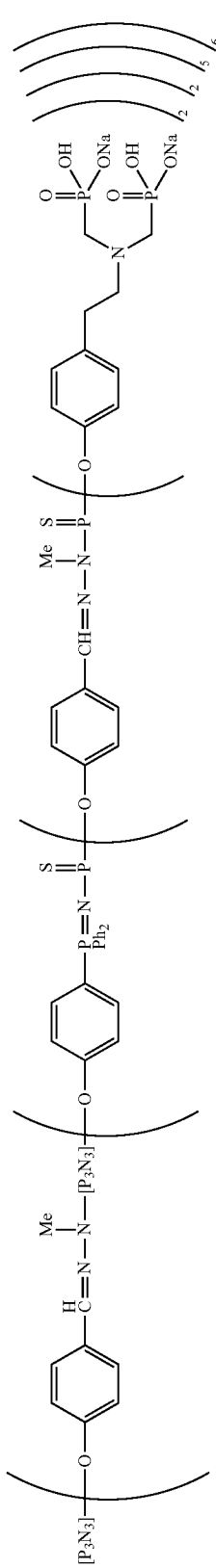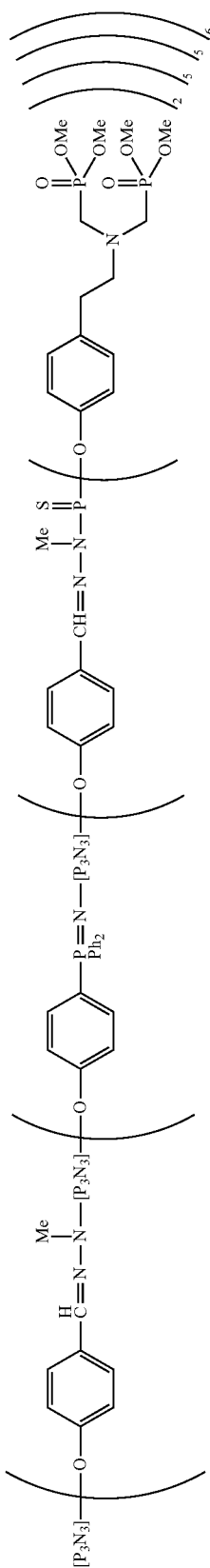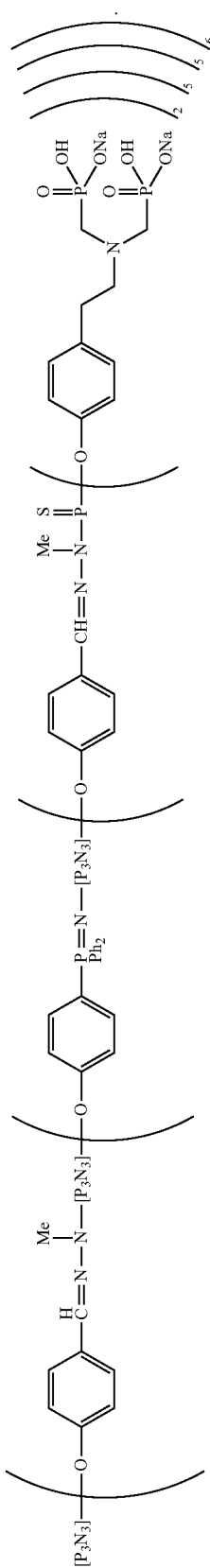

The present invention also relates to the use as defined above of dendrimers with monophosphonic or bisphosphonic terminations of the following formula:

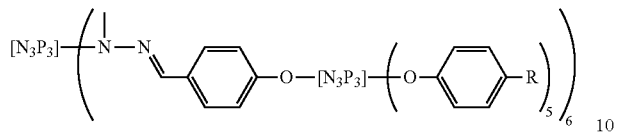

in which R represents a group chosen from

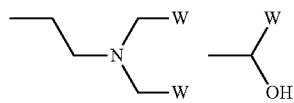

where W represents $PO_3Me_2$, $PO_3HNa$, or $PO_3H_2$.

The present invention also relates to the use as defined above of dendrimers with bisphosphonic terminations of the following formula:

lp;4p

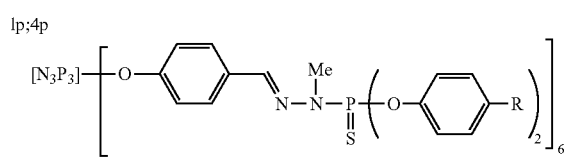

in which R represents a group chosen from:

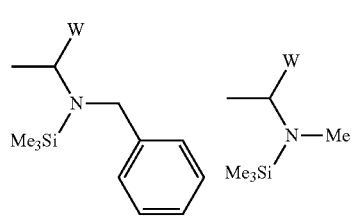

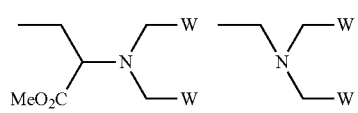

where W represents $PO_3Si_2Me_6$, $PO_3Me_2$, $PO_3HNa$, or $PO_3H_2$.

The present invention also relates to the use as defined above of dendrimers with monophosphonic terminations of the following formula:

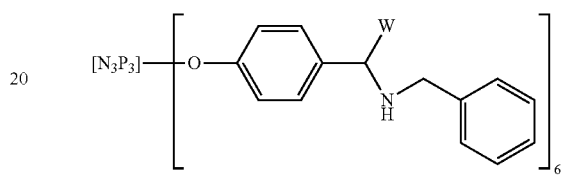

in which W represents $PO_3Me_2$, $PO_3HNa$, or $PO_3H_2$.

The present invention also relates to the use as defined above of dendrimers with bisphosphonic terminations of the following formula:

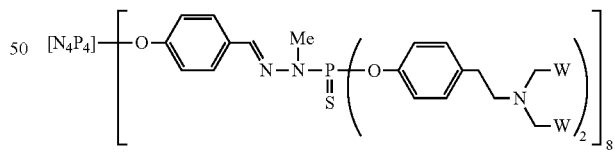

in which W represents $PO_3Me_2$, $PO_3HNa$, or $PO_3H_2$.

The present invention also relates to the use of dendrimers with bisphosphonic terminations of the following formula:

in which W represents PO$_3$Me$_2$, PO$_3$HNa, or PO$_3$H$_2$ and k represents 1, 2 or 3.

The present invention also relates to the use of dendrimers with bisphosphonic terminations of the following formula:

in which W represents PO$_3$Me$_2$, PO$_3$HNa, or PO$_3$H$_2$ and n represents 0, 1 or 2.

In a specific embodiment of the invention, the dendrimer with bisphosphonic terminations has the following formula:

The present invention also relates to the use as defined above of dendrimers with bisphosphonic terminations of the following formula:

in which W represents PO$_3$Me$_2$, PO$_3$HNa, or PO$_3$H$_2$, in particular compound of the following formula:

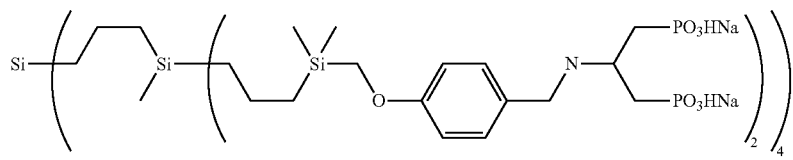
The present invention also relates to the use of dendrimers with bisphosphonic terminations of the following formula:
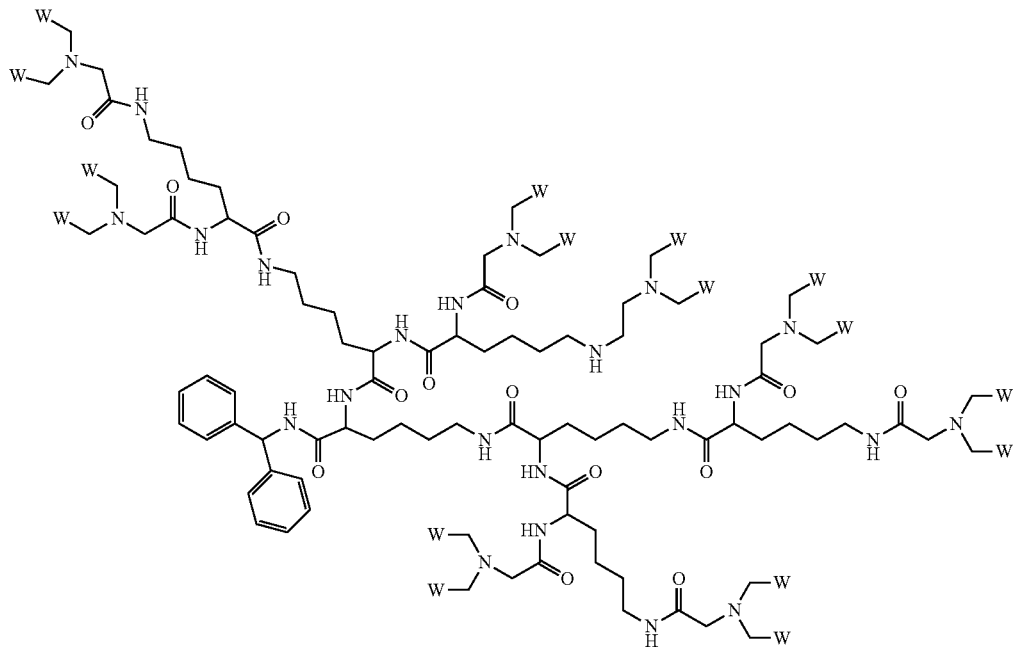
in which W represents $PO_3Me_2$, $PO_3HNa$, or $PO_3H_2$.
In a particular embodiment, the present invention relates to the use of the compounds of the following formulae:
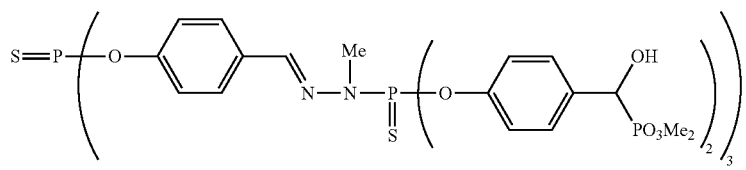
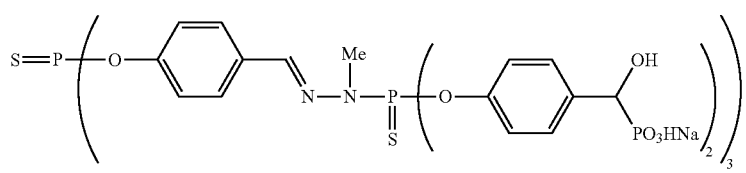
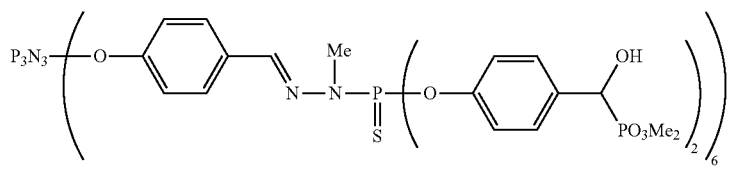

-continued
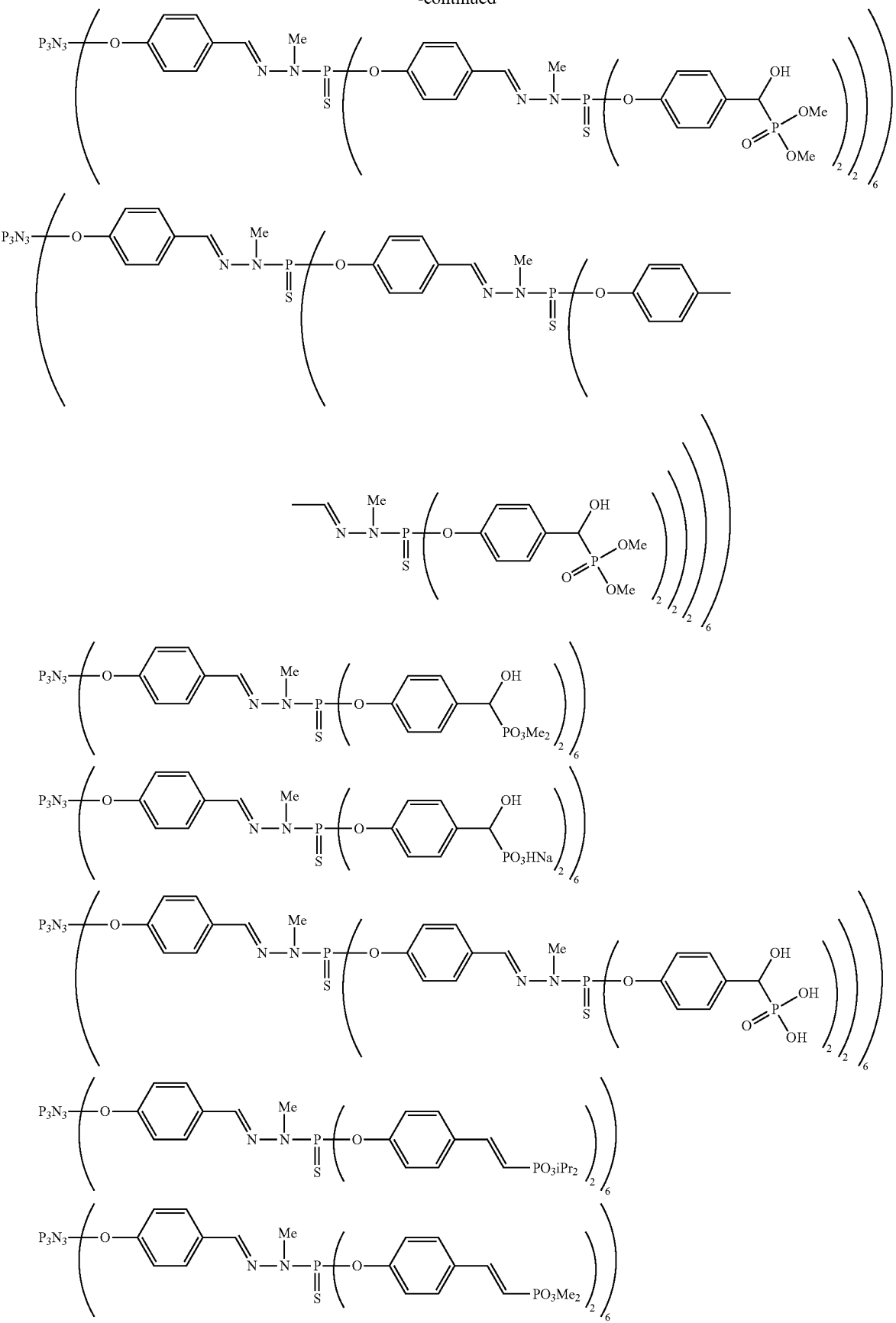

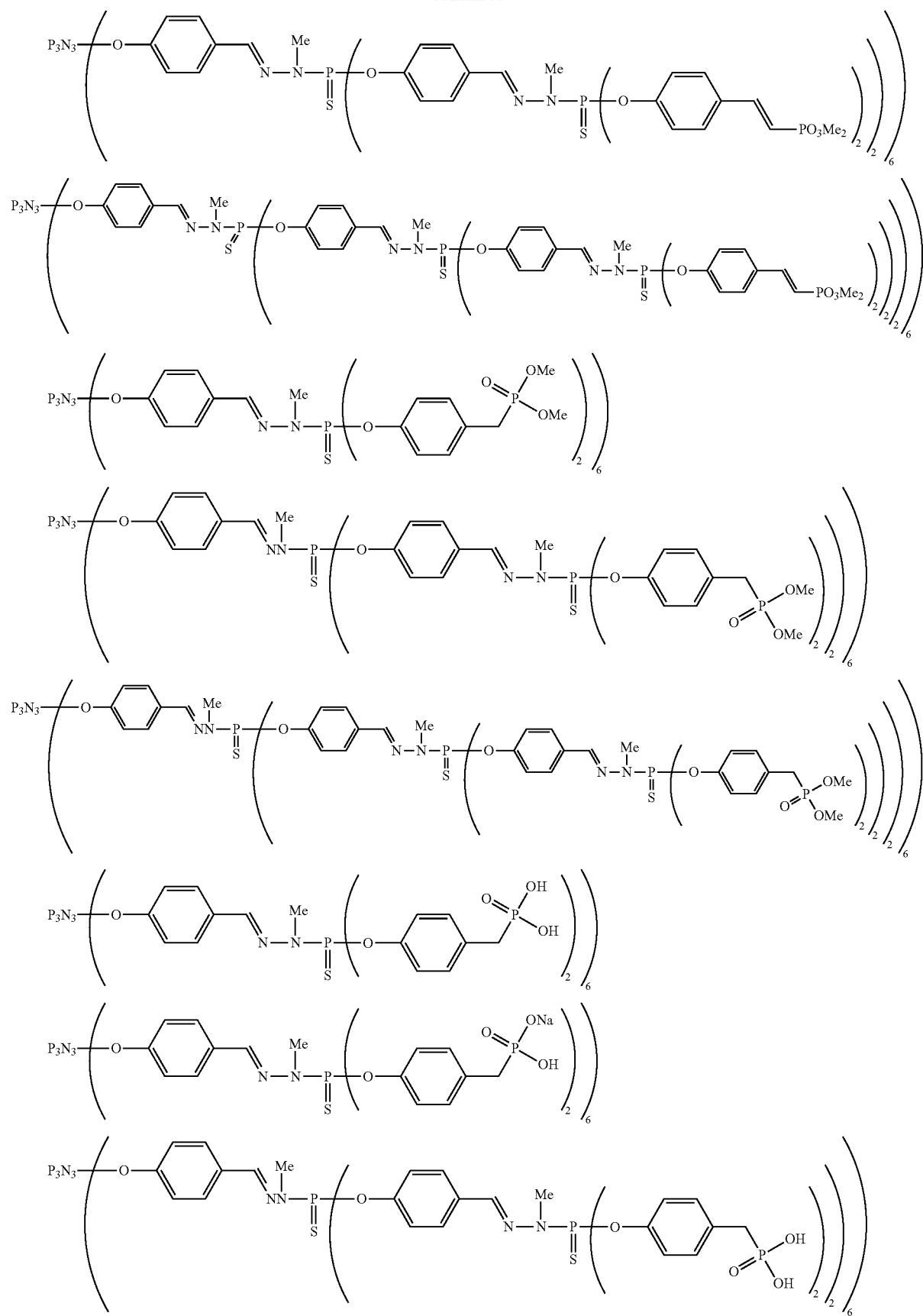

-continued
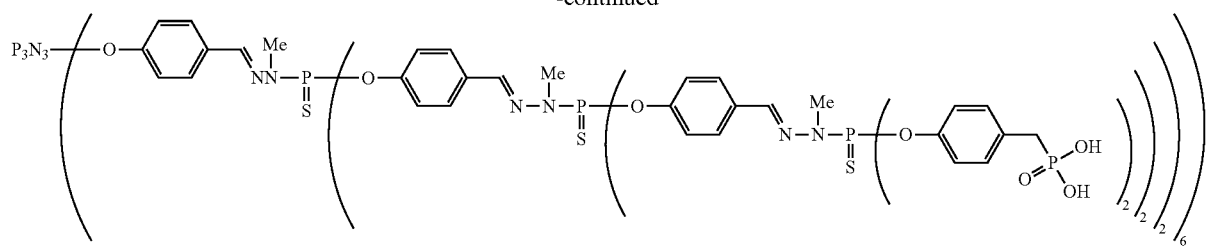
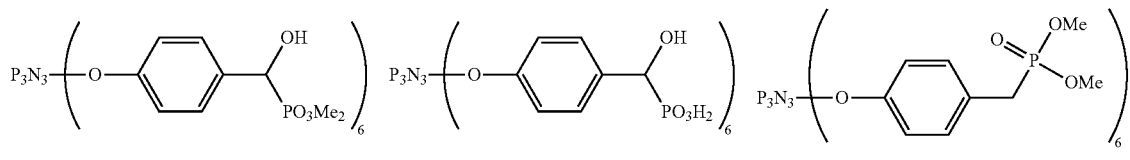
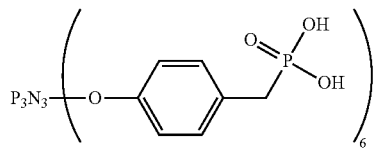
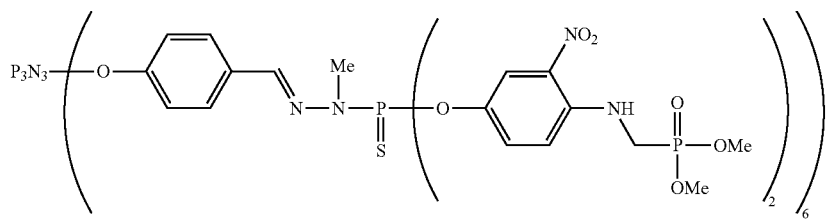
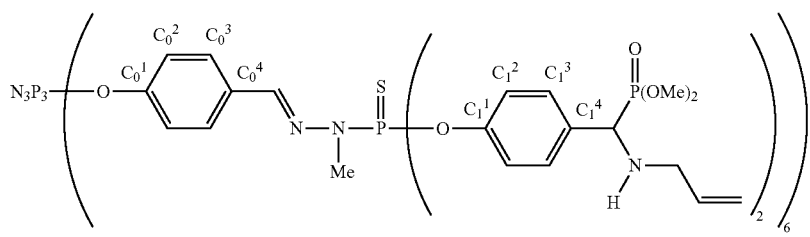
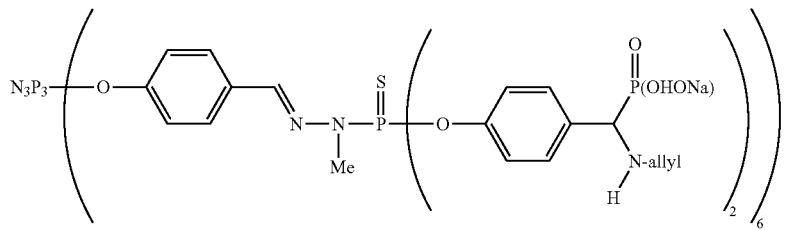
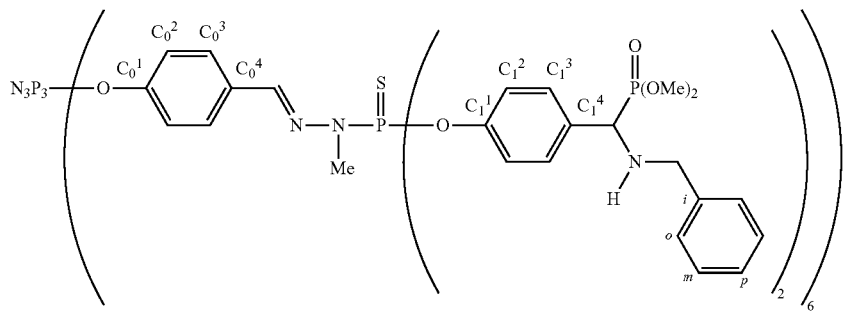

-continued
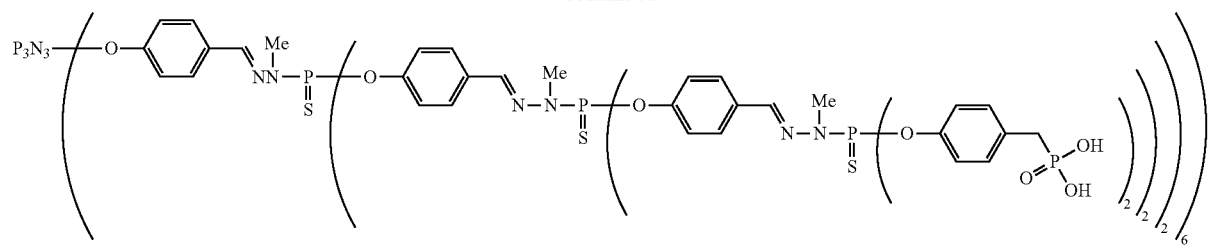
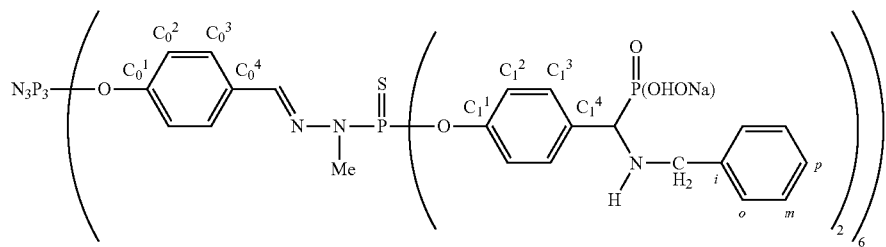
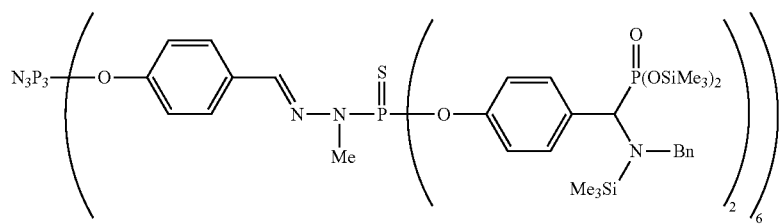
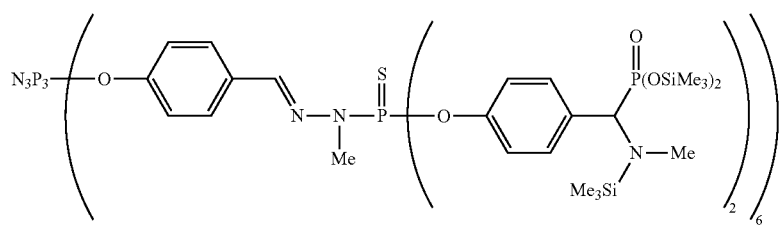
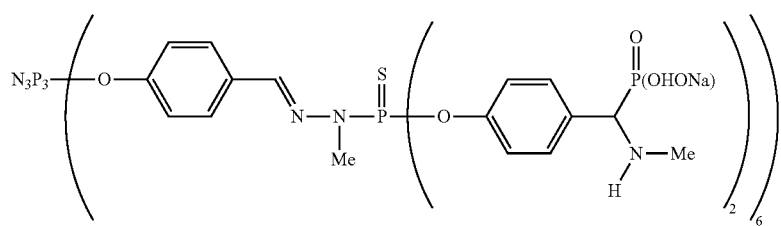
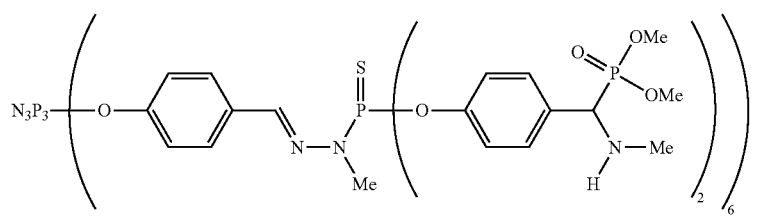
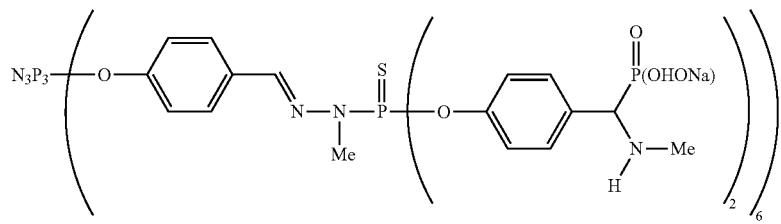

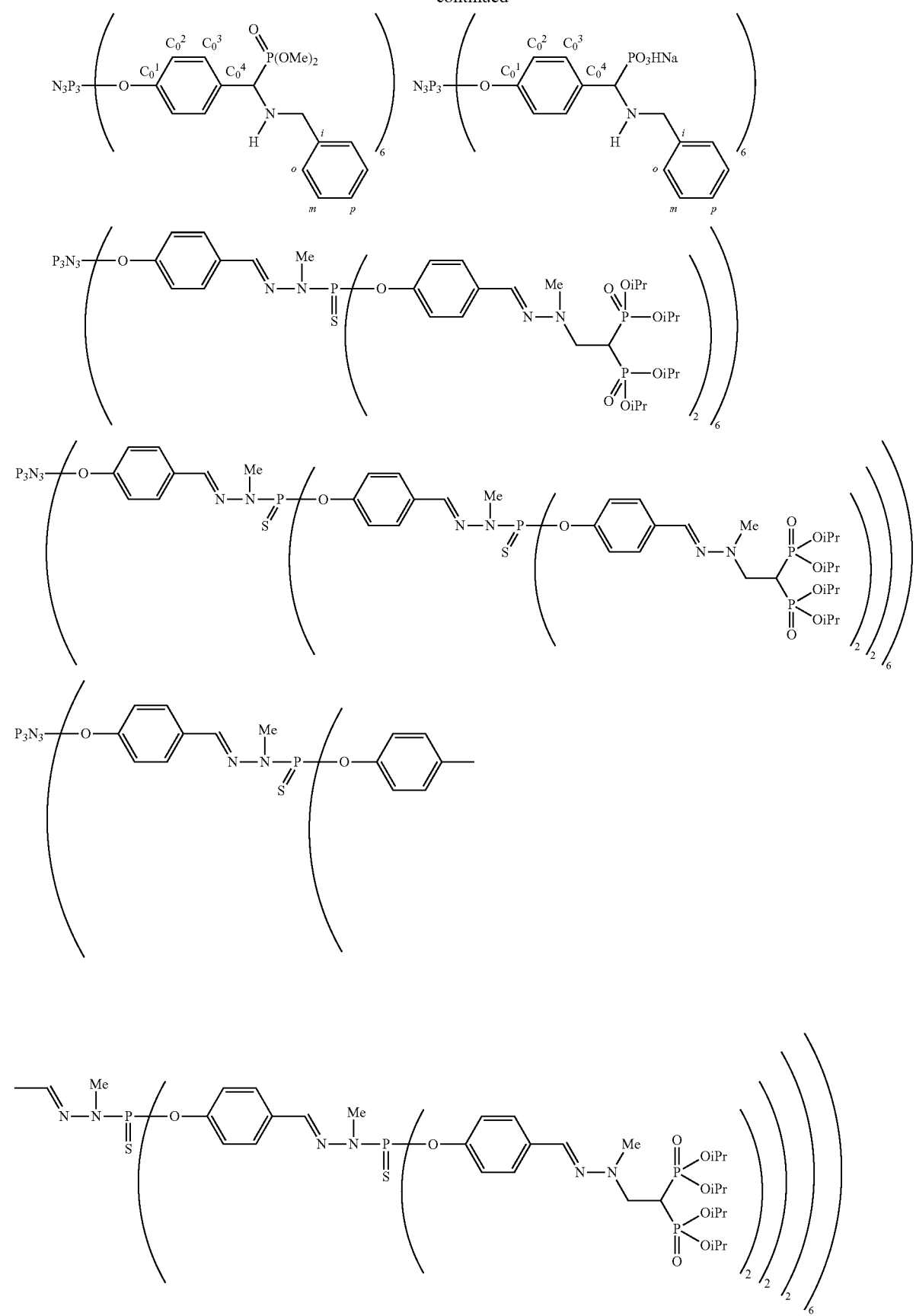

-continued
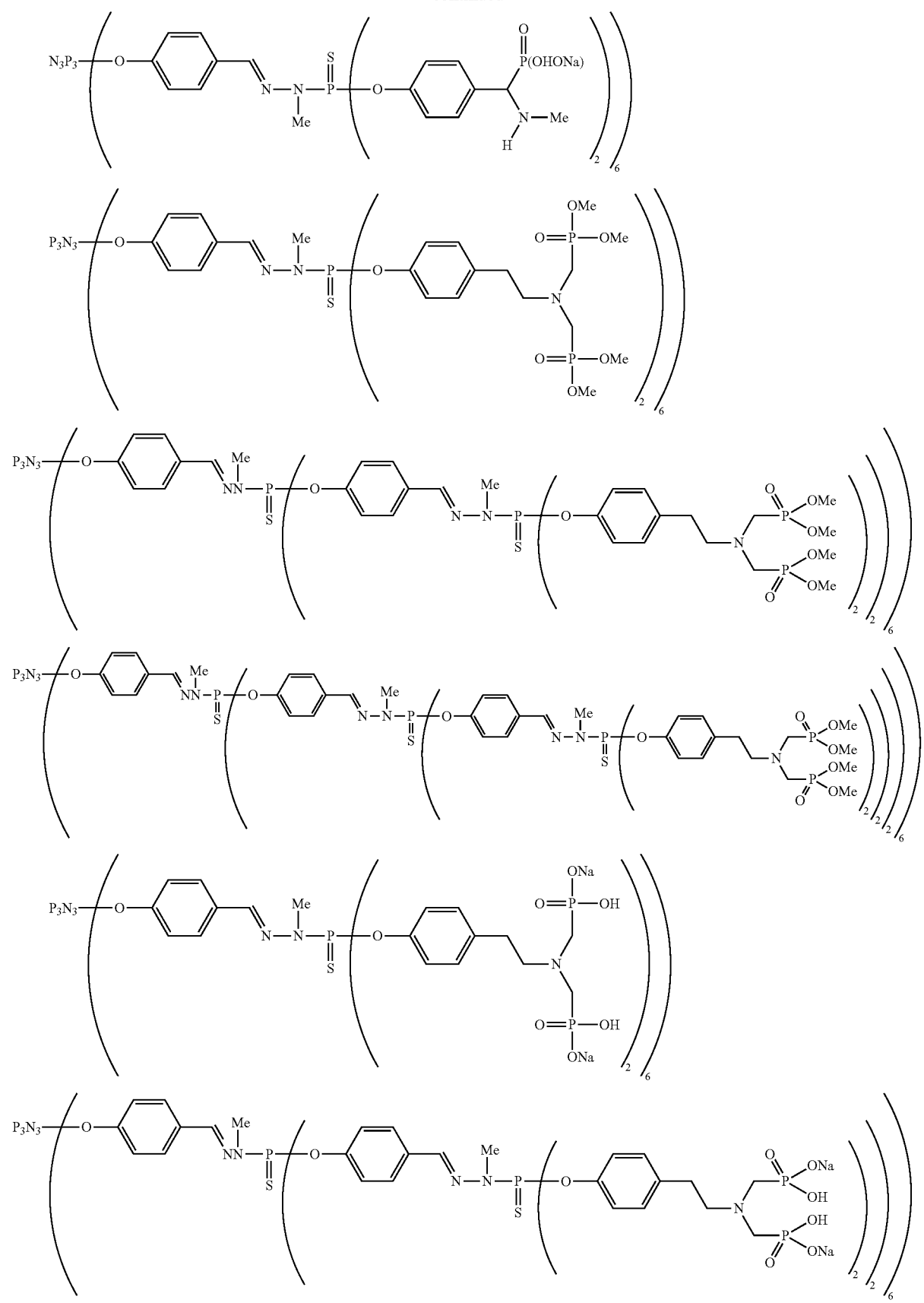

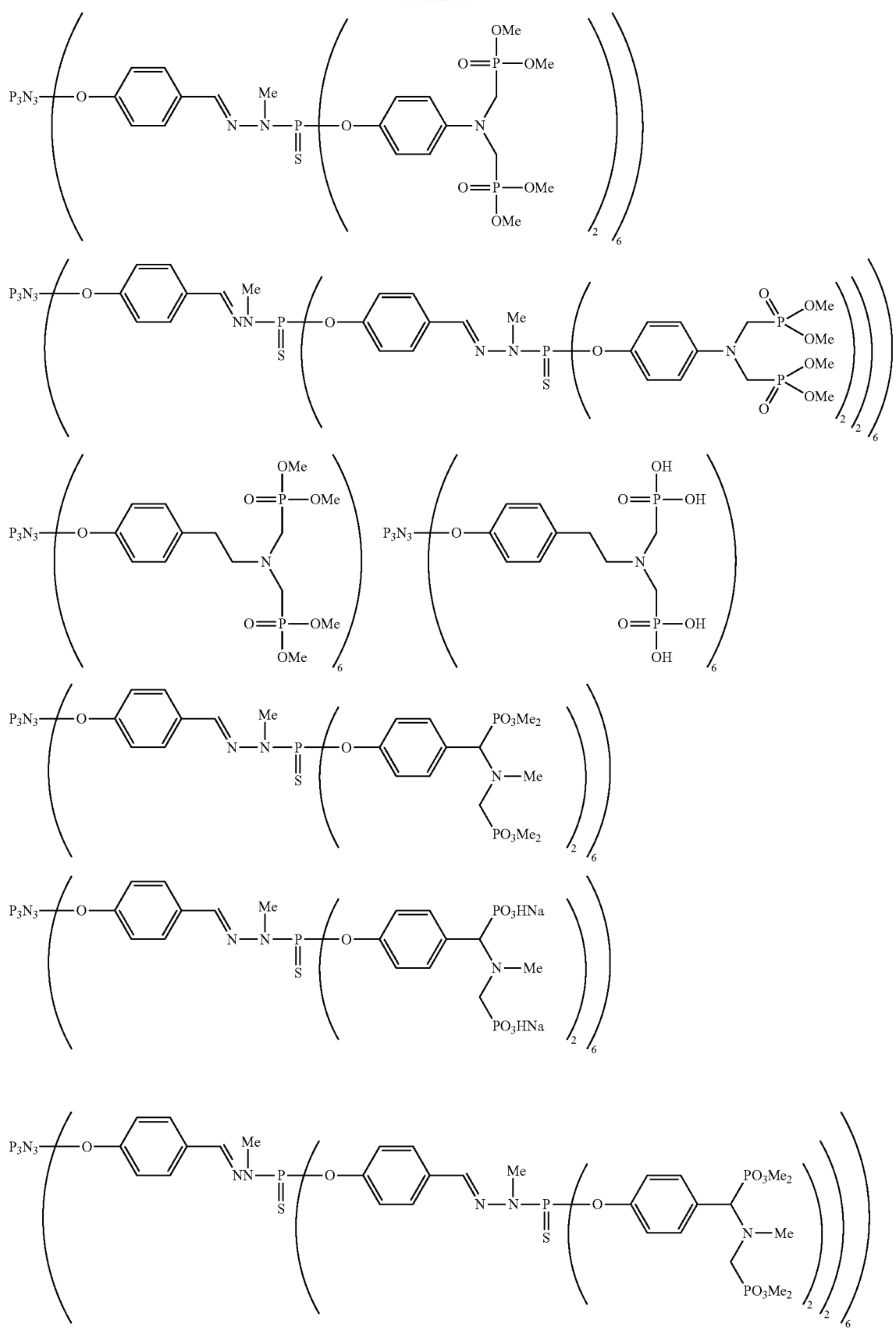

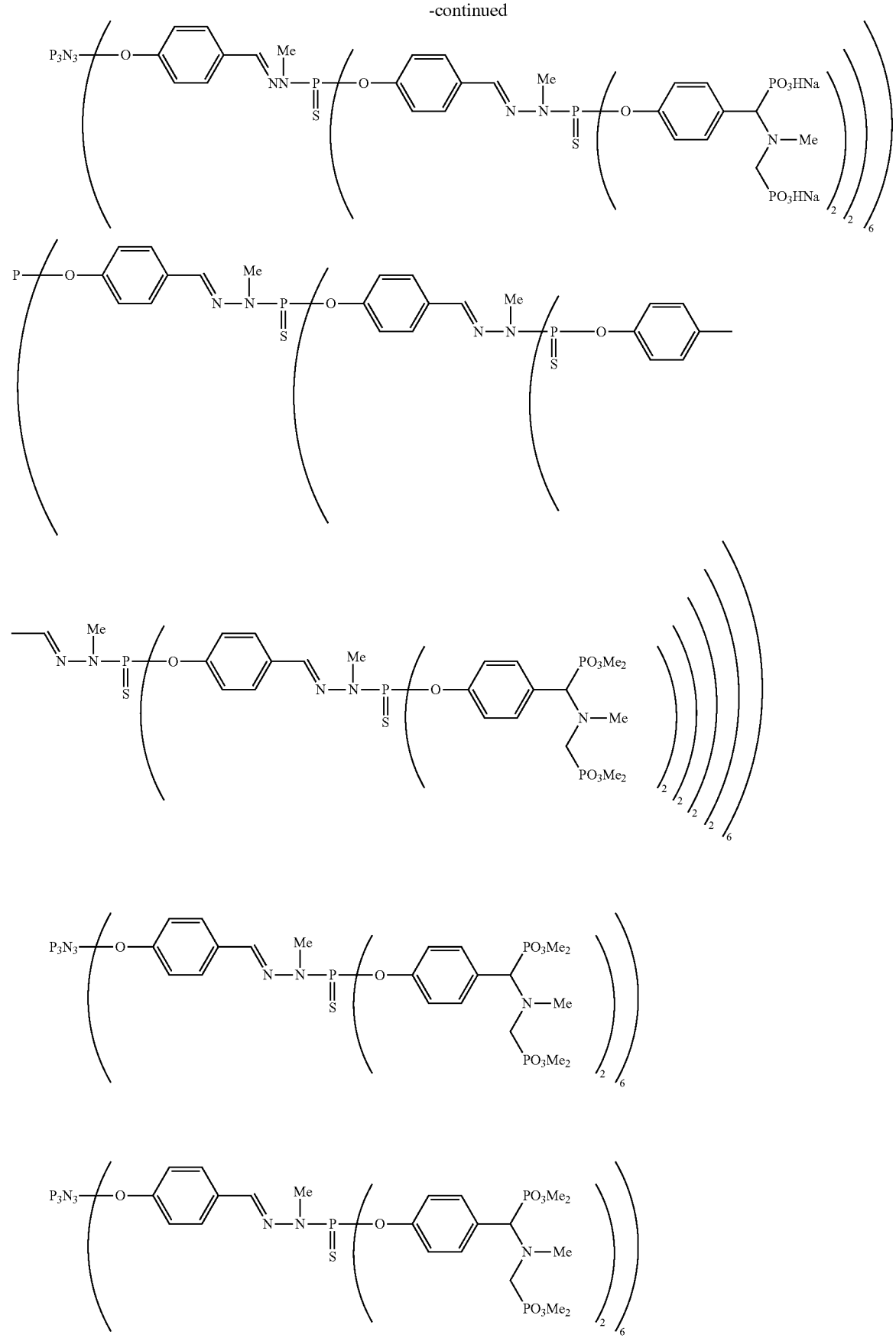

-continued
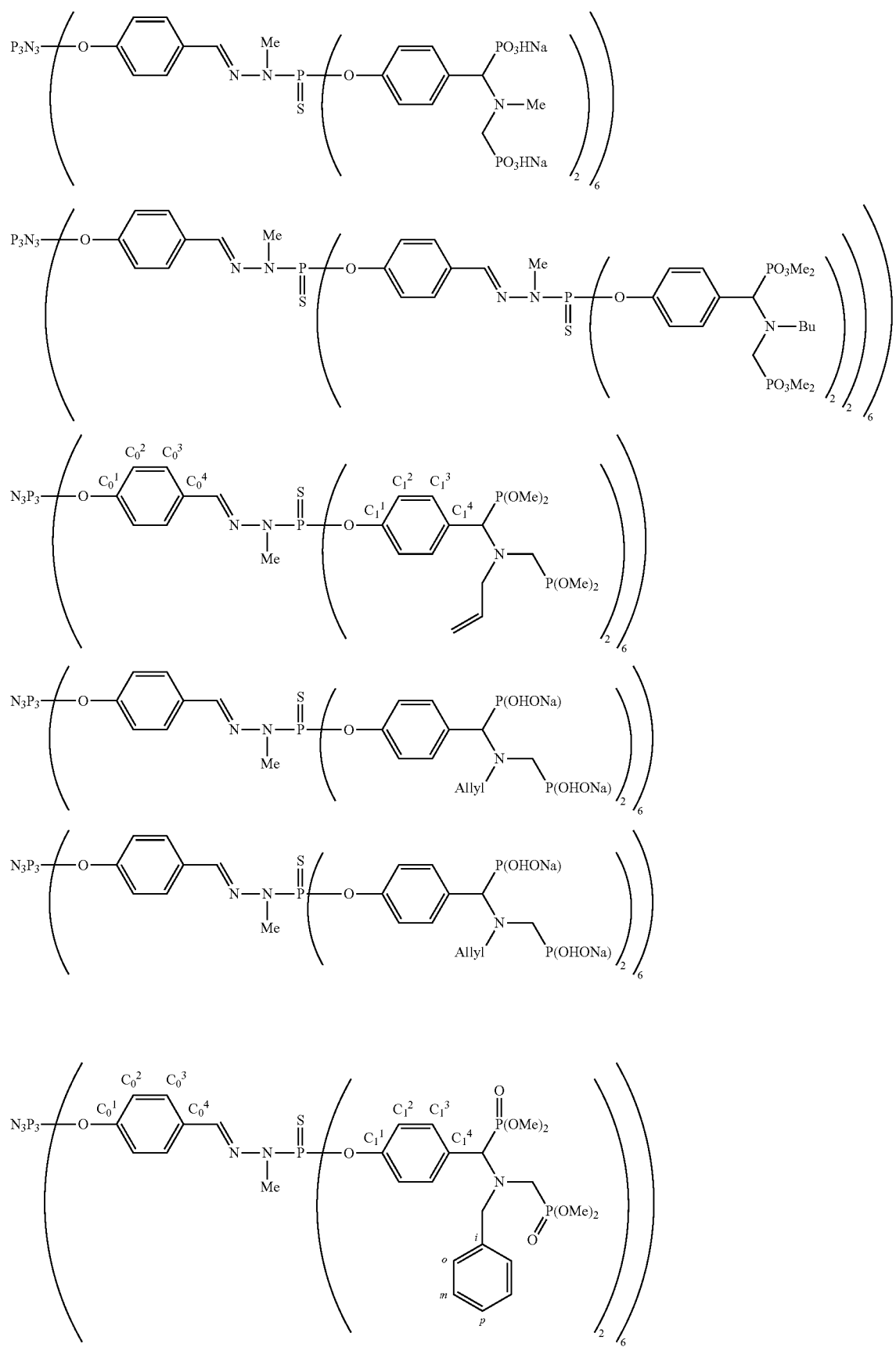

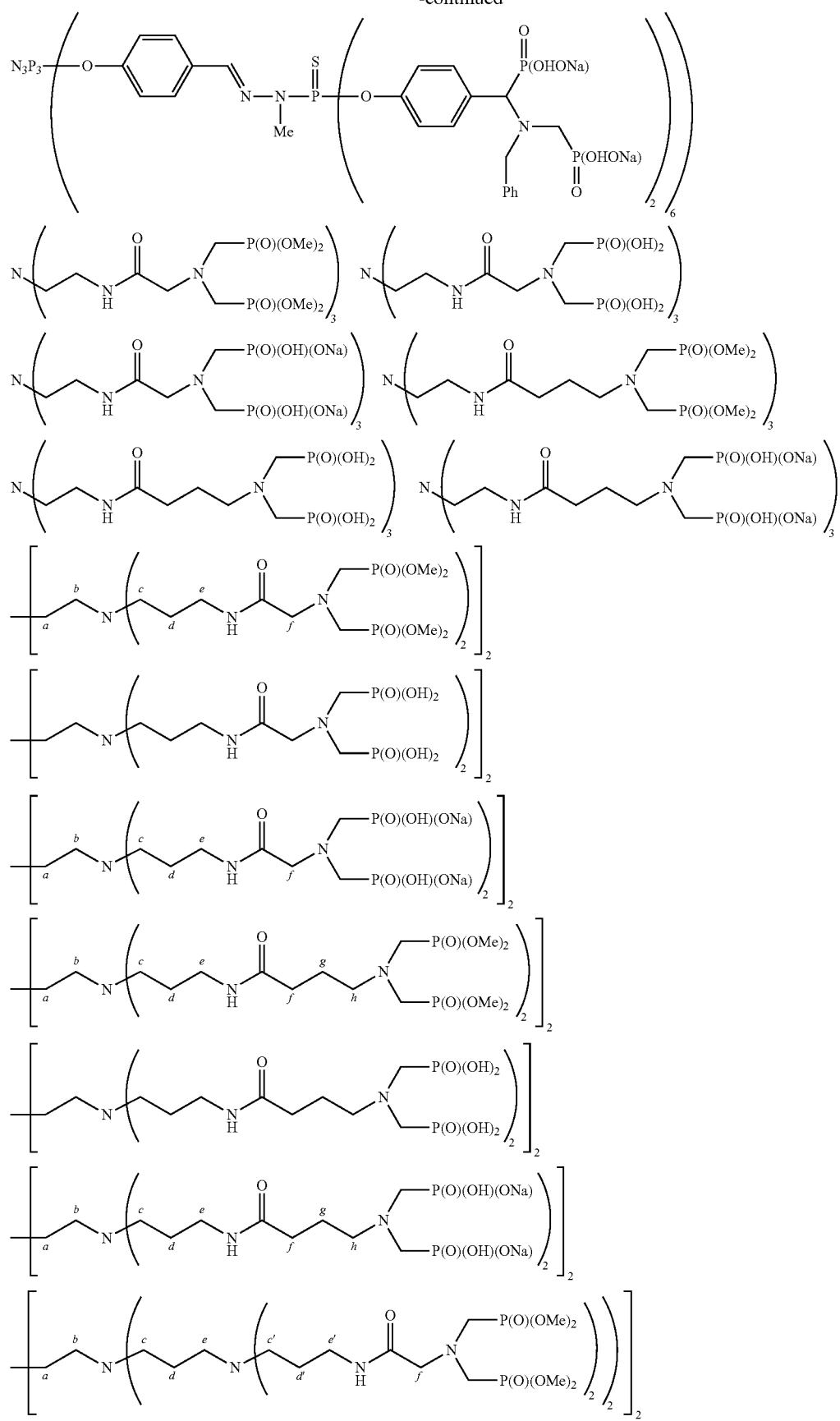

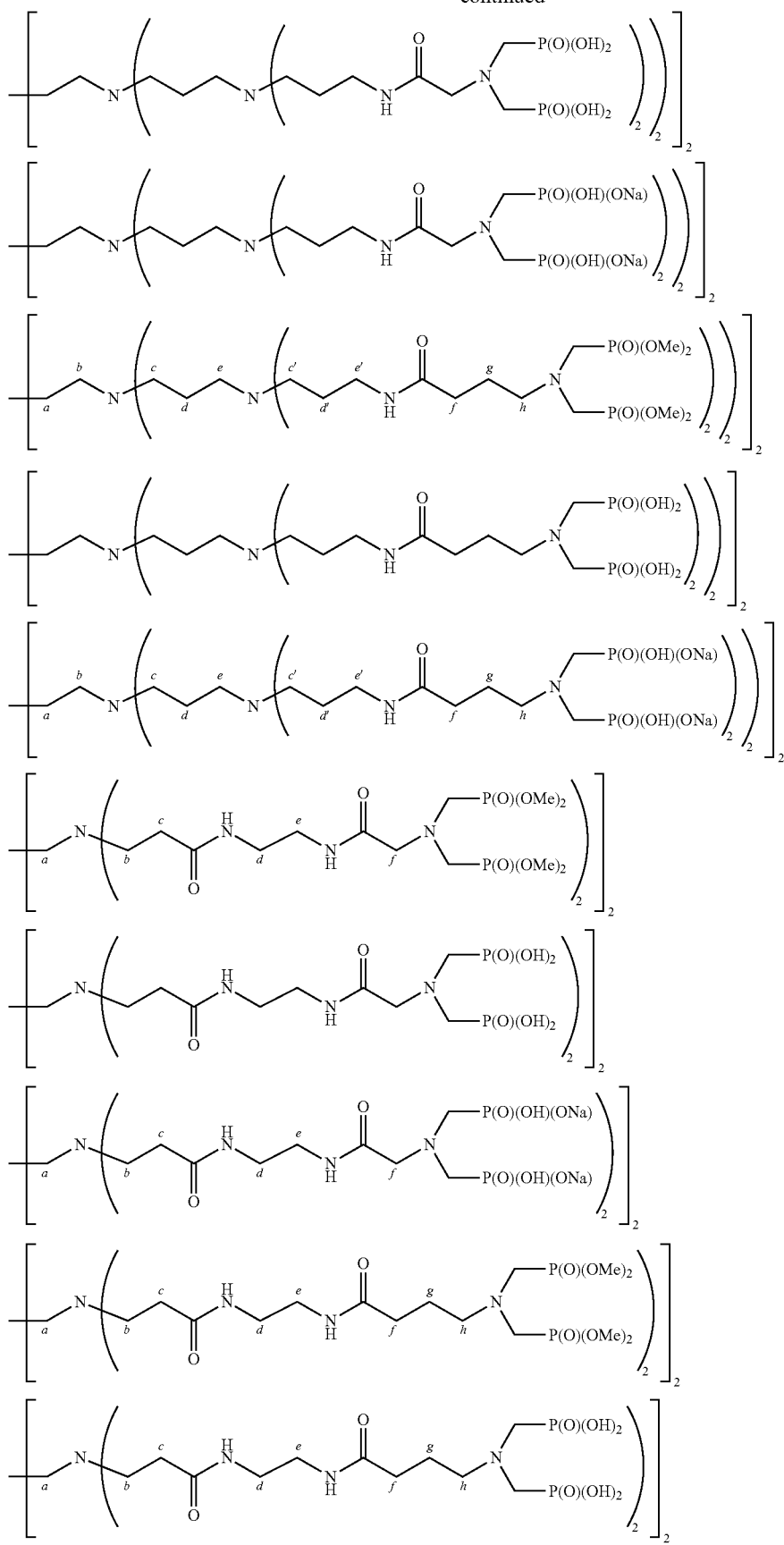

-continued
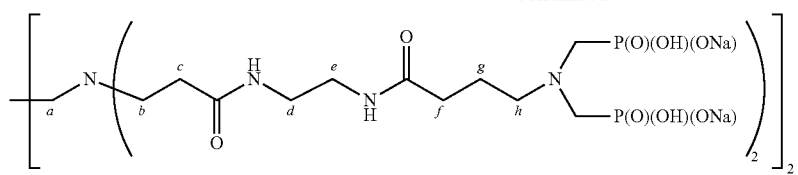
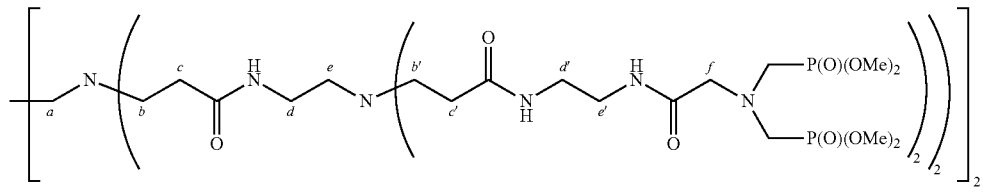
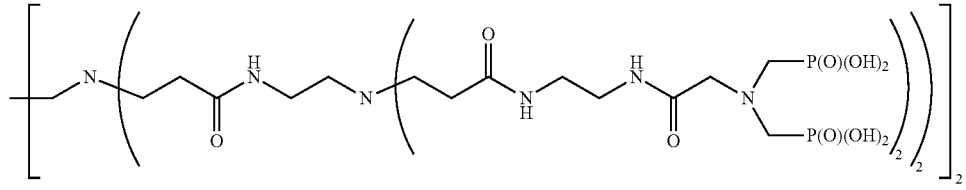
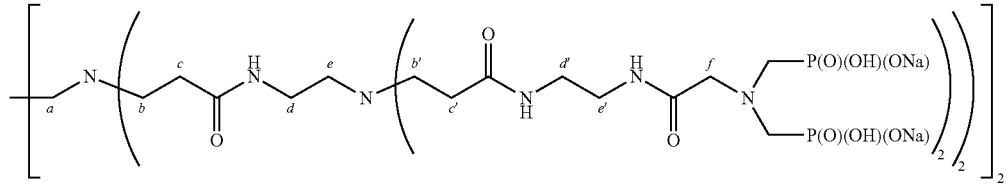
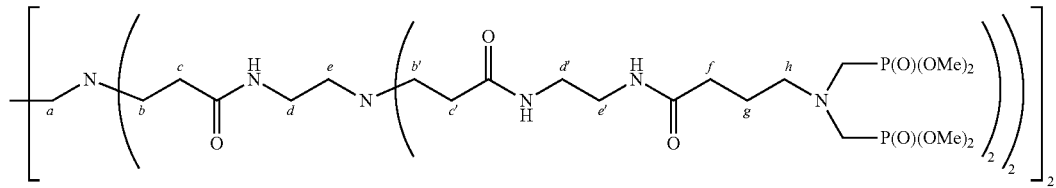
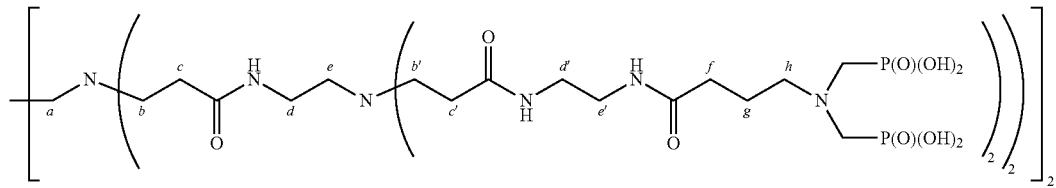
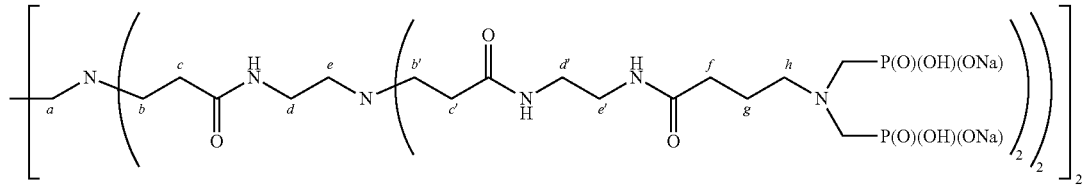
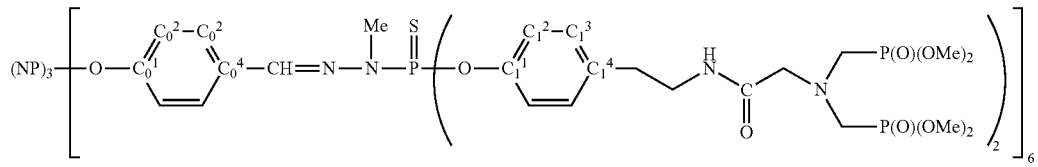
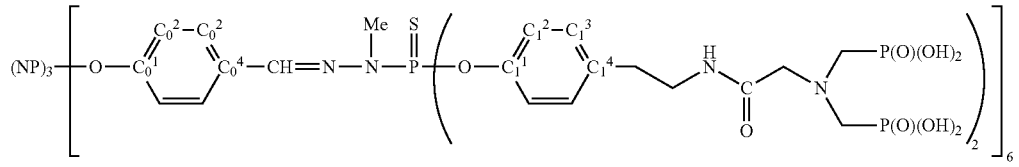

111              112
-continued
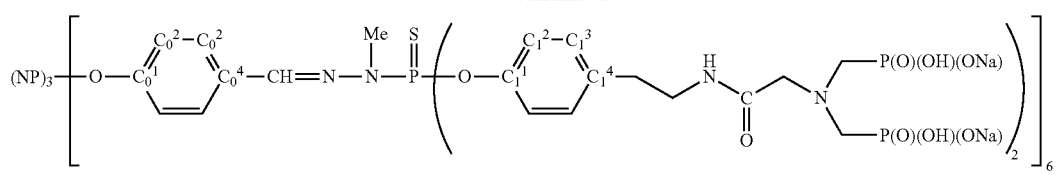
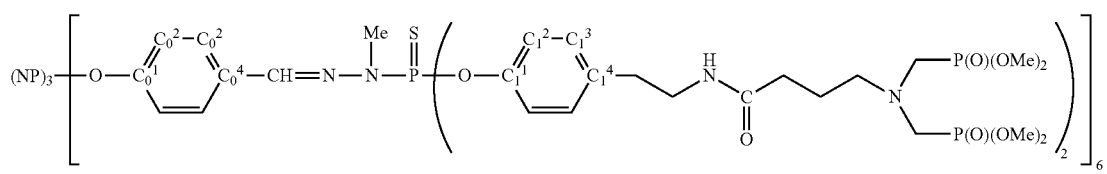
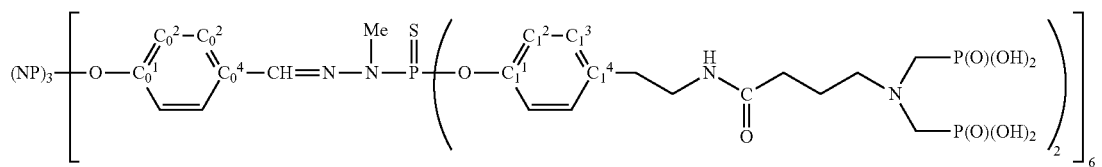
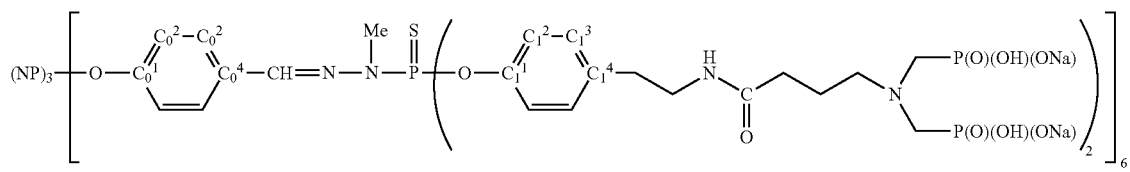
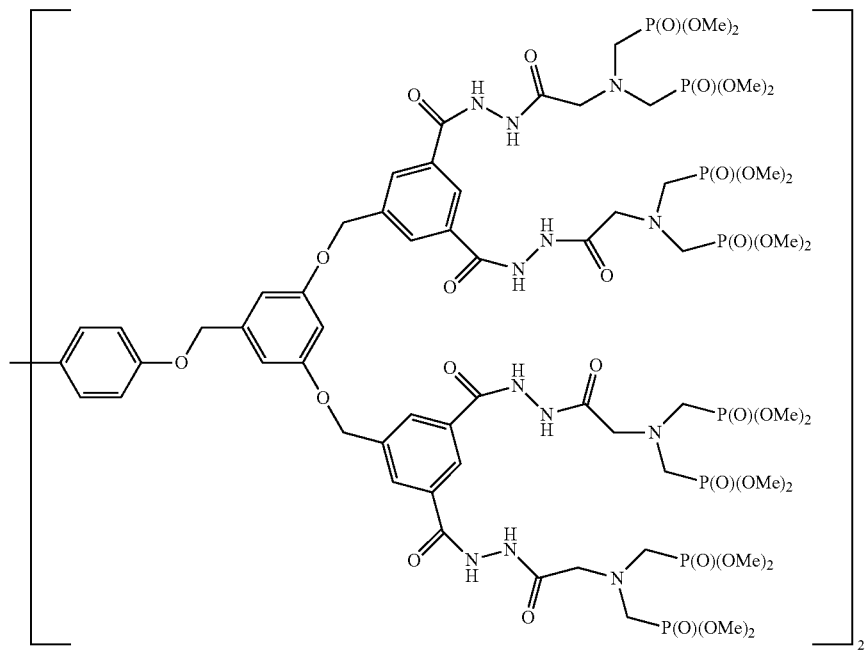

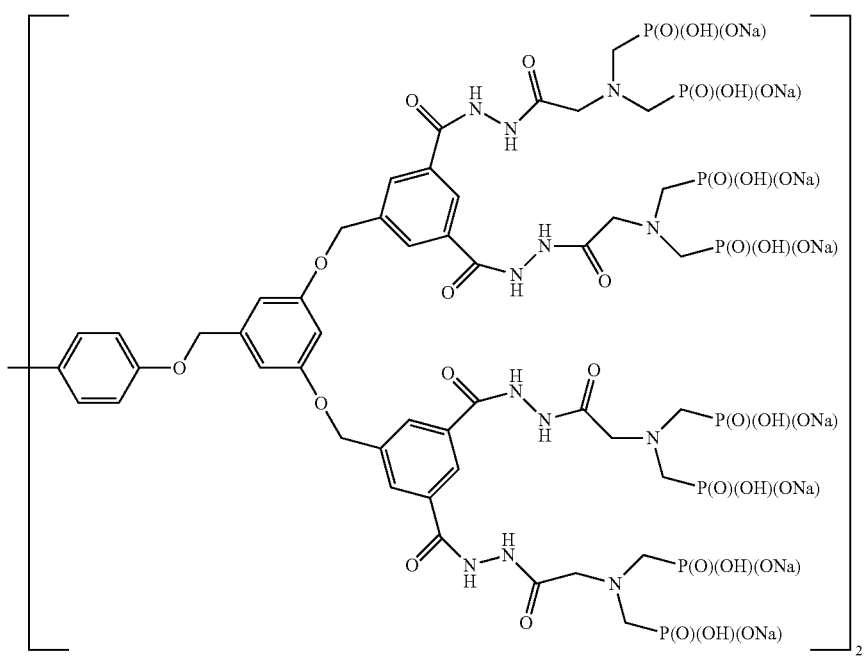
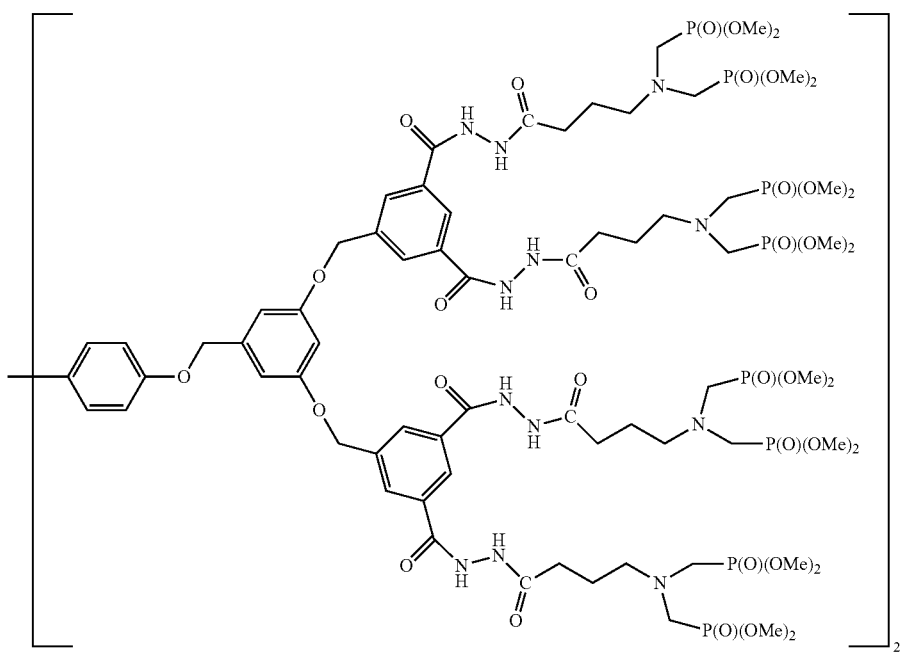

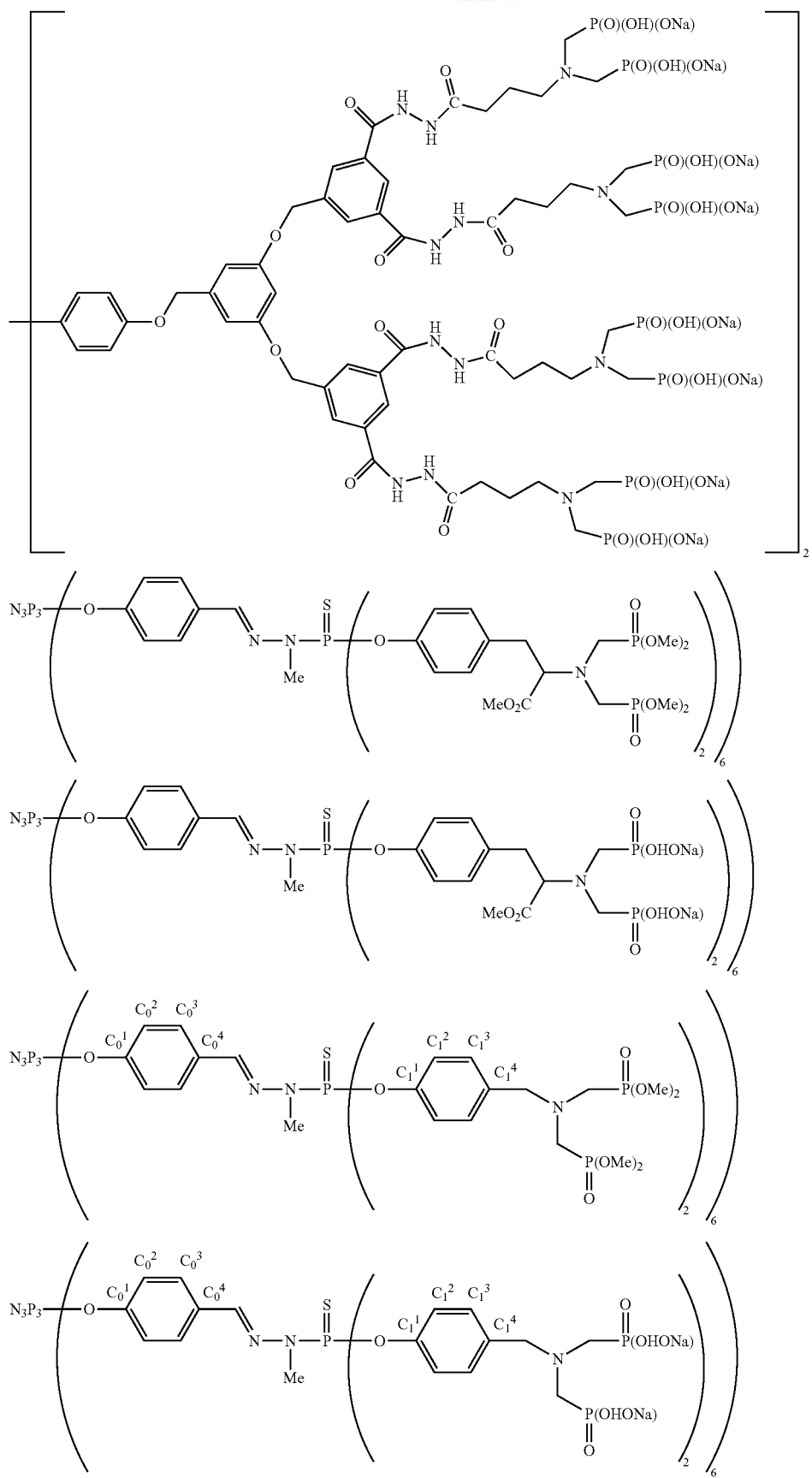

-continued
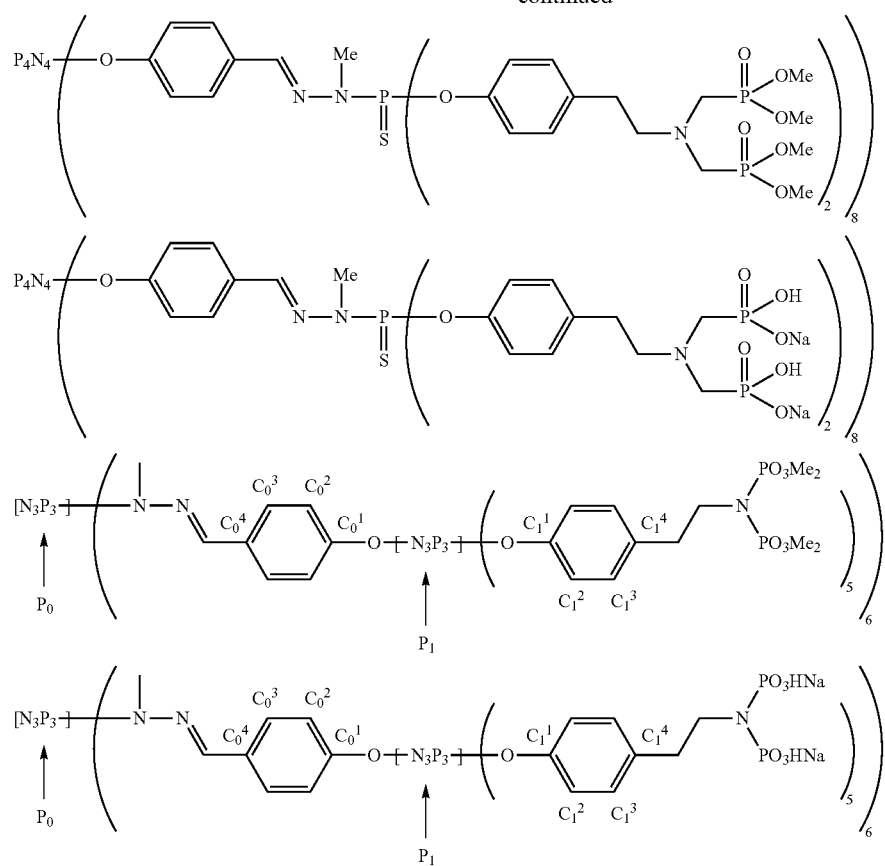
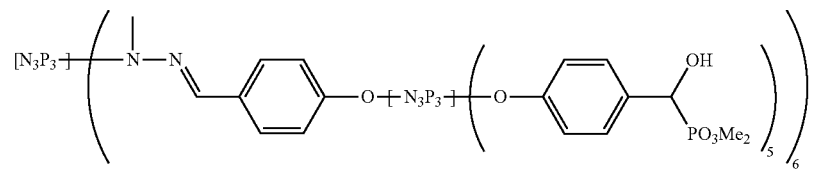
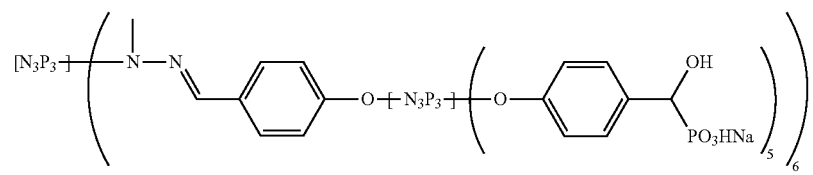
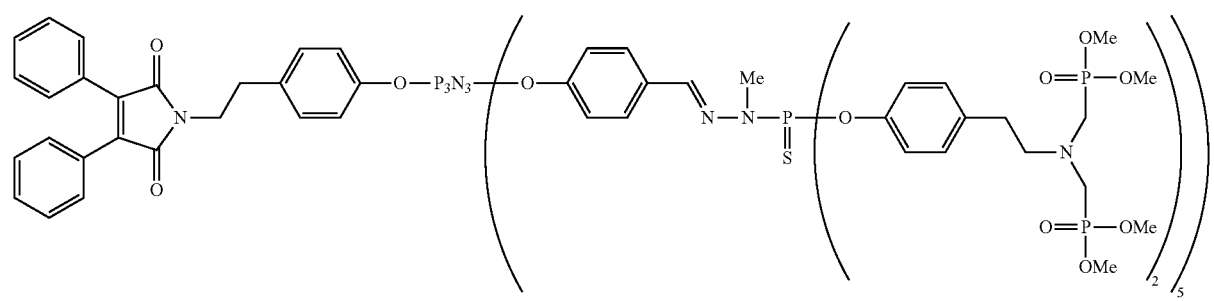

-continued
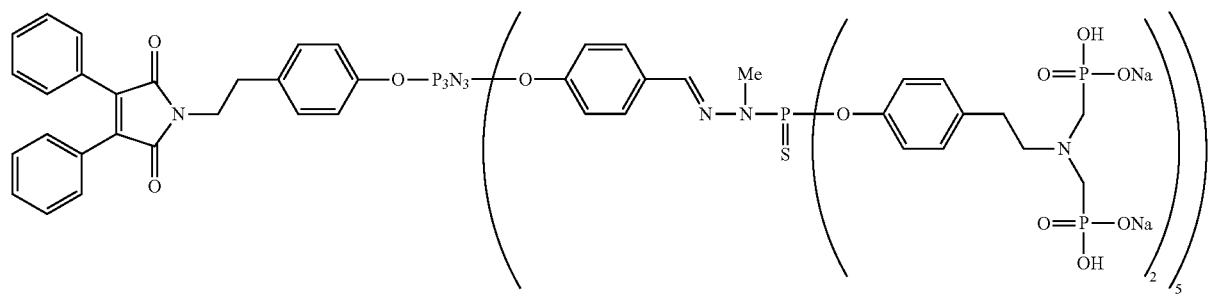
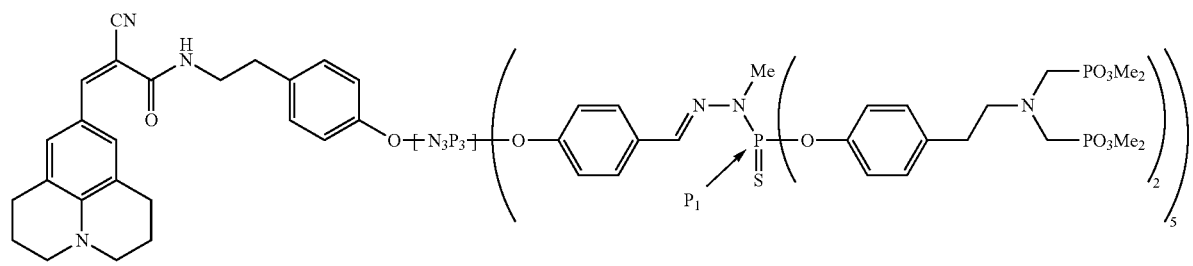
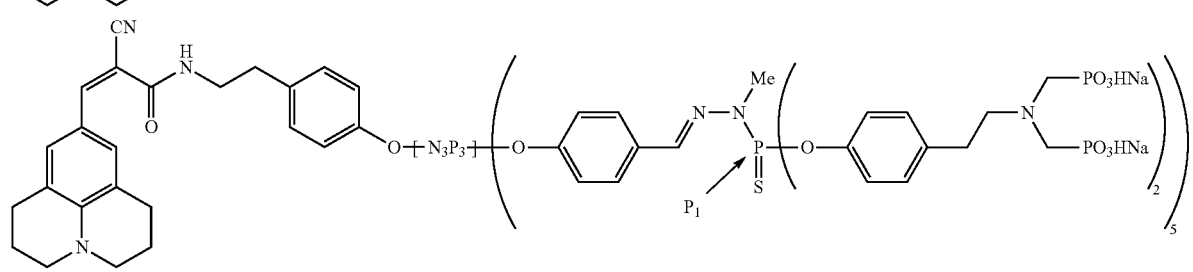
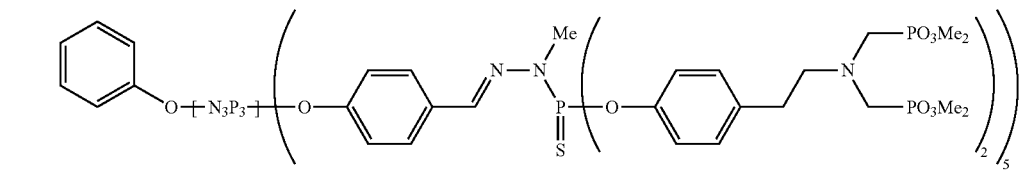
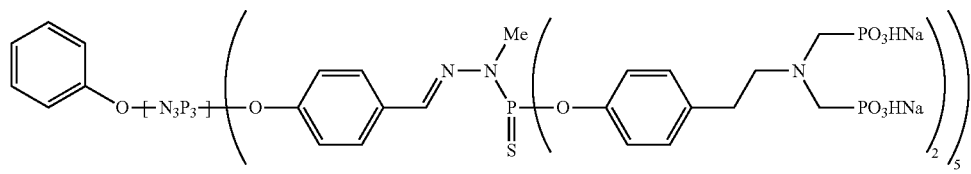
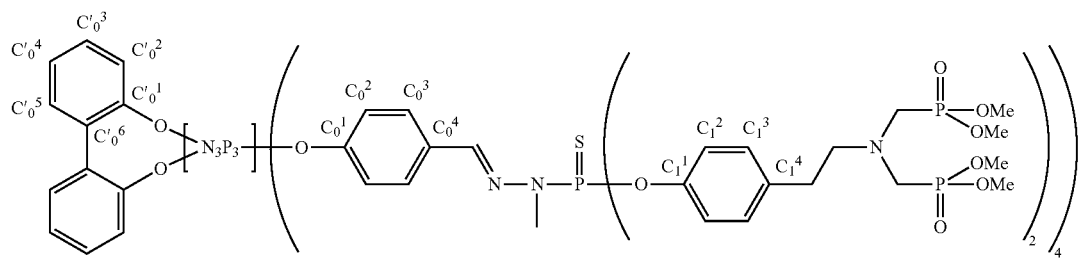
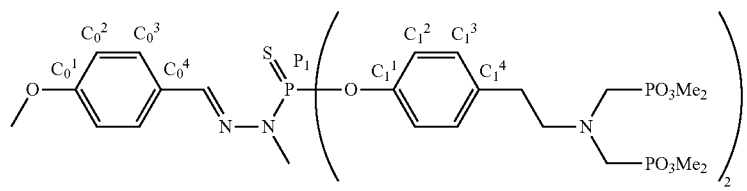

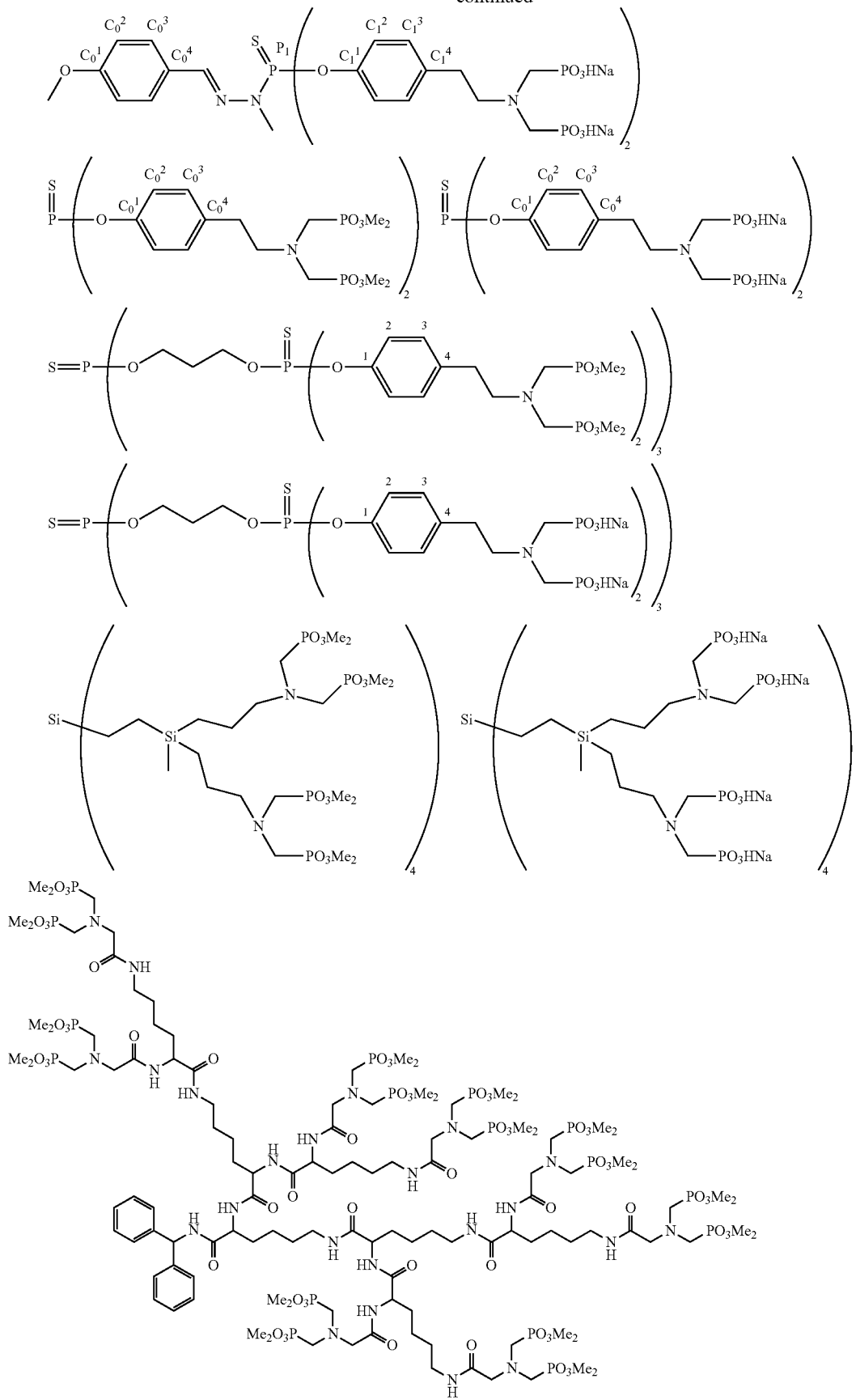

123 124
-continued
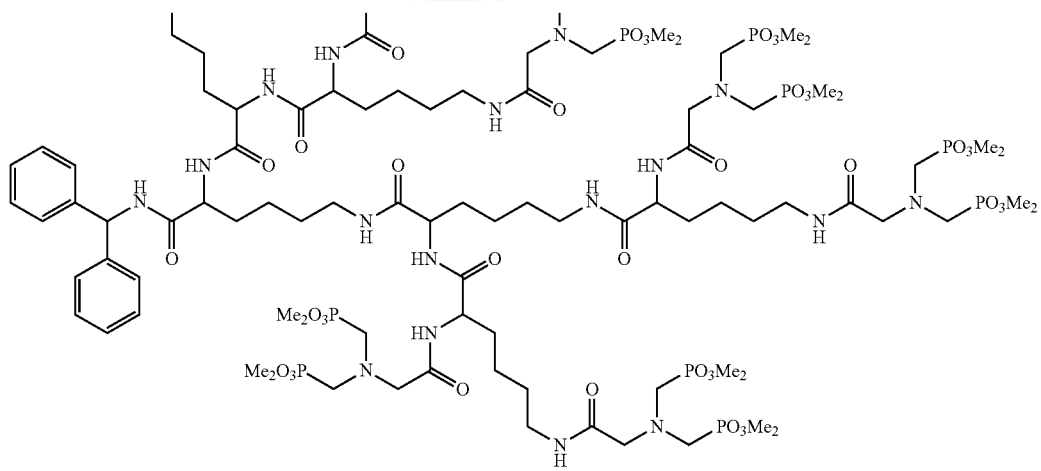
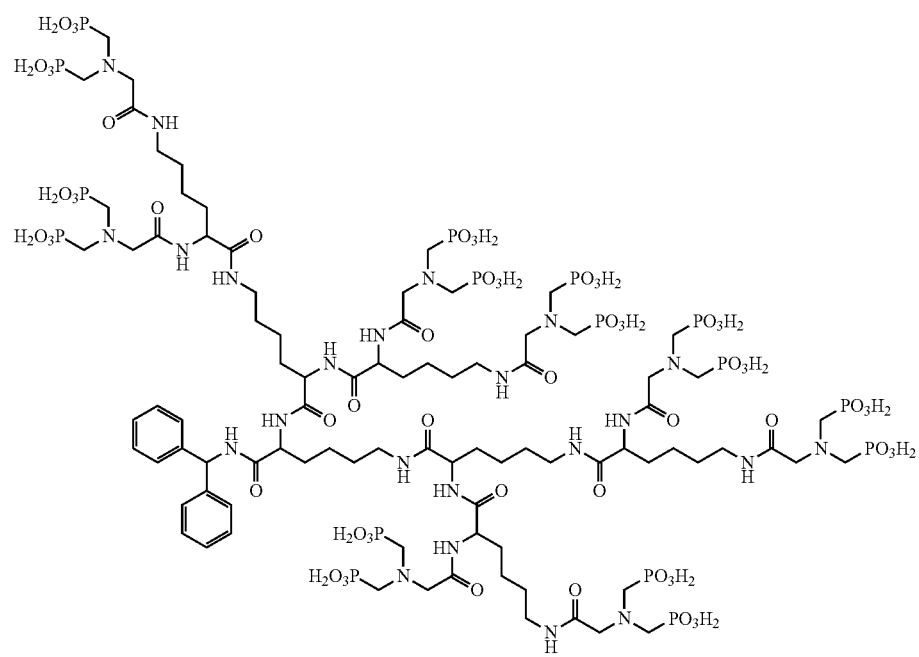

-continued

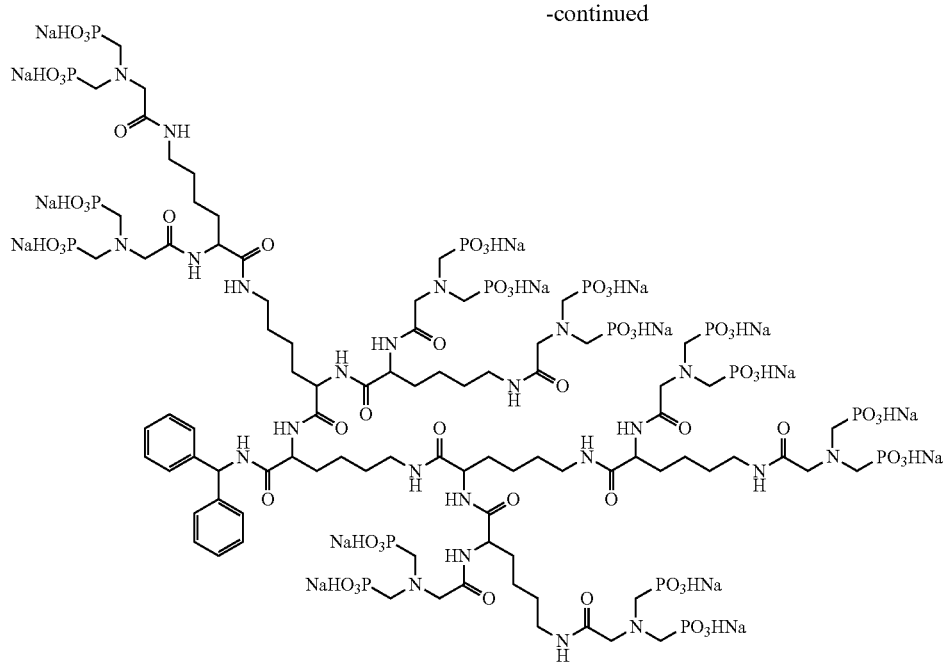

The instant invention also concerns the use of dendrimers with mono- or biphosphonic terminations for the preparation of drugs useful for the treatment of inflammatory diseases, said drugs acting through an anti-inflammatory type activation of monocytes.

The present invention also concerns the use of at least one dendrimer with mono- or biphosphonic terminations for the preparation of drugs useful for the treatment of inflammatory diseases, in particular from auto-immune origin.

The present invention also deals with a method for treating inflammatory diseases through an anti-inflammatory type activation of monocytes, said method comprising the administration to a patient in need thereof of an effective quantity of at least one dendrimer with mono- or biphosphonic terminations.

The present invention also deals with a method for treating inflammatory diseases comprising the administration to a patient in need thereof of an effective quantity of at least one dendrimer with mono- or biphosphonic terminations in association with a pharmaceutical acceptable carrier.

According to the present invention, inflammatory diseases are selected from the group comprising chronic inflammatory diseases, chronic inflammatory diseases of auto-immune origin, pro-inflammatory and inflammatory conditions in case of cancers.

In an advantageous embodiment of the invention, the chronic inflammatory disease is selected from the group comprising rheumatoid arthritis, psoriasis and juvenile idiotypical arthritis.

In an advantageous embodiment of the invention, the chronic inflammatory disease is selected from the group comprising rheumatoid arthritis, psoriasis, psoriatic arthritis, juvenile idiotypical arthritis and multiple sclerosis.

In an advantageous embodiment of the invention, the chronic inflammatory disease is multiple sclerosis.

The present invention also concerns pharmaceutical compositions containing as active substance at least one dendrimer with monophosphonic or bisphosphonic terminations associated with a pharmaceutically acceptable carrier for the treatment of inflammatory diseases, particularly those of auto-immune origin.

In another advantageous embodiment of the instant invention, the dendrimers with monophosphonic or bisphosphonic terminations may be associated with other active substances, in particular with other classical steroid or non-steroid anti-inflammatory compounds as a combined preparation for simultaneous, separate or sequential use in the treatment of inflammatory diseases.

Examples 1 to 11 and FIGS. 1 to 17 which follow illustrate the invention.

FIG. 7 shows the primer pairs used for quantitative RT-PCR. F: forward primer, R: reverse primer. Products (pb) correspond to the expected RT-PCR product size.

FIGS. 8(1), 8(2) and 8(3) show the 78 up-regulated genes in monocytes activated by dendrimer Gc1 (da-monocytes).

FIGS. 9(1), 9(2) and 9(3) show the 62 down-regulated genes in da-monocytes.

Figure 10:
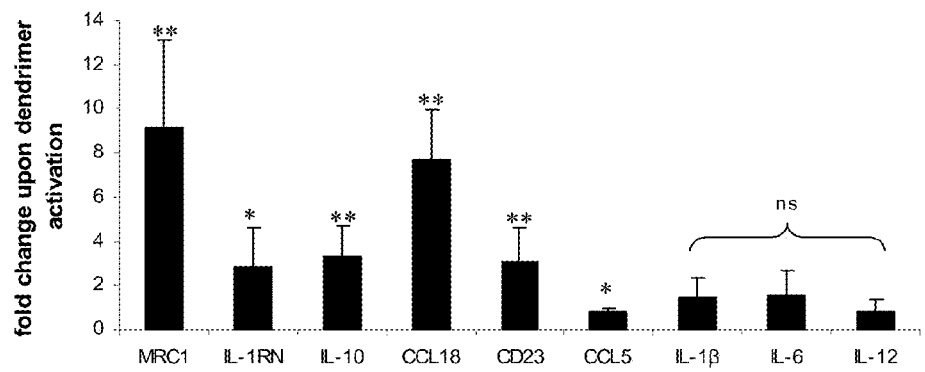

FIG. 10 shows the RT-PCR quantification of mRNA expression for 9 selected genes in da-monocytes. Expression levels are normalized to the GAPDH mRNA. Relative expressions are calculated using the ΔΔCt method and results represent the relative fold change induced by the dendrimer in comparison to non-stimulated monocytes. Data are expressed as mean±SD from 6 independent experiments. *p<0.05, **p<0.005, one tailed t-test.

Figure 11:
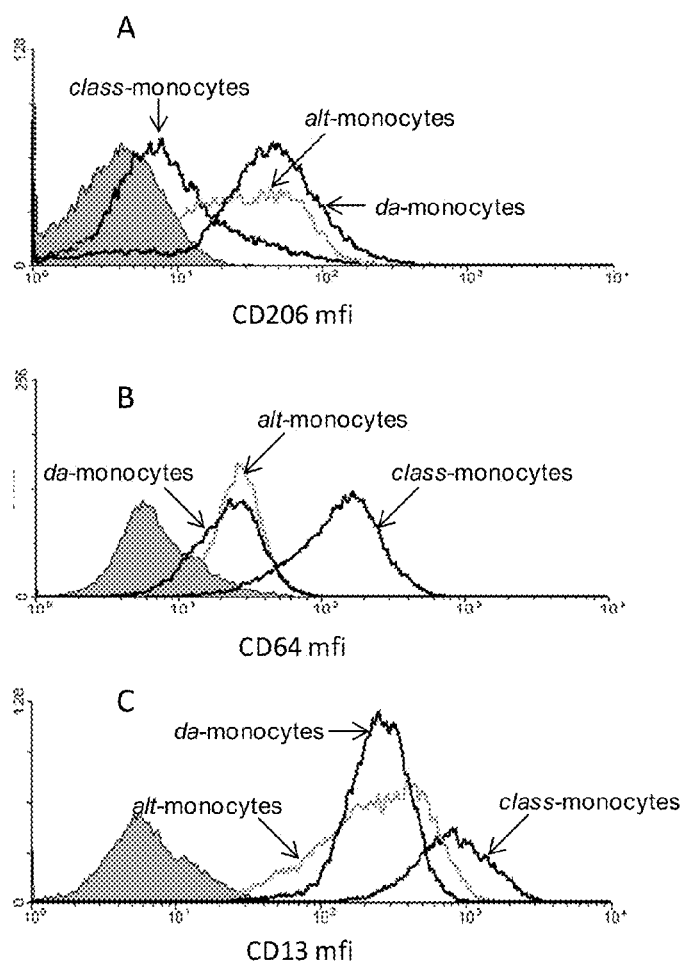

FIG. 11 shows the phenotype of da-monocytes compared to alt- and class-monocytes. Cell surface expression levels for (A) CD206 (the mannose receptor MRC1), (B) CD64 (a $F_c\gamma RI$) and (C) CD13 (the aminopeptidase N) are analyzed by flow cytometry. Mfi detected on class-monocytes labelled by isotype-matched mAbs are represented in grey as negative control. Data shown are representative of 3 independent experiments.

FIGS. 12(1) and 12(2) show the immuno-suppressive properties of da-monocytes (dendrimer Gc1 at 20 μM). FIG. 12(1) A shows flow cytometry analysis (showed as mfi) of the cell surface expression levels of antigen-presenting molecules (HLA-DR and HLA-A,B,C) and the co-stimulatory molecule CD86 on da- (black bars), alt- (grey bars) and class-monocytes (white bars). Data shown are representative of 3 independent experiments. In FIG. 12(1) B, CD4+ T lymphocytes are gated to quantify CFSE dilution by flow cytometry after MLR. For the different PBL:monocyte (• da-monocytes, ■ alt-monocytes and Δ class-monocytes) ratios, the percentages of divided CD4+ T cells represent cells having undergone at least one division. Each point is the mean of percentages of divided CD4+ T cells±SD from triplicates. The results for 3 different MLR are shown. FIG. 12(2) gives the statistical analysis of the results shown in FIG. 12(1) B.

Figure 13:
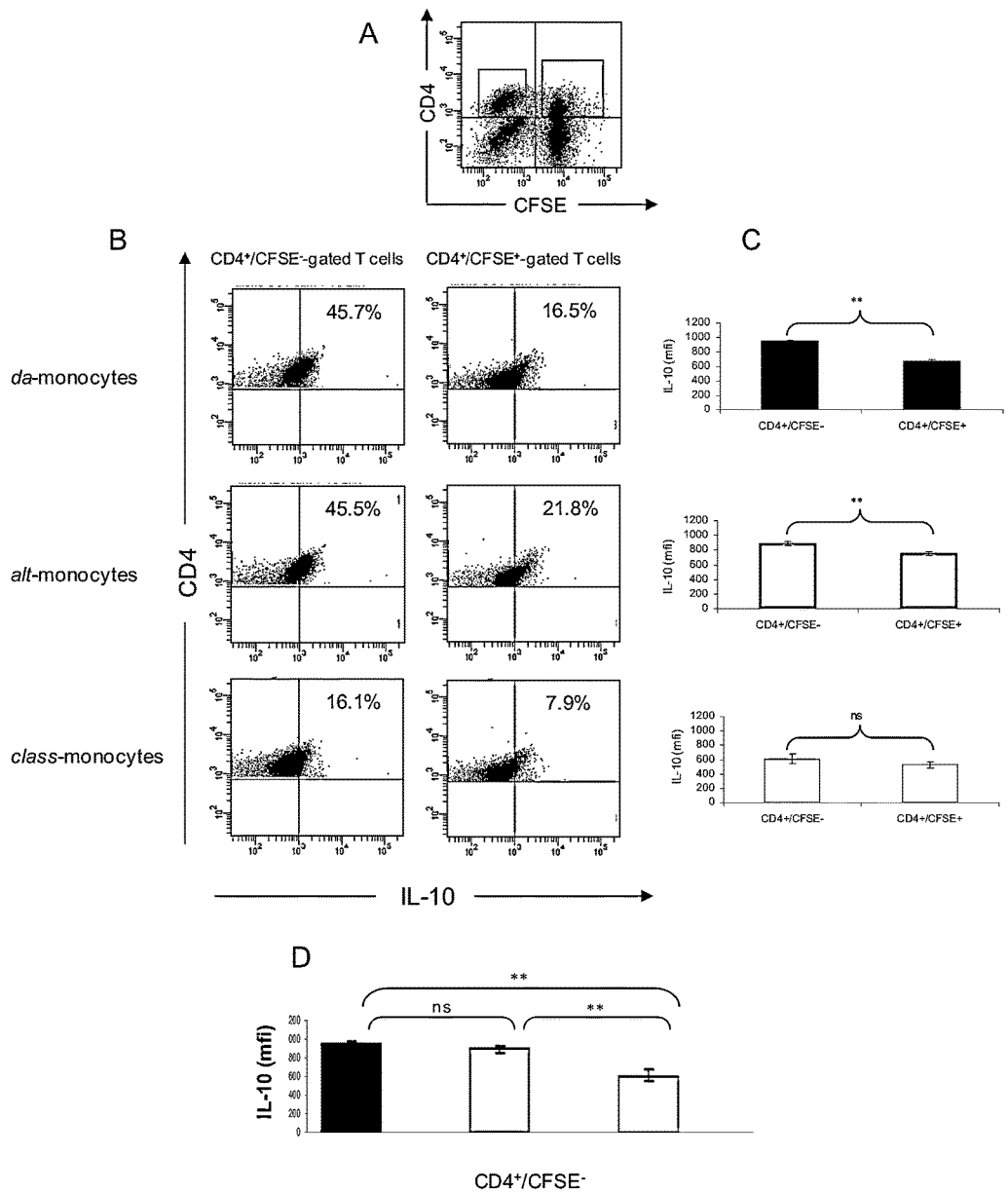

FIG. 13 shows that da- and alt-monocytes, but not class-monocytes, induce the proliferation of IL10-producing CD4+ T cells. A) After MLR and a 5 hour re-stimulation, divided CD4+/CFSE− T lymphocytes and non-divided CD4+/CFSE+ T lymphocytes are gated to quantify intracellular IL10 by flow cytometry. B) Flow cytometry analysis of intracellular IL10 (% of IL10+ CD4+ T cells) in divided (CD4+/CFSE−-gated, left column) and non-divided (CD4+/CFSE+-gated, right column) T cells. Presented results are representative of 3 independent MLR. C) Comparison (mean of mfi±SD from triplicates) of intracellular IL10 in divided and non-divided CD4+ T cells in MLR with da- (upper black bars), alt- (middle grey bars) and class-monocytes (lower white bars). p<0.005, Student's t-test. D) Comparison (mean of mfi±SD from triplicates) of intracellular IL10 in divided CD4+ T cells in MLR with da- (left black bar), alt- (middle grey bar) and class-monocytes (right white bar). p<0.001, one-way ANOVA. In flow cytometry dot plots, all quadrants are set using appropriate isotype controls.

FIG. 14 shows the inhibition of the differentiation of human monocytes in osteoclasts by dendrimer Gc1 at 20 μM, as in example 3. Picture 1: differentiation in control medium (without dendrimer Gc1); picture 2: differentiation in the presence of dendrimer Gc1 at 20 μM; picture 3: differentiation after pre-incubation (6 hours) with dendrimer Gc1 at 20 μM.

FIG. 15 shows the in vitro inhibition of bone resorption in presence of dendrimer Gc1 at different concentrations as explained in example 4; A) Gc1 added in the culture medium at different concentrations; B) after pre-incubation (6 hours) in Gc1 at 20 μM.

Figure 16:
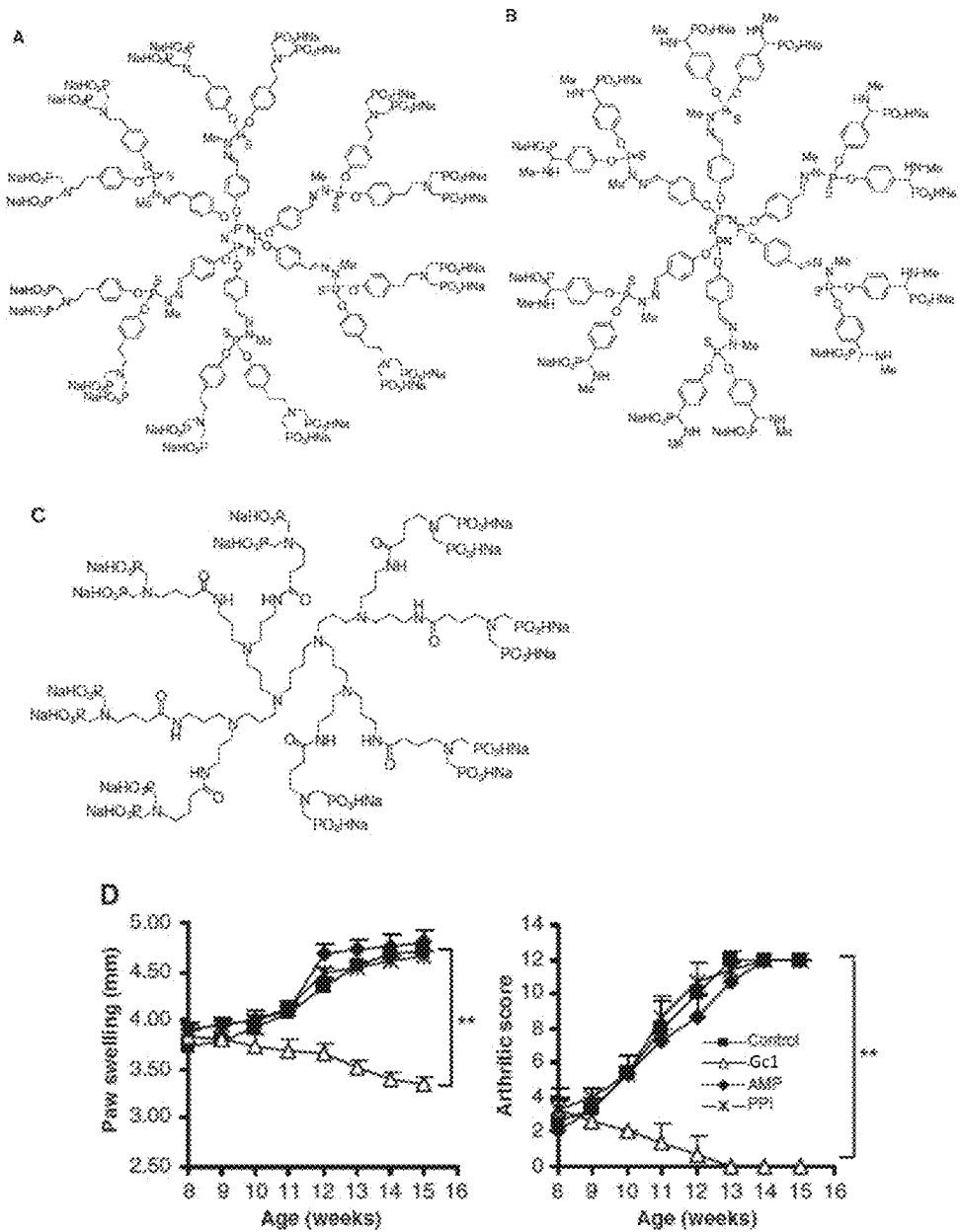

FIG. 16 shows A) Dendrimer Gc1 (or Aza-Bis-Phosphonate ABP); B) Dendrimer AMP (Aza-Mono-Phosphonate); C) Dendrimer PPI (PolyPropylenelmine) with aza-bis-phosphonate end groups; D) Comparison of the effect of 10 mg/kg of dendrimer Gc1, AMP, or PPI on the development of arthritis in IL-1ra−/− mice (n=3 per dendrimer treatment group). Control: untreated IL-1ra−/− mice (n=3). Values represent mean±SD. **p<0.01 versus control (p value was calculated using Student's t test).

Figure 17:
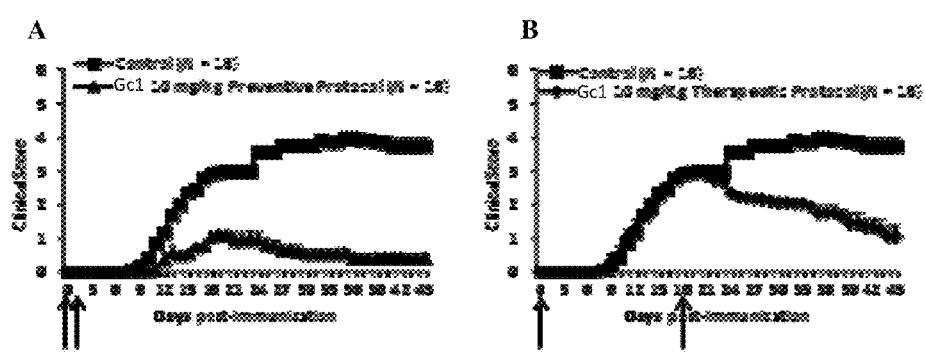

FIG. 17 shows Experimental Autoimmune Encephalomyelitis (EAE) score VS time after myelin oligodendrocyte protein (MΦG)-immunization in a dendrimer ABP preventive protocol (FIG. 17A) and in a dendrimer ABP therapeutic protocol (FIG. 17B).

Examples 1 to 4 illustrate the synthesis of some dendrimers.

GENERAL POINTS

The reactions were carried out under a dry argon atmosphere (argon U, Air Liquide). The following solvents were dried and distilled under argon immediately before use according to the techniques described by Perrin et al, *Purification of Laboratory Chemicals, Third Edition*; Press, P., Ed.: Oxford, 1988: tetrahydrofuran, dichloromethane, acetonitrile, pentane, toluene, diethyl ether, chloroform, triethylamine, pyridine.

Thin layer chromatography analyses were carried out on aluminium plates coated with silica of the Merck Kieselgel 60F$_{254}$ type.

The NMR spectra were recorded on Brüker devices (AC200, AM250, DPX 300). The chemical shifts are expressed in parts per million (ppm) relative to phosphoric acid at 85% in water for the $^{31}$P NMR and relative to tetramethylsilane for the $^1$H and $^{13}$C NMR. The following abbreviations were used in order to express the multiplicity of signals: s (singlet), d (doublet), bd (broad doublet), dd (doublet of doublets), AB syst. (AB system), t (triplet), dt (doublet of triplets), q (quadruplet), hept (heptuplet), m (unresolved multiplet).

Infrared vibrational spectroscopy was carried out on a Perkin Elmer FT 1725× spectrometer. The UV-visible spectroscopy was carried out on an HP 4852A device. The thermogravimetric measurements were carried out on a Netzch DSC 204 or Setaram TGA 92-16.18 device.

Numbering Used for the NMR Attribution:

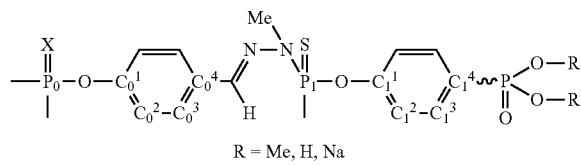

R = Me, H, Na

Example of Numbering for a First-Generation Dendrimer

Example 1: Synthesis of a Dendrimer of Polyether Type of First Generation with Azabis Phosphonic Acid Ends Derived from Tyramine

1.1. Synthesis of Phenol Aza-Bis-Dimethyl-Phosphonate Derived from Tyramine

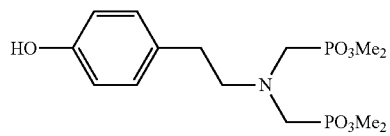

Tyramine (6 g, 43.7 mmol) and dimethyl-phosphite (10.32 ml, 112.5 mmol) are mixed at 0°, then a 37% solution of formaldehyde in water (12.6 ml) is slowly added, still at 0° C. The mixture is taken to ambient temperature for 30 minutes and refluxed for 1 hour with magnetic stirring. Finally the crude reaction product is placed under reduced pressure in order to evaporate the excess of formaldehyde. The product is extracted with a chloroform/water mixture (4/1) (3×100 ml of chloroform). The organic phase is recovered then subjected to chromatography on silica using acetone as eluent. The final product is isolated with a yield of 65%.

$^{31}$P-{$^1$H} NMR (CDCl$_3$): δ=30.2 (s, P(O)(OMe)$_2$) ppm.

$^1$H NMR (CDCl$_3$): δ=2.68 (deformed t, $^3J_{HH}$=7.2 Hz, 2H, —CH$_2$—CH$_2$—N); 3.05 (deformed t, $^3J_{HH}$=7.2 Hz, 2H, —CH$_2$—CH$_2$—N—); 3.20 (d, $^2J_{HP}$=8.9 Hz, 4H, N—CH$_2$—P); 3.75 (d, $^3J_{HP}$=10.7 Hz, 12H, —OMe); 6.6-7.1 (m, 4H, CH$_{arom}$); 8.16 (broad s, 1H, —OH) ppm.

$^{13}$C-{$^1$H} NMR (CDCl$_3$): δ=32.7 (s, C$_5$); 49.4 (dd, $^3J_{CP}$=6.8 Hz, $^1J_{CP}$=158.5 Hz, C$_7$); 52.8 (d, $^2J_{CP}$=3 Hz, C$_8$); 58.8 (t, $^3J_{CP}$=7.5 Hz, C$_6$); 115.4 (s, C$_3$); 129.8 (s, C$_2$); 129.8 (s, C$_4$); 155.9 (s, C$_1$) ppm.

1.2. Synthesis of a Dendrimer with Azabis Phosphonate Terminations Derived from Tyramine

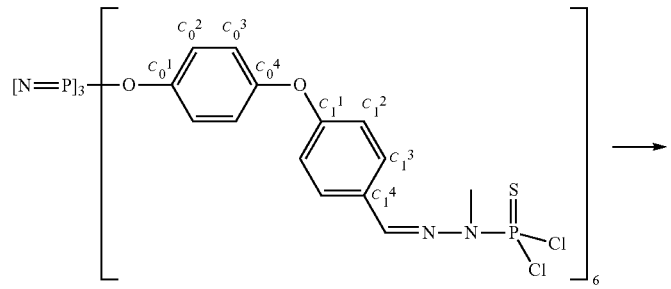

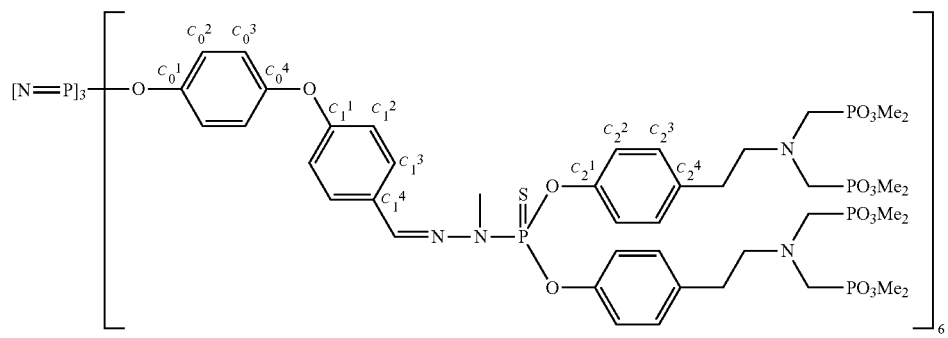

Tyramine aza-bisphosphonate of Example 1.1 (388 mg, 1.020 mmol) and caesium carbonate (565 mg, 1.734 mmol) are added to a solution of a dendrimer of polyether type of first generation with PSCl$_2$ terminations (177 mg, 0,074 mmol) in a mixture of aceton/THF (10 mL/3 mL). The reaction mixture is stirred at ambient temperature during 12 h, centrifuged and the resulting clear solution is evaporated to dryness under reduced pressure. The obtained oil is purified by chromatography on silica gel (gradient acetone/triethylamine (100:0 à 90:10), Rf=0.97 in aceton/triethylamine (90:10)) to afford the dendrimer with dimethylphosphonate ends as a pale yellow solid (yield: 91%).

$^{31}$P-{$^1$H} NMR (CDCl$_3$, 121.5 MHz): δ=9.27 (s, N$_3$P$_3$); 26.78 (s, PO$_3$Me$_2$); 63.18 (s, P$_1$); $^1$H NMR (CDCl$_3$, 300.13 MHz): δ=2.74 (t, $^3J_{HH}$=7.2 Hz, 24H, CH$_2$—CH$_2$—N); 3.05 (t, $^3J_{HH}$=7.2 Hz, 24H, CH$_2$—CH$_2$—N); 3.17 (d, $^2J_{HP}$=9.3 Hz, 48H, N—CH$_2$—P); 3.29 (d, $^3J_{HP}$=10.2 Hz, 18H, CH$_3$—N—P$_1$); 3.71 (dd, $^3J_{HP}$=10.5 Hz, $^7J_{HP}$=1.5 Hz, 144H, OMe); 6.93 (m, 12H, C$_0^3$—H); 6.94 (m, 12H, C$_1^2$—H); 7.00 (m, 12H, C$_0^3$—H); 7.10 (m, 24H, C$_2^2$—H); 7.16 (m, 24H, C$_2^3$—H); 7.60 (br s, 6H, CH=N); 7.67 (m, 12H, C$_0^2$—H); $^{13}$C-{$^1$H} NMR (CDCl$_3$, 75.6 MHz): δ=32.87 (br s, CH$_3$—N—P$_1$); 33.04 (s, CH$_2$—CH$_2$—N); 49.48 (dd, $^1J_{CP}$=157.5 Hz, $^3J_{CP}$=7.3 Hz, N—CH$_2$—P); 52.62 (d, $^2J_{CP}$=3.4 Hz, OMe); 52.66 (d, $^2J_{CP}$=3.4 Hz, OMe); 58.08 (t, $^3J_{CP}$=7.5 Hz, CH$_2$—CH$_2$—N); 118.50 (s, C$_1^2$); 120.40 (s, C$_0^3$); 121.27 (d, $^3J_{CP}$=4.5 Hz, C$_2^2$); 122.23 (s, C$_0^2$); 128.61 (s, C$_1^3$); 129.87 (s, C$_2^3$); 130.21 (s, C$_1^4$); 136.47 (d, $^5J_{CP}$=1.8 Hz, C$_2^4$); 138.89 (d, $^3J_{CP}$=13.8 Hz, CH=N); 146.37 (td, $^2J_{CP}$=5.2 Hz, $^4J_{CP}$=2.5 Hz, C$_0^1$); 148.96 (d, $^2J_{CP}$=7.0 Hz, C$_2^1$); 153.58 (s, C$_0^4$); 158.32 (s, C$_1^1$) ppm.

1.3. Synthesis of the Dendrimer with Sodium Salt of Azabisphosphonic Acid Ends Derived from Tyramine

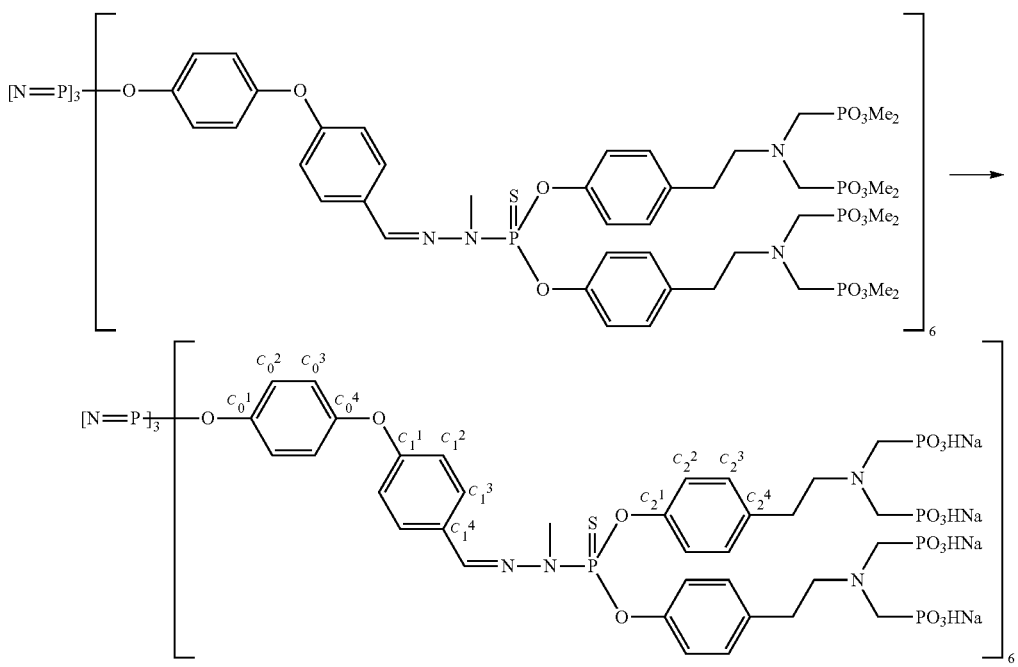

Trimethylsilyl bromide (535 µL, 4.00 mmol) is added to a solution of dendrimer dimethylphosphonate ends (440 mg, 5.75 10$^{-2}$ mmol) (obtained in example 1.2.) in acetonitrile (10 mL) at 0° C. The mixture is stirred at 25° C. during 12 h then evaporated to dryness under reduced pressure. The obtained residue is treated with methanol (2×15 mL), washed with ether (20 mL) and suspended in water (1 mL/100 mg) in the presence of one equivalent of NaOH for one phosphonic end. The solution is lyophilised to afford the dendrimer with sodium salt of phosphonic acid ends as a white solid (yield: 85%).

$^{31}$P-{$^1$H} NMR (D$_2$O/CD$_3$CN 7:3, 121.5 MHz): δ=6.82 (s, PO$_3$HNa); 10.43 (s, N$_3$P$_3$); 13.82 (s, PO$_3$Na$_2$); 64.56 (s, P$_1$); $^1$H NMR(H$_2$O/CD$_3$CN 7:3; 300.13 MHz): δ=3.25 (AA' part of a AA'BB' system, m, 24H, CH$_2$—CH$_2$—N); 3.51 (d, $^2J_{HP}$=11.7 Hz, 48H, N—CH$_2$—P and 18H, CH$_3$—N—P$_1$); 3.82 (BB' part of a AA'BB' system, m, 24H, CH$_2$—CH$_2$—N); 7.06 (m, 36H, C$_0^2$—H, C$_0^3$—H, C$_1^2$—H); 7.30 (m, 24H, C$_2^2$—H); 7.52 (m, 24H, C$_2^3$—H); 7.79 (br s, 6H, CH=N); 7.98 (m, 12H, C$_1^3$—H); $^{13}$C-{$^1$H} NMR (D$_2$O/CD$_3$CN 7:3, 75.6 MHz): δ=29.01 (s, CH$_2$—CH$_2$—N); 32.74 (br s, CH$_3$—N—P$_1$); 52.74 (br s, N—CH$_2$—P); 57.78 (s, CH$_2$—CH$_2$—N); 120.45 (s, C$_1^2$); 121.35 (s, C$_0^3$); 121.27 (d, $^3J_{CP}$=4.5 Hz, C$_2^2$); 122.53 (s, C$_0^2$); 128.94 (s, C$_1^3$); 130.50 (s, C$_1^4$); 130.85 (s, C$_2^3$); 134.55 (s, C$_2^4$); 141.00 (br s, CH=N); 146.01 (m, C$_0^1$); 149.36 (d, $^2J_{CP}$=6.1 Hz, C$_2^1$); 153.79 (s, C$_0^4$); 158.17 (s, C$_1^1$) ppm.

Example 2: Synthesis of a Dendrimer of Carbosilane Type of First Generation with Azabis Phosphonic Acid Ends Derived from Tyramine

2.1: Synthesis of the Dendrimer with Azabisphosphonate Ends Derived from Tyramine

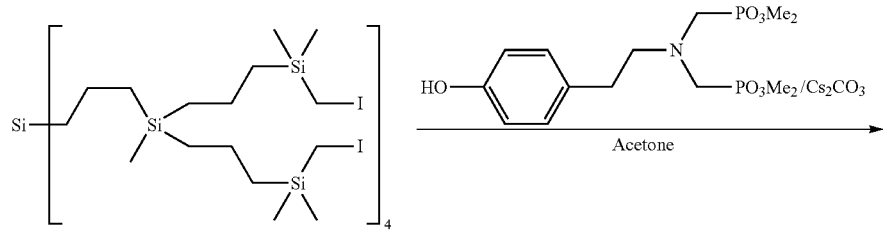

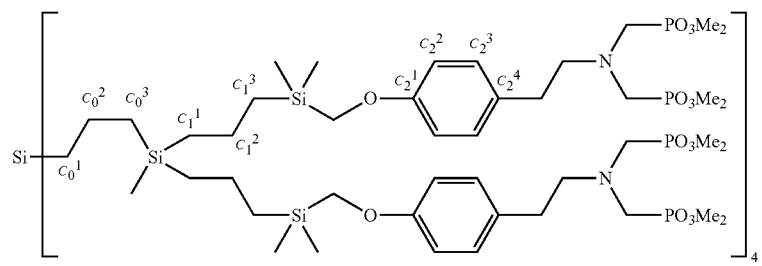

Tyramine aza-bisphosphonate obtained according to example 1.1 (320 mg, 0.830 mmol) and caesium carbonate (540 mg, 1.66 mmol) are added to a solution of carbosilane type dendrimer of first generation with $SiCH_2I$ ends (200 mg, $8.7.10^{-5}$ mmol) in acetone (2 mL). The mixture is stirred at 40° C. during 20 h, centrifuged and the resulting clear solution is evaporated to dryness under reduced pressure. The obtained oil is purified by chromatography on silica gel (gradient acetone/methanol (100:0 to 0:100), Rf=0.38 in acetone/methanol (90:10)) to afford the dendrimer with dimethylphosphonate ends as a pale yellow solid (yield: 65%).

$^{31}P$-$\{^{1}H\}$ NMR (acetone-d6, 162.0 MHz): δ=26.44 (s, $PO_3Me_2$); $^{1}H$ NMR ($CDCl_3$, 400.13 MHz): δ=0.00 (s, 12H, Si—$CH_3$); 0.14 (s, 48H, Si—$(CH_3)_2$); 0.67 (br s, 32H, $C_0^1$—H, $C_0^3$—H, $C_1^1$—H); 0.77-0.80 (m, 16H, $C_1^3$—H); 1.45-1.52 (m, 24H, $C_0^2$—H, $C_1^2$—H); 2.75 (AA' part of a AA'BB' system, m, 16H, $\underline{CH_2}$—$CH_2$—N); 3.03 (BB' part of a AA'BB' system, m, 16H, $CH_2$—$\underline{CH_2}$—N); 3.17 (d, $^{2}J_{HP}$=9.3 Hz, 32H, N—$CH_2$—P); 3.61 (s, 16H, Si—$CH_2$—O); 3.72 (d, $^{3}J_{HP}$=10.4 Hz, 96H, OMe); 6.89 (m, 16H, $C_2^2$—H); 7.18 (m, 16H, $C_2^3$—H); $^{13}C$-$\{^{1}H\}$ NMR ($CDCl_3$, 100.6 MHz): δ=-5.25 (s, Si—$CH_3$); -5.12 (s, Si—$(CH_3)_2$); 17.60 (s, $C_0^2$); 18.32 (s, $C_1^2$); 18.37 ($C_1^3$); 18.37 ($C_1^1$); 18.71 (s, $C_0^1$); 18.97 (s, $C_0^3$); 32.23 (s, $\underline{CH_2}$—$CH_2$—N); 49.98 (dd, $^{1}J_{CP}$=156.9 Hz, $^{3}J_{CP}$=7.7 Hz, N—$CH_2$—P); 51.94 (br s, OMe); 58.74 (t, $^{3}J_{CP}$=7.0 Hz, $CH_2$—$CH_2$—N); 59.99 (s, Si—$CH_2$—O); 113.88 (s, $C_2^2$); 129.65 (s, $C_2^3$); 131.48 (s, $C_2^4$); 160.02 (s, $C_2^1$); $^{29}Si$ NMR ($CDCl_3$; 79.5 MHz): δ=-0.30 (s, Si—$CH_2$-0); 1.07 (s, Si—$CH_3$); 3.98 (s, Si at the core) ppm.

2.2: Synthesis of the Dendrimer with Sodium Salt of Azabisphosphonic Acid Ends Derived from Tyramine

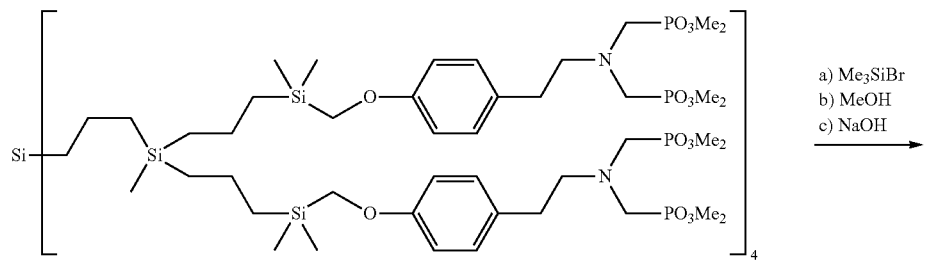

-continued

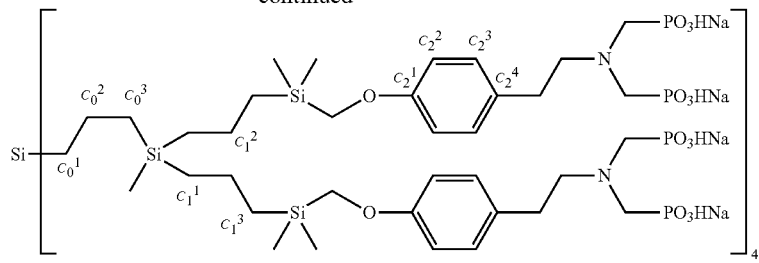

Trimethylsilyl bromide (120 μL, 8.56.10⁴ mmol) is added to a solution of dendrimer with dimethylphosphonate end obtained in example 2.1 (92.9 mg, 2.14 10⁻² mmol) in acetonitrile (2.5 mL) at 0° C. The mixture is stirred at 25° C. during 12 h then evaporated to dryness under reduced pressure. The obtained residue is treated with methanol (2×15 mL), washed with ether (20 mL) and suspended in water (1 mL/100 mg) in the presence of one equivalent of NaOH for one phosphonic end. The solution is lyophilised to afford the dendrimer with sodium salt phosphonic acid ends as a white solid (yield: 85%).

$^{31}P-\{^1H\}$ NMR (D₂O/acetone-d6 7:3, 162.0 MHz): δ=6.64 (s, PO₃HNa); $^1H$ NMR (D₂O/acetone-d6 7:3; 400.13 MHz): δ=-0.14 (br s, 60H, Si—CH₃ and Si—(CH₃)₂); 0.45 (br s, 48H, $C_0^1$—H, $C_0^3$—H, $C_1^1$—H, $C_1^3$—H); 1.23 (br s, 24H, $C_0^2$—H, $C_1^2$—H); 2.83 (AA' part of a AA'BB' system, br s, 16H, C$\underline{H}_2$—CH₂—N); 3.11 (br s, 32H, N—CH₂—P); 3.31 (BB' part of a AA'BB' system, br s, 32H, CH₂—C$\underline{H}_2$—N and Si—CH₂—O); 6.65 (m, 16H, $C_2^2$—H); 7.05 (m, 16H, $C_2^3$—H); $^{13}C-\{^1H\}$ NMR (D₂O/acetone-d6 7:3, 100.6 MHz): δ=-5.04 (br s, Si—CH₃ and Si—(CH₃)₂); 17.5-19.2 ($C_0^1$, $C_0^2$, $C_0^3$, $C_1^1$, $C_1^2$, $C_1^3$); 29.30 (s, C$\underline{H}_2$—CH₂—N); 53.74 (d, $^1J_{CP}$=122.7 Hz, N—CH₂—P); 57.69 (s, CH₂—C$\underline{H}_2$—N); 60.08 (s, CH₂—C$\underline{H}_2$—N); 114.14 (s, $C_2^2$); 128.57 (s, $C_2^4$); 130.14 (s, $C_2^3$); 159.86 (s, $C_2^1$).

Example 3: Synthesis of Salamonczyk-Type of Second Generation with Azabis Phosphonic Acid Ends Derived from Tyramine

3.1. Synthesis of the Diphenoxyamino Phosphine Derived from Tyramine

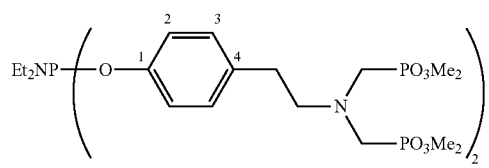

The experimental protocol used for preparing this molecule was inspired by that used by Salamonczyk in order to create his dendrimers (*Tetrahedron Lett.* 2000, 41, 1643). The aza bis phosphonate tyramine derivative obtained in Example 1.1 is weighed in a Schlenk tube under argon (2.3 g) and dissolved in 10 mL of distilled THF. The diethylaminodichlorophosphine is introduced into another Schlenk tube (0.5 mL) and placed in solution in 5 mL of distilled THF. The two Schlenk tubes are taken to −70° C. 1.4 mL of triethylamine are then added to the dichlorophosphine solution then the tyramine aza bis phosphonate solution is cannulated onto the mixture still at −70° C. The stirring is continued for half an hour at a low temperature then for 4 hours at ambient temperature. The mixture is then filtered on celite under argon then the solvent is eliminated under reduced pressure. The dry residue is kept under argon at a low temperature and used without other treatment in the rest of the synthesis.

$^{31}P$ $\{^1H\}$ NMR (CDCl₃): δ=30.4 (s, PO₃Me₂); 144.5 (s, Et₂NP) ppm.

$^1H$ NMR (CDCl₃): δ=1.00 (t, $^3J_{HH}$=7.2 Hz, 6H, C$\underline{H}_3$CH₂); 2.70 (m, 4H, N—C$\underline{H}_2$CH₂); 3.00 (m, 4H, CH₂C$\underline{H}_2$P); 3.11-3.23 (m, 12H, CH₂P, CH₃C$\underline{H}_2$); 3.69 (d, $^3J_{HP}$=6.9 Hz, 24H, CH₃O); 6.90 (d, $^3J_{HH}$=8.4 Hz, 4H, C²H); 6.97 (d, $^3J_{HH}$=8.4 Hz, 4H, C³H) ppm.

3.2.: Synthesis of the Dendrimer with Azabisphosphonate Ends Derived from Tyramine

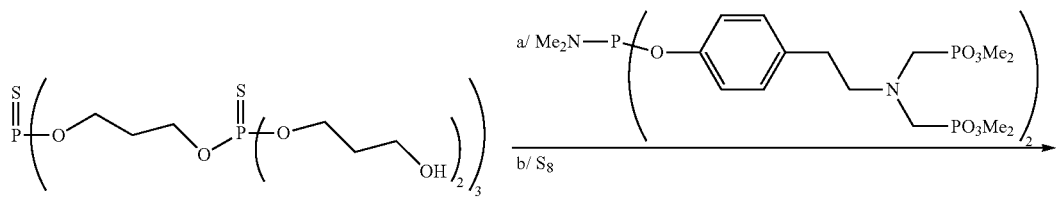

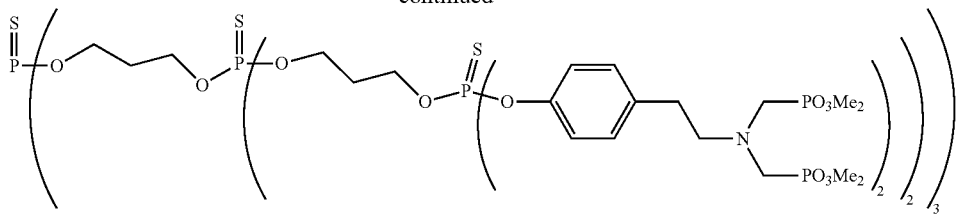

The phosphoramide derived from tyramine aza-bisphosphonate obtained as described in example 3.1 (160 mg, 0.17 mmol solubilized in dichloromethane/acetonitrile (1 mL/1 mL)) and tetrazole (180 mg, 2.60 mmol) are added to the dendrimer Salamonczyk with hydroxyle ends (1.64 g, 1.9 mmol) in solution in dichloromethane (4 mL). The mixture is stirred at 25° C. during 3 h 30 before addition of $S_8$ (512 mg, 2 mmol). The heterogeneous mixture is stirred during 12 h at 25° C. then filtered. The filtrate is evaporated to dryness under reduced pressure and purified by chromatography on silica gel (elution gradient: dichloromethane/acetone (50:50 à 0:100) then acetone/methanol (100:0 à 0:100), Rf=0.95 in methanol) to afford the dendrimer with dimethyphosphonate ends as a white solid (yield: 43%).

$^{31}$P-{$^1$H} NMR (acetone-d6, 101.25 MHz): δ=26.53 (s, $PO_3Me_2$), 58.72 (s, $P^2$), 68.23 (s, $P^0$ and $P^1$); $^1$H NMR (acetone-d6, 300.13 MHz): δ=2.15 (m, 18H, $C_1^2$—H and $C_0^2$—H); 2.85 (AA' part of a AA'BB' system, m, 24H, CH$_2$—CH$_2$—N); 3.17 (BB' part of a AA'BB' system, m, 24H, CH$_2$—CH$_2$—N); 3.25 (d, $^2J_{HP}$=9.9 Hz, 48H, N—CH$_2$—P); 3.72 (d, $^3J_{HP}$=10.5 Hz, 144H, OMe); 4.24 (m, 24H, $C_0^1$—H, $C_0^3$—H and $C_1^1$—H); 4.44 (m, 12H, $C_1^3$—H); 7.19 (m, 24H, $C_2^2$—H); 7.36 (m, 24H, $C_2^3$—H); $^{13}$C-{$^1$H} NMR (acetone-d6, 75.5 MHz): δ=30.62 (m, $C_0^2$ and $C_1^2$); 32.26 (s, CH$_2$—CH$_2$—N); 49.06 (dd, $^1J_{CP}$=157.6 Hz, $^3J_{CP}$=8.2 Hz, N—CH$_2$—P); 52.13 (d, $^2J_{CP}$=5.0 Hz, OMe); 58.13 (t, $^3J_{CP}$=7.8 Hz, CH$_2$—CH$_2$—N); 64.49 (m, $C_0^1$, $C_0^3$ and $C_1^3$); 65.90 (m, $^2J_{CP}$=6.0 Hz, $C_1^1$); 120.82 (d, $^3J_{CP}$=4.5 Hz, $C_2^2$); 130.28 (s, $C_2^3$); 137.54 (s, $C_2^4$); 148.99 (d, $^2J_{CP}$=7.6 Hz, $C_2^1$).

3.3.: Synthesis of the Dendrimer with Sodium Salt Azabis Phosphonic Acid Ends Derived from Tyramine Trimethylsilyl bromide (190 μL, 1.44 mmol) is added to a solution of dendrimer with dimethylphosphonate ends obtained in example 3.2 (140 mg, 2.39 $10^{-2}$ mmol) in acetonitrile (3.5 mL) at 0° C. The mixture is stirred at 25° C. during 12 h then evaporated to dryness under reduced pressure. The residue thus obtained is treated with methanol (2×15 mL), washed with ether (20 mL) and suspended in water (1 mL/100 mg) in presence of one equivalent of NaOH for one phosphonic end. The obtained solution is lyophilised to afford the dendrimer with sodium salt of phosphonic acid ends as a white solid (yield: 70%).

$^{31}$P-{$^1$H} NMR (D$_2$O/CD$_3$CN 9:1, 81.0 MHz): δ=10.19 (s, $PO_3HNa$), 14.63 (s, $PO_3Na_2$), 62.78 (s, $P^2$), 70.58 (s, $P^0$ and $P^1$); $^1$H NMR (D$_2$O/CD$_3$CN 9:1, 300.13 MHz): δ=2.03 (m, 18H, $C_1^2$—H and $C_0^2$—H); 3.07 (AA' part of a AA'BB' system, m, 24H, CH$_2$—CH$_2$—N); 3.40 (br s, 48H, N—CH$_2$—P); 3.63 (BB' part of a AA'BB' system, m, 24H, CH$_2$—CH$_2$—N); 4.13 (br s, 24H, $C_0^1$—H, $C_0^3$—H and $C_1^1$—H); 4.38 (br s, 12H, $C_1^3$—H); 7.12 (m, 24H, $C_2^2$—H); 7.31 (m, 24H, $C_2^3$—H); $^{13}$C-{$^1$H} RMN (CDCl$_3$; 75.5 MHz): δ=29.12 (s, CH$_2$—CH$_2$—N); 32.26 (m, $C_0^2$ and $C_1^2$); 52.64 (d, $^1J_{CP}$=131.7 Hz, N—CH$_2$—P); 58.03 (br s, CH$_2$—CH$_2$—N); 64.90 (m, $C_0^1$, $C_0^3$, $C_1^1$ and $C_1^3$); 121.45 (s, $C_2^2$); 130.83 (s, $C_2^3$); 134.51 (s, $C_2^4$); 149.31 (d, $^2J_{CP}$=7.2 Hz, $C_2^1$).

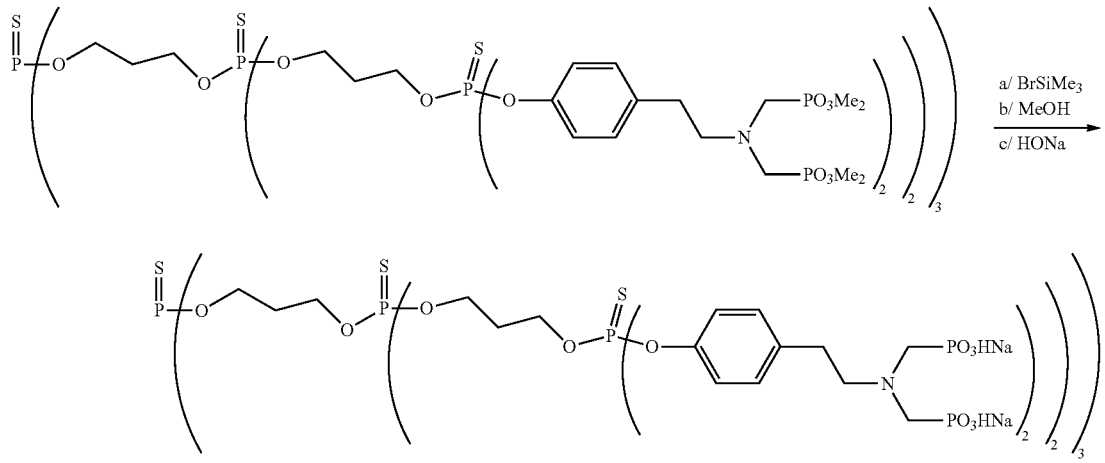

Figure 1:
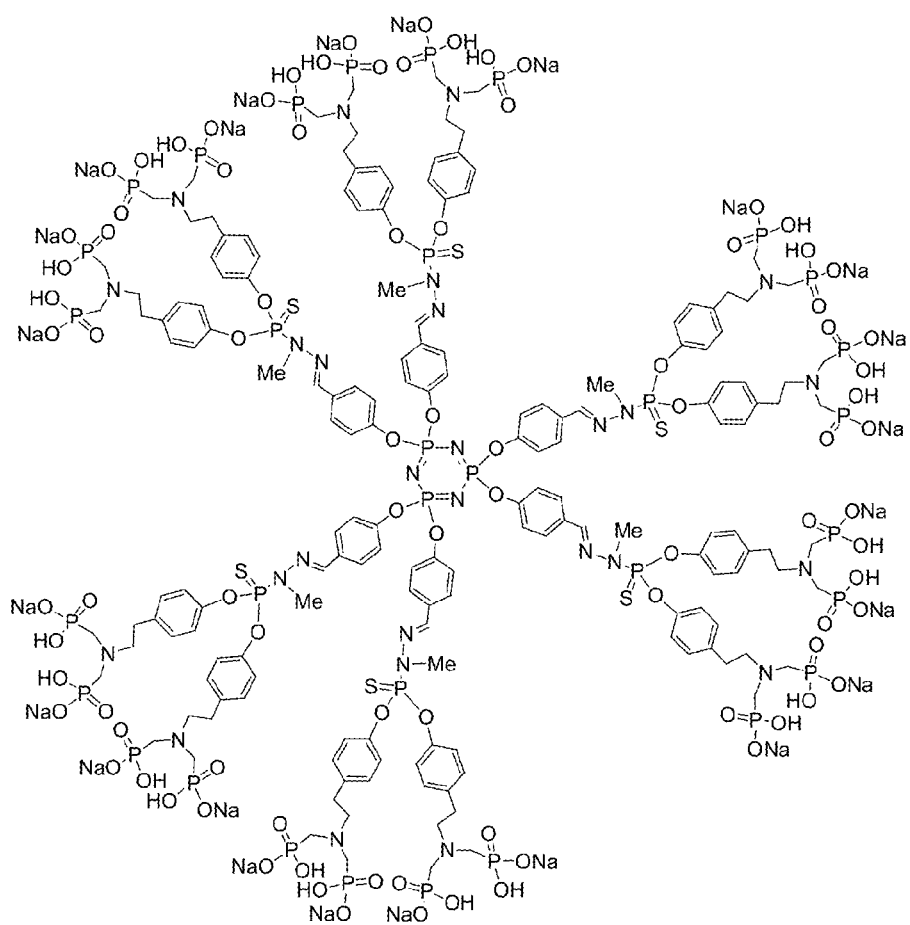
FIGS. 1 to 3 show the structure of the bisphosphonic-capped dendrimers tested in examples 5 to 7.
Figure 2:
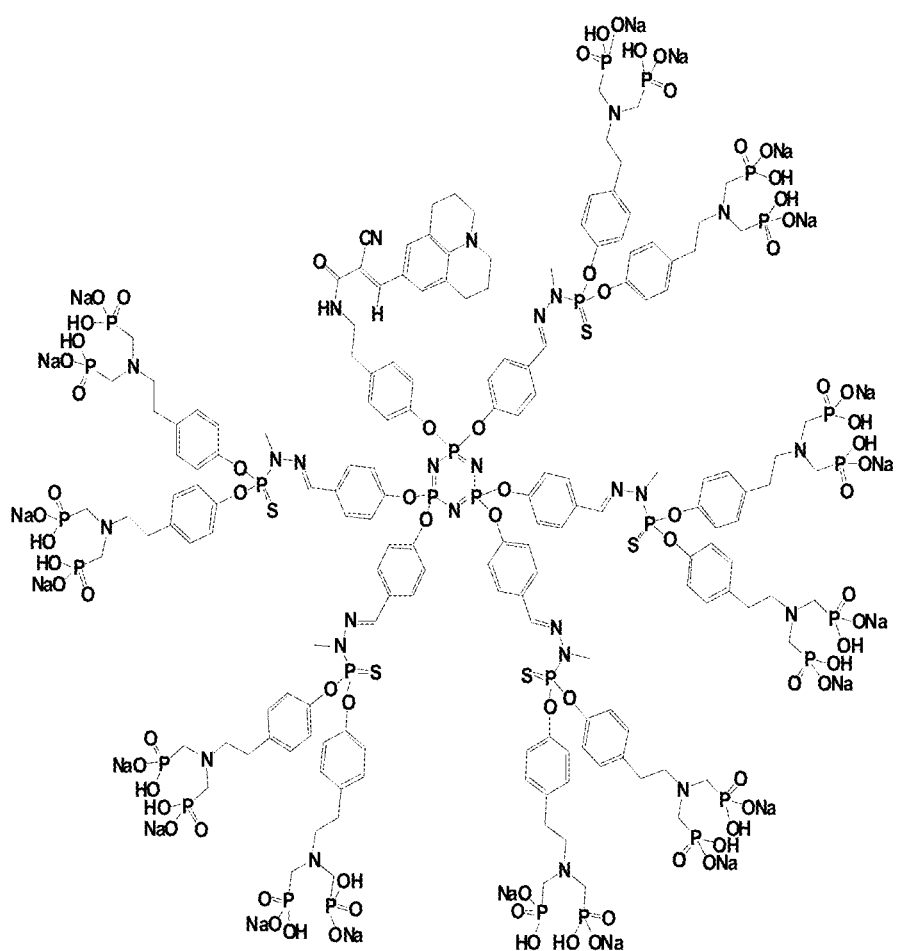
Figure 3:
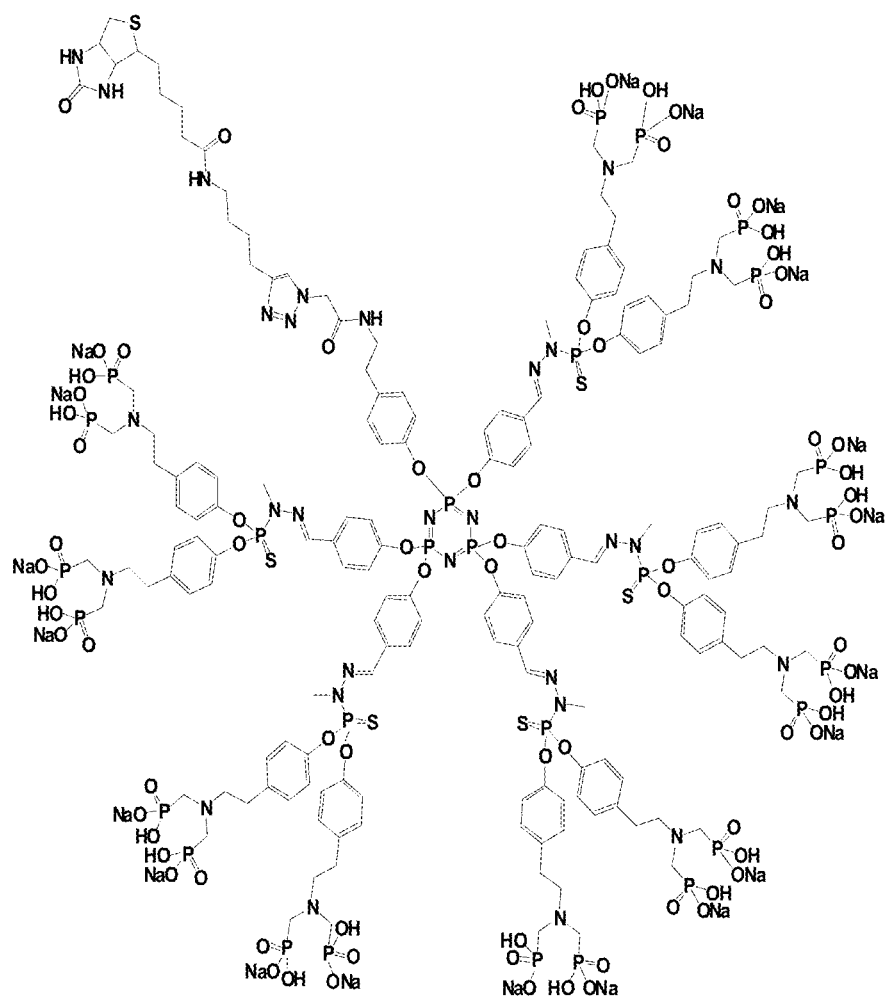

Example 4: Synthesis of Dimethylphosphonate Terminated Dendrimer with a Biotinylated Spacer (Aza 2P)$_{10}$-Biot-D (Voir FIG. 3)

4.1. Synthesis of 2-chloro-N-[2-(4-hydroxy-phenyl)-ethyl]-acetamide

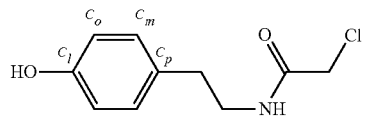

To a solution of tyramine (1.543 g, 11.25 mmol) in 25 mL of dichloromethane/saturated aqueous sodium carbonate mixture (1:1) was added chloroacetyl chloride (0.896 mL, 11.25 mmol) and the mixture was stirred at room temperature for 2 h. It was then diluted in water (50 mL) and extracted with dichloromethane (150 mL). The organic phase was dried over magnesium sulfate, filtered and evaporated to give a white solid which was purified by column chromatography (silica, dichloromethane/methanol, 97:3) to give 2-chloro-N-[2-(4-hydroxy-phenyl)-ethyl]-acetamide as a white solid (yield=75%).

$^1$H NMR (DMSO-d6, 300.1 MHz): δ=2.61 (t, $^3J_{HH}$=7.5 Hz, 2H, C$_6$H$_4$—CH$_2$—CH$_2$—NH), 3.24 (td, $^3J_{HH}$=7.5 Hz, $^3J_{HH}$=5.1 Hz, 2H, C$_6$H$_4$—CH$_2$—CH$_2$—NH), 4.03 (s, 2H, CO—CH$_2$), 6.68 (m, 2H, C$_o$—H), 6.99 (d, $^3J_{HH}$=8.4 Hz, 2H, C$_m$—H), 8.23 (t, $^3J_{HH}$=5.1 Hz, 1H, NH), 9.17 (s, 1H, OH); $^{13}$C{$^1$H} NMR (CDCl$_3$, 50.3 MHz): δ=34.3 (s, C$_6$H$_4$—CH$_2$—CH$_2$—NH), 41.2 (s, CO—CH$_2$—Cl), 42.5 (s, C$_6$H$_4$—CH$_2$—CH$_2$—NH), 115.5 (s, C$_o$), 128.9 (s, C$_p$), 129.5 (s, C$_m$), 155.7 (s, C$_i$), 165.9 (s, CO) ppm. DCI-MS (NH$_3$): m/z=231 [M+NH$_4$]$^+$, 214 [M+H]$^+$.

4.2. Synthesis of 2-Azido-N-[2-(4-hydroxy-phenyl)-ethyl]-acetamide

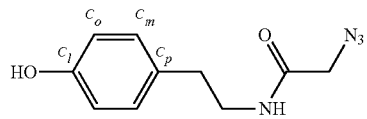

To a solution of 2-chloro-N-[2-(4-hydroxy-phenyl)-ethyl]-acetamide obtained in example 4.1 (250 mg, 1.17 mmol) in DMSO (3 mL) was added sodium azide (152 mg, 2.34 mmol) and the mixture was stirred at room temperature for 12 h. The reaction mixture was then diluted in water (70 mL) and extracted with ethyl acetate (140 mL) The organic phase was dried over magnesium sulfate, filtered and evaporated to give 2-Azido-N-[2-(4-hydroxy-phenyl)-ethyl]-acetamide as a viscous solid (yield=90%) that crystalises upon standing.

$^1$H NMR (CDCl$_3$, 300.1 MHz): δ=2.75 (t, $^3J_{HH}$=6.9 Hz, 2H, C$_6$H$_4$—CH$_2$—CH$_2$—NH), 3.51 (td, $^3J_{HH}$=6.9 Hz, $^3J_{HH}$=6.3 Hz, 2H, C$_6$H$_4$—CH$_2$—CH$_2$—NH), 3.95 (s, 2H, CO—CH$_2$), 6.51 (broad s, 1H, NH), 6.82 (m, 2H, C$_o$—H), 7.02 (m, 2H, C$_m$—H), 7.38 (broad s, 1H, OH); $^{13}$C{$^1$H} NMR (CDCl$_3$, 75.5 MHz): δ=34.6 (s, C$_6$H$_4$—CH$_2$—CH$_2$—NH), 40.9 (s, C$_6$H$_4$—CH$_2$—CH$_2$—NH), 52.6 (s, CO—CH$_2$—N), 115.7 (s, C$_o$), 129.5 (s, C$_p$), 129.7 (s, C$_m$), 155.3 (s, C$_i$), 167.1 (s, CO) ppm. DCI-MS (NH$_3$): m/z=238 [M+NH$_4$]$^+$.

4.3. Synthesis of 2-{4-[4-(1,3-Dioxo-1,3-dihydro-isoindol-2-yl)-butyl]-[1,2,3]triazol-1-yl}-N-[2-(4-hydroxy-phenyl)-ethyl]-acetamide

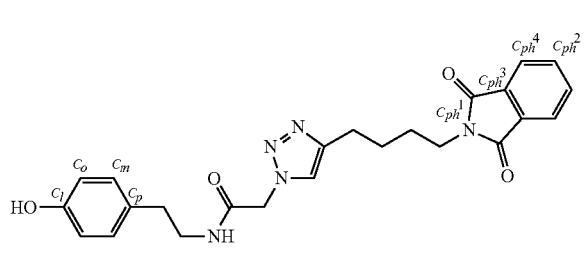

To 2.4 mL of tert-butanol/water mixture (1:1) were suspended 2-Azido-N-[2-(4-hydroxy-phenyl)-ethyl]-acetamide obtained in example 4.2 (385 mg, 1.750 mmol), N-(5-hexynyl)phthalimide (398 mg, 1.750 mmol), sodium ascorbate (35 mg, 0.175 mmol) and copper sulfate (140 mg, 0.088 mmol). The reaction mixture was stirred at room temperature for 12 h and was then diluted in water, and filtered. The solid was washed with water and ether to give 2-{4-[4-(1,3-Dioxo-1,3-dihydro-isoindol-2-yl)-butyl]-[1,2,3]triazol-1-yl}-N-[2-(4-hydroxy-phenyl)-ethyl]-acetamide as a white solid (yield=90%). $^1$H NMR (CD$_3$CN, 300.1 MHz): δ=1.71 (m, 4H, CH$_2$—CH$_2$—CH$_2$—CH$_2$—N, CH$_2$—CH$_2$—CH$_2$—CH$_2$—N), 2.70 (m, 4H, C$_6$H$_4$—CH$_2$—CH$_2$—NH, CH$_2$—CH$_2$—CH$_2$—CH$_2$—N), 3.37 (q, $^3J_{HH}$=6.9 Hz, $^3J_{HH}$=6.3 Hz, 2H, C$_6$H$_4$—CH$_2$—CH$_2$—NH), 3.67 (t, $^3J_{HH}$=6.3 Hz, 2H, CH$_2$—CH$_2$—CH$_2$—CH$_2$—N), 4.92 (s, 2H, CO—CH$_2$—N), 6.59 (broad s, 1H, NH), 6.73 (d, $^3J_{HH}$=8.1 Hz, 2H, C$_o$—H), 7.02 (d, $^3J_{HH}$=8.1 Hz, 2H, C$_m$—H), 7.50 (s, 1H, N—CH=C), 7.79 (m, 4H, C$_{ph}$—H); $^{13}$C{$^1$H} NMR (CD$_3$CN, 75.5 MHz): δ=24.7 (s, CH$_2$—CH$_2$—CH$_2$—CH$_2$—N), 26.5 (s, CH$_2$—CH$_2$—CH$_2$—CH$_2$—N), 27.7 (s, CH$_2$—CH$_2$—CH$_2$—CH$_2$—N), 34.1 (s, C$_6$H$_4$—CH$_2$—CH$_2$—NH), 37.4 (s, CH$_2$—CH$_2$—CH$_2$—CH$_2$—N), 40.8 (s, C$_6$H$_4$—CH$_2$—CH$_2$—NH), 52.1 (s, CO—CH$_2$—N), 115.1 (s, C$_o$), 122.7 (s, C$_{ph}^4$), 122.9 (s, N—CH=C), 129.8 (s, C$_m$), 130.2 (s, C$_p$), 132.3 (s, C$_{ph}^3$), 134.1 (s, C$_{ph}^2$), 147.5 (N—CH=C), 155.4 (s, C$_i$), 165.6 (HN—CO—CH$_2$), 168.5 (s, C$_{ph}^1$) ppm. DCI-MS (NH$_3$): m/z=448 [M+NH$_4$]$^+$.

4.4. Synthesis of tert-butyl 6-heptynoate ester

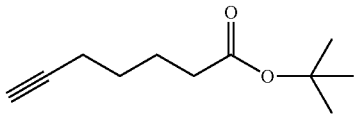

To a solution of 6-heptynoic acid (0.750 mL, 5.970 mmol), tert-butanol (1.7 mL, 17.91 mmol), and DMAP (73 mg, 0.597 mmol) in dichloromethane (12 mL) was added N,N'-dicyclohexylcarbodiimide (1.416 g, 6.864 mmol). The reaction mixture was stirred for 12 h at rt, and then the dicyclohexylurea was filtrated off and washed with dichloromethane (60 mL) and diethyl ether (30 mL). The organic phases were combined, dried over sodium sulfate and evaporated to dryness. The residue was purified by column chromatography (silica, pentane/ether, 98:2) to afford the tert-butyl 6-heptynoate ester as a colourless oil (yield=30%). $^1$H NMR (CDCl$_3$, 300.1 MHz): δ=1.45 (s, 9H, CH$_3$), 1.57 (m, 2H, CH$_2$—CH$_2$—CO), 1.70 (m, 2H, CH$_2$—CH$_2$—CH$_2$—CO), 1.96 (t, $^4J_{HH}$=2.6 Hz, 1H, CH), 2.23 (m, 2H, CH$_2$—CO, C—CH$_2$); $^{13}$C{$^1$H} NMR (CDCl$_3$, 62.9 MHz): δ=18.2 (C—CH$_2$), 24.1 (s, CH$_2$—CH$_2$—CO), 27.8 (s, CH$_2$—CH$_2$—CH$_2$—CO), 28.1 (s, CH$_3$), 35.0 (s, CH$_2$—CO), 68.5 (s, CH), 84.1 (s, C—CH$_2$), 172.8 (s, CO) ppm.

4.5. Synthesis of 5-(1-{[2-(4-Hydroxy-phenyl)-ethylcarbamoyl]-methyl}-1H-[1,2,3]triazol-4-yl)-pentanoic acid tert-butyl ester

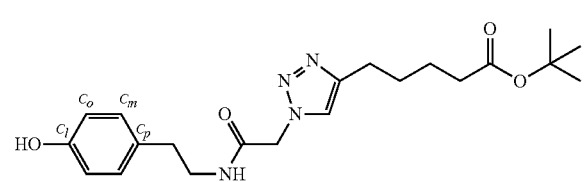

To 1.5 mL of tert-butanol/water mixture (1:1) were suspended 2-Azido-N-[2-(4-hydroxy-phenyl)-ethyl]-acetamide obtained in example 4.2 (254 mg, 1.152 mmol), tert-butyl 6-heptynoate ester obtained in example 4.4 (210 mg, 1.152 mmol), sodium ascorbate (23 mg, 0.015 mmol) and copper sulfate (9 mg, 0.057 mmol). The reaction mixture was stirred at room temperature for 12 h. It was then diluted in 0.6 mL of THF and 10 mL of water, stirred for 10 min, and extracted with ethyl acetate (60 mL). The organic phase was washed with brine (30 mL), dried over sodium sulfate, filtered and evaporated to give a sticky solid which was purified by column chromatography (silica, ether/acetone, 1:0 to 8:2) to give 5-(1-{[2-(4-Hydroxy-phenyl)-ethylcarbamoyl]-methyl}-1H-[1,2,3]triazol-4-yl)-pentanoic acid tert-butyl ester as a sticky solid (yield=85%). $^1$H NMR (CDCl$_3$, 300.1 MHz): δ=1.47 (s, 9H, CH$_3$), 1.69 (m, 4H, CH$_2$—CH$_2$—CH$_2$—CH$_2$CO, CH$_2$—CH$_2$—CH$_2$—CH$_2$—CO), 2.30 (t, $^3J_{HH}$=6.4 Hz, 2H, CH$_2$—CH$_2$—CH$_2$—CH$_2$—CO), 2.71 (m, 4H, C$_6$H$_4$—CH$_2$—CH$_2$—NH, CH$_2$—CH$_2$—CH$_2$—CH$_2$—CO), 3.47 (q, $^3J_{HH}$=6.3 Hz, 2H, C$_6$H$_4$—CH$_2$—CH$_2$—NH), 4.95 (s, 2H, CO—CH$_2$—N), 6.13 (t, $^3J_{HH}$=5.5 Hz, 1H, NH), 6.76 (d, $^3J_{HH}$=8.4 Hz, 2H, C$_o$—H), 6.89 (d, $^3J_{HH}$=8.4 Hz, 2H, C$_m$—H), 7.31 (s, 1H, OH), 7.61 (s, 1H, N—CH=C); $^{13}$C{$^1$H} NMR (CDCl$_3$, 75.5 MHz): δ=24.6 (s, CH$_2$—CH$_2$—CH$_2$—CH$_2$—CO), 25.6 (s, CH$_2$—CH$_2$—CH$_2$—CH$_2$—CO), 28.1 (s, CH$_3$), 28.4 (s, CH$_2$—CH$_2$—CH$_2$—CH$_2$—CO), 34.0 (s, C$_6$H$_4$—CH$_2$—CH$_2$—NH), 35.2 (s, CH$_2$—CH$_2$—CH$_2$—CH$_2$—CO), 40.8 (s, C$_6$H$_4$—CH$_2$—CH$_2$—NH), 53.0 (s, CO—CH$_2$—N), 80.8 (s, C(CH$_3$)), 115.6 (s, C$_o$), 122.3 (s, N—CH=C), 129.3 (s, C$_p$), 129.7 (s, C$_m$), 148.5 (N—CH=C), 155.4 (s, C$_i$), 165.4 (HN—CO—CH$_2$), 173.8 (s, CO$_2$) ppm. FAB-MS (>0): m/z=403 [M+H]$^+$, 347 [M–C$_4$H$_9$+2H]$^+$.

4.6. Synthesis of penta(4-formylphenoxy)-chlorocyclotriphosphazene

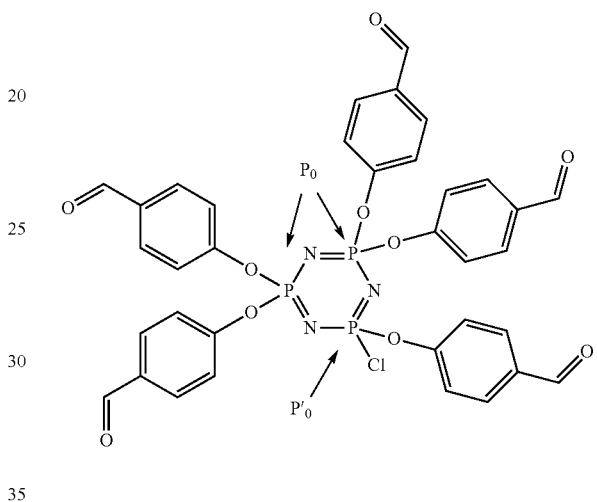

2591 mg of 4-hydroxybenzaldehyde sodium salt (18 mmol) are added at 0° C. and under an inert atmosphere to a solution containing 1.2 g of hexachlorocyclotriphosphazene (3.45 mmol) in THF (300 mL). The reaction medium is stirred for 12 hours while the temperature is allowed to gradually return to ambient temperature. The crude reaction product is evaporated to dryness then purified by "flash" chromatography on a silica column. The product is isolated in the form of translucent oil with a yield of 70%.

$^{31}$P{$^1$H} NMR (CDCl$_3$, 81 MHz): δ=9.2 (d, $^2J_{PP}$=86.6 Hz, P$_0$); 24.3 (t, $^2J_{PP}$=86.6 Hz, P'$_0$) ppm.

4.7. Synthesis of Persubstituted Cyclotriphosphazene Derivative with a Protected Amine Terminated Spacer

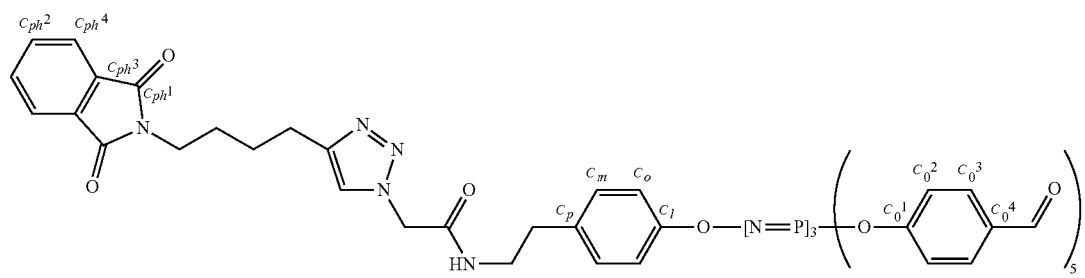

To a mixture of 2-{4-[4-(1,3-Dioxo-1,3-dihydro-isoindol-2-yl)-butyl]-[1,2,3]triazol-1-yl}-N-[2-(4-hydroxy-phenyl)-ethyl]-acetamide obtained in example 4.3 (173 mg, 0.386 mmol) and of compound of example 4.6 (272 mg, 0.351 mmol) in THF (15 mL) was added caesium carbonate (126 mg, 0.386 mmol), and the mixture was stirred at rt for 12 h. The reaction mixture was centrifugated, filtered and evaporated. The residue was purified by column flash chromatography (silica, pentane/ethyl acetate, 1:1) to give the title compound as a white oil (yield=85%). $^{31}P\ \{^1H\}$ NMR (CDCl$_3$, 121.5 MHz): δ=7.4 (s, N$_3$P$_3$); $^1H$ NMR (CDCl$_3$, 300.1 MHz): δ=1.74 (m, 4H, CH$_2$—CH$_2$—CH$_2$—CH$_2$—N, CH$_2$—CH$_2$—CH$_2$—CH$_2$—N), 2.76 (m, 4H, C$_6$H$_4$—CH$_2$—CH$_2$—CH$_2$—NH, CH$_2$—CH$_2$—CH$_2$—CH$_2$—N), 3.46 (q, $^3J_{HH}$=6.7 Hz, 2H, C$_6$H$_4$—CH$_2$—CH$_2$—NH), 3.71 (t, $^3J_{HH}$=6.5 Hz, 2H, CH$_2$—CH$_2$—CH$_2$—CH$_2$—N), 4.99 (s, 2H, CO—CH$_2$—N), 6.32 (t, $^3J_{HH}$=5.7 Hz, 1H, NH), 6.91 (d, $^3J_{HH}$=8.6 Hz, 2H, C$_o$—H), 6.98 (d, $^3J_{HH}$=8.6 Hz, 2H, C$_m$—H), 7.14 (m, 10H, C$_o^2$—H), 7.44 (s, 1H, N—CH=C), 7.73 (m, 12H, C$_o^3$—H, C$_{ph}$—H), 7.82 (m, 2H, C$_{ph}$—H), 9.94 (s, 5H, CHO); $^{13}C\ \{^1H\}$ NMR (CDCl$_3$, 75.5 MHz): δ=25.0 (s, CH$_2$—CH$_2$—CH$_2$—CH$_2$—N), 26.4 (s, CH$_2$—CH$_2$—CH$_2$—CH$_2$—N), 27.9 (s, CH$_2$—CH$_2$—CH$_2$—CH$_2$—N), 34.7 (s, C$_6$H$_4$—CH$_2$—CH$_2$—NH), 37.5 (s, CH$_2$—CH$_2$—CH$_2$—CH$_2$—N), 40.8 (s, C$_6$H$_4$—CH$_2$—CH$_2$—NH), 53.0 (s, CO—CH$_2$—N), 120.7 (s, C$_o$), 121.3 (2 s, C$_o^2$), 122.6 (s, N—CH=C), 123.2 (s, C$_{ph}^4$), 129.9 (s, C$_m$), 131.4 (s, C$_o^3$), 132.1 (s, C$_{ph}^3$), 133.6 (2 s, C$_o^4$), 133.7 (s, C$_o^4$), 134.0 (s, C$_{ph}^2$), 136.0 (s, C$_p$), 148.3 (s, N—CH=C), 148.7 (m, C$_i$), 154.6 (s, C$_o^1$), 154.7 (s, C$_o^1$), 165.4 (s, HN—CO—CH$_2$—N), 168.4 (s, 190.4 (s, CHO), 190.5 (s, CHO), 190.6 (s, CHO) ppm. FAB-MS: m/z=1187 [M+H]$^+$.

4.8. Synthesis of Chlorinated Dendrimer with a Protected Amine Terminated Spacer

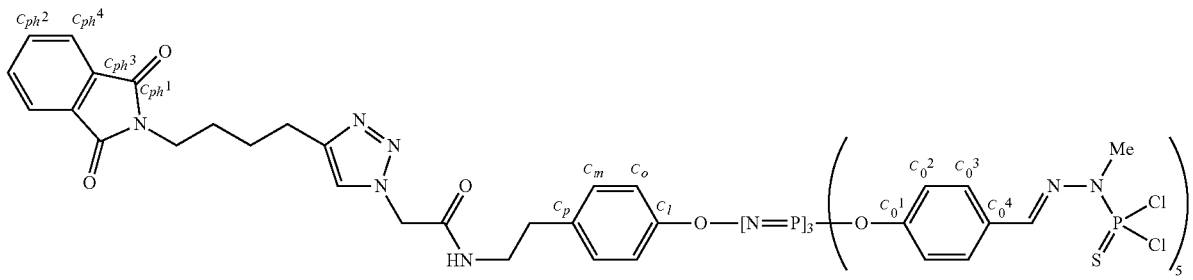

To an ice-cooled solution of N-methyldichlorothiophosphorhydrazide 2 (0.969 mmol) in chloroform (6.4 mL) was added the compound obtained in example 4.7 (200 mg, 0.169 mmol) and the mixture was stirred at rt for 2 h. After the evaporation of the solvent, the residue was diluted in the minimum of chloroform and precipitated by the addition of a large amount of pentane. This purification step was repeated twice to give dendrimer the title compound as a white solid (yield=80%). $^{31}P\{^1H\}$ NMR (CDCl$_3$, 121.5 MHz): δ=8.3 (broad s, N$_3$P$_3$), 62.4 (2 s, P=S), 62.5 (s, P=S); $^1H$ NMR (CDCl$_3$, 300.1 MHz): δ=1.76 (broad s, 4H, CH$_2$—CH$_2$—CH$_2$—CH$_2$—N, CH$_2$—CH$_2$—CH$_2$—CH$_2$—N), 2.77 (m, 4H, C$_6$H$_4$—CH$_2$—CH$_2$—NH, CH$_2$—CH$_2$—CH$_2$—CH$_2$—N), 3.43 (m, 2H, C$_6$H$_4$—CH$_2$—CH$_2$—NH), 3.49 (d, $^3J_{HP}$=14.0 Hz, 9H, N—CH$_3$), 3.50 (d, $^3J_{HP}$=14.0 Hz, 6H, N—CH$_3$), 3.71 (t, $^3J_{HH}$=6.3 Hz, 2H, CH$_2$—CH$_2$—CH$_2$—CH$_2$—N), 5.00 (s, 2H, CO—CH$_2$—N), 6.41 (broad s, 1H, NH), 6.90 (d, $^3J_{HH}$=8.5 Hz, 2H, C$_o$—H), 6.98 (m, 7H, C$_m$—H, C$_o^2$—H), 7.04 (m, 5H, C$_o^2$—H), 7.49 (s, 1H, N—CH=C), 7.61 (m, 13H, C$_o^3$—H, CH=N), 7.70 (m, 4H, CH=N, C$_{ph}$—H), 7.82 (m, 2H, C$_{ph}$—H); $^{13}C\{^1H\}$ NMR (CDCl$_3$, 75.5 MHz): δ=24.7 (s, CH$_2$—CH$_2$—CH$_2$—CH$_2$—N), 26.3 (s, CH$_2$—CH$_2$—CH$_2$—N), 27.9 (s, CH$_2$—CH$_2$—CH$_2$—CH$_2$—N), 32.0 (2 d, $^2J_{CP}$=12.9 Hz, N—CH$_3$), 34.8 (s, C$_6$H$_4$—CH$_2$—CH$_2$—NH), 37.5 (s, CH$_2$—CH$_2$—CH$_2$—CH$_2$—N), 41.0 (s, C$_6$H$_4$—CH$_2$—CH$_2$—NH), 53.2 (s, CO—CH$_2$—N), 121.1 (s, C$_o$), 121.4 (s, C$_o^2$), 123.1 (s, N—CH=C), 123.2 (s, C$_{ph}^4$), 128.6 (s, C$_o^3$), 129.8 (s, C$_m$), 131.3 (s, C$_{ph}^3$), 132.0 (s, C$_o^4$), 134.0 (s, C$_{ph}^2$), 135.3 (s, C$_p$), 140.7 (m, CH=N), 147.8 (s, N—CH=C), 148.9 (m, C$_i$), 151.7 (broad s, C$_o^1$), 165.0 (s, HN—CO—CH$_2$—N), 168.4 (s, C$_{ph}^1$) ppm.

4.9. Synthesis of Dimethylphosphonate Terminated Dendrimer with a Protected Amine Terminated Spacer

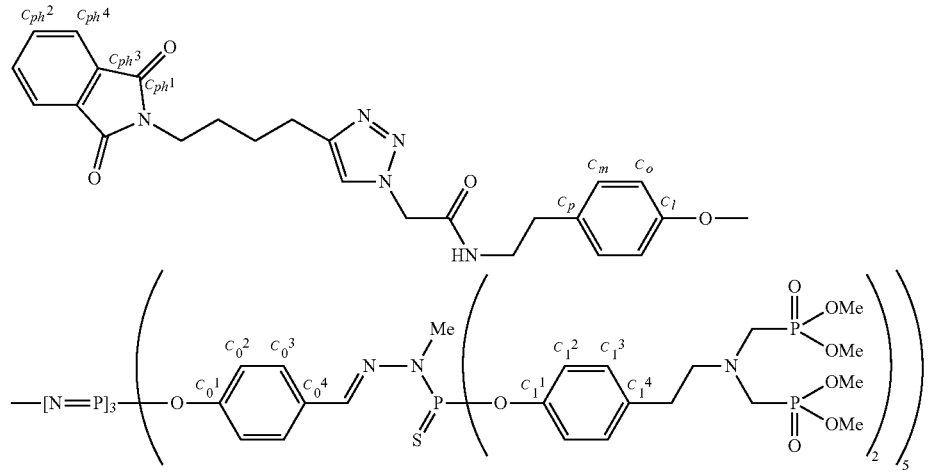

To a solution of dendrimer obtained in example 4.7 (316 mg, 0.159 mmol) in acetone (17 mL) were added phenol obtained in example 1.1 (666 mg, 1.747 mmol) and caesium carbonate (569 mg, 1.747 mmol) and the mixture was stirred at rt for 12 h. The reaction mixture was centrifugated, filtered and evaporated. The resulting crude oil was eluted on a plug of silica with acetone to remove the unreacted phenol then with acetone/methanol/water mixture (7:2:1). The resulting dendrimer solution was concentrated to dryness under reduced pressure, dissolved in 10 mL of dichloromethane, dried over sodium sulfate, filtered (micropore, 0.2 μm) and finally evaporated to dryness under reduced pressure to afford the title compound as a colourless oil (yield=85%) $^{31}P\{^{1}H\}$ NMR (CDCl$_3$, 121.5 MHz): δ=8.4 (s, N$_3$P$_3$), 26.7 (2 s, PO$_3$Me$_2$), 26.8 (2 s, PO$_3$Me$_2$), 63.1 (2 s, P=S), 63.2 (s, P=S); $^{1}$H NMR (CDCl$_3$, 300.1 MHz): δ=1.70 (broad s, 4H, CH$_2$—CH$_2$—$\underline{CH_2}$—CH$_2$—N, CH$_2$—$\underline{CH_2}$—CH$_2$—CH$_2$—N), 2.69 (m, 24H, C$_6$H$_4$—$\underline{CH_2}$—CH$_2$—N, C$_6$H$_4$—$\underline{CH_2}$—CH$_2$—NH, $\underline{CH_2}$—CH$_2$—CH$_2$—CH$_2$—N), 3.03 (m, 20H, C$_6$H$_4$—CH$_2$—$\underline{CH_2}$—N), 3.16 (d, $^{2}J_{HP}$=9.3 Hz, 40H, N—CH$_2$—P), 3.26 (m, 17H, N—CH$_3$, C$_6$H$_4$—CH$_2$—$\underline{CH_2}$—NH), 3.71 (broad d, $^{3}J_{HP}$=10.4 Hz, 122H, P(O)(OCH$_3$), CH$_2$—CH$_2$—CH$_2$—$\underline{CH_2}$—N), 4.87 (s, 2H, CO—CH$_2$—N), 6.84 (d, $^{3}J_{HH}$=8.3 Hz, 2H, C$_o$—H), 6.97 (m, 7H, C$_m$—H, C$_o^2$—H), 7.06 (m, 15H, C$_o^2$—H, C$_1^2$—H), 7.15 (d, $^{3}J_{HH}$=8.3 Hz, 20H, C$_1^3$—H), 7.41 (s, 1H, N—CH=C), 7.28 (m, 17H, C$_o^3$—H, CH=N, C$_{ph}$—H), 7.79 (m, 3H, C$_{ph}$—H); $^{13}$C{$^{1}$H} NMR (CDCl$_3$, 75.5 MHz): δ=25.1 (s, $\underline{CH_2}$—CH$_2$—CH$_2$—CH$_2$—N), 26.6 (s, CH$_2$—$\underline{CH_2}$—CH$_2$—CH$_2$—N), 28.1 (s, CH$_2$—CH$_2$—$\underline{CH_2}$—CH$_2$—N), 32.9 (m, C$_6$H$_4$—$\underline{CH_2}$—CH$_2$—N, N—CH$_3$), 34.7 (s, C$_6$H$_4$—$\underline{CH_2}$—CH$_2$—NH), 37.6 (s, CH$_2$—CH$_2$—CH$_2$—$\underline{CH_2}$—N), 40.9 (s, C$_6$H$_4$—CH$_2$—$\underline{CH_2}$—NH), 49.5 (dd, $^{1}J_{CP}$=157.5 Hz, $^{3}J_{CP}$=7.3 Hz, N—CH$_2$—P), 52.4 (s, CO—$\underline{CH_2}$—N), 52.6 (m, P(O)(OCH$_3$)), 58.1 (t, $^{3}J_{CP}$=7.6 Hz, C$_6$H$_4$—CH$_2$—$\underline{CH_2}$—N), 121.0 (s, C$_o$), 121.2 (broad d, $^{3}J_{CP}$=4.2 Hz, C$_1^2$, C$_o^2$), 122.4 (s, N—$\underline{CH}$=C), 123.2 (s, C$_{ph}^4$), 128.2 (s, C$_o^3$), 128.3 (s, C$_o^3$), 129.6 (s, C$_m$), 129.9 (s, C$_1^3$), 132.1 (s, C$_o^4$ or C$_{ph}^3$), 132.2 (s, C$_o^4$ or C$_{ph}^3$), 133.9 (s, C$_{ph}^2$), 135.6 (s, C$_p$), 136.6 (s, C$_1^4$), 138.7 (m, CH=N), 147.8 (s, N—CH=$\underline{C}$), 148.9 (broad d, $^{2}J_{CP}$=7.1 Hz, C$_1^1$, C$_i$), 151.2 (m, C$_o^1$), 165.4 (s, HN—$\underline{CO}$—CH$_2$—N), 168.3 (s, C$_{ph}^1$) ppm.

4.10. Synthesis of Persubstituted Cyclotriphosphazene Derivative with a Protected Acid Terminated Spacer

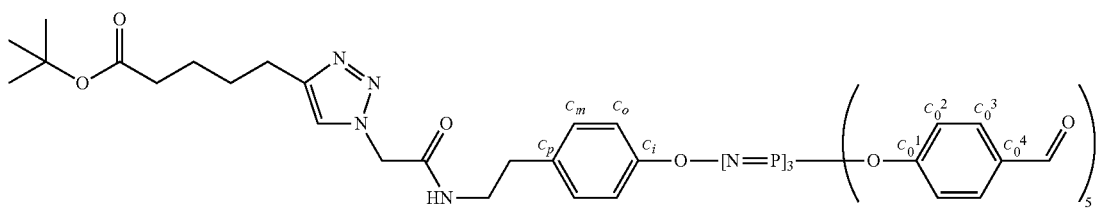

To a mixture of the compound obtained in example 4.5 (140 mg, 0.348 mmol) and compound of example 4.6 (270 mg, 0.348 mmol) in THF (5 mL) was added caesium carbonate (113 mg, 0.348 mmol), and the mixture was stirred at room temperature for 12 h. The reaction mixture was centrifugated, filtered and evaporated. The residue was purified by column flash chromatography (silica, pentane/ethyl acetate, 1:1) to give the title compound as a colourless viscous oil (yield=87%). $^{31}P\{^{1}H\}$ NMR (CDCl$_3$, 101.3 MHz): δ=7.4 (s, N$_3$P$_3$); $^{1}$H NMR (CDCl$_3$, 200.1 MHz): δ=1.41 (s, 9H, CH$_3$), 1.65 (m, 4H, CH$_2$—CH$_2$—$\underline{CH_2}$—CH$_2$—CO, CH$_2$—$\underline{CH_2}$—CH$_2$—CH$_2$—CO), 2.22 (t, $^{3}J_{HH}$=6.8 Hz, 2H, CH$_2$—CH$_2$—CH$_2$—$\underline{CH_2}$—CO), 2.72 (broad t, $^{3}J_{HH}$=7.0 Hz, 4H, C$_6$H$_4$—$\underline{CH_2}$—CH$_2$—NH, CH$_2$—CH$_2$—CH$_2$—CH$_2$—CO), 3.47 (q, $^3J_{HH}$=6.8 Hz, 2H, C$_6$H$_4$—CH$_2$—CH$_2$—NH), 4.97 (s, 2H, CO—CH$_2$—N), 6.37 (t, $^3J_{HH}$=5.4 Hz, 1H, NH), 6.91 (m, 4H, C$_o$—H, C$_m$—H), 7.11 (m, 10H, C$_0^2$—H), 7.42 (s, 1H, N—CH=C), 7.70 (m, 10H, C$_0^3$—H), 9.92 (s, 5H, CHO); $^{13}$C{$^1$H} NMR (CDCl$_3$, 62.9 MHz): δ=24.5 (s, CH$_2$—CH$_2$—CH$_2$—CH$_2$—CO), 25.3 (s, CH$_2$—CH$_2$—CH$_2$—CH$_2$—CO), 28.1 (s, CH$_3$), 28.6 (s, CH$_2$—CH$_2$—CH$_2$—CH$_2$—CO), 34.7 (s, C$_6$H$_4$—CH$_2$—CH$_2$—NH), 35.1 (s, CH$_2$—CH$_2$—CH$_2$—CH$_2$—CO), 40.8 (s, C$_6$H$_4$—CH$_2$—CH$_2$—NH), 53.0 (s, CO—CH$_2$—N), 80.2 (s, C(CH$_3$)), 120.7 (s, C$_o$), 121.3 (broad s, C$_0^2$), 122.5 (s, N—CH=C), 129.9 (s, C$_m$), 130.9 (s, C$_0^3$), 133.7 (2 s, C$_0^4$), 135.9 (s, C$_p$), 148.7 (broad s, N—CH=C, C$_i$), 154.6 (s, C$_0^1$), 165.4 (s, HN—CO—CH$_2$), 172.9 (s, CO$_2$), 190.4 (s, CHO), 190.5 (s, CHO), 190.6 (s, CHO) ppm.

4.11. Synthesis of a Fluorescent Dendrimer with a Tyramine Derived Aza-Bis-Phosphonic Acid Termination

4.11.1. Synthesis of 2,3,6,7-tetrahydro-1H,5H-3-formyl-benzo(ij)quinolizine (or paraformylated julolidine)

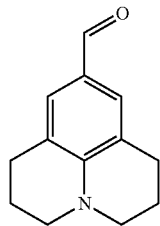 [SMILES: O=Cc1cc2c3c(c1)CCCN3CCC2]

Synthesis of this compound has been performed according to the procedure described by M. A. Haidekk et al. *Chemistry and Biology* 2001, 8, 123-131.

4.11.2. Synthesis of 2-cyano-N-[2-(4-hydroxy-phenyl)-ethyl]-acetamide

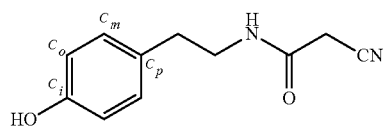

To a solution containing 1.00 g (8.84 mmol) of ethyl cyanoacetate in 13 mL of dimethylformamide under inert atmosphere were added 1.28 g (9.33 mmol) of tyramine. The mixture was stirred at 110° C. for 4 hours and then at room temperature for 12 h. The reaction mixture was then diluted with 100 mL of ethyl acetate and washed with 50 ml of an aqueous acid solution to pH=3. The aqueous phase was extracted again with 50 mL of ethyl acetate. The organic phases were combined, dried over magnesium sulfate, filtered and the solvent was evaporated under reduced pressure. The resulting brown viscous solid was then dissolved in toluene several times and the azeotropic toluene/DMF was evaporated. Finally, the solid was washed with dichloromethane and ether. The product was isolated as a pale brown solid with a yield of 65%.

RMN $^1$H (acetone d6, 200.13 MHz): δ=2.71 (t, $^3J_{HH}$=7.0 Hz, 2H, CH$_2$—C$_6$H$_4$); 3.41 (m, 2H, HN—CH$_2$); 3.56 (s, 2H, CH$_2$—CN); 6.76 (d, $^3J_{HH}$=8.3 Hz, 2H, C$_o$—H); 7.05 (d, $^3J_{HH}$=8.2 Hz, 2H, C$_m$—H); 7.52 (bs, 1H, OH); 8.21 (bs, 1H, NH) ppm.

RMN $^{13}$C{$^1$H} (acetone d$_6$, 50.32 MHz): δ=26.1 (s, CH$_2$—CN); 35.1 (s, CH$_2$—C$_6$H$_4$); 42.3 (s, HN—CH$_2$); 116.0 (s, C$_o$ et CN); 130.4 (s, C$_m$ et C$_p$); 156.6 (s, C$_i$); 162.7 (s, CO) ppm.

4.11.3. Synthesis of 2-cyano-N-[2-(4-hydroxy-phenyl)-ethyl]-3-(2,3,6,7-tetrahydro-1H,5H-3-formyl-benzo(ij)quinolizine)-acrylamide

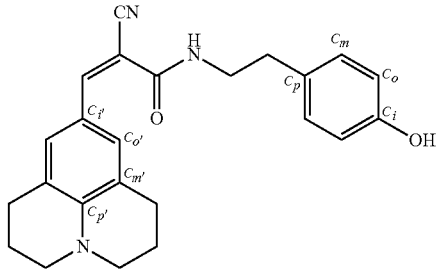

To a solution of 130 mg (0.646 mmol) of formylated julolidine in 14 mL THF were added 198 mg (0.969 mmol) of 2-cyano-N-[2-(4-hydroxyphenyl)ethyl]acetamide and 360 µl (2.580 mmol) of triethylamine. The reaction mixture was refluxed for 18 hours. The solvent was then evaporated under reduced pressure and the residue was purified by silica gel chromatography (eluent: dichloromethane containing 2% methanol). The product obtained (Rf=0.29) was isolated as an orange solid with a yield of 67%.

RMN $^1$H (DMSO d$_6$, 500.33 MHz): δ=1.86 (m, 4H, CH$_2$—CH$_2$—N); 2.64 (m, 6H, CH$_2$—CH$_2$—CH$_2$—N, HN—CH$_2$—CH$_2$); 3.31 (m, 6H, CH$_2$—CH$_2$—CH$_2$—N, HN—CH$_2$—CH$_2$); 6.66-7.01 (m, 4H, C$_m$—H, C$_o$—H); 7.42 (s, 2H, C$_{o'}$—H); 7.79 (s, 1H, HC=C—CN); 7.97 (t, $^3J_{HH}$=7.5 Hz, 1H, NH); 9.18 (s, 1H, OH) ppm.

RMN $^{13}$C{$^1$H} (DMSO d$_6$, 125.81 MHz): δ=21.1 (s, CH$_2$—CH$_2$—N); 27.6 (s, CH$_2$—CH$_2$—CH$_2$—N); 34.8 (s, CH$_2$—CH$_2$—NH); 42.0 (s, CH$_2$—NH); 49.8 (s, CH$_2$—N); 95.2 (s, C—CN); 115.6 (s, C$_o$); 118.1 (s, C$_i$); 119.0 (s, CN); 120.9 (s, C$_{m'}$); 129.9 (s, C$_m$, C$_p$); 130.6 (s, C$_o$); 147.1 (s, C$_{p'}$); 150.6 (s, HC=C—CN); 156.1 (s, C$_i$); 162.7 (s, CO) ppm.

4.11.4. Synthesis of a Dendritic AB5 Type Core with a Fluorophore Derived from Julolidine and 5 Aldehyde Functions

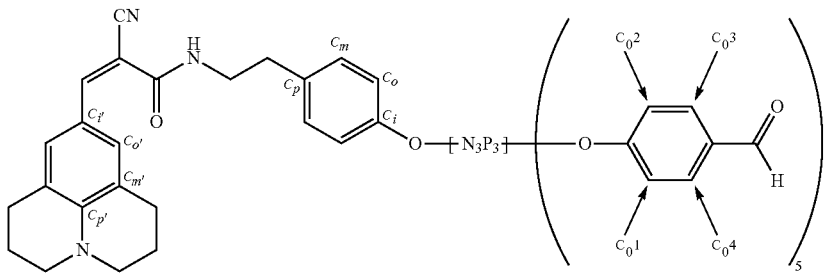

To a solution containing 92 mg (237 mmol) of 2-cyano-N-[2-(4-hydroxy-phenyl)-ethyl]-3-(2,3,6,7-tetrahydro-1H,5H-3-formyl-benzo(ij)quinolizine)-acrylamide obtained in example 4.11.3 in 10 ml of THF were added 184 mg (237 mmol) of penta (4-formyl-phenoxy)-phosphazene chlorocyclotri obtained in example 4.6 and then 155 mg (475 mmol) of cesium carbonate. The reaction mixture was stirred at room temperature for 12 hours. The cesium salts were removed by centrifugation, and after evaporation of the solvent under reduced pressure the crude residue was purified by silica gel chromatography (eluent: ethyl acetate/pentane, 1:1 acetate). The product (Rf=0.26) was isolated as an orange oil.

RMN $^{31}$P {$^1$H} (CDCl$_3$, 81.02 MHz): δ=10.9 (bs) ppm.

RMN $^1$H (acetone d$_6$, 200.13 MHz): δ=1.90 (m, 4H, CH$_2$—CH$_2$—N); 2.67 (t, $^3J_{HH}$=6.3 Hz, 4H, CH$_2$—CH$_2$—CH$_2$—N); 2.84 (distorted t, $^3J_{HH}$=6.9 Hz, 2H, HN—CH$_2$—CH$_2$); 3.25 (t, $^3J_{HH}$=6.0 Hz, 4H, CH$_2$—N); 3.58 (t, $^3J_{HH}$=6.0 Hz, 2H, HN—CH$_2$); 6.37 (t, $^3J_{HH}$=5.4 Hz, 1H, NH); 6.92 (d, $^3J_{HH}$=8.4 Hz, 2H, C$_o$—H); 7.10 (m, 12H, C$_m$—H et C$_o{}^2$—H); 7.36 (s, 2H, C$_{o'}$—H), 7.69 (d, $^3J_{HH}$=8.6 Hz, 10H, C$_o{}^3$—H); 7.95 (s, 1H, HC═C—CN); 9.90 (s; 3H, CHO), 9.92 (s; 2H, CHO) ppm.

4.11.5. Synthesis of Fluorescent Dendrimer with a PSCl$_2$ Termination

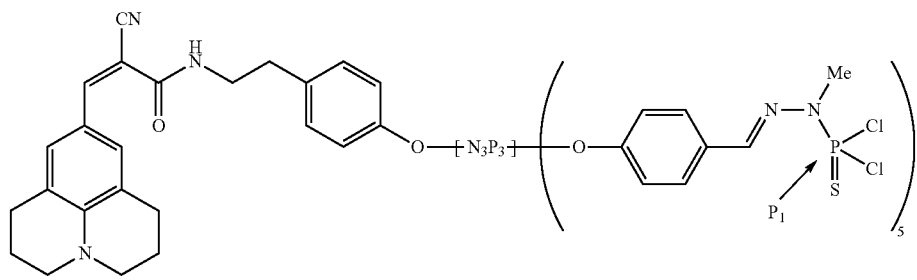

Dichlorothiophospho-(N-methyl)-hydrazide was obtained by reaction of methylhydrazine with P(S)Cl$_3$ in chloroform at −60° C.

100 mg of the compound obtained in example 4.11.4 (0.05 mmol) is added at 0° C. to a solution of dichlorothiophospho-(N-methyl)-hydrazide (0.3 mmol) in chloroform (1.5 mL). The reaction mixture is stirred for 12 hours. After evaporation of the reaction solvent, the product is diluted in a minimum amount of dichloromethane and precipitated by addition of a large volume of pentane. This treatment is carried out three times. The product is isolated with a yield of 90%.

NMR $^{31}$P {$^1$H} (CDCl$_3$, 81.02 MHz): δ=11.8 (bs, N$_3$P$_3$); 65.9 (s, P$_1$); 66.0 (s, P$_1$); 66.1 (s, P$_1$) ppm.

4.11.6. Synthesis of a Fluorescent Dendrimer with a Tyramine Derived Aza-Bis-Phosphonate Termination

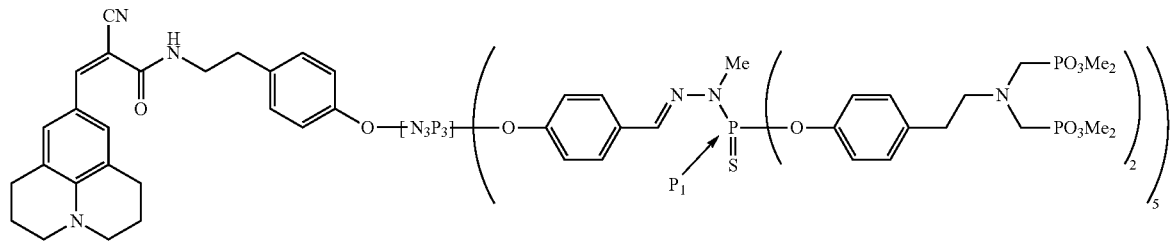

To a solution of 100 mg of the fluorescent dendrimer with PSCl2 termination obtained in example 4.11.5 (0.052 mmol) in 5 mL of THF were added 339 mg of cesium carbonate (1.04 mmol) and 198 mg of phenol aza-bis-dimethyl-phosphonate derivative tyramine obtained in example 1.1 (0.520 mmol). The mixture was stirred for 12 hours at room temperature and the salts formed were removed by centrifugation. After evaporation of the reaction solvent, the product was dissolved in a minimum amount of THF and precipitated by adding a large volume of pentane. The product was isolated with a yield of 70%.

RMN $^{31}$P {$^1$H} (CDCl$_3$, 81.02 MHz): δ=11.9 (s, N$_3$P$_3$); 30.3 (s, PO$_3$Me$_2$); 30.6 (s, PO$_3$Me$_2$); 66.7 (s, P$_1$); 66.8 (s, P$_1$) ppm.

4.11.7. Synthesis of a Fluorescent Dendrimer with a Sodium Salt Tyramine Derived Aza-Bis-Phosphonic Acid Termination

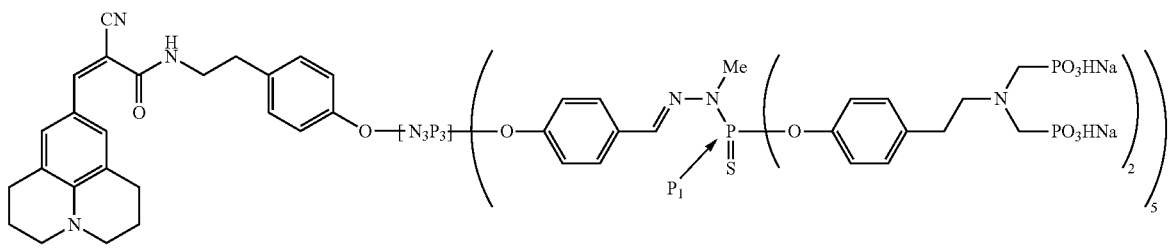

To a solution containing 100 mg of the fluorescent dendrimer obtained in example 4.11.6 (0.019 mmol) in acetonitrile (5 mL) at 0° C. under an inert atmosphere was slowly added 110 µl of bromotrimethylsilane (0.838 mmol). At the end of the addition, the reaction mixture was stirred at room temperature for 12 hours. The reaction mixture was then evaporated to dryness and then were added 2.5 mL of methanol at room temperature. The reaction mixture was stirred for 1 hour and then evaporated to dryness. This methanolysis was repeated a second time and the product was washed several times with diethyl ether. The resulting product, for NMR considerations, was then converted to its sodium salt. The product was first brought into contact with water (1 mL) and 4.8 mL of aqueous sodium hydroxide (0.1966 N) were then added. After complete dissolution of the dendrimer, the solution was lyophilized to provide the dendrimer as a white powder with a yield of 75%.

RMN $^{31}$P {$^1$H} (D$_2$O/CD$_3$CN, 81.02 MHz): δ=10.3 (bs, PO$_3$HNa); 13.1 (s, N$_3$P$_3$); 64.5 (s, P$_1$) ppm.

4.12. Synthesis of Chlorinated Dendrimer with a Protected Acid Terminated Spacer

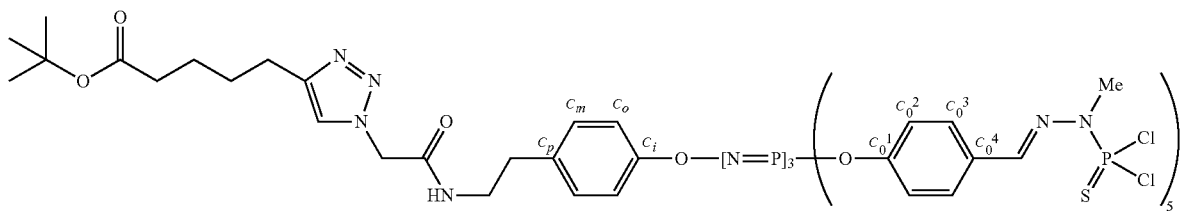

To an ice-cooled solution of N-methyldichlorothiophosphorhydrazide described in example 4.11.5 (0.655 mmol) in chloroform (4.3 mL) was added the compound of example 4.10 (130 mg, 0.114 mmol) and the mixture was stirred at room temperature for 2 h. After the evaporation of the solvent, the residue was diluted in the minimum of chloroform and precipitated by the addition of a large amount of pentane. This purification step was repeated twice to give the title compound as a white solid (yield=85%). $^{31}P\{^1H\}$ NMR (CDCl$_3$, 121.5 MHz): δ=8.3 (broad s, N$_3$P$_3$), 62.4 (2 s, P=S), 62.5 (s, P=S); $^1$H NMR (CDCl$_3$, 300.1 MHz): δ=1.45 (s, 9H, C(CH$_3$)), 1.71 (m, 4H, CH$_2$—CH$_2$—CH$_2$—CH$_2$—CO, CH$_2$—CH$_2$—CH$_2$—CH$_2$—CO), 2.27 (t, $^3J_{HH}$=7.1 Hz, 2H, CH$_2$—CH$_2$—CH$_2$—CH$_2$—CO), 2.79 (m, 4H, C$_6$H$_4$—CH$_2$—CH$_2$—NH, CH$_2$—CH$_2$—CH$_2$—CH$_2$—CO), 3.45 (broad s, 2H, C$_6$H$_4$—CH$_2$—CH$_2$—NH), 3.50 (d, $^3J_{HP}$=14.0 Hz, 9H, N—CH$_3$), 3.51 (d, $^3J_{HP}$=14.0 Hz, 6H, N—CH$_3$), 5.07 (broad s, 2H, CO—CH$_2$—N), 6.68 (broad s, 1H, NH), 6.90 (d, $^3J_{HH}$=8.0 Hz, 2H, C$_o$—H), 6.99 (broad d, $^3J_{HH}$=8.6 Hz, 6H, C$_o$,—H, C$_o^2$—H), 7.05 (d, $^3J_{HH}$=8.6 Hz, 6H, C$_o^2$—H), 7.47 (s, 1H, N—CH=C), 7.60 (d, 10H, C$_o^3$—H), 7.64 (broad s, 3H, CH=N), 7.68 (broad s, 2H, CH=N); $^{13}$C{$^1$H} NMR (CDCl$_3$, 75.5 MHz): δ=24.4 (s, CH$_2$—CH$_2$—CH$_2$—CH$_2$—CO), 24.9 (s, CH$_2$—CH$_2$—CH$_2$—CH$_2$—CO), 28.1 (s, C(CH$_3$)), 28.4 (s, CH$_2$—CH$_2$—CH$_2$—CH$_2$—CO), 32.0 (d, $^2J_{CP}$=12.9 Hz, N—CH$_3$), 32.1 (d, $^2J_{CP}$=12.9 Hz, N—CH$_3$), 34.8 (s, C$_6$H$_4$—CH$_2$—CH$_2$—NH), 35.1 (s, CH$_2$—CH$_2$—CH$_2$—CH$_2$—CO), 41.1 (s, C$_6$H$_4$—CH$_2$—CH$_2$—NH), 53.4 (s, CO—CH$_2$—N), 80.3 (s, C(CH$_3$)), 121.1 (s, C$_o$), 121.4 (broad s, C$_o^2$), 123.5 (s, N—CH=C), 128.6 (s, C$_o^3$), 129.7 (s, C$_m$), 131.3 (broad s, C$_o^4$), 135.3 (s, C$_p$), 140.7 (m, CH=N), 147.7 (s, N—CH=C), 148.9 (m, C$_i$), 151.7 (m, C$_o^1$), 164.7 (s, HN—CO—CH$_2$), 172.8 (s, CO$_2$) ppm.

4.13 Synthesis of Dimethylphosphonate Terminated Dendrimer with a Protected Acid Terminated Spacer

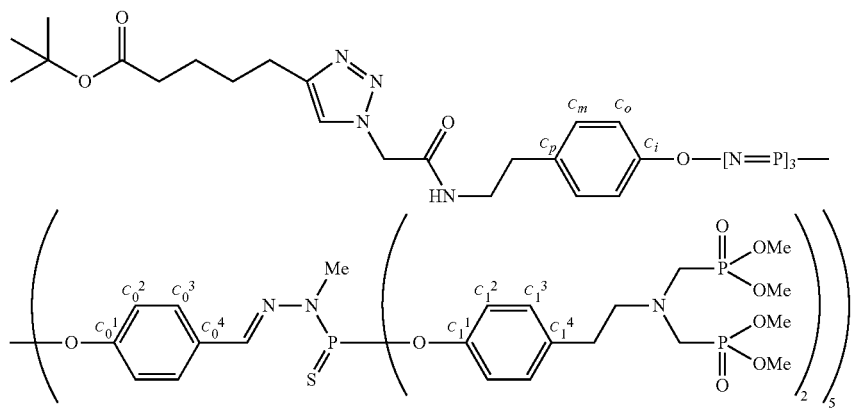

To a solution of compound obtained in example 4.12 (315 mg, 0.162 mmol) in acetone (17 mL) were added phenol of example 1.1 (680 mg, 1.783 mmol) and caesium carbonate (581 mg, 1.783 mmol) and the mixture was stirred at room temperature for 12 h. The reaction mixture was centrifugated, filtered and evaporated. The resulting crude oil was eluted on a plug of silica with acetone to remove the unreacted phenol then with acetone/methanol/water mixture (7:2:1). The resulting dendrimer solution was concentrated to dryness under reduced pressure, dissolved in 10 mL of dichloromethane, dried over sodium sulfate, filtered (micropore, 0.2 µm) and finally evaporated to dryness under reduced pressure to afford the title compound as a sticky solid (yield=90%) $^{31}$P{$^1$H} NMR (CDCl$_3$, 121.5 MHz): δ=8.4 (broad s, N$_3$P$_3$), 26.7 (2 s, PO$_3$Me$_2$), 26.8 (s, PO$_3$Me$_2$), 63.0 (s, P=S), 63.1 (s, P=S); $^1$H NMR (CDCl$_3$, 300.1 MHz): δ=1.38 (s, 9H, C(CH$_3$)), 1.62 (m, 4H, CH$_2$—CH$_2$—CH$_2$—CH$_2$—CO, CH$_2$—CH$_2$—CH$_2$—CH$_2$—CO), 2.19 (t, $^3J_{HH}$=7.1 Hz, 2H, CH$_2$—CH$_2$—CH$_2$—CH$_2$—CO), 2.70 (m, 24H, C$_6$H$_4$—CH$_2$—CH$_2$—NH, CH$_2$—CH$_2$—CH$_2$—CH$_2$—CO, C$_6$H$_4$—CH$_2$—CH$_2$—N), 2.99 (m, 20H, C$_6$H$_4$—CH$_2$—CH$_2$—N), 3.13 (d, $^2J_{HP}$=9.3 Hz, 40H, N—CH$_2$—P), 3.23 (m, 17H, N—CH$_3$, C$_6$H$_4$—CH$_2$—CH$_2$—NH), 3.67 (d, $^3J_{HP}$=10.5 Hz, 120H, P(O)(OCH$_3$)), 4.85 (broad s, 2H, CO—CH$_2$—N), 6.81 (d, $^3J_{HH}$=8.3 Hz, 2H, $C_o$—H), 6.99 (m, 52H, $C_m$—H, $C_o^2$—H, $C_1^2$—H, $C_1^3$—H), 7.39 (s, 1H, N—CH=C), 7.58 (m, 15H, $C_o^3$—H, CH=N); $^{13}$C{$^1$H} NMR (CDCl$_3$, 75.5 MHz): δ=24.5 (s, CH$_2$—CH$_2$—CH$_2$—CH$_2$—CO), 25.3 (s, CH$_2$—CH$_2$—CH$_2$—CH$_2$—CO), 28.1 (s, C(CH$_3$)), 28.6 (s, CH$_2$—CH$_2$—CH$_2$—CH$_2$—CO), 32.9 (broad s, C$_6$H$_4$—CH$_2$—CH$_2$—N, N—CH$_3$), 34.6 (s, C$_6$H$_4$—CH$_2$—CH$_2$—NH), 35.1 (s, CH$_2$—CH$_2$—CH$_2$—CH$_2$—CO), 40.9 (s, C$_6$H$_4$—CH$_2$—CH$_2$—NH), 49.4 (dd, $^1J_{CP}$=157.6 Hz, $^3J_{CP}$=7.2 Hz, N—CH$_2$—P), 52.7 (m, P(O)(OCH$_3$)), 53.4 (s, CO—CH$_2$—N), 58.1 (t, $^3J_{CP}$=7.5 Hz, C$_6$H$_4$—CH$_2$—CH$_2$—N), 80.1 (s, C(CH$_3$)), 121.0 (s, C$_o$), 121.2 (broad d, $^3J_{CP}$=4.1 Hz, C$_1^2$, C$_o^2$), 122.4 (s, N—CH=C), 128.3 (s, C$_o^3$), 129.6 (s, C$_m$), 129.9 (s, C$_1^3$), 132.1 (d, $^4J_{CP}$=5.3 Hz, C$_o^4$), 135.6 (s, C$_p$), 136.5 (s, C$_1^4$), 138.7 (d, $^3J_{CP}$=13.9 Hz, CH=N), 147.9 (s, N—CH=C), 148.9 (broad d, $^2J_{CP}$=6.9 Hz, C$_1^1$, C$_i$), 151.2 (m, C$_o^1$), 165.4 (s, HN—CO—CH$_2$), 172.9 (s, CO$_2$) ppm.

4.14. Synthesis of Dimethylphosphonate Terminated Dendrimer with a Deprotected Acid Terminated Spacer

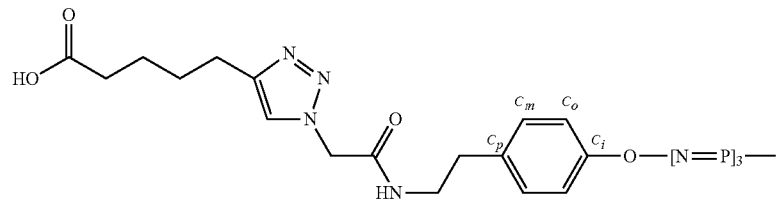

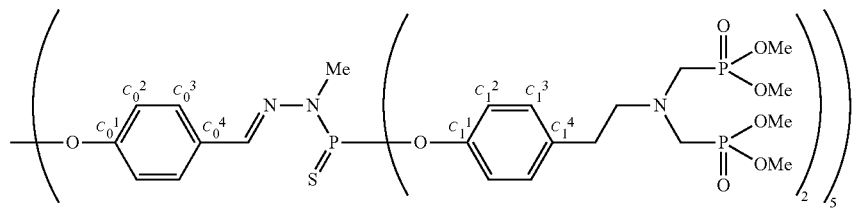

Compound of example 4.13 (107 mg, 0.020 mmol) was dissolved in a solution of 30% of TFA in dichloromethane, and the reaction mixture was allowed to stir at rt for 1.5 h and evaporated to dryness. This sequence was repeated 6 times and the residue was suspended into ethyl acetate so that remaining traces of TFA were removed upon evaporation to dryness. The residue was purified by column chromatography (silica, dichloromethane/methanol, 85:15) to give title compound as a sticky solid (yield=85%). $^{31}$P {$^1$H} NMR (CDCl$_3$, 121.5 MHz): δ=8.4 (broad s, N$_3$P$_3$), 26.8 (s, PO$_3$Me$_2$), 63.1 (s, P=S), 63.2 (s, P=S); $^1$H NMR (CDCl$_3$, 300.1 MHz): δ=1.63 (m, 4H, CH$_2$—CH$_2$—CH$_2$—CH$_2$—CO, CH$_2$—CH$_2$—CH$_2$—CH$_2$—CO), 2.25 (m, 2H, CH$_2$—CH$_2$—CH$_2$—CH$_2$—CO), 2.73 (m, 24H, C$_6$H$_4$—CH$_2$—CH$_2$—NH, CH$_2$—CH$_2$—CH$_2$—CH$_2$—CO, C$_6$H$_4$—CH$_2$—CH$_2$—N), 3.03 (m, 20H, C$_6$H$_4$—CH$_2$—CH$_2$—N), 3.17 (d, $^2J_{HP}$=9.3 Hz, 40H, N—CH$_2$—P), 3.26 (m, 17H, N—CH$_3$, C$_6$H$_4$—CH$_2$—CH$_2$—NH), 3.70 (d, $^3J_{HP}$=10.5 Hz, 120H, P(O)(OCH$_3$)), 4.82 (broad s, 2H, CO—CH$_2$—N), 6.88 (d, $^3J_{HH}$=8.3 Hz, 2H, C$_O$—H), 7.08 (m, 52H, C$_m$—H, C$_o^2$—H, C$_1^2$—H, C$_1^3$—H), 7.30 (s, 1H, N—CH=C), 7.61 (m, 15H, C$_o^3$—H, CH=N); $^{13}$C{$^1$H} NMR (CDCl$_3$, 75.5 MHz): δ=24.3 (s, CH$_2$—CH$_2$—CH$_2$—CH$_2$—CO), 25.2 (s, CH$_2$—CH$_2$—CH$_2$—CH$_2$—CO), 28.5 (s, CH$_2$—CH$_2$—CH$_2$—CH$_2$—CO), 32.9 (broad s, C$_6$H$_4$—CH$_2$—CH$_2$—N, N—CH$_3$), 33.6 (s, CH$_2$—CH$_2$—CH$_2$—CH$_2$—CO), 34.5 (s, C$_6$H$_4$—CH$_2$—CH$_2$—NH), 40.7 (s, C$_6$H$_4$—CH$_2$—CH$_2$—NH), 49.4 (dd, $^1J_{CP}$=157.9 Hz, $^3J_{CP}$=7.1 Hz, N—CH$_2$—P), 52.7 (broad s, P(O)(OCH$_3$)), 53.4 (s, CO—CH$_2$—N), 58.1 (t, $^3J_{CP}$=7.4 Hz, C$_6$H$_4$—CH$_2$—CH$_2$—N), 120.4 (s, C$_o$), 121.2 (broad d, $^3J_{CP}$=4.1 Hz, C$_1^2$, C$_o^2$), 122.5 (s, N—CH=C), 128.3 (s, C$_o^3$), 129.7 (s, C$_m$), 129.9 (s, C$_1^3$), 132.2 (d, $^4J_{CP}$=5.5 Hz, C$_o^4$), 135.6 (s, C$_p$), 136.5 (s, C$_1^4$), 138.8 (m, CH=N), 147.9 (s, N—CH=C), 148.9 (broad d, $^2J_{CP}$=7.4 Hz, C$_1^1$, C$_i$), 151.4 (broad s, C$_o^1$), 165.3 (s, HN—CO—CH$_2$), 175.1 (s, CO$_2$) ppm.

4.15. Synthesis of Amine Terminated Spacer

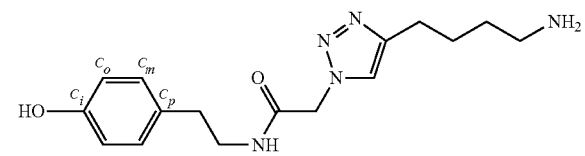

To a solution of 2-{4-[4-(1,3-Dioxo-1,3-dihydro-isoindol-2-yl)-butyl]-[1,2,3]triazol-1-yl}-N-[2-(4-hydroxy-phenyl)-ethyl]-acetamide obtained in example 4.3 (200 mg, 0.047 mmol) in ethanol (5 mL) was added hydrazine hydrate (0.070 mL, 2.23 mmol) and the reaction mixture was refluxed for 3 h. The mixture was evaporated to dryness to remove solvent and excess of hydrazine, resulting in a residue made of the title compound and by-product phthalhydrazide. The crude product was used without further purification. $^1$H NMR (CD$_3$OD, 200.3 MHz): δ=1.70 (m, 4H, CH$_2$—CH$_2$—CH$_2$—CH$_2$—N, CH$_2$—CH$_2$—CH$_2$—CH$_2$—N), 2.72 (m, 4H, C$_6$H$_4$—CH$_2$—CH$_2$—NH, CH$_2$—CH$_2$—CH$_2$—CH$_2$—N), 2.86 (m, 2H, C$_6$H$_4$—CH$_2$—CH$_2$—NH), 3.41 (m, 2H, CH$_2$—CH$_2$—CH$_2$—CH$_2$—N), 5.07 (s, 2H, CO—CH$_2$—N), 6.72 (d, $^3J_{HH}$=8.5 Hz, 2H, C$_o$—H), 7.02 (d, $^3J_{HH}$=8.5 Hz, 2H, C$_m$—H), 7.68 (s, 1H, N—CH=C) ppm.

4.16 Synthesis of the Biotinylated Spacer

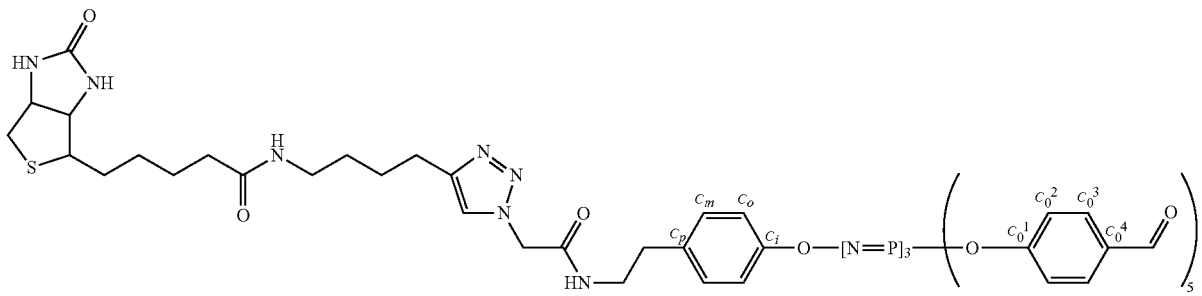

To a solution of biotin (65 mg, 0.265 mmol) and DIPEA (0.046 mL, 0.265 mmol) in DMF (2 mL) were added a solution of TBTU (89 mg, 0.277 mmol) in DMF (3 mL) and a solution of the compound of example 4.15 (80 mg, 0.252 mmol) in DMF (5 mL). The reaction mixture was stirred at room temperature for 24 h. The solvent was evaporated to dryness and the residue was purified by column chromatography (silica, dichloromethane/methanol, 9:1) to give title compound as a colourless oil (yield=70%). $^1$H NMR (CD$_3$OD, δ00.3 MHz): δ=1.45 (m, 2H, CO—CH$_2$—CH$_2$—CH$_2$—CH$_2$), 1.67 (m, 8H, CO—CH$_2$—CH$_2$—CH$_2$—CH$_2$, CO—CH$_2$—CH$_2$—CH$_2$—CH$_2$, CH$_2$—CH$_2$—CH$_2$—CH$_2$—NH, CH$_2$—CH$_2$—CH$_2$—CH$_2$—NH), 2.21 (t, $^3J_{HH}$=7.3 Hz, 2H, CO—CH$_2$—CH$_2$—CH$_2$—CH$_2$), 2.74 (m, 5H, C$_6$H$_4$—CH$_2$—CH$_2$—NH, CH$_2$—CH$_2$—CH$_2$—CH$_2$—NH, CH$_2$—S), 2.93 (dd, $^2J_{HH}$=5.0 Hz, $^3J_{HH}$=12.7 Hz, 1H, CH$_2$—S), 3.22 (m, 3H, CH$_2$—CH$_2$—CH$_2$—CH$_2$—NH, CH—S), 3.43 (t, $^3J_{HH}$=7.2 Hz, 2H, C$_6$H$_4$—CH$_2$—CH$_2$—NH), 4.30 (m, 1H, CH—CH—NH), 4.50 (m, 1H, CH$_2$—CH—NH), 5.06 (s, 2H, CO—CH$_2$—N), 6.72 (m, 2H, C$_o$—H), 7.03 (broad d, $^3J_{HH}$=8.4 Hz, 2H, C$_m$—H), 7.69 (s, 1H, N—CH=C); $^{13}$C{$^1$H} NMR (CD$_3$OD, 125.8 MHz): δ=24.5 (s, CH$_2$—CH$_2$—CH$_2$—CH$_2$—NH), 25.5 (s, CO—CH$_2$—CH$_2$—CH$_2$—CH$_2$), 26.3 (s, CH$_2$—CH$_2$—CH$_2$—CH$_2$—NH), 28.1 (s, CO—CH$_2$—CH$_2$—CH$_2$—CH$_2$), 28.4 (2 s, CO—CH$_2$—CH$_2$—CH$_2$—CH$_2$, CH$_2$—CH$_2$—CH$_2$—CH$_2$—NH), 34.1 (s, C$_6$H$_4$—CH$_2$—CH$_2$—NH), 35.4 (s, CO—CH$_2$—CH$_2$—CH$_2$—CH$_2$), 38.6 (s, CH$_2$—CH$_2$—CH$_2$—CH$_2$—NH), 39.6 (s, CH$_2$—S), 41.0 (s, C$_6$H$_4$—CH$_2$—CH$_2$—NH), 51.8 (s, CO—CH$_2$—N), 55.6 (s, CH—S), 60.2 (s, CH$_2$—CH—NH), 61.9 (s, CH—CH—NH), 114.9 (s, C$_o$), 123.3 (s, N—CH=C), 129.4 (s, C$_m$), 129.5 (s, C$_p$), 147.5 (N—CH=C), 155.6 (s, C$_i$), 164.7 (s, HN—CO—NH), 166.4 (s, HN—CO—CH$_2$—N), 174.6 (s, (CH$_2$)$_4$—NH—CO) ppm.

4.17. Synthesis of Persubstituted Cyclotriphosphazene Derivative with a Biotinylated Spacer To a mixture of the compound of example 4.16 (65 mg, 0.120 mmol) and compound of example 4.6 (93 mg, 0.120 mmol) in DMF (5 mL) was added caesium carbonate (39 mg, 0.120 mmol), and the mixture was stirred at room temperature for 12 h. The reaction mixture was centrifugated, filtered and evaporated. The residue was purified by column flash chromatography (silica, dichloromethane/methanol, 9:1) to give title compound as a white oil (yield=85%). $^{31}$P {$^1$H} NMR (CDCl$_3$, 81.0 MHz): δ=8.4 (s, N$_3$P$_3$); $^1$H NMR (CDCl$_3$, 300.1 MHz): δ=1.42 (broad s, 2H, CO—CH$_2$—CH$_2$—CH$_2$—CH$_2$), 1.72 (m, 8H, CO—CH$_2$—CH$_2$—CH$_2$—CH$_2$, CO—CH$_2$—CH$_2$—CH$_2$—CH$_2$, CH$_2$—CH$_2$—CH$_2$—CH$_2$—NH, CH$_2$—CH$_2$—CH$_2$—CH$_2$—NH), 2.24 (broad s, 2H, CO—CH$_2$—CH$_2$—CH$_2$—CH$_2$), 2.72 (m, 5H, C$_6$H$_4$—CH$_2$—CH$_2$—NH, CH$_2$—CH$_2$—CH$_2$—CH$_2$—NH, CH$_2$—S), 2.88 (m, 1H, CH$_2$—S), 3.18 (m, 3H, CH$_2$—CH$_2$—CH$_2$—CH$_2$—NH, CH—S), 3.43 (broad s, 2H, C$_6$H$_4$—CH$_2$—CH$_2$—NH), 4.32 (broad s, 1H, CH—CH—NH), 4.49 (broad s, 1H, CH$_2$—CH—NH), 5.03 (broad s, 2H, CO—CH$_2$—N), 6.53 (broad s, 1H, CH—CH—NH—CO or CH$_2$—CH—NH—CO), 6.73 (broad s, 1H, CH$_2$—CH—NH—CO), 6.88 (broad s, 2H, C$_o$—H), 7.00 (broad s, 2H, C$_m$—H), 7.12 (m, 10H, C$_o^2$—H), 7.29 (m, 1H, (CH$_2$)$_4$—NH—CO), 7.51 (broad s, 1H, NH—CO—CH$_2$—N), 7.55 (broad s, 1H, N—CH=C), 7.72 (m, 10H, C$_o^3$—H), 9.93 (2 s, 5H, CHO); $^{13}$C{$^1$H} NMR (CDCl$_3$, 75.5 MHz): δ=24.9 (s, CH$_2$—CH$_2$—CH$_2$—CH$_2$—NH), 25.7 (s, CO—CH$_2$—CH$_2$—CH$_2$—CH$_2$), 26.4 (s, CH$_2$—CH$_2$—CH$_2$—CH$_2$—NH), 28.1 (s, CO—CH$_2$—CH$_2$—CH$_2$—CH$_2$), 28.5 (2 s, CO—CH$_2$—CH$_2$—CH$_2$—CH$_2$, CH$_2$—CH$_2$—CH$_2$—CH$_2$—NH), 34.6 (s, C$_6$H$_4$—CH$_2$—CH$_2$—NH), 35.9 (s, CO—CH$_2$—CH$_2$—CH$_2$—CH$_2$), 39.0 (s, CH$_2$—CH$_2$—CH$_2$—CH$_2$—NH), 40.6 (s, CH$_2$—S), 41.0 (s, C$_6$H$_4$—CH$_2$—CH$_2$—NH), 52.8 (s, CO—CH$_2$—N), 55.7 (s, CH—S), 60.2 (s, CH$_2$—CH—NH), 61.9 (s, CH—CH—NH), 120.7 (s, C$_o$), 121.3 (s, C$_o^2$), 123.0 (s, N—CH=C), 129.9 (s, C$_m$), 133.4 (s, C$_o^3$), 133.6 (s, C$_o^4$), 133.7 (s, C$_o^4$), 136.3 (s, C$_p$), 148.0 (s, N—CH=C)), 148.5 (s, C$_i$), 154.6 (broad s, C$_o^1$), 164.0 (s, HN—CO—NH), 165.7 (s, HN—CO—CH$_2$—N), 173.4 (s, (CH$_2$)$_4$—NH—CO), 190.5 (s, CHO), 190.6 (s, CHO), 190.8 (s, CHO) Ppm.

4.18. Synthesis of Chlorinated Dendrimer with a Biotinylated Spacer

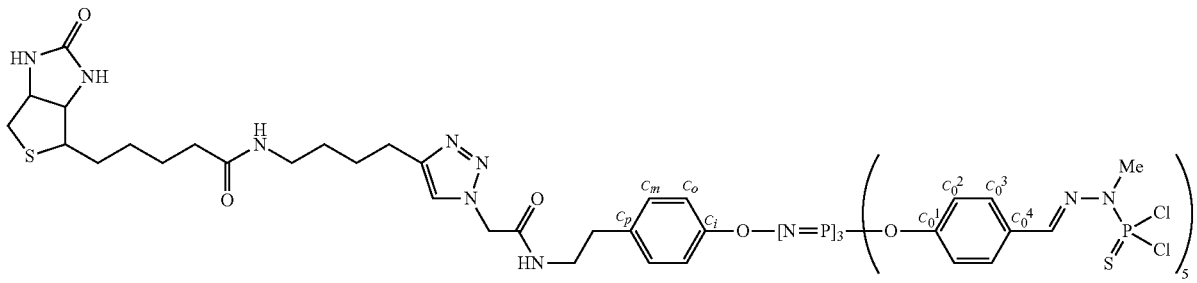

To an ice-cooled solution of N-methyldichlorothiophosphorhydrazide described in example 4.11.5 (0.355 mmol) in chloroform (2.3 mL) was added the compound of example 4.17 (70 mg, 0.055 mmol) and the mixture was stirred at room temperature for 2 h. After the evaporation of the solvent, the residue was diluted in the minimum of chloroform and precipitated by the addition of a large amount of pentane. This purification step was repeated twice to give the title compound as a white solid (yield=90%). $^{31}$P {$^1$H} NMR (CDCl$_3$, 101.3 MHz): δ=8.3 (broad s, N$_3$P$_3$), 62.3 (s, P=S), 62.6 (s, P=S); $^1$H NMR (CDCl$_3$, 300.1 MHz): δ=1.42 (m, 2H, CO—CH$_2$—CH$_2$—CH$_2$—CH$_2$), 1.70 (m, 8H, CO—CH$_2$—CH$_2$—CH$_2$—CH$_2$, CO—CH$_2$—CH$_2$—CH$_2$—CH$_2$, CH$_2$—CH$_2$—CH$_2$—CH$_2$—NH, CH$_2$—CH$_2$—CH$_2$—CH$_2$—NH), 2.28 (m, 2H, CO—CH$_2$—CH$_2$—CH$_2$—CH$_2$), 2.83 (broad s, 6H, C$_6$H$_4$—CH$_2$—CH$_2$—NH, CH$_2$—CH$_2$—CH$_2$—CH$_2$—NH, CH$_2$—S), 3.12 (m, 3H, CH$_2$—CH$_2$—CH$_2$—CH$_2$—NH, CH—S), 3.48 (broad d, $^3$J$_{HP}$=13.8 Hz, 17H, N—CH$_3$, C$_6$H$_4$—CH$_2$—CH$_2$—NH), 4.34 (broad s, 1H, CH—CH—NH), 4.52 (broad s, 1H, CH$_2$—CH—NH), 5.31 (broad s, 2H, CO—CH$_2$—N), 6.95 (m, 16H, C$_o$—H, C$_m$—H, C$_o^2$—H, CH—CH—NH—CO, CH$_2$—CH—NH—CO), 7.63 (m, 17H, N—CH=C, C$_o^3$—H, CH=N), 7.96 (s, 1H, (CH$_2$)$_4$—NH—CO), 8.28 (s, 1H, NH—CO—CH$_2$—N); $^{13}$C{$^1$H} NMR (CDCl$_3$, 75.5 MHz): δ=24.1 (s, CH$_2$—CH$_2$—CH$_2$—CH$_2$—NH), 25.9 (broad s, CO—CH$_2$—CH$_2$—CH$_2$—CH$_2$, CH$_2$—CH$_2$—CH$_2$—CH$_2$—NH), 28.0 (s, CO—CH$_2$—CH$_2$—CH$_2$—CH$_2$), 28.3 (broad s, CO—CH$_2$—CH$_2$—CH$_2$—CH$_2$, CH$_2$—CH$_2$—CH$_2$—CH$_2$—NH), 32.0 (d, $^2$J$_{CP}$=12.8 Hz, N—CH$_3$), 32.1 (d, $^2$J$_{CP}$=12.8 Hz, N—CH$_3$), 34.7 (s, C$_6$H$_4$—CH$_2$—CH$_2$—NH), 35.4 (s, CO—CH$_2$—CH$_2$—CH$_2$—CH$_2$), 39.1 (s, CH$_2$—CH$_2$—CH$_2$—CH$_2$—NH), 40.7 (s, CH$_2$—S), 41.2 (s, C$_6$H$_4$—CH$_2$—CH$_2$—NH), 53.3 (s, CO—CH$_2$—N), 55.7 (s, CH—S), 60.5 (s, CH$_2$—CH—NH), 61.9 (s, CH—CH—NH), 121.0 (s, C$_o$), 121.3 (s, C$_o^2$), 123.0 (s, N—CH=C), 128.9 (s, C$_o^3$), 129.8 (s, C$_m$), 131.3 (s, C$_o^4$), 135.8 (s, C$_p$), 140.9 (m, CH=N), 145.7 (N—CH=C), 148.7 (broad s, C$_i$), 151.7 (s, C$_o^1$), 164.2 (s, HN—CO—NH), 164.6 (HN—CO—CH$_2$—N), 174.6 (s, (CH$_2$)$_4$—NH—CO) ppm.

4.19. Synthesis of Dimethylphosphonate Terminated Dendrimer with a Biotinylated Spacer

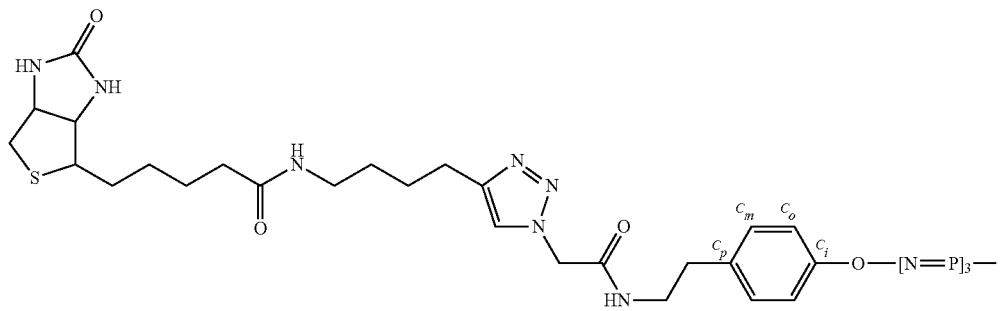

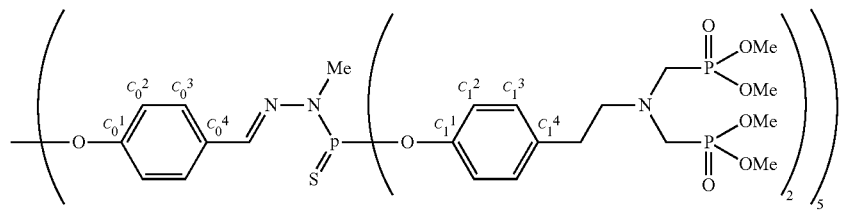

To a solution of the compound of example 4.18 (48 mg, 0.023 mmol) in acetone (5 mL) were added phenol of example 1.1 (92 mg, 0.241 mmol) and caesium carbonate (79 mg, 0.241 mmol) and the mixture was stirred at room temperature for 12 h. The reaction mixture was centrifugated, filtered and evaporated. The resulting crude oil was eluted on a plug of silica with acetone to remove the unreacted phenol then with acetone/methanol/water mixture (7:2:1). The resulting dendrimer solution was concentrated to dryness under reduced pressure, dissolved in 10 mL of dichloromethane, dried over sodium sulfate, filtered (micropore, 0.2 μm) and finally evaporated to dryness under reduced pressure to afford title compound as a colourless oil (yield=90%). $^{31}P$ $\{^1H\}$ NMR (acetone-d6, 202.5 MHz): δ=8.9 (s, $N_3P_3$), 26.3 (2 s, $PO_3Me_2$), 26.4 (2 s, $PO_3Me_2$), 62.8 (2 s, P=S); $^1H$ NMR (acetone-d6, 500.3 MHz): δ=1.42 (m, 2H, CO—$CH_2$—$CH_2$—$\underline{CH_2}$—$CH_2$), 1.53 (m, 2H, $CH_2$—$CH_2$—$\underline{CH_2}$—$CH_2$—NH), 1.62 (m, 2H, CO—$CH_2$—$\underline{CH_2}$—$CH_2$—$CH_2$), 1.67 (m, 2H, $CH_2$—$\underline{CH_2}$—$CH_2$—$CH_2$—NH), 1.74 (m, 2H, CO—$CH_2$—$CH_2$—$CH_2$—$\underline{CH_2}$), 2.16 (broad t, $^3J_{HH}$=7.2 Hz, 2H, CO—$\underline{CH_2}$—$CH_2$—$CH_2$—$CH_2$), 2.67 (m, 3H, $\underline{CH_2}$—$CH_2$—$CH_2$—$CH_2$—NH, $CH_2$—S), 2.75 (m, 2H, $C_6H_4$—$\underline{CH_2}$—$CH_2$—NH), 2.80 (m, 20H, $C_6H_4$—$\underline{CH_2}$—$CH_2$—N), 2.89 (m, 1H, $CH_2$—S), 3.06 (m, 20H, $C_6H_4$—$CH_2$—$\underline{CH_2}$—N), 3.20 (2 broad d, $^2J_{HP}$=12.7 Hz, 43H, N—$CH_2$—P, $CH_2$—$CH_2$—$CH_2$—$\underline{CH_2}$—NH, CH—S), 3.48 (m, 17H, N—$CH_3$, $C_6H_4$—$CH_2$—$\underline{CH_2}$—NH), 3.69 (2 d, 120H, $^3J_{HP}$=10.5 Hz, P(O)(OCH$_3$)), 4.27 (m, 1H, CH—$\underline{CH}$—NH), 4.45 (m, 1H, $CH_2$—$\underline{CH}$—NH), 5.07 (s, 2H, CO—$\underline{CH_2}$—N), 5.90 (broad s, 1H, CH—CH—$\underline{NH}$—CO), 6.10 (s, 1H, $CH_2$—CH—$\underline{NH}$—CO), 6.90 (d, $^3J_{HH}$=8.3 Hz, 2H, $C_o$—H), 7.04-7.17 (m, 32H, $C_m$—H, $C_o{}^2$—H, $C_1{}^2$—H), 7.27 (m, 20H, $C_1{}^3$—H), 7.32 (t, $^3J_{HH}$=5.6 Hz, 1H, $(CH_2)_4$—$\underline{NH}$—CO), 7.65 (s, 1H, N—CH=C), 7.73 (m, 10H, $C_o{}^3$—H), 7.88 (broad s, 3H, CH=N), 7.94 (broad s, 2H, CH=N), 8.00 (t, $^3J_{HH}$=5.5 Hz, 1H, $\underline{NH}$—CO—$CH_2$—N); $^{13}C\{^1H\}$ NMR (acetone-d6, 125.8 MHz): δ=25.0 (s, $\underline{CH_2}$—$CH_2$—$CH_2$—$CH_2$—NH), 25.6 (s, CO—$CH_2$—$\underline{CH_2}$—$CH_2$—$CH_2$), 26.6 (s, $CH_2$—$\underline{CH_2}$—$CH_2$—$CH_2$—NH), 28.2 (broad s, CO—$CH_2$—$CH_2$—$CH_2$—$\underline{CH_2}$, CO—$CH_2$—$CH_2$—$\underline{CH_2}$—$CH_2$), 28.2 (s, $CH_2$—$CH_2$—$\underline{CH_2}$—$CH_2$—NH), 32.2 (s, $C_6H_4$—$\underline{CH_2}$—$CH_2$—N), 32.8 (2 d, $^2J_{CP}$=12.2 Hz, N—$CH_3$), 34.5 (s, $C_6H_4$—$\underline{CH_2}$—$CH_2$—NH), 35.5 (s, CO—$\underline{CH_2}$—$CH_2$—$CH_2$—$CH_2$), 38.5 (s, $CH_2$—$CH_2$—$CH_2$—$\underline{CH_2}$—NH), 40.2 (s, $CH_2$—S), 40.7 (s, $C_6H_4$—$CH_2$—$\underline{CH_2}$—NH), 49.1 (dd, $^1J_{CP}$=157.3 Hz, $^3J_{CP}$=8.2 Hz, N—$CH_2$—P), 52.0 (m, P(O)(OCH$_3$), CO—$\underline{CH_2}$—N), 55.7 (s, CH—S), 58.1 (t, $^3J_{CP}$=7.7 Hz, $C_6H_4$—$CH_2$—$\underline{CH_2}$—N), 59.9 (s, $CH_2$—$\underline{CH}$—NH), 61.5 (s, CH—$\underline{CH}$—NH), 120.8 (s, $C_o$), 121.0 (d, $^3J_{CP}$=4.0 Hz, $C_1{}^2$), 121.3 (m, $C_o{}^2$), 122.8 (s, N—$\underline{CH}$=C), 128.4 (broad s, $C_o{}^3$), 129.9 (s, $C_m$), 130.1 (s, $C_1{}^3$), 132.6 (m, $C_o{}^4$), 136.6 (s, $C_p$), 137.3 (s, $C_1{}^4$), 139.5 (broad t, $^3J_{CP}$=4.9 Hz, CH=N), 147.2 (s, N—CH=$\underline{C}$), 148.9 (m, $C_1{}^1$), 151.2 (m, $C_i$, $C_o{}^1$), 162.8 (s, HN—CO—NH), 165.7 (HN—$\underline{CO}$—$CH_2$—N), 172.1 (s, $(CH_2)_4$—NH—$\underline{CO}$) ppm.

4.20. Synthesis of Dimethylphosphonate Salt Terminated Dendrimer with a Biotinylated Spacer [(Aza2P)$_{10}$-Biot-D]

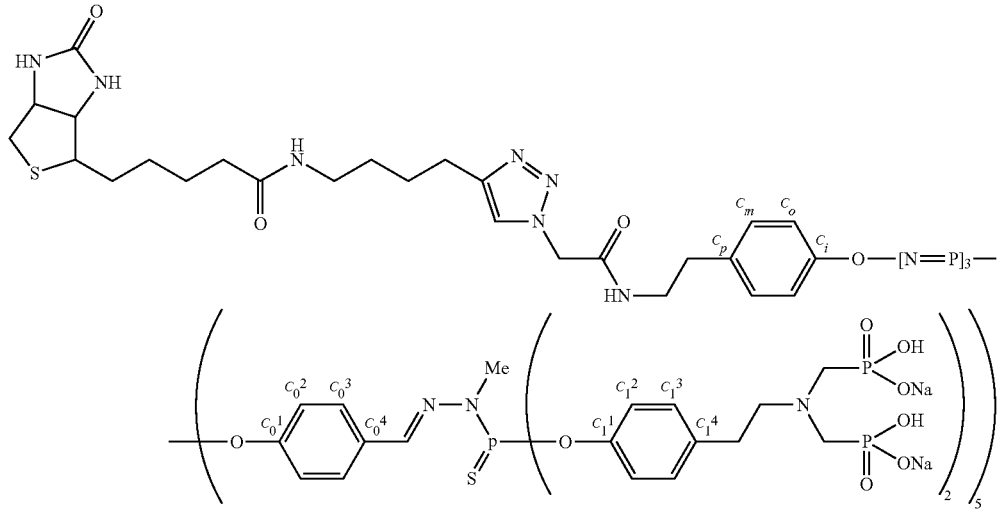

To a vigorously stirred solution of the compound of example 4.19 (36 mg, 0.007 mmol) in dry dichloromethane (2 mL) was added at 0° C., under a dry argon atmosphere, bromotrimethylsilane (40 µL, 0.299 mmol). The reaction mixture was stirred at room temperature overnight and then evaporated to dryness under reduced pressure. The crude residue was washed twice with methanol (2 mL) for 1 h at rt and evaporated to dryness under reduced pressure. The resulting white solid was washed once with diethylether (4 mL) and then transformed into its sodium salt as follows: the dendrimer was suspended in water (1 mL/100 mg) and one equivalent of sodium hydroxide per terminal phosphonic acid was added. The resulting solution was lyophilised to afford title compound as a white powder (yield=85%). $^{31}$P{$^{1}$H} NMR (D$_2$O/CD$_3$CN 7:1, 202.5 MHz): δ=7.1 (s, PO$_3$HNa), 9.5 (s, N$_3$P$_3$), 64.5 (s, P=S), 64.6 (s, P=S); $^{1}$H NMR (D$_2$O/CD$_3$CN 7:1, 500.3 MHz): δ=1.64 (m, 2H, CO—CH$_2$—CH$_2$—CH$_2$—CH$_2$)), 1.82 (m, 4H, CO—CH$_2$—CH$_2$—CH$_2$—CH$_2$, CH$_2$—CH$_2$—CH$_2$—CH$_2$—NH), 1.93 (m, 4H, CH$_2$—CH$_2$—CH$_2$—CH$_2$—NH, CO—CH$_2$—CH$_2$—CH$_2$—CH$_2$), 2.47 (s, 2H, CO—CH$_2$—CH$_2$—CH$_2$—CH$_2$), 3.10 (m, 7H, CH$_2$—CH$_2$—CH$_2$—CH$_2$—NH, CH$_2$—S, C$_6$H$_4$—CH$_2$—CH$_2$—NH, CH—S), 3.54 (broad s, 22H, C$_6$H$_4$—CH$_2$—CH$_2$—N, CH$_2$—CH$_2$—CH$_2$—CH$_2$—NH), 3.75 (broad d, $^{2}$J$_{HP}$=10.1 Hz, 42H, N—CH$_2$—P, C$_6$H$_4$—CH$_2$—CH$_2$—NH), 3.81 (m, 15H, N—CH$_3$), 4.13 (m, 20H, C$_6$H$_4$—CH$_2$—CH$_2$—N), 4.54 (broad s, 1H, CH—CH—NH), 4.70 (broad s, 1H, CH$_2$—CH—NH), 5.33 (broad s, 2H, CO—CH$_2$—N), 7.26 (broad s, 2H, C$_o$—H), 7.42 (m, 12H, C$_m$—H, C$_o^{2}$—H), 7.60 (m, 20H, C$_1^{2}$—H), 7.69 (s, 1H, N—CH=C), 7.82 (m, 20H, C$_1^{3}$—H), 8.06 (m, 10H, C$_o^{3}$—H), 8.29 (broad s, 3H, CH=N), 8.33 (broad s, 2H, CH=N) ppm. $^{13}$C{$^{1}$H} NMR (D$_2$O/CD$_3$CN 7:1, 125.8 MHz): δ=24.8 (s, CH$_2$—CH$_2$—CH$_2$—CH$_2$—NH), 25.8 (s, CO—CH$_2$—CH$_2$—CH$_2$—CH$_2$), 26.4 (s, CH$_2$—CH$_2$—CH$_2$—NH), 28.3 (broad s, CO—CH$_2$—CH$_2$—CH$_2$), 28.5 (s, CO—CH$_2$—CH$_2$—CH$_2$, CH$_2$—CH$_2$—CH$_2$—CH$_2$—NH), 29.3 (s, C$_6$H$_4$—CH$_2$—CH$_2$—N), 33.1 (d, $^{2}$J$_{CP}$=8.9 Hz, N—CH$_3$), 34.3 (s, C$_6$H$_4$—CH$_2$—CH$_2$—NH), 36.1 (s, CO—CH$_2$—CH$_2$—CH$_2$—CH$_2$), 39.3 (s, CH$_2$—CH$_2$—CH$_2$—CH$_2$—NH), 40.3 (s, CH$_2$—S), 40.6 (s, C$_6$H$_4$—CH$_2$—CH$_2$—NH), 52.2 (s, CO—CH$_2$—N), 55.4 (broad d, $^{1}$J$_{CP}$=125.6 Hz, N—CH$_2$—P), 55.8 (s, CH—S), 57.9 (broad s, C$_6$H$_4$—CH$_2$—CH$_2$—N), 60.6 (s, CH$_2$—CH—NH), 62.3 (s, CH—CH—NH), 121.0 (s, C$_o$), 121.9 (broad s, $^{3}$J$_{CP}$=4.0 Hz, C$_o^{2}$, C$_1^{2}$), 122.5 (s, N—CH=C), 128.9 (s, C$_o^{3}$), 130.7 (s, C$_m$), 131.1 (s, C$_1^{3}$), 133.0 (m, C$_o^{4}$), 135.1 (broad s, C$_p$, C$_1^{4}$), 141.1 (broad m, CH=N), 148.7 (s, N—CH=C), 149.7 (broad s, C$_1^{1}$), 151.1 (m, C$_i$, C$_o^{1}$), 164.2 (s, HN—CO—NH), 167.2 (HN—CO—CH$_2$—N), 175.9 (s, (CH$_2$)$_4$—NH—CO) ppm.

Example 5: Inhibition of the Proliferation of CD4 T Lymphocytes by Dendrimer Gc1

5.1. Methods

Peripheral blood samples are obtained from adult healthy volunteers through the Etablissement Français du Sang (Toulouse, France). Peripheral Blood Mononuclear Cells (PBMC) are isolated by Ficoll density gradient (Amersham Biosciences AB).

PBMC are cultured at a final concentration of 1.5×10$^{6}$ cells/mL in complete RPMI 1640 medium, i.e. supplemented with 10% of heat inactivated fetal calf serum (FCS) (Invitrogen), 1 mM sodium pyruvate (Invitrogen), 2 mM L-glutamine, 100 U/mL penicillin and 100 µg/mL streptomycin (Cambrex Bioscience). Proliferation is activated by 400 U/mL of interleukin 2 (IL2) (Sanofi-Aventis) (a "growth factor" for lymphocytes). Dendrimer Gc1 is made soluble in sterile water at 2 mM and filtered through a 0.2 µm membrane before use at 20 µM in culture.

Proliferation of CD4 T lymphocytes is evaluated by flow cytometry by analyzing the intracellular dilution of a fluorescent probe: the 5,6-carboxyfluorescein diacetate N-succinimidylester (CFSE). Briefly, PBMC are labelled with 1 µM CFSE in serum free PBS for 8 minutes at 37° C. and then labelling is stopped by adding an equal volume of FCS. The unconjugated CFSE is eliminated by 2 washes in PBS, and the CFSE-labelled PBMC are cultured for 6 days. Then, CFSE dilution is analyzed by flow cytometry to measure the proliferation CD4 T cells. After gating for CD4 positive cells (mouse anti-human CD4-PE-Cy5 clone 13B8.2, Beckman-Coulter), CFSE fluorescence intensities are analyzed, and the percentage of CD4 T cells which have proliferated during the culture is taken into account. Each condition is done in triplicate. The overall differences are evaluated by analysis of variance test (ANOVA) with Sigma Stat software (Systat Software).

5.2. Results

Figure 4:
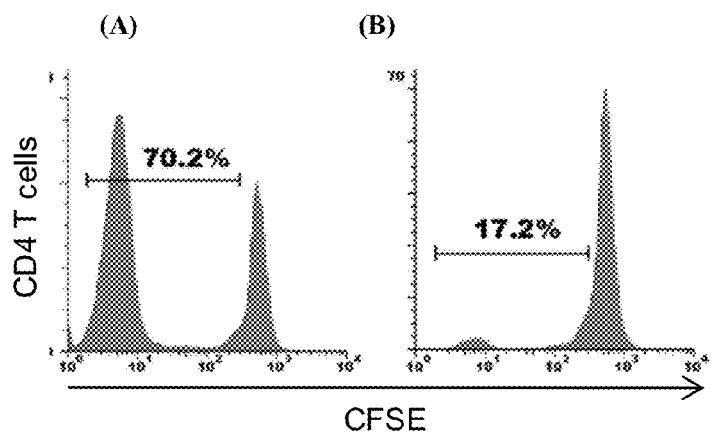
FIG. 4 shows the inhibitory properties of dendrimer Gc1 at 20 µM toward the proliferation of CD4 T lymphocytes in PBMC induced by IL2; (A) proliferation with IL2 alone (positive control); (B) proliferation with IL2 and Gc1 at 20 µM.

They are shown in FIG. 4.

T lymphocytes, especially CD4 T lymphocytes, proliferate in presence of IL2. We observe that, after a few days with IL2 alone, 70.2% of CD4 T lymphocytes have divided (left peak in FIG. 4A, the right peak corresponds to non-divided CD4 T lymphocytes).

In the same conditions but with 20 μM of Gc1, only 17.2% of CD4 T lymphocytes have divided (left signal FIG. 4B, the right peak corresponds to non-divided CD4 T lymphocytes).

Example 6: Inhibition of the Proliferation of Purified CD4 T Lymphocytes by Bisphosphonic Dendrimers

6.1. Methods

PBMC from adult healthy volunteers are prepared as described in example 5.1.

CD4 T lymphocytes are then purified from PBMC by positive selection using microbeads conjugated with anti-CD4 mAb, according to the manufacturer's instructions (Miltenyi Biotec). The cells obtained after the purification are >98% pure (as verified by flow cytometry).

Purified CD4 T lymphocytes are cultured at a final concentration of $1.5 \times 10^6$ cells/mL in complete RPMI 1640 medium (as described in example 5.1). Then, their proliferation is triggered by microbeads coated with anti-CD3 and anti-CD28 mAbs (Dynabeads®, Dynal Biotech ASA). Dendrimer Gc1 and its analogs are made soluble in sterile water at 2 mM and filtered through a 0.2 μm membrane before use at 20 μM in culture.

Proliferation of purified CD4 T lymphocytes is evaluated by flow cytometry by analyzing the intracellular dilution of a fluorescent probe: the CFSE.

6.2. Results

Figure 5:
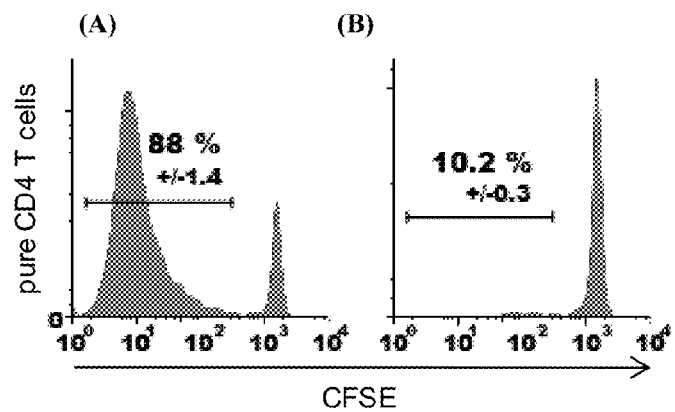
FIG. 5 shows the inhibitory properties of dendrimer Gc1 at 20 µM toward the proliferation of purified CD4 T lymphocytes stimulated by anti-CD3/anti-CD28 monoclonal antibodies (mAbs) and IL2; (A) proliferation with mAbs and IL2; (B) proliferation with mAbs and IL2 in presence of Gc1 at 20 µM.
Figure 6:
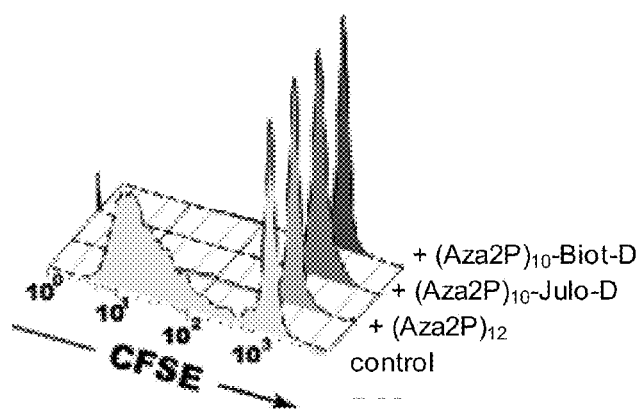
FIG. 6 shows the inhibitory properties of dendrimer Gc1 and of its analogs (Aza2P)$_{11}$-Julo-D and (Aza2P)$_{10}$-Biot-D at 20 µM toward the proliferation of purified CD4 T lymphocytes stimulated by anti-CD3/anti-CD28 mAbs and IL2.

They are shown in FIGS. 5 and 6.

CD4 T lymphocytes strongly proliferate after triggering by microbeads coated with anti-CD 3 and anti-CD28 mAbs in presence of IL2. We observe that, after a few days with microbeads and IL2, 88% of purified CD4 T lymphocytes have divided (FIG. 5A).

In the same conditions but with 20 μM of Gc1, only 10.2% of purified CD4 T lymphocytes have divided (FIG. 5B).

We observe the same inhibitory effect with the julolidin ((Aza2P)$_{10}$-Julo-D) and the biotinylated ((Aza2P)$_{10}$-Biot-D) analogs of Gc1 (FIG. 6).

These results show a direct inhibitory effect of azabisphosphonic dendrimers on the proliferation of CD4 T lymphocytes.

Example 7: Transcriptomic Study of Monocytes Activated by Dendrimer Gc1

7.1. Methods

7.1.1. Cell Preparation and Purification

Peripheral Blood Mononuclear Cells (PBMC) from adult healthy volunteers are prepared as described in example 1.

Monocytes are then purified by positive selection using microbeads conjugated with anti-CD14 mAb, according to the manufacturer's instructions (Miltenyi Biotec). The cells obtained after the purification are >95% pure. The CD14 negative fraction is collected as Peripheral Blood Lymphocytes (PBL).

7.1.2. Monocyte Culture and Activation

Monocytes are cultured at a final concentration of $1 \times 10^6$ cells/mL in complete RPMI 1640 medium (as described in example 1.1).

For genechip analysis, $10 \times 10^6$ monocytes from 3 donors (and from 3 more donors for quantitative PCR) are cultured in 25 cm² dishes. They are stimulated with 20 μM of dendrimer for 6 hours or remain untreated (control cells).

For the functional experiments, freshly purified monocytes are cultured in 6-well plates. The cells are stimulated for 24 hours (immunophenotyping by flow cytometry analyses, MLR) or 96 hours (CD206 detection) with different stimuli or remain untreated (control). Dendrimer-activated monocytes (da-monocytes) are obtained with 20 μM of the dendrimer Gc1, alternatively-activated monocytes (alt-monocytes) with 10 U/mL recombinant human IL4 (Peprotech). The classical activation of monocytes is obtained by priming the cells over night (18 hours) with 100 U/mL of human recombinant IFN-γ (R&D Systems) and, after a washing step in PBS, by stimulation with 10 ng/mL LPS from *E. coli* 011/B4 strain (InvivoGen) for the remaining 6 hours or 78 hours.

7.1.3. RNA Extraction and Complementary RNA (cRNA) Synthesis

Total RNA are extracted from $10 \times 10^6$ monocytes using TRIzol™ Reagent (Invitrogen), according to the manufacturer's instructions. The quality and integrity of the RNA obtained are assessed by using an Agilent 2100 Bioanalyser (Agilent Technologies) after a denaturating step at 70° C. for 2 minutes. cRNA are prepared according to one-Cycle Target Labelling protocol (Affymetrix) starting from 1 μg of total RNA.

7.1.4. Affymetrix Genechip Analysis cRNA are fragmented and hybridized to Affymetrix HG-U133 plus 2.0 arrays. The chips are then washed and scanned, according to the manufacturer's instructions. HG-U133 plus 2.0 arrays contain 54,675 sets of oligonucleotide probes that correspond to ≈39,000 unique human genes or predicted genes. GeneChip operating Software, Version 1.1 (Affymetrix), is used for the primary image analysis of the array, for the normalization (global scaling method, target value of 100), and for the comparisons between control and dendrimer-treated samples. Monocytes from 3 donors are analyzed after 6 hour incubation in the presence or absence of the dendrimer Gc1. Genes are considered to be differentially regulated in da-monocytes compared to control cells if they have a fold change of ≥2.0 or ≤−2.0 for at least two donors of the three. The annotation tool, which is an automated method for the functional annotation of gene lists, is performed with the Affymetrix NetAffx data base (http://www.affymetrix.com/analysis/netaffx/index.affx). Gene Ontology data mining for biological process at level 4 and 5 is conducted on line via the DAVID website (http://david.abcc.ncifcrf.gov/).

7.1.5. Quantitative RT-PCR

Total RNA are purified as described above, and 5 μg are used to synthesize single-strand cDNA using M-MLV reverse transcriptase RNase H Minus (Promega), according to the manufacturer's instructions. Quantitative RT-PCR is then performed using the Platinium SYBR Green qPCR SuperMix UDG (Invitrogen) with forward and reverse primers at a final concentration of 300 nM. The primers are designed using Primer Express software from mRNA sequences submitted to Ensembl data base, and are listed in FIG. 7. Quantification of the different mRNA is performed on a 7000 Sequence Detection System (Applied Biosystems). PCR amplification begins with 1 cycle of 50° C. for 2 minutes and 95° C. for 10 minutes, followed with 40 cycles of denaturation at 95° C. for 15 seconds and annealing/extension at 60° C. for 60 seconds. All experiments are performed in duplicate. For each donor, the relative expression is calculated as $2^{-\Delta\Delta Ct}$ where ΔΔCt is the difference between ΔCt of the sample and the ΔCt of the reference consisting of the control monocytes. ΔCt is the difference between the Ct of the target gene and the GAPDH gene. For statistical analysis, a one-tailed paired t test is performed comparing the ΔCt values for the da-monocytes and the corresponding control monocytes with Sigma Stat software (Systat Software).

7.1.6. Flow Cytometry

Flow cytometry is performed on a LSR-II cytometer (BD Biosciences). The data are analyzed with FACSDiva (BD Biosciences) or WinMDI softwares. The expression of surface markers is performed using mouse anti-human fluorochrome-conjugated mAbs specific for MHC class II-FITC (clone Tü36), CD86-PE (clone 2331), MHC class I-PE-Cy5 (clone G46-2.6) and CD13-PE (clone WM15) from BD Biosciences and specific for CD64-FITC (clone 22) and CD206-PE (clone 3.29B1.10) from Beckman-Coulter. Appropriate isotype-matched antibodies are used as negative control.

7.1.7. Allogenic Mixed Leucocyte Reactions (MLR)

MLR are performed in 96-well round bottom plates in a total volume of 200 μL in complete RPMI 1640 medium. Stimulation is assayed by incubating responder PBL ($10^5$ cells) with different numbers of allogenic stimulating monocytes (activated with the different stimuli for 24 hours) (PBL:monocyte ratios ranging from 4:1 to 100:1). The proliferation of the CD4 T cells is analyzed by measuring the cytoplasmic dilution of CFSE (as described in 5.1. Methods). The CFSE-labelled PBL and the differently activated monocytes are then co-cultured for 6 days. Then, CFSE dilution is analyzed by flow cytometry to measure the proliferation of alloantigen-induced CD4 T cells. After gating for CD4 positive cells CFSE fluorescence intensities are analyzed, and the percentage of CD4 T cells which have proliferated during the MLR is taken into account. Each condition is done in triplicate. The overall differences are evaluated by analysis of variance test (ANOVA) with Sigma Stat software (Systat Software).

7.1.8. Intracellular Detection of IL10

Six days following the primary stimulation with one of the differently activated monocytes at a ratio of PBL: monocytes of 4:1, cells were restimulated with 10000 anti-CD 3/anti-CD28 beads for 5 hours (according to the technical description by J. P. Edwards et al., (2006) *J Leukoc Biol* 80, 1298-1307) and with 10 μg/mL Brefeldin A (Sigma-Aldrich) to inhibit cytokine secretion. Cells are then harvested, washed with PBS and incubated 15 minutes at 4° C. with mouse mAb anti-human CD4-PE (clone 13B8.2, Beckman-Coulter) in PBS with 5% FCS. Cells washed twice, are then fixed by 2% paraformaldehyde in PBS and permeabilized with 1% saponin in PBS. Intracellular staining is performed with AlloPhycoCyanin-conjugated rat anti-human IL10 (clone JES3-19F1, BD Bioscience) for 30 minutes at 4° C. in PBS with 1% saponin and analyzed by flow cytometry. Each condition is done in triplicate and results are expressed as the mean±SD. Intracellular IL10 mean fluorescence intensity (mfi) means across the differently activated monocytes are compared by one-way analysis of variance, the comparisons between CD4$^+$/CFSE$^-$ and CD4$^+$/CFSE$^+$ cells are done with Student's t-test using Sigma Stat software (Systat Software).

7.2. Results

7.2.1. Human Monocyte Transcriptional Profile after Activation by Dendrimer Gc1

Results are shown in FIGS. 8 and 9.

78 genes were found over-expressed and 62 genes were found under-expressed by da-monocytes. On the one hand, up-regulation of genes coding for proteins characterizing the alternative activation of monocytes/macrophages such as the mannose receptor (MRC), the IL1 receptor antagonist (IL1 RN), the immuno-suppressive cytokine IL10, and the chemokine CCL18 (also called AMAC-1 for Alternative Macrophage Activation-associated CC-chemokine-1) is detected. C1QR1 (important for the anti-inflammatory phagocytosis of apoptotic cells), CHI3L1, matrix metalloproteinases (of which MMP1) and SLAMF1 are also found over-expressed. On the other hand, down-regulation of genes coding for CXCR4 (receptor for the pro-inflammatory CXL12 chemokine), metallothioneins and IFITs (gene clusters induced by IFN-γ) is detected. These genes are likely to be expressed after IFN-γ and/or LPS treatment. Moreover, we detect a down-regulated expression of adhesion molecules such as CD9, CD11a and CD18. CD11a/CD18 also know as lymphocyte function antigen 1 (LFA-1) are implicated in mechanisms of leukocyte recruitment on inflamed tissue (42).

7.2.2. Validation of the Alternative-Like Activation of Human Monocytes by Quantitative RT-PCR and Analysis of da-monocyte Phenotype Results are shown in FIG. 10.

9 gene transcripts of high relevance for the classical activation pathway (one pro-inflammatory chemokine: CCL5 and 3 pro-inflammatory cytokines: IL1 (3, IL6, IL12) or for the alternative activation pathway (MRC1, IL1 RN, IL10, CCL18 and CD23) are quantified. Results of quantitative RT-PCR are compared in da-monocytes and untreated monocytes of the 3 donors enlisted for the transcriptional study plus 3 supplementary donors. 5 genes whose products indicate an alternative activation (MRC1, IL1 RN, IL10, CCL18 and CD23) are significantly up-regulated in da-monocytes, whereas the expression levels of 3 genes out of 4 selected to indicate a classical activation (IL1β, IL6 and IL12) are not significantly modified and the fourth gene (coding for CCL5) is significantly under-expressed. These results confirm those of example 3.2.1.

7.2.3. Phenotype of da-monocytes

Results are shown in FIG. 11.

Expression of the mannose receptor MRC1 (CD206) is strongly enhanced by alt-monocytes and by da-monocytes, whereas this marker is weakly expressed by class-monocytes. On the contrary, CD64 (a FcγRI) is overexpressed in class-monocytes, but not in alt- or da-monocytes. Finally, FIG. 11 shows that CD13, a cell membrane-associated aminopeptidase N, also discriminates between the different types of monocyte activation. Class-monocytes express a higher level of CD13 than alt- and da-monocytes. Taken together, the quantitative study of gene transcripts and the analysis of the phenotype of differently activated monocytes strengthen the hypothesis of an alternative activation of human monocytes by bisphosphonic dendrimers.

7.2.4. The Activation of Monocytes by the Dendrimer Gc1 is Anti-Inflammatory and Immuno-Suppressive Results are shown in FIGS. 12 (1) and (2).

After 24 hours stimulations, the phenotypes of alt-, class- and da-monocytes are compared for the expression of HLA-DR, HLA-A,B,C (antigen presenting molecules) and CD86 (co-stimulatory molecule) markers by flow cytometry (FIG. 12(1) A). As expected, class-monocytes express high levels of antigen-presenting molecules and CD86, whereas alt-monocytes express lower levels of these molecules and appear as poor antigen-presenting cells (APC). In this respect, da-monocytes are closely related to alt-monocytes and also appear as poor APC. To compare the stimulatory capacity of differently activated monocytes, MLR with PBL and allogeneic activated-monocytes are performed. MLR activation is conducted for 4 different PBL/monocyte ratios from 4:1 to 100:1. MLR are measured as the percentage of divided CD4$^+$ T lymphocytes among the PBL by using the dilution of the fluorescent dye CFSE. The results for 3 representative donors are compiled in FIG. 12(1) B with alt-, class- and da-monocytes as activators of MLR. As awaited, MLR activation by class-monocytes is always significantly higher than activation by alt-monocytes, except for the 4:1 ratio of donor 1. Statistical analysis is given in FIG. 12(2). It is noteworthy that da-monocytes systematically give the lowest activating effect on MLR. In detail, MLR activations by da-monocytes are always lower than activations by class-monocytes. When compared to activations by alt-monocytes, activations by da-monocytes are also significantly lower, except for donor 2, 25:1 ratio of donor 1 and 10:1 and 25:1 ratios of donor 3.

7.2.5. Intracellular Detection of IL10

Results are shown in FIG. 13.

Intracellular labelling of IL10 is compared in divided (CFSE) and in non-divided (CFSE$^+$) CD4$^+$ T cells (FIG. 13 (A)) resulting from the different MLR contexts after re-stimulation for 5 hours with anti-CD3/anti-CD28 mAbs coated on microbeads. The results from a representative donor out of 3 show an increase of the percentage of IL10$^+$ CD4$^+$ dividing cells in all MLR (FIG. 13 (B)). FIG. 13 (C) shows a comparison of the production of IL10 in divided and non-divided CD4$^+$ T cells for the three MLR contexts independently. Statistical analysis of the mfi detected after labelling of IL10 gained in experiments with 3 donors indicates a significantly increased production of IL10 in divided (CFSE) CD4$^+$ T lymphocytes in MLR with da- and alt-monocytes. Conversely, the divided and non-divided CD4$^+$ T cells in MLR with class-monocytes do not show significantly different levels of IL10 production. FIG. 13 (D) shows the comparison of the production of IL10 in divided cells aroused from the three different MLR. The production of IL10 by CD4$^+$ T cells is significantly enhanced in MLR with da- and alt-monocytes when compared to MLR with class-monocytes.

Thus, alt- and da-monocytes are poor inducers of CD4 T cell proliferation. What is more, da-monocytes induced IL10-producing CD4 T cells.

All the results described in example 7 were also reported by Fruchon et al. *J. Leukocyte Biol.* 2009, 85, 553-562.

Example 8: Inhibition of the Differentiation of Monocytes in Osteoclasts by 20 µM of Dendrimer Gc1

8.1. Introduction

The combination of cytokines such as RANK-Ligand and M-CSF induces the differentiation of human monocytes in osteoclasts. In bone biology, osteoclasts are responsible for bone resorption whereas osteoblasts rebuilt it. In some pathological contexts, the balance between the activities of osteoclasts and osteoblasts is compromised in the direction of the osteoclastic activity resulting in bone resorption.

8.2. Methods

PBMC from adult healthy volunteers are prepared as described in example 1.

Monocytes are then purified by negative selection using a kit containing a mixture of mouse anti-human mAbs and superparamagnetic polystyrene beads coated with a human anti-mouse IgG mAbs, according to the manufacturer's instructions (Dynal). The cells obtained after the purification are >90% pure.

Pure monocytes are activated or not during 6 hours with 20 µM of dendrimer Gc1. After three washings, activated and not activated monocytes are cultured for 21 days in α-MEM complete medium, i.e. supplemented with 10% of heat inactivated fetal calf serum (FCS) (Invitrogen), 2 mM L-glutamine, 100 U/mL penicillin and 100 µg/mL streptomycin (Cambrex Bioscience) in presence or not of 20 µM of dendrimer Gc1. To generate osteoclasts, 50 ng/mL of M-CSF (PeproTech) and 30 ng/mL of sRANK-Ligand (PeproTech) are added to the culture medium. Each three days, half medium is changed and 25 ng/mL of M-CSF and 100 ng/mL of sRANK-Ligand are added. At day 21, the cells are fixed and stained with the leucocyte phosphatase acid kit according to the manufacturer's instructions (Sigma-Aldrich).

8.3. Results

They are shown in FIG. 14.

When added at 20 µM in the culture medium, dendrimer Gc1 inhibits the differentiation of human monocytes in osteoclasts (picture 1 of FIG. 14 shows osteoclasts as giant multinuclear cells whereas picture 2 shows nucleus of undifferenciated monocytes).

When monocytes are pre-incubated with 20 µM of dendrimer Gc1 during 6 hours, then rinsed before stimulation with RANK-Ligand and M-CSF, we also observe an inhibition of their differentiation in osteoclasts (picture 3 of FIG. 14 shows only a few osteoclasts among undifferenciated monocytes).

Example 9: Inhibition of Bone Resorption In Vitro

9.1. Methods

PBMC from adult healthy volunteers are prepared as described in example 1.

Monocytes are then purified as described in section 4.2.

Monocytes were cultured in bone matrix 96-well plates (OsteoAssay Human bone plate, Lonza, USA) and differentiated into osteoclasts in the presence of M-CSF and sRANK-Ligand as described in section 4.2. Supernatants were collected and bone resorption was evaluated using a Crosslaps assay (Nordicbioscience, Danemark) which measures collagen degradation fragments.

9.2. Results

They are shown in FIG. 15.

Results show the release of fragments of bone matrix collagen (CTX, in nM) measured at days (D) 12 and 16. Dendrimer Gc1 inhibits the in vitro resorption of bone when added directly in the differentiating medium (FIG. 15 (A)) or when monocytes have been pre-incubated for 6 hours and rinsed before stimulation by RANK-Ligand et M-CSF (FIG. 15 B). Dendrimer Gc1 at 200 nM inhibits approximatively 60% of bone resorption at day 12, and 80% at day 15 (FIG. 15 (A)).

When monocytes have been pre-incubated with the dendrimer Gc1 before induction of the differentiation, inhibition of bone resorption is around 80% at day 12 and 50% at day 15 (FIG. 15 (B)).

Taken together, these results show that bisphosphonic dendrimers activate human monocytes toward an «alternative-like» response and thus can be used as drugs for the treatment of uncontrolled inflammatory disorders in chronic or acute diseases such as psoriasis, rheumatoid arthritis or auto-immune disorders.

Example 10: Antiarthritic Properties of Dendrimer ABP In Vivo

Dendrimer ABP (azabisphosphonate) or Gc1 (FIG. 16A) was initially compared to two other dendrimer-based systems, dendrimer azamonophosphonate (AMP) and dendrimer polypropyleneimine (PPI), for antiarthritic activity in mice, according to the following protocole, described by Hayder et al. *Science Transl. Med.* 2011, 3, 81ra35.

Dendrimer AMP (FIG. 16B) is a phosphorus-based dendrimer that is similar in structure and composition to dendrimer ABP, but with different surface moieties, whereas dendrimer PPI (FIG. 16C) is a second-generation diaminobutane-core dendrimer that has the same ABP surface moieties as dendrimer ABP.

IL-1ra−/− mice develop spontaneous arthritis beginning at 4 weeks of age. By 10 weeks, 100% of mice show full-blown disease, with marked paw swelling. We assessed the effect of dendrimers ABP, AMP, and PPI in this model of arthritis via weekly intravenous injections (10 mg/kg) starting at 8 weeks of age. The evolution of inflammation and arthritis was followed by measuring the hind paw swelling and by clinical arthritic score. The arthritic score per animal was the sum of the scores attributed to the four paws (28).

Only dendrimer ABP showed a significant decrease in paw swelling and in arthritic score at the age of 15 weeks (FIG. 16D).

Example 11: Efficacy of Dendrimer G1-ABP in a Mouse Model of Experimental Autoimmune Encephalomyelitis (EAE)

Experimental Autoimmune Encephalomyelitis (EAE) is an inflammatory disease of the Central Nervous System (CNS) that shares clinical and immunopathological similarities with Multiple Sclerosis (MS). The model we have chosen is the classical model of active EAE induced by an immunization against myelin oligodendrocyte protein (MΦG) peptide 35-55 in mice. This leads to a chronic-progressive form of EAE resembling MS. Therefore, it is considered as a good model. Disease severity is scored on a clinical scale of 0 to 5 (0 being no detectable sign of EAE, 4 being tetraparalysis and 5 moribund or death). After MΦG-immunization, EAE scores for motor functions have been evaluated daily for 45 days for each animal. A preventive protocol (FIG. 17A) and a therapeutic protocol (FIG. 17B) have been tested. In both cases, mice are immunized with the MΦG peptide at Day 0 (first arrow of FIGS. 17A and 17B, corresponding to day 0 post-immunization). In the preventive protocol, intravenous administration of 10 mg/kg of dendrimer ABP started at Day 1 (FIG. 17A, second arrow, corresponding to 1 day post-immunization) and then every three days. In the therapeutic protocol, administration of ABP started once the disease is established at Day 18 (FIG. 17B, second arrow, corresponding to 18 days post-immunization), in the same conditions as the preventive protocol.

After 45 days post-immunization and without any ABP-based protocol, the disease severity clinical score is about 4 (control). In contrast, the disease severity clinical score is about 1 with the ABP-base therapeutic protocol, and is even less than 1 with the ABP-base preventive protocol, after 45 days post-immunization.

The invention claimed is:

1. A method for treating an inflammatory disease through an anti-inflammatory type activation of monocytes, said disease being selected from the group consisting of rheumatoid arthritis, psoriasis, and multiple sclerosis, said method comprising:

administering to a patient in need thereof of an effective quantity of at least one dendrimer with biphosphonic terminations selected from:

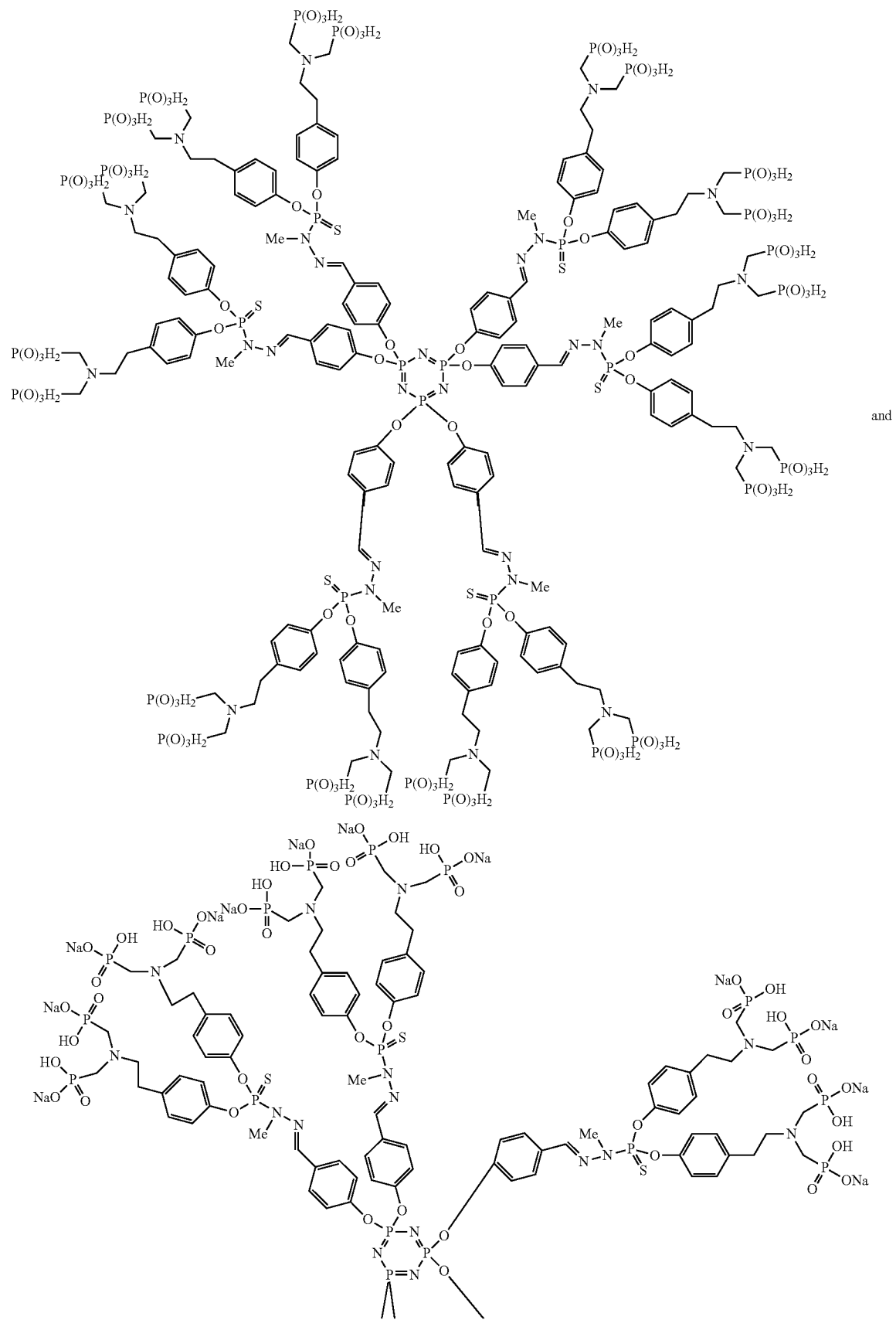
173
174
and

175
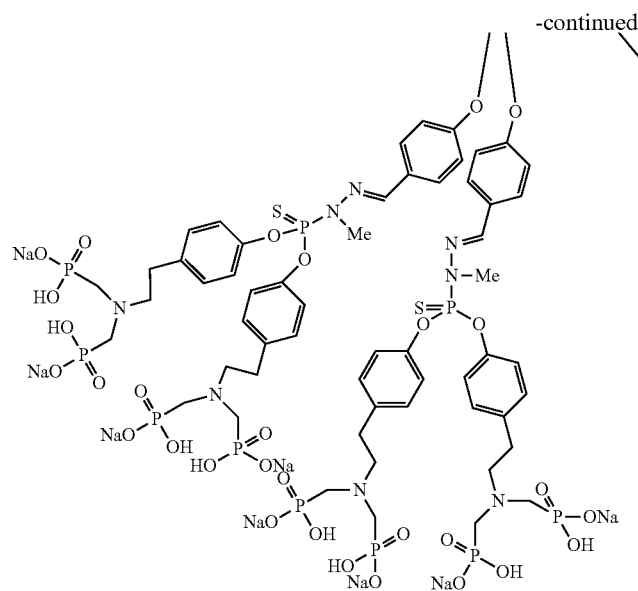
-continued
176
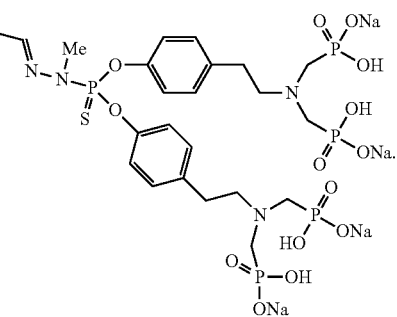
* * * * *